US009951347B2

(12) United States Patent
Flasinski

(10) Patent No.: US 9,951,347 B2
(45) Date of Patent: Apr. 24, 2018

(54) PLANT REGULATORY ELEMENTS FROM THE UBQ10 GENE OF C. LACRYMA-JOBI

(71) Applicant: Monsanto Technology LLC, St. Louis, MO (US)

(72) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/046,914

(22) Filed: Feb. 18, 2016

(65) Prior Publication Data

US 2016/0177326 A1 Jun. 23, 2016

Related U.S. Application Data

(62) Division of application No. 14/133,599, filed on Dec. 18, 2013, now Pat. No. 9,303,266.

(60) Provisional application No. 61/739,720, filed on Dec. 19, 2012.

(51) Int. Cl.
*C12N 15/82* (2006.01)

(52) U.S. Cl.
CPC ..... *C12N 15/8216* (2013.01); *C12N 15/8279* (2013.01)

(58) Field of Classification Search
None
See application file for complete search history.

(56) References Cited

U.S. PATENT DOCUMENTS

| | | | | |
|---|---|---|---|---|
| 5,510,474 | A | 4/1996 | Quail et al. | |
| 6,054,574 | A | 4/2000 | Quail et al. | |
| 6,635,806 | B1 * | 10/2003 | Kriz | C07K 14/415 536/24.1 |
| 7,371,848 | B2 * | 5/2008 | Conner | C12N 15/8216 536/24.1 |
| 8,168,859 | B2 | 5/2012 | Abbitt | |
| 2007/0061917 | A1 | 3/2007 | McCutchen et al. | |
| 2007/0204367 | A1 * | 8/2007 | Flasinski | C12N 15/8216 800/278 |
| 2009/0138985 | A1 | 5/2009 | Martinell et al. | |
| 2010/0058495 | A1 | 3/2010 | Abbitt | |
| 2011/0023183 | A1 | 1/2011 | Stewart et al. | |
| 2012/0180158 | A1 | 7/2012 | Abbitt | |
| 2012/0198584 | A1 | 8/2012 | Nuccio | |
| 2012/0246763 | A1 | 9/2012 | Flasinski | |
| 2016/0177325 | A1 | 6/2016 | Flasinski | |

FOREIGN PATENT DOCUMENTS

| | | |
|---|---|---|
| WO | WO 1989/012059 A1 | 12/1989 |
| WO | WO 1998/044781 A1 | 10/1998 |
| WO | WO 2001/094394 A2 | 12/2001 |
| WO | WO 2009/149304 A2 | 10/2009 |
| WO | WO 2011/130894 | 10/2011 |
| WO | WO 2012/134921 | 10/2012 |
| WO | WO 2012/158535 A1 | 11/2012 |

OTHER PUBLICATIONS

Donald & Cashmore, EMBO J 9:1717-26 (1990).*
Kim et al., Plant Mol Biol 24:105-17 (1994).*
Dolferus et al., Plant Physiol 105:1075-87 (1994).*
Kiran et al., Plant Physiol 142(1):364-76 (2006).*
Grefen et al., Plant J 64:355-65 (2010).*
Potenza et al., In Vitro Cell Dev Biol Plant 40:1-22 (2004).*
Saha et al., In Silico Biol 7(1):7-19 (2007).*
Rose, Curr Top Microbiol Immunol, 326:277-90 (2008).*
Joung & Kamo, Plant Cell Rep 25:1081-88 (2006).*
Wang & Oard, Plant Cell Rep 22:129-34 (2003).*
USPTO Written Description Training Materials (2008).*
Welsch et al., Planta 216:523-34 (2003).*
Cho & Cosgrove, Plant Cell 14:3237-53 (2002).*
Partial Supplementary European Search Report regarding European Application No. 13866064, dated May 20, 2016.
Benfey et al., "The CaMV 35S enhancer contains at least two domains which can confer different developmental and tissue-specific expression patterns," *EMBO J.*, 8(8):2195-2202, 1989.
Callis et al., "Introns increase gene expression in cultured maize cells," *Genes & Dev.* 1:1183-1200, 1987.
Cho et al., "Regulation of root-hair initiation and expansin gene expression in *Arabidopsis*," *The Plant Cell*, 14:3237-3253, 2002.
Christensen et al., "Ubiquitin promoter-based vectors for high-level expression of selectable and/or screenable marker genes in monocotyledonous plants," *Transgenic Research* 5:213-218, 1996.
Christiansen et al., "Maize polyubiquitin genes: structure, thermal perturbation of expression and transcript splicing, and promoter activity following transfer to protoplasts by electroporation," *Plant Mol. Biol*, 18:675-689, 1992.
Dolferus et al., "Differential Interactions of Promoter Elements in Stress Responses of the *Arabidopsis* Adh Gene," *Plant Physiol.* 105:1075-1087, 1994.
Donald et al., "Mutation of either G box or I box sequences profoundly affects expression from the *Arabidopsis* rbcS-1A promoter," *EMBO J.* 9:1717-1726, 1990.
International Search Report and Written Opinion for International Application No. PCT/US2013/075813, dated Jun. 10, 2014.
Jeon et al., "Tissue-Preferential Expression of a Rice a-Tubulin Gene, OsTubA1, Mediated by the First Intron," *Plant Physiol.* 123:1005-1014, 2000.

(Continued)

*Primary Examiner* — Cathy Kingdon Worley
*Assistant Examiner* — Russell T Boggs
(74) *Attorney, Agent, or Firm* — Dentons US LLP; Carine M. Doyle, Esq.

(57) ABSTRACT

The invention provides novel recombinant DNA molecules and constructs useful for modulating gene expression in plants, plant cells, seeds, and progeny plants. Plant regulatory elements comprising sequences from the Ubq10 gene of *C. lacryma-jobi*, as well as variants and fragments thereof having gene regulatory activity, are provided. The invention also provides transgenic plants, plant cells, plant parts, seeds, and progeny plants comprising the recombinant DNA molecules of the invention, along with methods of their use.

20 Claims, 9 Drawing Sheets

(56) References Cited

OTHER PUBLICATIONS

Kim et al., "A 20 nucleotide upstream element is essential for the nopaline synthase (nos) promoter activity," *Plant Molecular Biology* 24:105-117, 1994.
Mascarenhas et al., "Intron-mediated enhancement of heterologous gene expression in maize," Plant Mol. Biol 15:913-920, 1990.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Mol. Biol.*, 38:655-662, 1998.
Potenza et al., "Invited Review: Targeting Transgene Expression in Research, Agricultural, and Environmental Applications: Promoters Used in Plant Transformation," *In Vitro Cell. Dev. Biol.-Plant* 40:1-22, 2004.
Vasil et al., "Increased Gene Expression by the First Intron of Maize Shrunken-1 Locus in Grass Species," *Plant Physiol.* 91:1575-1579, 1989.
Welsch et al., "Structural and functional characterization of the phytoene synthase promoter from *Arabidopsis thaliana*," *Planta*, 216:523-534, 2003.
USPTO: Non-Final Office Action regarding U.S. Appl. No. 15/046,906, dated Oct. 5, 2017.
Response to Non-Final Office Action regarding U.S. Appl. No. 15/046,906, dated Nov. 17, 2017.
USPTO: Final Office Action regarding U.S. Appl. No. 15/046,906, dated Feb. 16, 2018.

* cited by examiner

P-ARUdo.Ubq1-1:1:4
(SEQ ID NO: 10; 4114 bp)

P-ARUdo.Ubq1-1:1:5
(SEQ ID NO: 14; 2012 bp)

P-ARUdo.Ubq1-1:1:6
(SEQ ID NO: 17; 1000 bp)

P-ARUdo.Ubq1-1:1:8
(SEQ ID NO: 22; 755 bp)

▬▬▬▬▬▬▬▬▬▬▬▬▬▬▬ P-ARUdo.Ubq2-1:1:4
(SEQ ID NO: 24; 2033 bp)

▬▬▬▬▬▬▬▬▬▬ P-ARUdo.Ubq2-1:1:6
(SEQ ID NO: 28; 2004 bp)

▬▬▬▬ P-ARUdo.Ubq2-1:1:5
(SEQ ID NO: 31; 1001 bp)

▬▬ P-ARUdo.Ubq2-1:1:7
(SEQ ID NO: 33; 696 bp)

P-BOUgr.Ubq1-1:1:2
(SEQ ID NO: 35; 2371 bp)

P-BOUgr.Ubq1-1:1:3
(SEQ ID NO: 39; 1999 bp)

P-BOUgr.Ubq1-1:1:5
(SEQ ID NO: 42; 1022 bp)

P-BOUgr.Ubq1-1:1:6
(SEQ ID NO: 44; 760 bp)

P-BOUgr.Ubq2-1:1:4
(SEQ ID NO: 46; 2100 bp)

P-BOUgr.Ubq2-1:1:7
(SEQ ID NO: 50; 2043 bp)

P-BOUgr.Ubq2-1:1:5
(SEQ ID NO: 53; 2002 bp)

P-BOUgr.Ubq2-1:1:6
(SEQ ID NO: 56; 1024 bp)

P-BOUgr.Ubq2-1:1:8
(SEQ ID NO: 61; 749 bp)

P-MISsi.Ubq1-1:1:2
(SEQ ID NO: 63; 5359bp)

P-MISsi.Ubq1-1:1:11
(SEQ ID NO: 67; 2423bp)

P-MISsi.Ubq1-1:1:10
(SEQ ID NO: 71; 1447bp)

P-MISsi.Ubq1-1:1:13
(SEQ ID NO: 73; 899bp)

P-MISsi.Ubq1-1:1:14
(SEQ ID NO: 75; 691bp)

P-MISsi.Ubq1-1:1:9
(SEQ ID NO: 77; 506bp)

P-SCHsc.Ubq1-1:1:12
(SEQ ID NO: 79; 2831 bp)

P-SCHsc.Ubq1-1:1:11
(SEQ ID NO: 83; 2033 bp)

P-SCHsc.Ubq1-1:1:10
(SEQ ID NO: 85; 1046 bp)

P-SCHsc.Ubq1-1:1:14
(SEQ ID NO: 87; 547 bp)

P-SORnu.Ubq1-1:1:4
(SEQ ID NO: 89; 2218 bp)

P-SORnu.Ubq1-1:1:5
(SEQ ID NO: 93; 1964 bp)

P-SORnu.Ubq1-1:1:6
(SEQ ID NO: 96; 1023 bp)

P-SORnu.Ubq1-1:1:7
(SEQ ID NO: 98; 724 bp)

Expression Cassette Configuration 1

Promoter
or
chimeric
promoter | Leader | Intron | Coding Region | 3' UTR
[A] | [B] | [C] | [D] | [E]

Expression Cassette Configuration 2

Promoter
or
chimeric
promoter | Leader | Intron | Leader | Coding Region | 3' UTR
[F] | [G] | [H] | [I] | [J] | [K]

Expression Cassette Configuration 3

Promoter
or
chimeric
promoter | Leader | Coding Region | Intron | Coding Region | 3' UTR
[L] | [M] | [N] | [O] | [P] | [Q]

PLANT REGULATORY ELEMENTS FROM THE UBQ10 GENE OF C. LACRYMA-JOBI

REFERENCE TO RELATED APPLICATIONS

This application is a divisional of co-pending U.S. application Ser. No. 14/133,599, filed Dec. 18, 2013 (pending), which claims the benefit of priority to U.S. provisional application Ser. No. 61/739,720, filed Dec. 19, 2012, the disclosures of which are incorporated by reference herein in their entirety.

INCORPORATION OF SEQUENCE LISTING

The sequence listing that is contained in the file named "38-21-59465-0000Seq.txt", which is 341,857 bytes (as measured in Microsoft Windows®) and was created on Sep. 27, 2012, is filed herewith by electronic submission and is incorporated by reference herein.

FIELD OF THE INVENTION

The invention relates to the field of plant molecular biology, plant genetic engineering, and DNA molecules useful for modulating gene expression in plants.

BACKGROUND

Regulatory elements are genetic elements that regulate gene activity by modulating the transcription of an operably linked transcribable DNA molecule. Such elements include promoters, leaders, enhancers, introns, and 3' untranslated regions, and are useful in the field of plant molecular biology and plant genetic engineering.

SUMMARY OF THE INVENTION

The invention provides novel regulatory elements for use in plants and constructs comprising the regulatory elements. The invention also provides transgenic plant cells, plants, plant parts, and seeds comprising the regulatory elements. In one embodiment, the invention provides the regulatory elements disclosed herein operably linked to a transcribable DNA molecule. In certain embodiments, the transcribable DNA molecule is heterologous with respect to a regulatory element sequence provided herein. Also provided herein are methods for making and using the regulatory elements disclosed herein, including constructs comprising the regulatory elements, and transgenic plants, plant cells, plant parts, and seeds comprising the regulatory elements operably linked to a transcribable DNA molecule that is heterologous with respect to the regulatory element.

Thus, in one aspect, the invention provides a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. By "heterologous transcribable DNA molecule," it is meant that the transcribable DNA molecule is heterologous with respect to the DNA sequence. In specific embodiments, the recombinant DNA molecule comprises a DNA sequence having at least 90 percent, at least 91 percent, at least 92 percent, at least 93 percent, at least 94 percent, at least about 95 percent, at least 96 percent, at least 97 percent, at least 98 percent, or at least 99 percent sequence identity to the DNA sequence of any of SEQ ID NOs: 1-98 and 168-171. In particular embodiments, the heterologous transcribable DNA molecule comprises a gene of agronomic interest, such as a gene capable of conferring herbicide resistance or pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. In specific embodiments, the transgenic plant is a progeny plant of any generation relative to a starting transgenic plant and comprises the recombinant DNA molecule. A transgenic seed comprising the recombinant DNA molecule that produces such a transgenic plant when grown is also provided by the invention.

In still yet another aspect, the invention provides a method of expressing a transcribable DNA molecule, such as a gene of agronomic interest, in a transgenic plant by obtaining a transgenic plant containing a recombinant DNA molecule of the invention and cultivating the plant.

Also provided herein is a method of providing a transgenic plant by transforming a plant cell with a recombinant DNA molecule of the invention to produce a transformed plant cell, and regenerating the transformed plant cell to produce a transgenic plant.

BRIEF DESCRIPTION OF THE FIGURES

FIG. 1 shows an alignment of a 2005 base pair (bp) promoter P-AGRne.Ubq1-1:1:5 (SEQ ID NO: 2), contained in the regulatory expression element group (EXP) EXP-AGRne.Ubq1:1:7 (SEQ ID NO: 1), with promoter variants of P-AGRne.Ubq1-1:1:5. Deletion, for instance of the 5' end of P-AGRne.Ubq1-1:1:5, produced the promoter P-AGRne.Ubq1-1:1:4 (SEQ ID NO: 6), a 999 by sequence that is contained in EXP-AGRne.Ubq1:1:8 (SEQ ID NO: 5). Another promoter variant shown in FIG. 1 is P-AGRne.Ubq1-1:1:6 (SEQ ID NO: 8), a 762 by sequence contained in EXP-AGRne.Ubq1:1:9 (SEQ ID NO: 7).

FIG. 2: Shows an alignment of multiple promoter variants of various sizes corresponding to promoter elements from

*Arundo donax*. In particular, FIG. 2 shows an alignment of a 4114 by promoter P-ARUdo.Ubq1-1:1:4 (SEQ ID NO: 10), contained in the regulatory expression element group EXP-ARUdo.Ubq1:1:4 (SEQ ID NO: 9), with promoter variants of P-ARUdo.Ubq1-1:1:4. Included in the alignment are a 2012 by promoter P-ARUdo.Ubq1-1:1:5 (SEQ ID NO: 14); a 1000 by promoter P-ARUdo.Ubq1-1:1:6 (SEQ ID NO: 17); and a 755 by promoter P-ARUdo.Ubq1-1:1:8 (SEQ ID NO: 22).

FIG. 3 shows an alignment of a 2033 by promoter P-ARUdo.Ubq2-1:1:4 (SEQ ID NO: 24) with promoter variants of P-ARUdo.Ubq2-1:1:4. Included in the alignment are a 2004 by promoter P-ARUdo.Ubq2-1:1:6 (SEQ ID NO: 28); a 1001 by promoter P-ARUdo.Ubq2-1:1:5 (SEQ ID NO: 31); and a 696 by promoter P-ARUdo.Ubq2-1:1:7 (SEQ ID NO: 33).

FIG. 4 shows an alignment of a 2371 by promoter P-BOUgr.Ubq1-1:1:2 (SEQ ID NO: 35) with promoter variants of the 5' end of P-BOUgr.Ubq1-1:1:2. Included in the alignment are a 1999 by promoter P-BOUgr.Ubq1-1:1:3 (SEQ ID NO: 39); a 1022 by promoter P-BOUgr.Ubq1-1:1:5 (SEQ ID NO: 42); and a 760 by promoter P-BOUgr.Ubq1-1:1:6 (SEQ ID NO: 44).

FIG. 5 shows alignment of a 2100 by promoter element, P-BOUgr.Ubq2-1:1:4 (SEQ ID NO: 46) with promoter variants of P-BOUgr.Ubq2-1:1:4. Included in the alignment are a 2043 by promoter P-BOUgr.Ubq2-1:1:7 (SEQ ID NO: 50); a 2002 by promoter P-BOUgr.Ubq2-1:1:5 (SEQ ID NO: 53); a 1024 by promoter P-BOUgr.Ubq2-1:1:6 (SEQ ID NO: 56); and a 749 by promoter P-BOUgr.Ubq2-1:1:8 (SEQ ID NO: 61).

FIG. 6 shows an alignment of a 5359 by promoter element, P-MISsi.Ubq1-1:1:2 (SEQ ID NO: 63) with promoter variants of P-MISsi.Ubq1-1:1:2. Included in the alignment are a 2423 by promoter P-MISsi.Ubq1-1:1:11 (SEQ ID NO: 67); a 1447 by promoter P-MISsi.Ubq1-1:1:10 (SEQ ID NO: 71); a 899 by promoter P-MISsi.Ubq1-1:1:13 (SEQ ID NO: 73); a 691 by promoter P-MISsi.Ubq1-1:1:14 (SEQ ID NO: 75); and a 506 by promoter P-MISsi.Ubq1-1:1:9 (SEQ ID NO: 77).

FIG. 7 shows an alignment of a 2831 by promoter element, P-SCHsc.Ubq1-1:1:12 (SEQ ID NO: 79) with promoter variants of P-SCHsc.Ubq1-1:1:12. Included in the alignment are a 2033 by promoter P-SCHsc.Ubq1-1:1:11 (SEQ ID NO: 83); a 1046 by promoter P-SCHsc.Ubq1-1:1:10 (SEQ ID NO: 85); and a 547 by promoter P-SCHsc.Ubq1-1:1:14 (SEQ ID NO: 87).

FIG. 8 shows an alignment of a 2218 by promoter element, P-SORnu.Ubq1-1:1:4 (SEQ ID NO: 89) with promoter variants of P-SORnu.Ubq1-1:1:4. Included in the alignment are a 1964 by promoter P-SORnu.Ubq1-1:1:5 (SEQ ID NO: 93); a 1023 by promoter P-SORnu.Ubq1-1:1:6 (SEQ ID NO: 96); and a 724 by promoter P-SORnu.Ubq1-1:1:7 (SEQ ID NO: 98).

BRIEF DESCRIPTION OF THE SEQUENCES

Figure 1:
FIG. 1: Shows an alignment of multiple promoter variants of various sizes corresponding to promoter elements from *Agrostis nebulosa*. In particular.
Figure 2:
Figure 3:
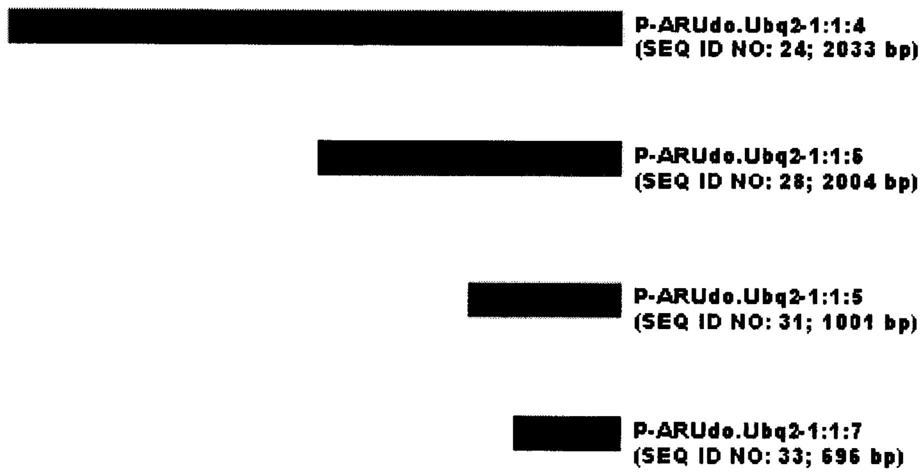
FIG. 3: Shows an alignment of multiple promoter variants of various sizes corresponding to promoter elements from *Arundo donax*. In particular.
Figure 4:
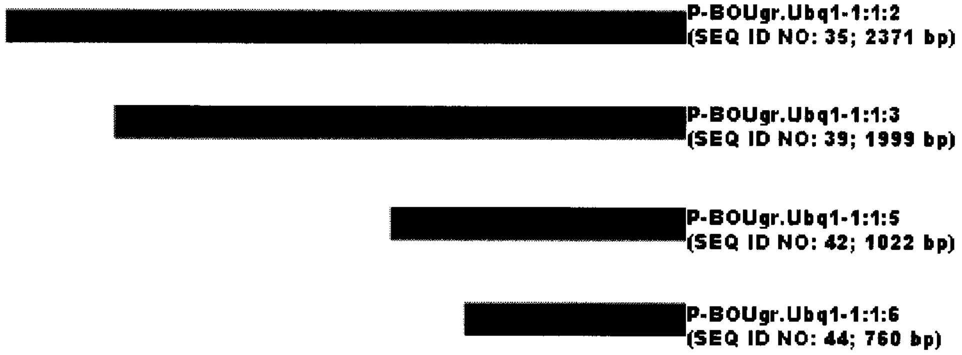
FIG. 4: Shows an alignment of multiple promoter variants of various sizes corresponding to promoter elements from *Bouteloua gracilis*. In particular.
Figure 5:
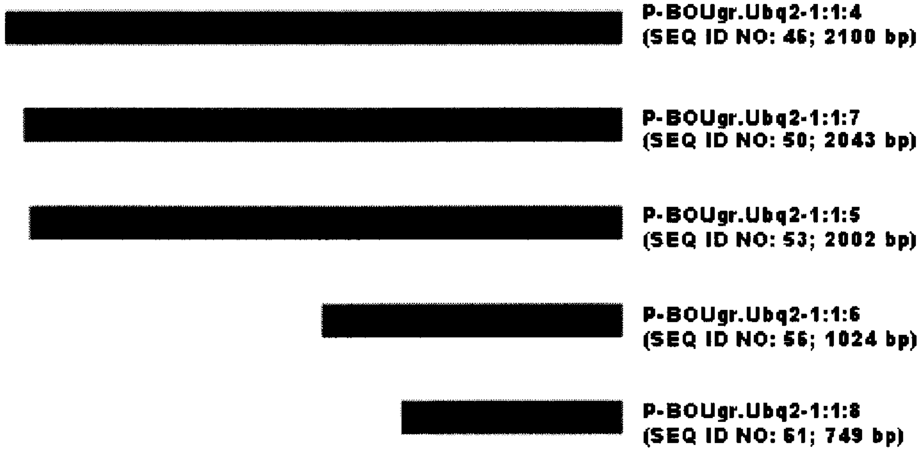
FIG. 5: Shows an alignment of multiple promoter variants of various sizes corresponding to promoter elements from *Bouteloua gracilis*. In particular.
Figure 6:
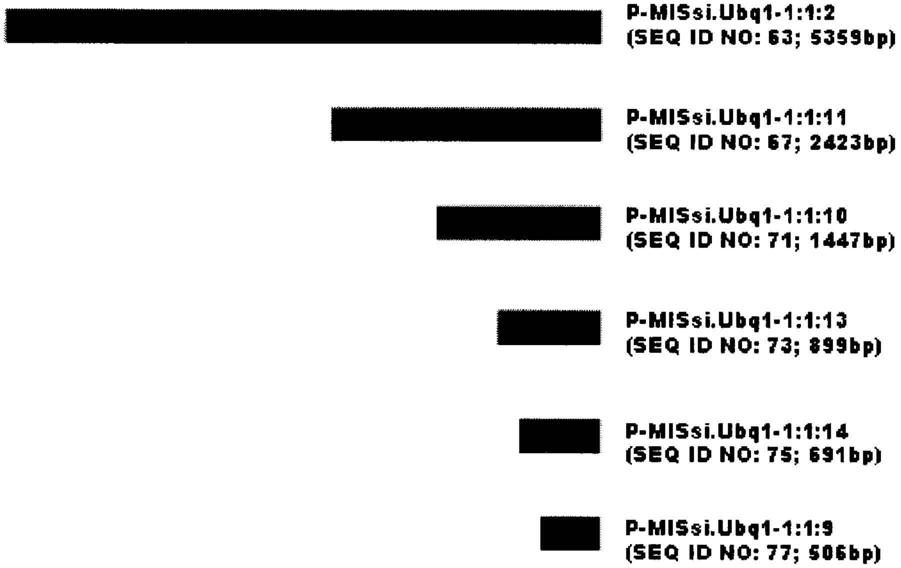
FIG. 6: Shows an alignment of multiple promoter variants of various sizes corresponding to promoter elements from *Miscanthus sinesis*. In particular.
Figure 7:
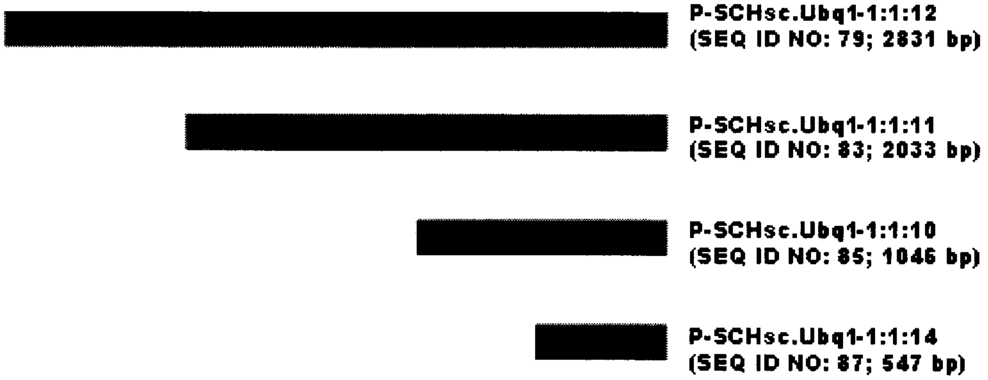
FIG. 7: Shows an alignment of multiple promoter variants of various sizes corresponding to promoter elements from *Schizachyium scoparium*. In particular.
Figure 8:
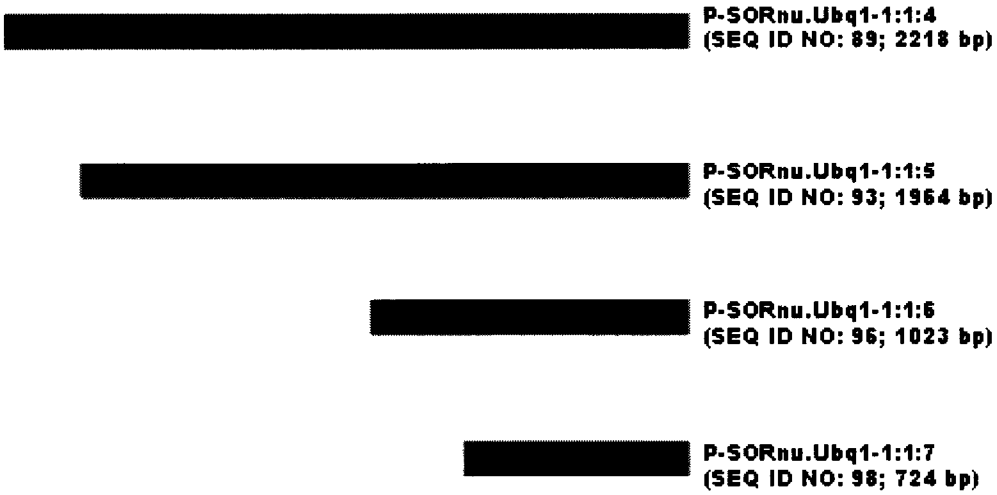
FIG. 8: Shows an alignment of multiple promoter variants of various sizes corresponding to promoter elements from *Sorghastrum nutans*. In particular.

SEQ ID NOs: 1, 5, 7, 9, 13, 16, 18, 19, 21, 23, 27, 30, 32, 34, 38, 41, 43, 45, 49, 52, 55, 58, 60, 62, 66, 70, 72, 74, 76, 78, 82, 84, 86, 88, 92, 95, 97, 99, 103, 106, 108, 110, 114, 116, 118, 120, 122, 126, 128, 132, 134, 138, 140, 144, 148, 150 and 168 are DNA sequences of regulatory expression element groups (EXPs) comprising a promoter sequence operably linked 5' to a leader sequence which is operably linked 5' to an intron sequence.

SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98, 100, 104, 107, 109, 111, 117, 119, 121, 123, 129, 135, 141, 145, 151 and 169 are promoter sequences.

SEQ ID NOs: 3, 11, 25, 36, 47, 64, 68, 80, 90, 101, 112, 124, 130, 136, 142, 146, 152 and 170 are leader sequences.

SEQ ID NOs: 4, 12, 15, 20, 26, 29, 37, 40, 48, 51, 54, 57, 59, 65, 69, 81, 91, 94, 102, 105, 113, 115, 125, 127, 131, 133, 137, 139, 143, 147, 149, 153 and 171 are intron sequences.

DETAILED DESCRIPTION OF THE INVENTION

The invention provides DNA molecules having gene-regulatory activity in plants. The nucleotide sequences of these DNA molecules are provided as SEQ ID NOs: 1-98 and 168-171. These DNA molecules are, for instance, capable of affecting the expression of an operably linked transcribable DNA molecule in plant tissues, and therefore regulating gene expression of an operably linked transgene in transgenic plants. The invention also provides methods of modifying, producing, and using the same. The invention also provides compositions that include transgenic plant cells, plants, plant parts, and seeds containing recombinant DNA molecules of the invention, and methods for preparing and using the same.

The following definitions and methods are provided to better define the invention and to guide those of ordinary skill in the art in the practice of the invention. Unless otherwise noted, terms are to be understood according to conventional usage by those of ordinary skill in the relevant art.

DNA Molecules

As used herein, the term "DNA" or "DNA molecule" refers to a double-stranded DNA molecule of cellular or synthetic origin, i.e., a polymer of deoxyribonucleotide bases. As used herein, the term "DNA sequence" refers to the nucleotide sequence of a DNA molecule. The nomenclature used herein corresponds to that of by Title 37 of the United States Code of Federal Regulations §1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation.

As used herein, the term "sequence identity" refers to the extent to which two optimally aligned DNA sequences are identical. An optimal sequence alignment is created by manually aligning two DNA sequences, e.g., a reference sequence and another DNA sequence, to maximize the number of nucleotide matches in the sequence alignment with appropriate internal nucleotide insertions, deletions, or gaps. As used herein, the term "reference sequence" refers to a DNA sequence provided as SEQ ID NOs: 1-98 and 168-171.

As used herein, the term "percent sequence identity" or "percent identity" or "% identity" is the identity fraction multiplied by 100. The "identity fraction" for a DNA sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a DNA sequence that when optimally aligned to a reference sequence, provided herein as SEQ ID NOs: 1-98 and 168-171, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders, enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, a "regulatory expression element group" or "EXP" sequence may refer to a group of operably linked regulatory elements, such as enhancers, promoters, leaders, and introns. Thus, a regulatory expression element group may be comprised, for instance, of a promoter operably linked 5' to a leader sequence, which is in turn operably linked 5' to an intron sequence.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. Chimeric promoters are produced through the fusion of two or more heterologous DNA molecules. Promoters useful in practicing the invention include SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169, including fragments or variants thereof. In specific embodiments of the invention, such DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments are provided of a promoter sequence disclosed herein. Promoter fragments may comprise promoter activity, as described above, and may be useful alone or in combination with other promoters and promoter fragments, such as in constructing chimeric promoters. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. Methods for producing such fragments from a starting promoter molecule are well known in the art.

Compositions derived from any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169, such as internal or 5' deletions, for example, can be produced using well known methods in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 comprised of 3' deletions in which the TATA box element or equivalent DNA sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 and fragments or enhancers derived therefrom can be used to make chimeric regulatory element compositions comprised of any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 and the fragments or enhancers derived therefrom operably linked to other enhancers and promoters.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Promoter molecules of the invention may thus be operably linked to their native leader or may be operably linked to a heterologous leader. Leaders useful in practicing the invention include SEQ ID NOs: 3, 11, 25, 36, 47, 64, 68, 80, 90 and 170 or fragments or variants thereof. In specific embodiments, such DNA sequences may be defined as being capable of acting as a leader in a host cell, including, for example, a transgenic plant cell. In one embodiment, such DNA sequences may be decoded as comprising leader activity.

The leader sequences (5' UTR) presented as SEQ ID NOs: 3, 11, 25, 36, 47, 64, 68, 80, 90 and 170 may be comprised of regulatory elements or may adopt secondary structures that can have an effect on transcription or translation of an operably linked DNA molecule. The leader sequences presented as SEQ ID NOs: 3, 11, 25, 36, 47, 64, 68, 80, 90 and 170 can be used in accordance with the invention to make chimeric regulatory elements that affect transcription or translation of an operably linked DNA molecule. In addition, the leader sequences presented as SEQ ID NOs: 3, 11, 25, 36, 47, 64, 68, 80, 90 and 170 can be used to make chimeric leader sequences that affect transcription or translation of an operably linked DNA molecule.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements.

Introns useful in practicing the invention include SEQ ID NOs: 4, 12, 15, 20, 26, 29, 37, 40, 48, 51, 54, 57, 59, 65, 69, 81, 91, 94 and 171. Compositions derived from any of the introns presented as SEQ ID NOs: 4, 12, 15, 20, 26, 29, 37, 40, 48, 51, 54, 57, 59, 65, 69, 81, 91, 94 and 171 can be comprised of internal deletions or duplications of cis regulatory elements; and/or alterations of the 5' and 3' DNA sequences comprising the intron/exon splice junctions can be used to improve expression or specificity of expression when operably linked to a promoter+leader or chimeric promoter+leader and coding sequence. When modifying intron/exon boundary sequences, it may be beneficial to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified in this manner. Introns and intron variants altered as described herein and through methods known in the art, can be tested empirically as described in the working examples to determine an intron's effect on expression of an operably linked DNA molecule.

As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. The 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. The 3' UTR should not cause a reduction in the transcriptional activity imparted by the promoter, leader, enhancers, and introns that are used to drive expression of the DNA molecule. In plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention.

As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the invention.

As used herein, the term "variant" refers to a second DNA molecule, such as a regulatory element, that is similar in composition, but not identical to, a first DNA molecule, and wherein the second DNA molecule still maintains the general functionality, i.e., same or similar expression pattern, for instance through more or less or equivalent transcriptional or translational activity, of the first DNA molecule. A variant may be a shortened or truncated version of the first DNA molecule and/or an altered version of the DNA sequence of the first DNA molecule, such as one with different restriction enzyme sites and/or internal deletions, substitutions, and/or insertions. Regulatory element "variants" also encompass variants arising from mutations that occur during or as a result of bacterial and plant cell transformation. In the invention, a DNA sequence provided as SEQ ID NOs: 1-98 and 168-171 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, a DNA sequence provided as SEQ ID NOs: 1-98 and 168-171 may provide a regulatory element reference sequence, wherein the constituent elements that comprise the reference sequence may be joined by methods known in the art and may comprise substitutions, deletions, and/or insertions of one or more nucleotides or mutations that naturally occur in bacterial and plant cell transformation.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs: 1-98 and 168-171, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Expression of a transcribable DNA molecule in a plant cell can also be used to suppress plant pests feeding on the plant cell, for example, compositions isolated from coleopteran pests and compositions isolated from nematode pests. Plant pests include, but are not limited to, arthropod pests, nematode pests, and fungal or microbial pests.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also includes progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants, of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique*, (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention.

However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel ubiquitin regulatory elements, or regulatory expression element group (EXP) sequences, were identified and isolated from genomic DNA of the monocot Cloud grass (*Agrostis nebulosa*), giant reed (*Arundo donax*), Blue grama (*Bouteloua gracilis*), Chinese silvergrass (*Miscanthus sinesis*), Little bluestem (*Schizachyium scoparium*), Yellow Indiangrass (*Sorghastrum nutans*) and Coix (*Coix lacryma-jobi*).

Ubiquitin 1 transcript sequences were identified from each of the above species. The 5' untranslated region (5' UTR) of each of the Ubiquitin 1 transcripts was used to design primers to amplify the corresponding regulatory elements for the identified Ubiquitin gene, which comprises a promoter, leader (5' UTR), and first intron operably linked. The primers were used with GenomeWalker™ (Clontech Laboratories, Inc, Mountain View, Calif.) libraries constructed following the manufacturer's protocol to clone the 5' region of the corresponding genomic DNA sequence. Ubiquitin regulatory elements were also isolated from the monocots *Setaria italica, Setaria viridis*, and *Zea mays* subsp. *Mexicana* (Teosinte) using GenomeWalker™ libraries as described above. In addition, ubiquitin regulatory elements were isolated from the monocot *Sorghum bicolor* using public sequences that are homologs to the Ubiquitin 4, 6, and 7 genes.

Using the identified sequences, a bioinformatic analysis was conducted to identify regulatory elements within the amplified DNA. Using the results of this analysis, regulatory elements were defined within the DNA sequences and primers designed to amplify the regulatory elements. The corresponding DNA molecule for each regulatory element was amplified using standard polymerase chain reaction (PCR) conditions with primers containing unique restriction enzyme sites and genomic DNA isolated from *A. nebulosa, A donax, B. gracilis, M. sinesis, S. scoparium, S. nutans*, and *C. lacryma-jobi*. The resulting DNA fragments were ligated into base plant expression vectors and sequenced. An analysis of the regulatory element transcription start site (TSS) and intron/exon splice junctions was then done using transformed plant protoplasts. Briefly, the protoplasts were transformed with the plant expression vectors comprising the cloned DNA fragments operably linked to a heterologous transcribable DNA molecule and the 5' RACE System for Rapid Amplification of cDNA Ends, Version 2.0 (Invitrogen, Carlsbad, California 92008) was used to confirm the regulatory element TSS and intron/exon splice junctions by analyzing the sequence of the messenger RNA (mRNA) transcripts produced thereby.

DNA sequences of the identified EXPs are provided herein as SEQ ID NOs: 1, 5, 7, 9, 13, 16, 18, 19, 21, 23, 27, 30, 32, 34, 38, 41, 43, 45, 49, 52, 55, 58, 60, 62, 66, 70, 72, 74, 76, 78, 82, 84, 86, 88, 92, 95, 97, 99, 103, 106, 108, 110, 114, 116, 118, 120, 122, 126, 128, 132, 134, 138, 140, 144, 148, 150 and 168, as listed in Table 1 below. Promoter sequences are provided herein as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98, 100, 104, 107, 109, 111, 117, 119, 121, 123, 129, 135, 141, 145, 151 and 169. Leader sequences are provided herein as SEQ ID NOs: 3, 11, 25, 36, 47, 64, 68, 80, 90, 101, 112, 124, 130, 136, 142, 146, 152 and 170. Intron sequences are provided herein as SEQ ID NOs: 4, 12, 15, 20, 26, 29, 37, 40, 48, 51, 54, 57, 59, 65, 69, 81, 91, 94, 102, 105, 113, 115, 125, 127, 131, 133, 137, 139, 143, 147, 149, 153 and 171.

TABLE 1

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| EXP-AGRne.Ubq1:1:7 | 1 | 3143 | *A. nebulosa* | EXP: P-AGRne.Ubq1-1:1:5 (SEQ ID NO: 2); L-AGRne.Ubq1-1:1:1 (SEQ ID NO: 3); I-AGRne.Ubq1-1:1:3 (SEQ ID NO: 4) |
| P-AGRne.Ubq1-1:1:5 | 2 | 2005 | *A. nebulosa* | Promoter |
| L-AGRne.Ubq1-1:1:1 | 3 | 85 | *A. nebulosa* | Leader |
| I-AGRne.Ubq1-1:1:3 | 4 | 1053 | *A. nebulosa* | Intron |
| EXP-AGRne.Ubq1:1:8 | 5 | 2137 | *A. nebulosa* | EXP: P-AGRne.Ubq1-1:1:4 (SEQ ID NO: 6); L-AGRne.Ubq1-1:1:1 (SEQ ID NO: 3); I-AGRne.Ubq1-1:1:3 (SEQ ID NO: 4) |
| P-AGRne.Ubq1-1:1:4 | 6 | 999 | *A. nebulosa* | Promoter |
| EXP-AGRne.Ubq1:1:9 | 7 | 1900 | *A. nebulosa* | EXP: P-AGRne.Ubq1-1:1:6 (SEQ ID NO: 8); L-AGRne.Ubq1-1:1:1 (SEQ ID NO: 3); I-AGRne.Ubq1-1:1:3 (SEQ ID NO: 4) |
| P-AGRne.Ubq1-1:1:6 | 8 | 762 | *A. nebulosa* | Promoter |
| EXP-ARUdo.Ubq1:1:4 | 9 | 5068 | *A. donax* | EXP: P-ARUdo.Ubq1-1:1:4 (SEQ ID NO: 10); L-ARUdo.Ubq1-1:1:1 (SEQ ID NO: 11); I-ARUdo.Ubq1-1:1:2 (SEQ ID NO: 12) |
| P-ARUdo.Ubq1-1:1:4 | 10 | 4114 | *A. donax* | Promoter |
| L-ARUdo.Ubq1-1:1:1 | 11 | 85 | *A. donax* | Leader |
| I-ARUdo.Ubq1-1:1:2 | 12 | 869 | *A. donax* | Intron |
| EXP-ARUdo.Ubq1:1:8 | 13 | 2969 | *A. donax* | EXP: P-ARUdo.Ubq1-1:1:5 (SEQ ID NO: 14); L-ARUdo.Ubq1-1:1:1 (SEQ ID NO: 11); I-ARUdo.Ubq1-1:1:3 (SEQ ID NO: 15) |
| P-ARUdo.Ubq1-1:1:5 | 14 | 2012 | *A. donax* | Promoter |
| I-ARUdo.Ubq1-1:1:3 | 15 | 872 | *A. donax* | Intron |
| EXP-ARUdo.Ubq1:1:6 | 16 | 1954 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:2 (SEQ ID NO: 12) |
| P-ARUdo.Ubq1-1:1:6 | 17 | 1000 | *A. donax* | Promoter |
| EXP-ARUdo.Ubq1:1:9 | 18 | 1957 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:3 (SEQ ID NO: 15) |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| EXP-ARUdo.Ubq1:1:12 | 19 | 1957 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:4 (SEQ ID NO: 20) |
| I-ARUdo.Ubq1-1:1:4 | 20 | 872 | *A. donax* | Intron |
| EXP-ARUdo.Ubq1:1:11 | 21 | 1712 | *A. donax* | EXP: P-ARUdo.Ubq1-1:1:8 (SEQ ID NO: 22); L-ARUdo.Ubq1-1:1:1 (SEQ ID NO: 11); I-ARUdo.Ubq1-1:1:3 (SEQ ID NO: 15) |
| P-ARUdo.Ubq1-1:1:8 | 22 | 755 | *A. donax* | Promoter |
| EXP-ARUdo.Ubq2:1:4 | 23 | 3276 | *A. donax* | EXP: P-ARUdo.Ubq2-1:1:4 (SEQ ID NO: 24); L-ARUdo.Ubq2-1:1:1 (SEQ ID NO: 25); I-ARUdo.Ubq2-1:1:1 (SEQ ID NO: 26) |
| P-ARUdo.Ubq2-1:1:4 | 24 | 2033 | *A. donax* | Promoter |
| L-ARUdo.Ubq2-1:1:1 | 25 | 88 | *A. donax* | Leader |
| I-ARUdo.Ubq2-1:1:1 | 26 | 1155 | *A. donax* | Intron |
| EXP-ARUdo.Ubq2:1:8 | 27 | 3250 | *A. donax* | EXP: P-ARUdo.Ubq2-1:1:6 (SEQ ID NO: 28); L-ARUdo.Ubq2-1:1:1 (SEQ ID NO: 25); I-ARUdo.Ubq2-1:1:2 (SEQ ID NO: 29) |
| P-ARUdo.Ubq2-1:1:6 | 28 | 2004 | *A. donax* | Promoter |
| I-ARUdo.Ubq2-1:1:2 | 29 | 1158 | *A. donax* | Intron |
| EXP-ARUdo.Ubq2:1:9 | 30 | 2247 | *A. donax* | EXP: P-ARUdo.Ubq2-1:1:5 (SEQ ID NO: 31); L-ARUdo.Ubq2-1:1:1 (SEQ ID NO: 25); I-ARUdo.Ubq2-1:1:2 (SEQ ID NO: 29) |
| P-ARUdo.Ubq2-1:1:5 | 31 | 1001 | *A. donax* | Promoter |
| EXP-ARUdo.Ubq2:1:10 | 32 | 1942 | *A. donax* | EXP: P-ARUdo.Ubq2-1:1:7 (SEQ ID NO: 33); L-ARUdo.Ubq2-1:1:1 (SEQ ID NO: 25); I-ARUdo.Ubq2-1:1:2 (SEQ ID NO: 29) |
| P-ARUdo.Ubq2-1:1:7 | 33 | 696 | *A. donax* | Promoter |
| EXP-BOUgr.Ubq1:1:1 | 34 | 3511 | *B. gracilis* | EXP: P-BOUgr.Ubq1-1:1:2 (SEQ ID NO: 35); L-BOUgr.Ubq1-1:1:1 (SEQ ID NO: 36); I-BOUgr.Ubq1-1:1:2 (SEQ ID NO: 37) |
| P-BOUgr.Ubq1-1:1:2 | 35 | 2371 | *B. gracilis* | Promoter |
| L-BOUgr.Ubq1-1:1:1 | 36 | 86 | *B. gracilis* | Leader |
| I-BOUgr.Ubq1-1:1:2 | 37 | 1054 | *B. gracilis* | Intron |
| EXP-BOUgr.Ubq1:1:6 | 38 | 3142 | *B. gracilis* | EXP: P-BOUgr.Ubq1-1:1:3 (SEQ ID NO: 39); L-BOUgr.Ubq1-1:1:1 (SEQ ID NO: 36); I-BOUgr.Ubq1-1:1:3 (SEQ ID NO: 40) |
| P-BOUgr.Ubq1-1:1:3 | 39 | 1999 | *B. gracilis* | Promoter |
| I-BOUgr.Ubq1-1:1:3 | 40 | 1057 | *B. gracilis* | Intron |
| EXP-BOUgr.Ubq1:1:7 | 41 | 2165 | *B. gracilis* | EXP: P-BOUgr.Ubq1-1:1:5 (SEQ ID NO: 42); L-BOUgr.Ubq1-1:1:1 (SEQ ID NO: 36); I-BOUgr.Ubq1-1:1:3 (SEQ ID NO: 40) |
| P-BOUgr.Ubq1-1:1:5 | 42 | 1022 | *B. gracilis* | Promoter |
| EXP-BOUgr.Ubq1:1:8 | 43 | 1903 | *B. gracilis* | EXP: P-BOUgr.Ubq1-1:1:6 (SEQ ID NO: 44); L-BOUgr.Ubq1-1:1:1 (SEQ ID NO: 36); I-BOUgr.Ubq1-1:1:3 (SEQ ID NO: 40) |
| P-BOUgr.Ubq1-1:1:6 | 44 | 760 | *B. gracilis* | Promoter |
| EXP-BOUgr.Ubq2:1:11 | 45 | 3234 | *B. gracilis* | EXP: P-BOUgr.Ubq2-1:1:4 (SEQ ID NO: 46); L-BOUgr.Ubq2-1:1:1 (SEQ ID NO: 47); I-BOUgr.Ubq2-1:1:3 (SEQ ID NO: 48) |
| P-BOUgr.Ubq2-1:1:4 | 46 | 2100 | *B. gracilis* | Promoter |
| L-BOUgr.Ubq2-1:1:1 | 47 | 91 | *B. gracilis* | Leader |
| I-BOUgr.Ubq2-1:1:3 | 48 | 1043 | *B. gracilis* | Intron |
| EXP-BOUgr.Ubq2:1:7 | 49 | 3176 | *B. gracilis* | EXP: P-BOUgr.Ubq2-1:1:7 (SEQ ID NO: 50); L-BOUgr.Ubq2-1:1:1 (SEQ ID NO: 47); I-BOUgr.Ubq2-1:1:1 (SEQ ID NO: 51) |
| P-BOUgr.Ubq2-1:1:7 | 50 | 2043 | *B. gracilis* | Promoter |
| I-BOUgr.Ubq2-1:1:1 | 51 | 1042 | *B. gracilis* | Intron |
| EXP-BOUgr.Ubq2:1:14 | 52 | 3139 | *B. gracilis* | EXP: P-BOUgr.Ubq2-1:1:5 (SEQ ID NO: 53); L-BOUgr.Ubq2-1:1:1 (SEQ ID NO: 47); I-BOUgr.Ubq2-1:1:4 (SEQ ID NO: 54) |
| P-BOUgr.Ubq2-1:1:5 | 53 | 2002 | *B. gracilis* | Promoter |
| I-BOUgr.Ubq2-1:1:4 | 54 | 1046 | *B. gracilis* | Intron |
| EXP-BOUgr.Ubq2:1:15 | 55 | 2160 | *B. gracilis* | EXP: P-BOUgr.Ubq2-1:1:6 (SEQ ID NO: 56); L-BOUgr.Ubq2-1:1:1 (SEQ ID NO: 47); I-BOUgr.Ubq2-1:1:5 (SEQ ID NO: 57) |
| P-BOUgr.Ubq2-1:1:6 | 56 | 1024 | *B. gracilis* | Promoter |
| I-BOUgr.Ubq2-1:1:5 | 57 | 1045 | *B. gracilis* | Intron |
| EXP-BOUgr.Ubq2:1:16 | 58 | 2160 | *B. gracilis* | EXP: P-BOUgr.Ubq2-1:1:6 (SEQ ID NO: 56); L-BOUgr.Ubq2-1:1:1 (SEQ ID NO: 47); I-BOUgr.Ubq2-1:1:6 (SEQ ID NO: 59) |
| I-BOUgr.Ubq2-1:1:6 | 59 | 1045 | *B. gracilis* | Intron |
| EXP-BOUgr.Ubq2:1:17 | 60 | 1885 | *B. gracilis* | EXP: P-BOUgr.Ubq2-1:1:8 (SEQ ID NO: 61); L-BOUgr.Ubq2-1:1:1 (SEQ ID NO: 47); I-BOUgr.Ubq2-1:1:6 (SEQ ID NO: 59) |
| P-BOUgr.Ubq2-1:1:8 | 61 | 749 | *B. gracilis* | Promoter |
| EXP-MISsi.Ubq1:1:2 | 62 | 6813 | *M. sinesis* | EXP: P-MISsi.Ubq1-1:1:2 (SEQ ID NO: 63); L-MISsi.Ubq1-1:1:1 (SEQ ID NO: 64); I-MISsi.Ubq1-1:1:1 (SEQ ID NO: 65) |
| P-MISsi.Ubq1-1:1:2 | 63 | 5359 | *M. sinesis* | Promoter |
| L-MISsi.Ubq1-1:1:1 | 64 | 63 | *M. sinesis* | Leader |
| I-MISsi.Ubq1-1:1:1 | 65 | 1391 | *M. sinesis* | Intron |
| EXP-MISsi.Ubq1:1:9 | 66 | 4402 | *M. sinesis* | EXP: P-MISsi.Ubq1-1:1:11 (SEQ ID NO: 67); L-MISsi.Ubq1-1:1:2 (SEQ ID NO: 68); I-MISsi.Ubq1-1:1:3 (SEQ ID NO: 69) |
| P-MISsi.Ubq1-1:1:11 | 67 | 2423 | *M. sinesis* | Promoter |
| L-MISsi.Ubq1-1:1:2 | 68 | 55 | *M. sinesis* | Leader |
| I-MISsi.Ubq1-1:1:3 | 69 | 1924 | *M. sinesis* | Intron |
| EXP-MISsi.Ubq1:1:8 | 70 | 3426 | *M. sinesis* | EXP: P-MISsi.Ubq1-1:1:10 (SEQ ID NO: 71); L-MISsi.Ubq1-1:1:2 (SEQ ID NO: 68); I-MISsi.Ubq1-1:1:3 (SEQ ID NO: 69) |
| P-MISsi.Ubq1-1:1:10 | 71 | 1447 | *M. sinesis* | Promoter |
| EXP-MISsi.Ubq1:1:10 | 72 | 2878 | *M. sinesis* | EXP: P-MISsi.Ubq1-1:1:13 (SEQ ID NO: 73); L-MISsi.Ubq1-1:1:2 (SEQ ID NO: 68); I-MISsi.Ubq1-1:1:3 (SEQ ID NO: 69) |
| P-MISsi.Ubq1-1:1:13 | 73 | 899 | *M. sinesis* | Promoter |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| EXP-MISsi.Ubq1:1:11 | 74 | 2670 | *M. sinesis* | EXP: P-MISsi.Ubq1-1:1:14 (SEQ ID NO: 75); L-MISsi.Ubq1-1:1:2 (SEQ ID NO: 68); I-MISsi.Ubq1-1:1:3 (SEQ ID NO: 69) |
| P-MISsi.Ubq1-1:1:14 | 75 | 691 | *M. sinesis* | Promoter |
| EXP-MISsi.Ubq1:1:7 | 76 | 2485 | *M. sinesis* | EXP: P-MISsi.Ubq1-1:1:9 (SEQ ID NO: 77); L-MISsi.Ubq1-1:1:2 (SEQ ID NO: 68); I-MISsi.Ubq1-1:1:3 (SEQ ID NO: 69) |
| P-MISsi.Ubq1-1:1:9 | 77 | 506 | *M. sinesis* | Promoter |
| EXP-SCHsc.Ubq1:1:9 | 78 | 4079 | *S. scoparium* | EXP: P-SCHsc.Ubq1-1:1:12 (SEQ ID NO: 79); L-SCHsc.Ubq1-1:1:3 (SEQ ID NO: 80); I-SCHsc.Ubq1-1:1:2 (SEQ ID NO: 81) |
| P-SCHsc.Ubq1-1:1:12 | 79 | 2831 | *S. scoparium* | Promoter |
| L-SCHsc.Ubq1-1:1:3 | 80 | 95 | *S. scoparium* | Leader |
| I-SCHsc.Ubq1-1:1:2 | 81 | 1153 | *S. scoparium* | Intron |
| EXP-SCHsc.Ubq1:1:8 | 82 | 3281 | *S. scoparium* | EXP: P-SCHsc.Ubq1-1:1:11 (SEQ ID NO: 83); L-SCHsc.Ubq1-1:1:3 (SEQ ID NO: 80); I-SCHsc.Ubq1-1:1:2 (SEQ ID NO: 81) |
| P-SCHsc.Ubq1-1:1:11 | 83 | 2033 | *S. scoparium* | Promoter |
| EXP-SCHsc.Ubq1:1:7 | 84 | 2294 | *S. scoparium* | EXP: P-SCHsc.Ubq1-1:1:10 (SEQ ID NO: 85); L-SCHsc.Ubq1-1:1:3 (SEQ ID NO: 80); I-SCHsc.Ubq1-1:1:2 (SEQ ID NO: 81) |
| P-SCHsc.Ubq1-1:1:10 | 85 | 1046 | *S. scoparium* | Promoter |
| EXP-SCHsc.Ubq1:1:10 | 86 | 1795 | *S. scoparium* | EXP: P-SCHsc.Ubq1-1:1:14 (SEQ ID NO: 87); L-SCHsc.Ubq1-1:1:3 (SEQ ID NO: 80); I-SCHsc.Ubq1-1:1:2 (SEQ ID NO: 81) |
| P-SCHsc.Ubq1-1:1:14 | 87 | 547 | *S. scoparium* | Promoter |
| EXP-SORnu.Ubq1:1:2 | 88 | 3357 | *S. nutans* | EXP: P-SORnu.Ubq1-1:1:4 (SEQ ID NO: 89); L-SORnu.Ubq1-1:1:1 (SEQ ID NO: 90); I-SORnu.Ubq1-1:1:1 (SEQ ID NO: 91) |
| P-SORnu.Ubq1-1:1:4 | 89 | 2218 | *S. nutans* | Promoter |
| L-SORnu.Ubq1-1:1:1 | 90 | 86 | *S. nutans* | Leader |
| I-SORnu.Ubq1-1:1:1 | 91 | 1053 | *S. nutans* | Intron |
| EXP-SORnu.Ubq1:1:6 | 92 | 3106 | *S. nutans* | EXP: P-SORnu.Ubq1-1:1:5 (SEQ ID NO: 93); L-SORnu.Ubq1-1:1:1 (SEQ ID NO: 90); I-SORnu.Ubq1-1:1:2 (SEQ ID NO: 94) |
| P-SORnu.Ubq1-1:1:5 | 93 | 1964 | *S. nutans* | Promoter |
| I-SORnu.Ubq1-1:1:2 | 94 | 1056 | *S. nutans* | Intron |
| EXP-SORnu.Ubq1:1:7 | 95 | 2165 | *S. nutans* | EXP: P-SORnu.Ubq1-1:1:6 (SEQ ID NO: 96); L-SORnu.Ubq1-1:1:1 (SEQ ID NO: 90); I-SORnu.Ubq1-1:1:2 (SEQ ID NO: 94) |
| P-SORnu.Ubq1-1:1:6 | 96 | 1023 | *S. nutans* | Promoter |
| EXP-SORnu.Ubq1:1:8 | 97 | 1866 | *S. nutans* | EXP: P-SORnu.Ubq1-1:1:7 (SEQ ID NO: 98); L-SORnu.Ubq1-1:1:1 (SEQ ID NO: 90); I-SORnu.Ubq1-1:1:2 (SEQ ID NO: 94) |
| P-SORnu.Ubq1-1:1:7 | 98 | 724 | *S. nutans* | Promoter |
| EXP-SETit.Ubq1:1:10 | 99 | 2625 | *S. italica* | EXP: P-SETit.Ubq1-1:1:4 (SEQ ID NO: 100); L-SETit.Ubq1-1:1:1 (SEQ ID NO: 101); I-SETit.Ubq1-1:1:3 (SEQ ID NO: 102) |
| P-SETit.Ubq1-1:1:4 | 100 | 1492 | *S. italica* | Promoter |
| L-SETit.Ubq1-1:1:1 | 101 | 127 | *S. italica* | Leader |
| I-SETit.Ubq1-1:1:3 | 102 | 1006 | *S. italica* | Intron |
| EXP-SETit.Ubq1:1:5 | 103 | 2625 | *S. italica* | EXP: P-SETit.Ubq1-1:1:1 (SEQ ID NO: 104); L-SETit.Ubq1-1:1:1 (SEQ ID NO: 101); I-SETit.Ubq1-1:1:2 (SEQ ID NO: 105) |
| P-SETit.Ubq1-1:1:1 | 104 | 1492 | *S. italica* | Promoter |
| I-SETit.Ubq1-1:1:2 | 105 | 1006 | *S. italica* | Intron |
| EXP-SETit.Ubq1:1:7 | 106 | 2167 | *S. italica* | EXP: P-SETit.Ubq1-1:1:2 (SEQ ID NO: 107); L-SETit.Ubq1-1:1:1 (SEQ ID NO: 101); I-SETit.Ubq1-1:1:2 (SEQ ID NO: 105) |
| P-SETit.Ubq1-1:1:2 | 107 | 1034 | *S. italica* | Promoter |
| EXP-SETit.Ubq1:1:6 | 108 | 1813 | *S. italica* | EXP: P-SETit.Ubq1-1:1:3 (SEQ ID NO: 109); L-SETit.Ubq1-1:1:1 (SEQ ID NO: 101); I-SETit.Ubq1-1:1:2 (SEQ ID NO: 105) |
| P-SETit.Ubq1-1:1:3 | 109 | 680 | *S. italica* | Promoter |
| EXP-Sv.Ubq1:1:7 | 110 | 2634 | *S. viridis* | EXP: P-Sv.Ubq1-1:1:1 (SEQ ID NO: 111); L-Sv.Ubq1-1:1:2 (SEQ ID NO: 112); I-Sv.Ubq1-1:1:2 (SEQ ID NO: 113) |
| P-Sv.Ubq1-1:1:1 | 111 | 1493 | *S. viridis* | Promoter |
| L-Sv.Ubq1-1:1:2 | 112 | 127 | *S. viridis* | Leader |
| I-Sv.Ubq1-1:1:2 | 113 | 1014 | *S. viridis* | Intron |
| EXP-Sv.Ubq1:1:11 | 114 | 2634 | *S. viridis* | EXP: P-Sv.Ubq1-1:1:1 (SEQ ID NO: 111); L-Sv.Ubq1-1:1:2 (SEQ ID NO: 112); I-Sv.Ubq1-1:1:3 (SEQ ID NO: 115) |
| I-Sv.Ubq1-1:1:3 | 115 | 1014 | *S. viridis* | Intron |
| EXP-Sv.Ubq1:1:8 | 116 | 2176 | *S. viridis* | EXP: P-Sv.Ubq1-1:1:2 (SEQ ID NO: 117); L-Sv.Ubq1-1:1:2 (SEQ ID NO: 112); I-Sv.Ubq1-1:1:2 (SEQ ID NO: 113) |
| P-Sv.Ubq1-1:1:2 | 117 | 1035 | *S. viridis* | Promoter |
| EXP-Sv.Ubq1:1:10 | 118 | 1822 | *S. viridis* | EXP: P-Sv.Ubq1-1:1:4 (SEQ ID NO: 119); L-Sv.Ubq1-1:1:2 (SEQ ID NO: 112); I-Sv.Ubq1-1:1:2 (SEQ ID NO: 113) |
| P-Sv.Ubq1-1:1:4 | 119 | 681 | *S. viridis* | Promoter |
| EXP-Sv.Ubq1:1:12 | 120 | 1822 | *S. viridis* | EXP: P-Sv.Ubq1-1:1:3 (SEQ ID NO: 121); L-Sv.Ubq1-1:1:2 (SEQ ID NO: 112); I-Sv.Ubq1-1:1:3 (SEQ ID NO: 115) |
| P-Sv.Ubq1-1:1:3 | 121 | 681 | *S. viridis* | Promoter |
| EXP-Zm.UbqM1:1:6 (Allele-1) | 122 | 1925 | *Z. mays* subsp. *Mexicana* | EXP: P-Zm.UbqM1-1:1:1 (SEQ ID NO: 123); L-Zm.UbqM1-1:1:1 (SEQ ID NO: 124); I-Zm.UbqM1-1:1:13 (SEQ ID NO: 125) |
| P-Zm.UbqM1-1:1:1 (Allele-1) | 123 | 850 | *Z. mays* subsp. *Mexicana* | Promoter |
| L-Zm.UbqM1-1:1:1 (Allele-1) | 124 | 78 | *Z. mays* subsp. *Mexicana* | Leader |
| I-Zm.UbqM1-1:1:13 (Allele-1) | 125 | 997 | *Z. mays* subsp. *Mexicana* | Intron |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| EXP-Zm.UbqM1:1:10 (Allele-1) | 126 | 1925 | *Z. mays* subsp. *Mexicana* | EXP: P-Zm.UbqM1-1:1:1 (SEQ ID NO: 123); L-Zm.UbqM1-1:1:1 (SEQ ID NO: 124); I-Zm.UbqM1-1:1:17 (SEQ ID NO: 127) |
| I-Zm.UbqM1-1:1:17 (Allele-1) | 127 | 997 | *Z. mays* subsp. *Mexicana* | Intron |
| EXP-Zm.UbqM1:1:7 (Allele-2) | 128 | 1974 | *Z. mays* subsp. *Mexicana* | EXP: P-Zm.UbqM1-1:1:4 (SEQ ID NO: 129); L-Zm.UbqM1-1:1:5 (SEQ ID NO: 130); I-Zm.UbqM1-1:1:14 (SEQ ID NO: 131) |
| P-Zm.UbqM1-1:1:4 (Allele-2) | 129 | 887 | *Z. mays* subsp. *Mexicana* | Promoter |
| L-Zm.UbqM1-1:1:5 (Allele-2) | 130 | 77 | *Z. mays* subsp. *Mexicana* | Leader |
| I-Zm.UbqM1-1:1:14 (Allele-2) | 131 | 1010 | *Z. mays* subsp. *Mexicana* | Intron |
| EXP-Zm.UbqM1:1:12 (Allele-2) | 132 | 1974 | *Z. mays* subsp. *Mexicana* | EXP: P-Zm.UbqM1-1:1:4 (SEQ ID NO: 129); L-Zm.UbqM1-1:1:5 (SEQ ID NO: 130); I-Zm.UbqM1-1:1:19 (SEQ ID NO: 133) |
| I-Zm.UbqM1-1:1:19 (Allele-2) | 133 | 1010 | *Z. mays* subsp. *Mexicana* | Intron |
| EXP-Zm.UbqM1:1:8 (Allele-2) | 134 | 2008 | *Z. mays* subsp. *Mexicana* | EXP: P-Zm.UbqM1-1:1:5 (SEQ ID NO: 135); L-Zm.UbqM1-1:1:4 (SEQ ID NO: 136); I-Zm.UbqM1-1:1:15 (SEQ ID NO: 137) |
| P-Zm.UbqM1-1:1:5 (Allele-2) | 135 | 877 | *Z. mays* subsp. *Mexicana* | Promoter |
| L-Zm.UbqM1-1:1:4 (Allele-2) | 136 | 78 | *Z. mays* subsp. *Mexicana* | Leader |
| I-Zm.UbqM1-1:1:15 (Allele-2) | 137 | 1053 | *Z. mays* subsp. *Mexicana* | Intron |
| EXP-Zm.UbqM1:1:11 (Allele-2) | 138 | 2008 | *Z. mays* subsp. *Mexicana* | EXP: P-Zm.UbqM1-1:1:5 (SEQ ID NO: 135); L-Zm.UbqM1-1:1:4 (SEQ ID NO: 136); I-Zm.UbqM1-1:1:18 (SEQ ID NO: 139) |
| I-Zm.UbqM1-1:1:18 (Allele-2) | 139 | 1053 | *Z. mays* subsp. *Mexicana* | Intron |
| EXP-Sb.Ubq4:1:2 | 140 | 1635 | *S. bicolor* | EXP: P-Sb.Ubq4-1:1:1 (SEQ ID NO: 141); L-Sb.Ubq4-1:1:1 (SEQ ID NO: 142); I-Sb.Ubq4-1:1:2 (SEQ ID NO: 143) |
| P-Sb.Ubq4-1:1:1 | 141 | 401 | *S. bicolor* | Promoter |
| L-Sb.Ubq4-1:1:1 | 142 | 154 | *S. bicolor* | Leader |
| I-Sb.Ubq4-1:1:2 | 143 | 1080 | *S. bicolor* | Intron |
| EXP-Sb.Ubq6:1:2 | 144 | 2067 | *S. bicolor* | EXP: P-Sb.Ubq6-1:1:1 (SEQ ID NO: 145); L-Sb.Ubq6-1:1:1 (SEQ ID NO: 146); I-Sb.Ubq6-1:1:2 (SEQ ID NO: 147) |
| P-Sb.Ubq6-1:1:1 | 145 | 855 | *S. bicolor* | Promoter |
| L-Sb.Ubq6-1:1:1 | 146 | 136 | *S. bicolor* | Leader |
| I-Sb.Ubq6-1:1:2 | 147 | 1076 | *S. bicolor* | Intron |
| EXP-Sb.Ubq6:1:3 | 148 | 2067 | *S. bicolor* | EXP: P-Sb.Ubq6-1:1:1 (SEQ ID NO: 145); L-Sb.Ubq6-1:1:1 (SEQ ID NO: 146); I-Sb.Ubq6-1:1:3 (SEQ ID NO: 149) |
| I-Sb.Ubq6-1:1:3 | 149 | 1076 | *S. bicolor* | Intron |
| EXP-Sb.Ubq7:1:2 | 150 | 2003 | *S. bicolor* | EXP: P-Sb.Ubq7-1:1:1 (SEQ ID NO: 151); L-Sb.Ubq7-1:1:1 (SEQ ID NO: 152); I-Sb.Ubq7-1:1:2 (SEQ ID NO: 153) |
| P-Sb.Ubq7-1:1:1 | 151 | 565 | *S. bicolor* | Promoter |
| L-Sb.Ubq7-1:1:1 | 152 | 77 | *S. bicolor* | Leader |
| I-Sb.Ubq7-1:1:2 | 153 | 1361 | *S. bicolor* | Intron |
| EXP-Cl.Ubq10 | 168 | 1790 | *C. lacryma-jobi* | EXP: P-Cl.UBQ10 (SEQ ID NO: 169); L-Cl.UBQ10 (SEQ ID NO: 170); I-Cl.UBQ10 (SEQ ID NO: 171) |
| P-Cl.Ubq10 | 169 | 481 | *C. lacryma-jobi* | Promoter |
| L-Cl.Ubq10 | 170 | 93 | *C. lacryma-jobi* | Leader |
| I-Cl.Ubq10 | 171 | 1216 | *C. lacryma-jobi* | Intron |

As shown in Table 1, for example, the regulatory EXP sequence designated EXP-AGRne.Ubq1:1:7 (SEQ ID NO: 1), with components isolated from *A. nebulosa*, comprises a promoter element, P-AGRne.Ubq1-1:1:5 (SEQ ID NO: 2), operably linked 5' to a leader element, L-AGRne.Ubq1-1:1:1 (SEQ ID NO: 3), operably linked 5' to an intron element, I-AGRne.Ubq1-1:1:3 (SEQ ID NO: 4). Other EXP sequences are linked similarly, as outlined in Table 1.

As shown in Table 1, the sequence listing, and FIGS. 1-8, variants of promoter sequences from *A. nebulosa, A donax, B. gracilis, M sinesis, S. scoparium*, and *S. nutans* were engineered, which comprise shorter promoter fragments of, for instance, P-AGRne.Ubq1-1:1:5 (SEQ ID NO:2), P-ARUdo.Ubq1-1:1:4 (SEQ ID NO:10), or other respective promoters from other species, and for instance resulting in P-AGRne.Ubq1-1:1:4 (SEQ ID NO: 6) and P-ARUdo.Ubq1-1:1:5 (SEQ ID NO: 14), as well as other promoter fragments.

Also listed in Table 1 are three allelic variants isolated using the same primer sets designed for amplification of genomic DNA from *Z. mays* subsp. *mexicana*. Allelic variants of the *Z. mays* subsp. *mexicana* EXP sequences are comprised of DNA sequences that share some identity within various regions of other DNA sequences, but insertions, deletions, and nucleotide mismatches may also be apparent within each promoter, leader and/or intron of each of the EXP sequences. The EXP sequences designated EXP-Zm.UbqM1:1:6 (SEQ ID NO: 122) and EXP-Zm.UbqM1:1:10 (SEQ ID NO: 126) represent a first allele (Allele-1) of the *Z. mays* subsp. *mexicana* Ubq1 gene regulatory expression element group, with the only difference between the two EXP sequences occurring in the last 3' nucleotides of each respective intron following the sequence 5"-AG-3' of the 3' intron splice junction. The EXP sequences designated EXP-Zm.UbqM1:1:7 (SEQ ID NO: 128) and EXP-Zm.UbqM1:1:12 (SEQ ID NO: 132) represent a second allele (Allele-2) of the *Z. mays* subsp. *mexicana* Ubq1 gene regulatory expression element group, with the only difference between the two EXP sequences occurring in the last 3' nucleotides of each respective intron following the sequence 5'-AG-3' of the 3' intron splice junction. The EXP sequences EXP-Zm.UbqM1:1:8 (SEQ ID NO: 134) and EXP-Zm.UbqM1:1:11 (SEQ ID NO: 138) represent a third allele (Allele-3) of the *Z. mays* subsp. *mexicana* Ubq1 gene regulatory expression element group, with the only difference between the two EXP sequences occurring in the last 3' nucleotides of each respective intron following the sequence 5'-AG-3' of the 3' intron splice junction.

Example 2

Analysis of Regulatory Elements Driving GUS in Corn Protoplasts Using GUS Expression Cassette Amplicons Corn leaf protoplasts were transformed with DNA amplicons derived from plant expression vectors containing an EXP sequence, driving expression of the β-glucuronidase transgene (GUS), and compared to leaf protoplasts in which expression of GUS is driven by known constitutive promoters in a series of experiments presented below.

In a first set of experiments, corn protoplast cells derived from leaf tissue were transformed as above with amplicons produced from amplification of GUS expression cassettes comprising plant expression vectors to compare expression of a transgene (GUS) driven by one of EXP-AGRne.Ubq1:1:7 (SEQ ID NO: 1), EXP-AGRne.Ubq1:1:8 (SEQ ID NO: 5), EXP-AGRne.Ubq1:1:9 (SEQ ID NO: 7), EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO: 20), EXP-ARUdo.Ubq2:1:8 (SEQ ID NO: 26), EXP-ARUdo.Ubq2:1:9 (SEQ ID NO: 29), EXP-ARUdo.Ubq2:1:10 (SEQ ID NO: 31), EXP-BOUgr.Ubq1:1:6 (SEQ ID NO: 37), EXP-BOUgr.Ubq1:1:7 (SEQ ID NO: 40), EXP-BOUgr.Ubq1:1:8 (SEQ ID NO: 42), EXP-BOUgr.Ubq2:1:14 (SEQ ID NO: 51), EXP-BOUgr.Ubq2:1:16 (SEQ ID NO: 57), EXP-BOUgr.Ubq2:1:17 (SEQ ID NO: 59), EXP-MISsi.Ubq1:1:8 (SEQ ID NO: 69), EXP-MISsi.Ubq1:1:10 (SEQ ID NO: 71), EXP-MISsi.Ubq1:1:11 (SEQ ID NO: 73), EXP-MISsi.Ubq1:1:7 (SEQ ID NO: 75), EXP-SCHsc.Ubq1:1:9 (SEQ ID NO: 77), EXP-SCHsc.Ubq1:1:7 (SEQ ID NO: 83), EXP-SCHsc.Ubq1:1:10 (SEQ ID NO: 85), EXP-SORnu.Ubq1:1:6 (SEQ ID NO: 91), EXP-SORnu.Ubq1:1:7 (SEQ ID NO: 94), EXP-SORnu.Ubq1:1:8 (SEQ ID NO: 96), EXP-SETit.Ubq1:1:5 (SEQ ID NO: 102), EXP-SETit.Ubq1:1:7 (SEQ ID NO: 105), EXP-SETit.Ubq1:1:6 (SEQ ID NO: 107), EXP-Sv.Ubq1:1:7 (SEQ ID NO: 109), EXP-Sv.Ubq1:1:8 (SEQ ID NO: 115), EXP-Sv.Ubq1:1:10 (SEQ ID NO: 117), EXP-Zm.UbqM1:1:6 (SEQ ID NO: 121), EXP-Zm.UbqM1:1:7 (SEQ ID NO: 127), EXP-Zm.UbqM1:1:8 (SEQ ID NO: 133), Exp-Sb.Ubq4:1:2 (SEQ ID NO: 139), and Exp-Sb.Ubq6:1:2 (SEQ ID NO: 143) with that of known constitutive promoters. Each EXP sequence comprising the amplification template from which the expression cassette amplicon is produced was cloned using methods known in the art into a plant expression vector shown in Table 2 below under the heading of "Amplicon Template." The resulting plant expression vectors comprise a expression cassette comprised of a EXP sequence, operably linked 5' to a coding sequence for GUS that either contains a processable intron ("GUS-2", SEQ ID NO: 154), or a contiguous GUS coding sequence ("GUS-1", SEQ ID NO: 153), operably linked 5' to a 3' UTR T-AGRtu.nos-1:1:13 (SEQ ID NO: 157) or T-Ta.Hsp17-1:1:1 (SEQ ID NO: 158). Amplicons were produced using methods known to those skilled in the art using the plasmid construct templates presented in Table 2 below. Briefly, a 5' oligonucleotide primer was designed to anneal to the promoter sequence and a 3' oligonucleotide primer, which anneals at the 3' end of the 3' UTR, was used for amplification of each expression cassette. Successive 5' deletions were introduced into the promoter sequences comprising the expression cassettes, giving rise to different EXP sequences, by the use of different oligonucleotide primers which were designed to anneal at different positions within the promoter sequence comprising each amplicon template.

TABLE 2

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145942 | pMON25455 | EXP-Os.Act1:1:9 | 162 | GUS-1 | T-AGRtu.nos-1:1:13 |
| PCR0145943 | pMON65328 | EXP-CaMV.35S-enh + Ta.Lhcb1 + Os.Act1:1:1 | 161 | GUS-2 | T-Ta.Hsp17-1:1:1 |
| PCR0145935 | pMON140890 | EXP-AGRne.Ubq1:1:7 | 1 | GUS-1 | T-AGRtu.nos-1:1:13 |
| PCR0145827 | pMON140890 | EXP-AGRne.Ubq1:1:8 | 5 | GUS-1 | T-AGRtu.nos-1:1:13 |
| PCR0145828 | pMON140890 | EXP-AGRne.Ubq1:1:9 | 7 | GUS-1 | T-AGRtu.nos-1:1:13 |
| PCR0145939 | pMON140894 | EXP-ARUdo.Ubq1:1:8 | 13 | GUS-1 | T-AGRtu.nos-1:1:13 |

TABLE 2-continued

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145837 | pMON140894 | EXP-ARUdo.Ubq1:1:9 | 18 | GUS-1 | T-AGRtu.nos-1:1:13 |
| PCR0145838 | pMON140894 | EXP-ARUdo.Ubq1:1:11 | 21 | GUS-1 | T-AGRtu.nos-1:1:13 |
| PCR0145940 | pMON140895 | EXP-ARUdo.Ubq2:1:8 | 27 | GUS-1 | T-AGRtu.nos-1:1:13 |
| PCR0145841 | pMON140895 | EXP-ARUdo.Ubq2:1:9 | 30 | GUS-1 | T-AGRtu.nos-1:1:13 |
| PCR0145842 | pMON140895 | EXP-ARUdo.Ubq2:1:10 | 32 | GUS-1 | T-AGRtu.nos-1:1:13 |
| PCR0145936 | pMON140891 | EXP-BOUgr.Ubq1:1:6 | 38 | GUS-1 | T-AGRtu.nos-1:1:13 |
| PCR0145829 | pMON140891 | EXP-BOUgr.Ubq1:1:7 | 41 | GUS-1 | T-AGRtu.nos-1:1:13 |
| PCR0145831 | pMON140891 | EXP-BOUgr.Ubq1:1:8 | 43 | GUS-1 | T-AGRtu.nos-1:1:13 |
| PCR0145937 | pMON140892 | EXP-BOUgr.Ubq2:1:14 | 52 | GUS-1 | T-AGRtu.nos-1:1:13 |
| PCR0145833 | pMON140892 | EXP-BOUgr.Ubq2:1:16 | 58 | GUS-1 | T-AGRtu.nos-1:1:13 |
| PCR0145836 | pMON140892 | EXP-BOUgr.Ubq2:1:17 | 60 | GUS-1 | T-AGRtu.nos-1:1:13 |
| PCR0145898 | pMON136265 | EXP-MISsi.Ubq1:1:8 | 70 | GUS-1 | T-AGRtu.nos-1:1:13 |
| PCR0145823 | pMON136265 | EXP-MISsi.Ubq1:1:10 | 72 | GUS-1 | T-AGRtu.nos-1:1:13 |
| PCR0145824 | pMON136265 | EXP-MISsi.Ubq1:1:11 | 74 | GUS-1 | T-AGRtu.nos-1:1:13 |
| PCR0145899 | pMON136260 | EXP-MISsi.Ubq1:1:7 | 76 | GUS-1 | T-AGRtu.nos-1:1:13 |
| PCR0145894 | pMON136262 | EXP-SCHsc.Ubq1:1:9 | 78 | GUS-1 | T-AGRtu.nos-1:1:13 |
| PCR0145895 | pMON136257 | EXP-SCHsc.Ubq1:1:7 | 84 | GUS-1 | T-AGRtu.nos-1:1:13 |
| PCR0145813 | pMON136257 | EXP-SCHsc.Ubq1:1:10 | 86 | GUS-1 | T-AGRtu.nos-1:1:13 |
| PCR0145938 | pMON140893 | EXP-SORnu.Ubq1:1:6 | 92 | GUS-1 | T-AGRtu.nos-1:1:13 |
| PCR0145839 | pMON140893 | EXP-SORnu.Ubq1:1:7 | 95 | GUS-1 | T-AGRtu.nos-1:1:13 |
| PCR0145840 | pMON140893 | EXP-SORnu.Ubq1:1:8 | 97 | GUS-1 | T-AGRtu.nos-1:1:13 |
| PCR0145900 | pMON140877 | EXP-SETit.Ubq1:1:5 | 103 | GUS-1 | T-AGRtu.nos-1:1:13 |
| PCR0145928 | pMON140877 | EXP-SETit.Ubq1:1:7 | 106 | GUS-1 | T-AGRtu.nos-1:1:13 |
| PCR0145905 | pMON140877 | EXP-SETit.Ubq1:1:6 | 108 | GUS-1 | T-AGRtu.nos-1:1:13 |

TABLE 2-continued

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145909 | pMON140878 | EXP-Sv.Ubq1:1:7 | 110 | GUS-1 | T-AGRtu.nos-1:1:13 |
| PCR0145929 | pMON140878 | EXP-Sv.Ubq1:1:8 | 116 | GUS-1 | T-AGRtu.nos-1:1:13 |
| PCR0145911 | pMON140878 | EXP-Sv.Ubq1:1:10 | 118 | GUS-1 | T-AGRtu.nos-1:1:13 |
| PCR0145914 | pMON140881 | EXP-Zm.UbqM1:1:6 | 122 | GUS-1 | T-AGRtu.nos-1:1:13 |
| PCR0145916 | pMON140883 | EXP-Zm.UbqM1:1:7 | 128 | GUS-1 | T-AGRtu.nos-1:1:13 |
| PCR0145915 | pMON140882 | EXP-Zm.UbqM1:1:8 | 134 | GUS-1 | T-AGRtu.nos-1:1:13 |
| PCR0145921 | pMON140887 | Exp-Sb.Ubq4:1:2 | 140 | GUS-1 | T-AGRtu.nos-1:1:13 |
| PCR0145920 | pMON140886 | Exp-Sb.Ubq6:1:2 | 144 | GUS-1 | T-AGRtu.nos-1:1:13 |

Plasmid constructs listed as amplicon templates in Table 2 served as templates for amplification of transgene expression cassettes comprising the listed EXP sequences of Table 2. Control plasmids used to generate GUS transgene amplicons for comparison were constructed as previously described with the constitutive EXP sequences EXP-Os-.Act1:1:9 (SEQ ID NO: 162) and EXP-CaMV.35S-enh+Ta.Lhcb1+Os.Act1:1:1 (SEQ ID NO: 161). An empty vector not designed for transgene expression was used as a negative control to assess background GUS and luciferase expression.

Two plasmids, for use in co-transformation and normalization of data, were also constructed using methods known in the art. Each plasmid contained a specific luciferase coding sequence that was driven by a constitutive EXP sequence. The plant vector pMON19437 comprises a expression cassette with a constitutive promoter operably linked 5' to an intron, (EXP-CaMV.35S-enh+Zm.DnaK:1:1, SEQ ID NO: 163), operably linked 5' to a firefly (*Photinus pyralis*) luciferase coding sequence (LUCIFERASE:1:3, SEQ ID NO: 156), operably linked 5' to a 3' UTR from the *Agrobacterium tumefaciens* nopaline synthase gene (T-AGRtu.nos-1:1:13, SEQ ID NO: 158). The plant vector pMON63934 comprises a expression cassette with a constitutive EXP sequence (EXP-CaMV.35S-enh-Lhcb1, SEQ ID NO: 164), operably linked 5' to a sea pansy (*Renilla reniformis*) luciferase coding sequence (CR-Ren.h*Renilla Lucife*-0:0:1, SEQ ID NO: 157), operably linked 5' to a 3' UTR from the *Agrobacterium tumefaciens* nopaline synthase gene (T-AGRtu.nos-1:1:13, SEQ ID NO: 158).

Corn leaf protoplasts were transformed using a PEG-based transformation method, which is well known in the art. Protoplast cells were transformed with pMON19437 plasmid DNA, pMON63934 plasmid DNA, and the amplicons presented in Table 2, and were incubated overnight in total darkness. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p.02). One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence amplicon per one of two transformation experiments. The mean GUS and luciferase expression levels are provided in Table 3. In this table, the firefly luciferase values (e.g., from expression of pMON19437) are provided in the column labeled "FLuc" and the *Renilla luciferase* values are provided as in the column labeled "RLuc."

TABLE 3

Mean GUS and Luciferase activity in transformed corn leaf protoplast cells.

| EXP Sequence | SEQ ID NO: | GUS | FLuc | RLuc |
|---|---|---|---|---|
| EMPTY | | 5 | 7840.58 | 205661 |
| EXP-Os.Act1:1:9 | 162 | 1540.25 | 2671.83 | 105417 |
| EXP-CaMV.35S-enh + Ta.Lhcb1 + Os.Act1:1:1 | 161 | 12530.8 | 3067.08 | 137723 |
| EXP-AGRne.Ubq1:1:7 | 1 | 39665 | 3645.83 | 137384 |
| EXP-AGRne.Ubq1:1:8 | 5 | 22805.5 | 4183.58 | 140991 |
| EXP-AGRne.Ubq1:1:9 | 7 | 5861.5 | 887.08 | 34034.3 |
| EXP-ARUdo.Ubq1:1:8 | 13 | 26965.5 | 1052.33 | 37774.8 |
| EXP-ARUdo.Ubq1:1:9 | 18 | 66126 | 3251.08 | 114622 |
| EXP-ARUdo.Ubq1:1:11 | 21 | 136163 | | 453851 |
| EXP-ARUdo.Ubq2:1:8 | 27 | 13222.3 | 2203.58 | 72339.1 |
| EXP-ARUdo.Ubq2:1:9 | 30 | 30095 | 6538.58 | 229201 |

TABLE 3-continued

Mean GUS and Luciferase activity in transformed corn leaf protoplast cells.

| EXP Sequence | SEQ ID NO: | GUS | FLuc | RLuc |
|---|---|---|---|---|
| EXP-ARUdo.Ubq2:1:10 | 32 | 16448.5 | 1842.58 | 65325.1 |
| EXP-BOUgr.Ubq1:1:6 | 38 | 32544.3 | 2765.08 | 80330.8 |
| EXP-BOUgr.Ubq1:1:7 | 41 | 3826.33 | 697.11 | 20709 |
| EXP-BOUgr.Ubq1:1:8 | 43 | 9935.5 | 3372.58 | 110965 |
| EXP-BOUgr.Ubq2:1:14 | 52 | 17828 | 1575.83 | 62286.8 |
| EXP-BOUgr.Ubq2:1:16 | 58 | 54970.3 | 3389.08 | 117616 |
| EXP-BOUgr.Ubq2:1:17 | 60 | 48601.3 | 7139.08 | 245785 |
| EXP-MISsi.Ubq1:1:8 | 70 | 11788.3 | 3264.58 | 87751.6 |
| EXP-MISsi.Ubq1:1:10 | 72 | 33329.5 | 2388.58 | 81000.6 |
| EXP-MISsi.Ubq1:1:11 | 74 | 4723.75 | 3135.33 | 98059.1 |
| EXP-MISsi.Ubq1:1:7 | 76 | 4499 | 3073.58 | 84015.1 |
| EXP-SCHsc.Ubq1:1:9 | 78 | 5972 | 1703.33 | 62310.6 |
| EXP-SCHsc.Ubq1:1:7 | 84 | 24173.5 | 5306.08 | 155122 |
| EXP-SCHsc.Ubq1:1:10 | 86 | 7260 | 1171.08 | 38698.1 |
| EXP-SORnu.Ubq1:1:6 | 92 | 3966.5 | 4175.08 | 129365 |
| EXP-SORnu.Ubq1:1:7 | 95 | 23375.5 | 616.83 | 25125.3 |
| EXP-SORnu.Ubq1:1:8 | 97 | 8431.75 | 1630.08 | 55095.6 |
| EXP-SETit.Ubq1:1:5 | 103 | 20496.5 | 2358.83 | 88695.8 |
| EXP-SETit.Ubq1:1:7 | 106 | 75728.5 | 4723.08 | 185224 |
| EXP-SETit.Ubq1:1:6 | 108 | 44148.3 | 4962.08 | 161216 |
| EXP-Sv.Ubq1:1:7 | 110 | 15043.8 | 1888.33 | 74670.6 |
| EXP-Sv.Ubq1:1:8 | 116 | 31997.8 | 3219.83 | 113787 |
| EXP-Sv.Ubq1:1:10 | 118 | 38952.8 | 7011.33 | 220209 |
| EXP-Zm.UbqM1:1:6 | 122 | 30528.3 | 2453.58 | 90113.1 |
| EXP-Zm.UbqM1:1:8 | 134 | 34986.3 | 2553.78 | 105725 |
| Exp-Sb.Ubq4:1:2 | 140 | 9982.25 | 2171.58 | 72593.8 |
| Exp-Sb.Ubq6:1:2 | 144 | 33689 | 3879.58 | 114710 |

To compare the relative activity of each EXP sequence, GUS values were expressed as a ratio of GUS to luciferase activity and normalized with respect to the expression levels observed for EXP-Os.Act1:1:1 and EXP-CaMV.35S-enh+Ta.Lhcb1+Os.Act1:1:1. Table 4 below shows the GUS/RLuc ratios of expression normalized with respect to EXP-Os-.Act1:1:1 and EXP-CaMV.35S-enh+Ta.Lhcb1+Os.Act1:1:1 driven expression in corn protoplasts. Table 5 below shows the GUS/FLuc ratios of expression normalized with respect to EXP-Os.Act1:1:1 and EXP-CaMV.35S-enh+Ta.Lhcb1+Os.Act1:1:1 driven expression in corn protoplasts.

TABLE 4

GUS/RLuc and GUS/FLuc ratios of expression normalized with respect to EXP-CaMV.35S-enh + Ta.Lhcb1 + Os.Act1:1:1 (SEQ ID NO: 161) in corn protoplasts.

| EXP Sequence | SEQ ID NO: | GUS/FLuc Relative to EXP-CaMV.35S-enh + Ta.Lhcb1 + Os.Act1:1:1 | GUS/RLuc Relative to EXP-CaMV.35S-enh + Ta.Lhcb1 + Os.Act1:1:1 |
|---|---|---|---|
| EXP-Os.Act1:1:9 | 162 | 0.14 | 0.16 |
| EXP-CaMV.35S-enh + Ta.Lhcb1 + Os.Act1:1:1 | 161 | 1 | 1 |
| EXP-AGRne.Ubq1:1:7 | 1 | 2.66 | 3.17 |
| EXP-AGRne.Ubq1:1:8 | 5 | 1.33 | 1.78 |
| EXP-AGRne.Ubq1:1:9 | 7 | 1.62 | 1.89 |
| EXP-ARUdo.Ubq1:1:8 | 13 | 6.27 | 7.85 |
| EXP-ARUdo.Ubq1:1:9 | 18 | 4.98 | 6.34 |
| EXP-ARUdo.Ubq1:1:11 | 21 | | 3.3 |
| EXP-ARUdo.Ubq2:1:8 | 27 | 1.47 | 2.01 |
| EXP-ARUdo.Ubq2:1:9 | 30 | 1.13 | 1.44 |
| EXP-ARUdo.Ubq2:1:10 | 32 | 2.18 | 2.77 |
| EXP-BOUgr.Ubq1:1:6 | 38 | 2.88 | 4.45 |
| EXP-BOUgr.Ubq1:1:7 | 41 | 1.34 | 2.03 |
| EXP-BOUgr.Ubq1:1:8 | 43 | 0.72 | 0.98 |
| EXP-BOUgr.Ubq2:1:14 | 52 | 2.77 | 3.15 |
| EXP-BOUgr.Ubq2:1:16 | 58 | 3.97 | 5.14 |

TABLE 4-continued

GUS/RLuc and GUS/FLuc ratios of expression normalized with respect to EXP-CaMV.35S-enh + Ta.Lhcb1 + Os.Act1:1:1 (SEQ ID NO: 161) in corn protoplasts.

| EXP Sequence | SEQ ID NO: | GUS/FLuc Relative to EXP-CaMV.35S-enh + Ta.Lhcb1 + Os.Act1:1:1 | GUS/RLuc Relative to EXP-CaMV.35S-enh + Ta.Lhcb1 + Os.Act1:1:1 |
|---|---|---|---|
| EXP-BOUgr.Ubq2:1:17 | 60 | 1.67 | 2.17 |
| EXP-MISsi.Ubq1:1:8 | 70 | 0.88 | 1.48 |
| EXP-MISsi.Ubq1:1:10 | 72 | 3.42 | 4.52 |
| EXP-MISsi.Ubq1:1:11 | 74 | 0.37 | 0.53 |
| EXP-MISsi.Ubq1:1:7 | 76 | 0.36 | 0.59 |
| EXP-SCHsc.Ubq1:1:9 | 78 | 0.86 | 1.05 |
| EXP-SCHsc.Ubq1:1:7 | 84 | 1.12 | 1.71 |
| EXP-SCHsc.Ubq1:1:10 | 86 | 1.52 | 2.06 |
| EXP-SORnu.Ubq1:1:6 | 92 | 0.23 | 0.34 |
| EXP-SORnu.Ubq1:1:7 | 95 | 9.28 | 10.23 |
| EXP-SORnu.Ubq1:1:8 | 97 | 1.27 | 1.68 |
| EXP-SETit.Ubq1:1:5 | 103 | 2.13 | 2.54 |
| EXP-SETit.Ubq1:1:7 | 106 | 3.92 | 4.49 |
| EXP-SETit.Ubq1:1:6 | 108 | 2.18 | 3.01 |
| EXP-Sv.Ubq1:1:7 | 110 | 1.95 | 2.21 |
| EXP-Sv.Ubq1:1:8 | 116 | 2.43 | 3.09 |
| EXP-Sv.Ubq1:1:10 | 118 | 1.36 | 1.94 |
| EXP-Zm.UbqM1:1:6 | 122 | 3.05 | 3.72 |
| EXP-Zm.UbqM1:1:8 | 134 | 3.35 | 3.64 |
| Exp-Sb.Ubq4:1:2 | 140 | 1.13 | 1.51 |
| Exp-Sb.Ubq6:1:2 | 144 | 2.13 | 3.23 |

TABLE 5

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-Os.Act1:1:9 | 162 | 1 | 1 |
| EXP-CaMV.35S-enh + Ta.Lhcb1 + Os.Act1:1:1 | 161 | 7.09 | 6.23 |
| EXP-AGRne.Ubq1:1:7 | 1 | 18.87 | 19.76 |
| EXP-AGRne.Ubq1:1:8 | 5 | 9.46 | 11.07 |
| EXP-AGRne.Ubq1:1:9 | 7 | 11.46 | 11.79 |
| EXP-ARUdo.Ubq1:1:8 | 13 | 44.45 | 48.86 |
| EXP-ARUdo.Ubq1:1:9 | 18 | 35.28 | 39.48 |
| EXP-ARUdo.Ubq1:1:11 | 21 | | 20.53 |
| EXP-ARUdo.Ubq2:1:8 | 27 | 10.41 | 12.51 |
| EXP-ARUdo.Ubq2:1:9 | 30 | 7.98 | 8.99 |
| EXP-ARUdo.Ubq2:1:10 | 32 | 15.49 | 17.23 |
| EXP-BOUgr.Ubq1:1:6 | 38 | 20.42 | 27.73 |
| EXP-BOUgr.Ubq1:1:7 | 41 | 9.52 | 12.65 |
| EXP-BOUgr.Ubq1:1:8 | 43 | 5.11 | 6.13 |
| EXP-BOUgr.Ubq2:1:14 | 52 | 19.63 | 19.59 |
| EXP-BOUgr.Ubq2:1:16 | 58 | 28.14 | 31.99 |
| EXP-BOUgr.Ubq2:1:17 | 60 | 11.81 | 13.53 |
| EXP-MISsi.Ubq1:1:8 | 70 | 6.26 | 9.19 |
| EXP-MISsi.Ubq1:1:10 | 72 | 24.21 | 28.16 |
| EXP-MISsi.Ubq1:1:11 | 74 | 2.61 | 3.3 |
| EXP-MISsi.Ubq1:1:7 | 76 | 2.54 | 3.67 |
| EXP-SCHsc.Ubq1:1:9 | 78 | 6.08 | 6.56 |
| EXP-SCHsc.Ubq1:1:7 | 84 | 7.9 | 10.67 |
| EXP-SCHsc.Ubq1:1:10 | 86 | 10.75 | 12.84 |
| EXP-SORnu.Ubq1:1:6 | 92 | 1.65 | 2.1 |
| EXP-SORnu.Ubq1:1:7 | 95 | 65.74 | 63.67 |
| EXP-SORnu.Ubq1:1:8 | 97 | 8.97 | 10.47 |
| EXP-SETit.Ubq1:1:5 | 103 | 15.07 | 15.82 |
| EXP-SETit.Ubq1:1:7 | 106 | 27.81 | 27.98 |
| EXP-SETit.Ubq1:1:6 | 108 | 15.43 | 18.74 |
| EXP-Sv.Ubq1:1:7 | 110 | 13.82 | 13.79 |
| EXP-Sv.Ubq1:1:8 | 116 | 17.24 | 19.25 |
| EXP-Sv.Ubq1:1:10 | 118 | 9.64 | 12.11 |

TABLE 5-continued

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-Zm.UbqM1:1:6 | 122 | 21.58 | 23.19 |
| EXP-Zm.UbqM1:1:8 | 134 | 23.76 | 22.65 |
| Exp-Sb.Ubq4:1:2 | 140 | 7.97 | 9.41 |
| Exp-Sb.Ubq6:1:2 | 144 | 15.06 | 20.1 |

As can be seen in Tables 9 and 10, all of the EXP sequences were capable of driving GUS transgene expression in corn cells. Average GUS expression was higher for all of the EXP sequences relative to EXP-Os.Act1:1:9. The EXP sequences, EXP-AGRne.Ubq1:1:7 (SEQ ID NO: 1), EXP-AGRne.Ubq1:1:8 (SEQ ID NO: 5), EXP-AGRne.Ubq1:1:9 (SEQ ID NO: 7), EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO: 21), EXP-ARUdo.Ubq2:1:8 (SEQ ID NO: 27), EXP-ARUdo.Ubq2:1:9 (SEQ ID NO: 30), EXP-ARUdo.Ubq2:1:10 (SEQ ID NO: 32), EXP-BOUgr.Ubq1:1:6 (SEQ ID NO: 38), EXP-BOUgr.Ubq1:1:7 (SEQ ID NO: 41), EXP-BOUgr.Ubq2:1:14 (SEQ ID NO: 52), EXP-BOUgr.Ubq2:1:16 (SEQ ID NO: 58), EXP-BOUgr.Ubq2:1:17 (SEQ ID NO: 60), EXP-MISsi.Ubq1:1:10 (SEQ ID NO: 72), EXP-SCHsc.Ubq1:1:7 (SEQ ID NO: 84), EXP-SCHsc.Ubq1:1:10 (SEQ ID NO: 86), EXP-SORnu.Ubq1:1:7 (SEQ ID NO: 95), EXP-SORnu.Ubq1:1:8 (SEQ ID NO: 97), EXP-SETit.Ubq1:1:5 (SEQ ID NO: 103), EXP-SETit.Ubq1:1:7 (SEQ ID NO: 106), EXP-SETit.Ubq1:1:6 (SEQ ID NO: 108), EXP-Sv.Ubq1:1:7 (SEQ ID NO: 110), EXP-Sv.Ubq1:1:8 (SEQ ID NO: 116), EXP-Sv.Ubq1:1:10 (SEQ ID NO: 118), EXP-Zm.UbqM1:1:6 (SEQ ID NO: 122), EXP-Zm.UbqM1:1:8 (SEQ ID NO: 134), EXP-Sb.Ubq4:1:2 (SEQ ID NO: 140), and EXP-Sb.Ubq6:1:2 (SEQ ID NO: 144) demonstrated GUS expression levels above that of EXP-CaMV.35S-enh+Ta.Lhcb1+Os.Act1:1:1.

In a second set of experiments, a GUS expression cassette amplicon comprising the EXP sequence EXP-Zm.UbqM1:1:7 (SEQ ID NO: 128) was compared to the control amplicons, PCR0145942 (EXP-Os.Act1:1:9, SEQ ID NO: 162) and PCR0145944 (EXP-CaMV.35S-enh+Zm.DnaK:1:1, SEQ ID NO: 161) with respect to GUS expression. GUS expression driven by the EXP sequence EXP-Zm.UbqM1:1:7 was higher than that of the two controls. Table 6 below shows the mean GUS and luciferase values determined for each amplicon. Table 7 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 6

Mean GUS and Luciferase activity in transformed corn leaf protoplast cells.

| EXP Sequence | SEQ ID NO: | GUS | FLuc | RLuc |
|---|---|---|---|---|
| EXP-Os.Act1:1:9 | 162 | 1512.25 | 11333.75 | 190461.00 |
| EXP-CaMV.35S-enh + Ta.Lhcb1 + Os.Act1:1:1 | 161 | 41176.50 | 13885.75 | 330837.25 |
| EXP-Zm.UbqM1:1:7 | 128 | 79581.50 | 15262.50 | 330755.75 |

TABLE 7

GUS/RLuc and GUS/FLuc ratios of expression normalized with respect to EXP-Os.Act1:1:9 (SEQ ID NO: 161) and EXP-CaMV.35S-enh + Zm.DnaK:1:1 (SEQ ID NO: 160) in corn leaf protoplasts.

| EXP Sequence | SEQ ID NO: | GUS | FLuc | RLuc |
|---|---|---|---|---|
| EXP-Os.Act1:1:9 | 162 | 1512.25 | 11333.75 | 190461.00 |
| EXP-CaMV.35S-enh + Ta.Lhcb1 + Os.Act1:1:1 | 161 | 41176.50 | 13885.75 | 330837.25 |
| EXP-Zm.UbqM1:1:7 | 128 | 79581.50 | 15262.50 | 330755.75 |

The efficacy of regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the GUS transgene, and compared to leaf protoplast in which expression of GUS is driven by known constitutive promoters.

Example 3

Analysis of Regulatory Elements Driving GUS in Wheat Protoplasts Using GUS Expression Cassette Amplicons Wheat leaf protoplasts were transformed with DNA amplicons derived from plant expression vectors containing an EXP sequence, driving expression of the GUS transgene, and compared to leaf protoplast in which expression of GUS was driven by known constitutive promoters.

Wheat protoplast cells derived from leaf tissue were transformed using methods known in the art with amplicons produced from amplification of GUS expression cassettes comprising plant expression vectors to compare expression of a transgene (GUS) driven by the EXP sequences listed in Table 3 with that of known constitutive promoters with methodology as described in a previous example (Example 2), using the same GUS expression cassette amplicons as that used for assay in corn in Example 2 above. Control GUS expression cassette amplicons and Luciferase plasmids used for wheat protoplast transformation were also the same as those presented in the previous example and provided in Table 3 above in Example 2. Likewise, negative controls were used for the determination of GUS and Luciferase background, as described above. Wheat leaf protoplasts were transformed using a PEG-based transformation method, as described in Example 2 above. Table 8 lists mean GUS and LUC activity seen in transformed wheat leaf protoplast cells, and Table 9 and 10 shows normalized GUS/FLuc and GUS/RLuc ratios of expression in wheat protoplasts relative to the constitutive EXP controls.

TABLE 8

Mean GUS and Luciferase activity in transformed wheat leaf protoplast cells.

| EXP Sequence | SEQ ID NO: | GUS | FLuc | RLuc |
|---|---|---|---|---|
| EMPTY | | 262.56 | 1109.78 | 61422.1 |
| EXP-Os.Act1:1:9 | 162 | 2976.33 | 730.11 | 53334.8 |
| EXP-CaMV.35S-enh + Ta.Lhcb1 + Os.Act1:1:1 | 161 | 29299.3 | 741.78 | 50717.4 |

TABLE 8-continued

Mean GUS and Luciferase activity in transformed wheat leaf protoplast cells.

| EXP Sequence | SEQ ID NO: | GUS | FLuc | RLuc |
|---|---|---|---|---|
| EXP-AGRne.Ubq1:1:7 | 1 | 27078.3 | 754.44 | 44235.8 |
| EXP-AGRne.Ubq1:1:8 | 5 | 22082.7 | 958.11 | 55774.8 |
| EXP-AGRne.Ubq1:1:9 | 7 | 13882.7 | 699.78 | 49273.4 |
| EXP-ARUdo.Ubq1:1:8 | 13 | 65628 | 791.44 | 56358.8 |
| EXP-ARUdo.Ubq1:1:9 | 18 | 87615 | 801.44 | 53246.4 |
| EXP-ARUdo.Ubq1:1:11 | 21 | 19224.3 | 143.44 | 14104.1 |
| EXP-ARUdo.Ubq2:1:8 | 27 | 25453.3 | 835.11 | 57679.4 |
| EXP-ARUdo.Ubq2:1:9 | 30 | 26720.7 | 702.44 | 47455.4 |
| EXP-ARUdo.Ubq2:1:10 | 32 | 37089.3 | 859.11 | 57814.4 |
| EXP-BOUgr.Ubq1:1:6 | 38 | 35146 | 995.44 | 64418.8 |
| EXP-BOUgr.Ubq1:1:7 | 41 | 18077 | 857.78 | 55793.4 |
| EXP-BOUgr.Ubq1:1:8 | 43 | 11723.7 | 938.44 | 59362.1 |
| EXP-BOUgr.Ubq2:1:14 | 52 | 38109.3 | 875.11 | 58048.1 |
| EXP-BOUgr.Ubq2:1:16 | 58 | 37384 | 860.44 | 52447.8 |
| EXP-BOUgr.Ubq2:1:17 | 60 | 24090.7 | 968.78 | 53057.8 |
| EXP-MISsi.Ubq1:1:8 | 70 | 16456.7 | 1021.78 | 61684.1 |
| EXP-MISsi.Ubq1:1:10 | 72 | 42816.7 | 839.78 | 46688.1 |
| EXP-MISsi.Ubq1:1:11 | 74 | 20625.7 | 987.78 | 61842.1 |
| EXP-MISsi.Ubq1:1:7 | 76 | 4913.67 | 764.78 | 64720.1 |
| EXP-SCHsc.Ubq1:1:9 | 78 | 9726 | 937.11 | 54725.4 |
| EXP-SCHsc.Ubq1:1:7 | 84 | 13374.7 | 1112.44 | 73815.4 |
| EXP-SCHsc.Ubq1:1:10 | 86 | 13650 | 936.78 | 62242.1 |
| EXP-SORnu.Ubq1:1:6 | 92 | 8188.17 | 753.83 | 50572.5 |
| EXP-SORnu.Ubq1:1:7 | 95 | 83233.7 | 854.44 | 54410.1 |
| EXP-SORnu.Ubq1:1:8 | 97 | 21904.7 | 1011.83 | 60852 |
| EXP-SETit.Ubq1:1:5 | 103 | 39427.7 | 908.78 | 57463.1 |
| EXP-SETit.Ubq1:1:7 | 106 | 108091 | 809.44 | 49330.4 |
| EXP-SETit.Ubq1:1:6 | 108 | 58703 | 809.11 | 46110.1 |
| EXP-Sv.Ubq1:1:7 | 110 | 29330 | 684.11 | 43367.1 |
| EXP-Sv.Ubq1:1:8 | 116 | 53359 | 698.11 | 40076.4 |
| EXP-Sv.Ubq1:1:10 | 118 | 49122.7 | 901.44 | 53180.8 |
| EXP-Zm.UbqM1:1:6 | 122 | 37268 | 945.78 | 54088.1 |
| EXP-Zm.UbqM1:1:8 | 134 | 51408 | 677.78 | 47297.4 |
| Exp-Sb.Ubq4:1:2 | 140 | 35660.3 | 1114.11 | 62591.1 |
| Exp-Sb.Ubq6:1:2 | 144 | 27543 | 915.11 | 57826.4 |

TABLE 9

GUS/RLuc and GUS/FLuc ratios of expression normalized with respect to EXP-CaMV.35S-enh + Ta.Lhcb1 + Os.Act1:1:1 (SEQ ID NO: 161) in wheat protoplasts.

| EXP Sequence | SEQ ID NO: | GUS | FLuc | RLuc |
|---|---|---|---|---|
| EMPTY | | 262.56 | 1109.78 | 61422.1 |
| EXP-Os.Act1:1:9 | 162 | 2976.33 | 730.11 | 53334.8 |
| EXP-CaMV.35S-enh + Ta.Lhcb1 + Os.Act1:1:1 | 161 | 29299.3 | 741.78 | 50717.4 |
| EXP-AGRne.Ubq1:1:7 | 1 | 27078.3 | 754.44 | 44235.8 |
| EXP-AGRne.Ubq1:1:8 | 5 | 22082.7 | 958.11 | 55774.8 |
| EXP-AGRne.Ubq1:1:9 | 7 | 13882.7 | 699.78 | 49273.4 |
| EXP-ARUdo.Ubq1:1:8 | 13 | 65628 | 791.44 | 56358.8 |
| EXP-ARUdo.Ubq1:1:9 | 18 | 87615 | 801.44 | 53246.4 |
| EXP-ARUdo.Ubq1:1:11 | 21 | 19224.3 | 143.44 | 14104.1 |
| EXP-ARUdo.Ubq2:1:8 | 27 | 25453.3 | 835.11 | 57679.4 |
| EXP-ARUdo.Ubq2:1:9 | 30 | 26720.7 | 702.44 | 47455.4 |
| EXP-ARUdo.Ubq2:1:10 | 32 | 37089.3 | 859.11 | 57814.4 |
| EXP-BOUgr.Ubq1:1:6 | 38 | 35146 | 995.44 | 64418.8 |
| EXP-BOUgr.Ubq1:1:7 | 41 | 18077 | 857.78 | 55793.4 |
| EXP-BOUgr.Ubq1:1:8 | 43 | 11723.7 | 938.44 | 59362.1 |
| EXP-BOUgr.Ubq2:1:14 | 52 | 38109.3 | 875.11 | 58048.1 |
| EXP-BOUgr.Ubq2:1:16 | 58 | 37384 | 860.44 | 52447.8 |
| EXP-BOUgr.Ubq2:1:17 | 60 | 24090.7 | 968.78 | 53057.8 |
| EXP-MISsi.Ubq1:1:8 | 70 | 16456.7 | 1021.78 | 61684.1 |
| EXP-MISsi.Ubq1:1:10 | 72 | 42816.7 | 839.78 | 46688.1 |
| EXP-MISsi.Ubq1:1:11 | 74 | 20625.7 | 987.78 | 61842.1 |
| EXP-MISsi.Ubq1:1:7 | 76 | 4913.67 | 764.78 | 64720.1 |
| EXP-SCHsc.Ubq1:1:9 | 78 | 9726 | 937.11 | 54725.4 |
| EXP-SCHsc.Ubq1:1:7 | 84 | 13374.7 | 1112.44 | 73815.4 |

TABLE 9-continued

GUS/RLuc and GUS/FLuc ratios of expression normalized with respect to EXP-CaMV.35S-enh + Ta.Lhcb1 + Os.Act1:1:1 (SEQ ID NO: 161) in wheat protoplasts.

| EXP Sequence | SEQ ID NO: | GUS | FLuc | RLuc |
|---|---|---|---|---|
| EXP-SCHsc.Ubq1:1:10 | 86 | 13650 | 936.78 | 62242.1 |
| EXP-SORnu.Ubq1:1:6 | 92 | 8188.17 | 753.83 | 50572.5 |
| EXP-SORnu.Ubq1:1:7 | 95 | 83233.7 | 854.44 | 54410.1 |
| EXP-SORnu.Ubq1:1:8 | 97 | 21904.7 | 1011.83 | 60852 |
| EXP-SETit.Ubq1:1:5 | 103 | 39427.7 | 908.78 | 57463.1 |
| EXP-SETit.Ubq1:1:7 | 106 | 108091 | 809.44 | 49330.4 |
| EXP-SETit.Ubq1:1:6 | 108 | 58703 | 809.11 | 46110.1 |
| EXP-Sv.Ubq1:1:7 | 110 | 29330 | 684.11 | 43367.1 |
| EXP-Sv.Ubq1:1:8 | 116 | 53359 | 698.11 | 40076.4 |
| EXP-Sv.Ubq1:1:10 | 118 | 49122.7 | 901.44 | 53180.8 |
| EXP-Zm.UbqM1:1:6 | 122 | 37268 | 945.78 | 54088.1 |
| EXP-Zm.UbqM1:1:8 | 134 | 51408 | 677.78 | 47297.4 |
| Exp-Sb.Ubq4:1:2 | 140 | 35660.3 | 1114.11 | 62591.1 |
| Exp-Sb.Ubq6:1:2 | 144 | 27543 | 915.11 | 57826.4 |

TABLE 10

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-Os.Act1:1:9 | 162 | 1 | 1 |
| EXP-CaMV.35S-enh + Ta.Lhcb1 + Os.Act1:1:1 | 161 | 9.69 | 10.35 |
| EXP-AGRne.Ubq1:1:7 | 1 | 8.8 | 10.97 |
| EXP-AGRne.Ubq1:1:8 | 5 | 5.65 | 7.09 |
| EXP-AGRne.Ubq1:1:9 | 7 | 4.87 | 5.05 |
| EXP-ARUdo.Ubq1:1:8 | 13 | 20.34 | 20.87 |
| EXP-ARUdo.Ubq1:1:9 | 18 | 26.82 | 29.49 |
| EXP-ARUdo.Ubq1:1:11 | 21 | 32.88 | 24.43 |
| EXP-ARUdo.Ubq2:1:8 | 27 | 7.48 | 7.91 |
| EXP-ARUdo.Ubq2:1:9 | 30 | 9.33 | 10.09 |
| EXP-ARUdo.Ubq2:1:10 | 32 | 10.59 | 11.5 |
| EXP-BOUgr.Ubq1:1:6 | 38 | 8.66 | 9.78 |
| EXP-BOUgr.Ubq1:1:7 | 41 | 5.17 | 5.81 |
| EXP-BOUgr.Ubq1:1:8 | 43 | 3.06 | 3.54 |
| EXP-BOUgr.Ubq2:1:14 | 52 | 10.68 | 11.76 |
| EXP-BOUgr.Ubq2:1:16 | 58 | 10.66 | 12.77 |
| EXP-BOUgr.Ubq2:1:17 | 60 | 6.1 | 8.14 |
| EXP-MISsi.Ubq1:1:8 | 70 | 3.95 | 4.78 |
| EXP-MISsi.Ubq1:1:10 | 72 | 12.51 | 16.43 |
| EXP-MISsi.Ubq1:1:11 | 74 | 5.12 | 5.98 |
| EXP-MISsi.Ubq1:1:7 | 76 | 1.58 | 1.36 |
| EXP-SCHsc.Ubq1:1:9 | 78 | 2.55 | 3.18 |
| EXP-SCHsc.Ubq1:1:7 | 84 | 2.95 | 3.25 |
| EXP-SCHsc.Ubq1:1:10 | 86 | 3.57 | 3.93 |
| EXP-SORnu.Ubq1:1:6 | 92 | 2.66 | 2.9 |
| EXP-SORnu.Ubq1:1:7 | 95 | 23.9 | 27.41 |
| EXP-SORnu.Ubq1:1:8 | 97 | 5.31 | 6.45 |
| EXP-SETit.Ubq1:1:5 | 103 | 10.64 | 12.3 |
| EXP-SETit.Ubq1:1:7 | 106 | 32.76 | 39.26 |
| EXP-SETit.Ubq1:1:6 | 108 | 17.8 | 22.81 |
| EXP-Sv.Ubq1:1:7 | 110 | 10.52 | 12.12 |
| EXP-Sv.Ubq1:1:8 | 116 | 18.75 | 23.86 |
| EXP-Sv.Ubq1:1:10 | 118 | 13.37 | 16.55 |
| EXP-Zm.UbqM1:1:6 | 122 | 9.67 | 12.35 |
| EXP-Zm.UbqM1:1:8 | 134 | 18.61 | 19.48 |
| Exp-Sb.Ubq4:1:2 | 140 | 7.85 | 10.21 |
| Exp-Sb.Ubq6:1:2 | 144 | 7.38 | 8.54 |

As can be seen in Tables 9 and 10 above, all of the EXP sequences were capable of driving GUS transgene expression in wheat cells. All of the EXP sequences drove GUS expression at levels higher than that of EXP-Os.Act1:1:9 in wheat cells. The EXP sequences EXP-ARUdo.Ubq1:1:8 (SEQ ID NO: 13), EXP-ARUdo.Ubq1:1:9 (SEQ ID NO:

18), EXP-ARUdo.Ubq1:1:11 (SEQ ID NO: 21), EXP-ARUdo.Ubq2:1:10 (SEQ ID NO: 32), EXP-BOUgr.Ubq2:1:14 (SEQ ID NO: 52), EXP-BOUgr.Ubq2:1:16 (SEQ ID NO: 58), EXP-BOUgr.Ubq2:1:17 (SEQ ID NO: 60), EXP-MISsi.Ubq1:1:10 (SEQ ID NO: 72), EXP-SORnu.Ubq1:1:7 (SEQ ID NO: 95), EXP-SETit.Ubq1:1:5 (SEQ ID NO: 103), EXP-SETit.Ubq1:1:7 (SEQ ID NO: 106), EXP-SETit.Ubq1:1:6 (SEQ ID NO: 108), EXP-Sv.Ubq1:1:7 (SEQ ID NO: 110), EXP-Sv.Ubq1:1:8 (SEQ ID NO: 116), EXP-Sv.Ubq1:1:10 (SEQ ID NO: 118), EXP-Zm.UbqM1:1:6 (SEQ ID NO: 122), and EXP-Zm.UbqM1:1:8 (SEQ ID NO: 134) demonstrated levels of GUS expression equal to or greater than GUS expression driven by EXP-CaMV.35S-enh+Ta.Lhcb1+Os.Act1:1:1 in wheat cells.

In a second set of experiments, the amplicon GUS expression cassette comprising EXP-ARUdo.Ubq1:1:11 (SEQ ID NO: 21) was compared to the controls EXP-Os.Act1:1:9 (SEQ ID NO: 162) and EXP-CaMV.35S-enh+Zm.DnaK:1:1 (SEQ ID NO: 161). Table 11 below shows the mean GUS and luciferase values determined for each amplicon. Table 12 below shows the GUS/RLuc ratios of expression normalized with respect to EXP-Os.Act1:1:9 and EXP-CaMV.35S-enh+Zm.DnaK:1:1 driven expression in wheat protoplasts.

TABLE 11

Mean GUS and Luciferase activity in transformed wheat leaf protoplast cells.

| EXP Sequence | SEQ ID NO: | GUS | RLuc |
|---|---|---|---|
| EMPTY | | 20.75 | 187112.50 |
| EXP-Os.Act1:1:9 | 162 | 1234.00 | 176970.50 |
| EXP-CaMV.35S-enh + Ta.Lhcb1 + Os.Act1:1:1 | 161 | 12883.50 | 119439.00 |
| EXP-ARUdo.Ubq1:1:11 | 21 | 30571.50 | 135037.50 |

TABLE 12

GUS/RLuc and GUS/FLuc ratios of expression normalized with respect to EXP-Os.Act1:1:9 (SEQ ID NO: 161) and EXP-CaMV.35S-enh + Zm.DnaK:1:1 (SEQ ID NO: 160) in wheat leaf protoplasts.

| EXP Sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 162 | 1.00 | 0.06 |
| EXP-CaMV.35S-enh + Ta.Lhcb1 + Os.Act1:1:1 | 161 | 15.47 | 1.00 |
| EXP-ARUdo.Ubq1:1:11 | 21 | 32.47 | 2.10 |

As can be seen in Table 12 above, GUS expression driven by EXP-ARUdo.Ubq1:1:11 (SEQ ID NO: 21) was higher than both constitutive controls, EXP-Os.Act1:1:9 and EXP-CaMV.35S-enh+Zm.DnaK:1:1.

Example 4

Analysis of Regulatory Elements Driving GUS in Corn and Wheat Protoplasts

Corn and Wheat leaf protoplasts were transformed with plant expression vectors containing an EXP sequence driving expression of the β-glucuronidase (GUS) transgene and compared to GUS expression in leaf protoplasts in which expression of GUS is driven by known constitutive promoters.

Expression of a transgene driven by EXP-Cl.Ubq10 (SEQ ID NO: 168) was compared with expression from known constitutive promoters. The foregoing EXP sequences were cloned into plant expression vectors as shown in Table 13 below to yield vectors in which an EXP sequence is operably linked 5' to a GUS reporter that contained a processable intron (referred to as GUS-2, SEQ ID NO: 160) derived from the potato light-inducible tissue-specific ST-LS1 gene (GenBank Accession: X04753) or a contiguous GUS coding sequence (GUS-1, SEQ ID NO: 159), which was operably linked 5' to a 3' UTR derived from the *A. tumefaciens* Nopaline synthase gene (T-AGRtu.nos-1:1:13, SEQ ID NO: 161) or the wheat Hsp17 gene (T-Ta.Hsp17-1:1:1, SEQ ID NO: 162).

TABLE 13

GUS plant expression plasmid construct and corresponding EXP sequence, GUS coding sequence and 3' UTR used for transformation of corn leaf protoplasts. "SEQ ID NO:" refers to given EXP sequence.

| EXP Sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 162 | 1.00 | 0.06 |
| EXP-CaMV.35S-enh + Ta.Lhcb1 + Os.Act1:1:1 | 161 | 15.47 | 1.00 |
| EXP-ARUdo.Ubq1:1:11 | 21 | 32.47 | 2.10 |

Two plasmids, for use in co-transformation and normalization of data, were also constructed using methods known in the art. Each plasmid contained a specific luciferase coding sequence that was driven by a constitutive EXP sequence. The plant vector pMON19437 comprises an expression cassette with a constitutive promoter operably linked 5' to an intron, (EXP-CaMV.35S-enh+Zm.DnaK:1:1, SEQ ID NO: 163), operably linked 5' to a firefly (*Photinus pyralis*) luciferase coding sequence (LUCIFERASE:1:3, SEQ ID NO: 156), operably linked 5' to a 3' UTR from the *Agrobacterium tumefaciens* nopaline synthase gene (T-AGRtu.nos-1:1:13, SEQ ID NO: 158). The plant vector pMON63934 comprises an expression cassette with a constitutive EXP sequence (EXP-CaMV.35S-enh-Lhcb1, SEQ ID NO: 164), operably linked 5' to a sea pansy (*Renilla reniformis*) luciferase coding sequence (CR-Ren.h*Renilla Lucife*-0:0:1, SEQ ID NO: 157), operably linked 5' to a 3' UTR from the *Agrobacterium tumefaciens* nopaline synthase gene (T-AGRtu.nos-1:1:13, SEQ ID NO: 158).

Corn leaf protoplasts were transformed using a PEG-based transformation method, which is well known in the art. Protoplast cells were transformed with pMON19437 plasmid DNA, pMON63934 plasmid DNA, and the plasmids presented in Table 13 and incubated overnight in total darkness. Measurements of both GUS and luciferase were conducted in a similar manner as that described in Example 2 above. One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence construct per one of two transformation experiments. The mean GUS and luciferase expression levels are provided in Table 14. In this table, the firefly luciferase values (e.g., from expression of pMON19437) are provided in the column labeled "FLuc" and the *Renilla luciferase* values are provided as in the column labeled "RLuc."

TABLE 14

Mean GUS and Luciferase activity in transformed corn leaf protoplast cells.

| EXP Sequence | SEQ ID NO: | GUS | FLuc | RLuc |
|---|---|---|---|---|
| EXP-Os.Act1:1:9 | 162 | 83997.3 | 80983 | 61619 |
| EXP-CaMV.35S-enh + Ta.Lhcb1 + Os.Act1:1:1 | 161 | 248832 | 83589.8 | 72064.3 |
| EXP-Cl.Ubq10 | 168 | 30790.8 | 65807.5 | 34846.3 |

Table 15 below shows the GUS/FLuc and GUS/RLuc ratios of expression normalized with respect to EXP-Os-.Act1:1:9 and EXP-CaMV.35S-enh+Zm.DnaK:1:1 driven expression in corn protoplasts.

TABLE 15

GUS/FLuc and GUS/RLuc ratios of expression normalized with respect to EXP-Os.Act1:1:9 (SEQ ID NO: 161) and EXP-CaMV.35S-enh + Zm.DnaK:1:1 (SEQ ID NO: 160) in wheat leaf protoplasts.

| EXP Sequence | SEQ ID NO: | GUS/Fluc normalized with respect to EXP-Os.Act1:1:9 | GUS/Rluc normalized with respect to EXP-Os.Act1:1:9 | GUS/Fluc normalized with respect to EXP-CaMV.35S-enh + Ta.Lhcb1 + Os.Act1:1:1 | GUS/Rluc normalized with respect to EXP-CaMV.35S-enh + Ta.Lhcb1 + Os.Act1:1:1 |
|---|---|---|---|---|---|
| EXP-Os.Act1:1:9 | 162 | 1.00 | 1.00 | 0.35 | 0.39 |
| EXP-CaMV.35S-enh + Ta.Lhcb1 + Os.Act1:1:1 | 161 | 2.87 | 2.53 | 1.00 | 1.00 |
| EXP-Cl.Ubq10 | 168 | 0.45 | 0.65 | 0.16 | 0.26 |

As can be seen in Table 15 above, EXP-CLUbq10 (SEQ ID NO: 168) was able to drive expression of GUS, but was at a level lower than that of both constitutive controls.

The plasmids listed in Table 13 above were also used to transform wheat leaf protoplast cells in a similar manner as that for corn leaf protoplasts described above. Mean GUS and luciferase values are shown in Table 16 below. Table 17 below shows the GUS/FLuc and GUS/RLuc ratios of expression normalized with respect to EXP-CaMV.35S-enh+Zm.DnaK:1:1 driven expression in corn protoplasts.

TABLE 16

Mean GUS and Luciferase activity in transformed corn leaf protoplast cells.

| EXP Sequence | SEQ ID NO: | GUS | FLuc | RLuc |
|---|---|---|---|---|
| EXP-CaMV.35S-enh + Ta.Lhcb1 + Os.Act1:1:1 | 161 | 134145 | 1076.67 | 6858.67 |
| EXP-Cl.Ubq10 | 168 | 104669 | 888.67 | 4516 |

TABLE 17

GUS/FLuc and GUS/RLuc ratios of expression normalized with respect to EXP-CaMV.35S-enh + Zm.DnaK:1:1 (SEQ ID NO: 160) in wheat leaf protoplasts.

| EXP Sequence | SEQ ID NO: | GUS/Fluc normalized with respect to EXP-CaMV.35S-enh + Ta.Lhcb1 + Os.Act1:1:1 | GUS/Rluc normalized with respect to EXP-CaMV.35S-enh + Ta.Lhcb1 + Os.Act1:1:1 |
|---|---|---|---|
| EXP-CaMV.35S-enh + Ta.Lhcb1 + Os.Act1:1:1 | 161 | 1.00 | 1.00 |
| EXP-Cl.Ubq10 | 168 | 0.95 | 1.19 |

As can be seen in Table 17 above, EXP-CLUbq10 (SEQ ID NO: 168) expressed GUS at a similar level as that of EXP-CaMV.35S-enh+Zm.DnaK:1:1 (SEQ ID NO: 160) in wheat protoplast cells.

Example 5

Analysis of Regulatory Elements Driving GUS in Transgenic Corn

Corn plants were transformed with plant expression vectors containing a EXP sequences driving expression of the GUS transgene, and the resulting plants were analyzed for GUS protein expression. The ubiquitin EXP sequences were cloned into plant binary transformation plasmid constructs using methods known in the art.

The resulting plant expression vectors contain a right border region from *A. tumefaciens*, a first expression cassette to assay the EXP sequence operably linked to a coding sequence for GUS that possesses the processable intron GUS-2, described above, operably linked 5' to the 3' UTR from the rice lipid transfer protein gene (T-Os.LTP-1:1:1, SEQ ID NO: 159); a second transgene selection cassette used for selection of transformed plant cells that confers resistance to the herbicide glyphosate (driven by the rice Actin 1 promoter), and a left border region from *A. tumefaciens*. The resulting plasmids were used to transform corn plants. Table 18 lists the plasmid designations, the EXP sequences and the SEQ ID NOs, which are also described in Table 1.

TABLE 18

| Binary plant transformation plasmids and the associated EXP sequences. | | |
|---|---|---|
| Plasmid Construct | EXP sequence | SEQ ID NO: |
| pMON140869 | EXP-AGRne.Ubq1:1:7 | 1 |
| pMON140870 | EXP-AGRne.Ubq1:1:8 | 5 |
| pMON142650 | EXP-ARUdo.Ubq1:1:8 | 13 |
| pMON142651 | EXP-ARUdo.Ubq1:1:9 | 18 |
| pMON142652 | EXP-ARUdo.Ubq2:1:8 | 27 |
| pMON142653 | EXP-ARUdo.Ubq2:1:9 | 30 |
| pMON140871 | EXP-BOUgr.Ubq1:1:6 | 38 |
| pMON140872 | EXP-BOUgr.Ubq1:1:7 | 41 |
| pMON140873 | EXP-BOUgr.Ubq2:1:14 | 52 |
| pMON140874 | EXP-BOUgr.Ubq2:1:15 | 55 |
| pMON142887 | EXP-MISsi.Ubq1:1:7 | 76 |
| pMON140875 | EXP-SORnu.Ubq1:1:6 | 92 |
| pMON140876 | EXP-SORnu.Ubq1:1:7 | 95 |
| pMON132037 | EXP-SETit.Ubq1:1:10 | 99 |
| pMON131958 | EXP-Sv.Ubq1:1:11 | 114 |
| pMON131959 | EXP-Sv.Ubq1:1:12 | 120 |
| pMON131961 | EXP-Zm.UbqM1:1:10 | 126 |
| pMON131963 | EXP-Zm.UbqM1:1:12 | 132 |
| pMON131962 | EXP-Zm.UbqM1:1:11 | 138 |
| pMON132932 | EXP-Sb.Ubq4:1:2 | 140 |
| pMON132931 | EXP-Sb.Ubq6:1:3 | 148 |
| pMON132974 | EXP-Sb.Ubq7:1:2 | 150 |
| pMON142738 | EXP-Cl.Ubq10 | 168 |

Plants were transformed using *Agrobacterium*-mediated transformations, for instance as described in U.S. Patent Application Publication 2009/0138985.

Histochemical GUS analysis was used for qualitative expression analysis of transformed plants. Whole tissue sections were incubated with GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues. The $R_0$ plants are inspected for expression in the roots and leaves, as well as the anther, silk, and developing seed and embryo, 21 days after pollination (21 DAP).

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 μl. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

The average $R_0$ GUS expression observed for each transformation is presented in Tables 19 and 20 below.

TABLE 19

Average $R_0$ GUS expression in root and leaf tissue.

| EXP sequence | SEQ ID NO: | V3 Root | V4 Root | V7 Root | VT Root | V3 Leaf | V4 Leaf | V7 Leaf | VT Leaf |
|---|---|---|---|---|---|---|---|---|---|
| EXP-AGRne.Ubq1:1:7 | 1 | 16 | | 25 | 14 | 49 | | 60 | 48 |
| EXP-AGRne.Ubq1:1:8 | 5 | 13 | | 20 | 22 | 38 | | 38 | 52 |
| EXP-ARUdo.Ubq1:1:8 | 13 | 18 | | 34 | 89 | 117 | | 48 | 106 |
| EXP-ARUdo.Ubq1:1:9 | 18 | 19 | | 20 | 68 | 105 | | 33 | 69 |
| EXP-ARUdo.Ubq2:1:8 | 27 | 14 | | 19 | 27 | 58 | | 57 | 47 |
| EXP-ARUdo.Ubq2:1:9 | 30 | 14 | | 15 | 25 | 40 | | 38 | 40 |
| EXP-BOUgr.Ubq1:1:6 | 38 | 12 | | 28 | 16 | 43 | | 46 | 27 |
| EXP-BOUgr.Ubq1:1:7 | 41 | 14 | | 24 | 114 | 51 | | 48 | 48 |
| EXP-BOUgr.Ubq2:1:14 | 52 | 17 | | 13 | 28 | 46 | | 33 | 41 |
| EXP-BOUgr.Ubq2:1:15 | 55 | 11 | | 67 | 36 | 86 | | 72 | 36 |
| EXP-MISsi.Ubq1:1:7 | 76 | 17 | | 28 | 13 | 18 | | 12 | 18 |
| EXP-SORnu.Ubq1:1:6 | 92 | 14 | | 45 | 33 | 44 | | 64 | 55 |
| EXP-SORnu.Ubq1:1:7 | 95 | 11 | | 18 | 20 | 31 | | 36 | 48 |
| EXP-SETit.Ubq1:1:10 | 99 | 0 | | 29 | 57 | 58 | | 37 | 46 |
| EXP-Sv.Ubq1:1:11 | 114 | nd | | nd | 9 | 20 | | 55 | 29 |
| EXP-Sv.Ubq1:1:12 | 120 | 63 | | 0 | 28 | 184 | | 27 | 16 |
| EXP-Zm.UbqM1:1:10 | 126 | 0 | | 237 | 18 | 221 | | 272 | 272 |
| EXP-Zm.UbqM1:1:12 | 132 | 0 | | 21 | 43 | 234 | | 231 | 196 |
| EXP-Zm.UbqM1:1:11 | 138 | 124 | | 103 | 112 | 311 | | 369 | 297 |
| EXP-Sb.Ubq4:1:2 | 140 | 125 | | 0 | 95 | 233 | | 150 | 88 |
| EXP-Sb.Ubq6:1:3 | 148 | 154 | | 13 | 128 | 53 | | 39 | 55 |
| EXP-Sb.Ubq7:1:2 | 150 | 37 | | 22 | 18 | 165 | | 89 | 177 |
| EXP-Cl.Ubq10 | 168 | | 61 | 67 | 32 | | 111 | 58 | 115 |

TABLE 20

Average $R_0$ GUS expression in corn reproductive organs (anther, silk) and developing seed (embryo and endosperm).

| EXP sequence | SEQ ID NO: | VT Anther | VT/R1 Silk | 21 DAP Embryo | 21 DAP Endosperm |
|---|---|---|---|---|---|
| EXP-AGRne.Ubq1:1:7 | 1 | 149 | 36 | 59 | 59 |
| EXP-AGRne.Ubq1:1:8 | 5 | 73 | 66 | 33 | 58 |
| EXP-ARUdo.Ubq1:1:8 | 13 | 321 | 253 | 177 | 355 |
| EXP-ARUdo.Ubq1:1:9 | 18 | 242 | 268 | 97 | 266 |
| EXP-ARUdo.Ubq2:1:8 | 27 | 104 | 99 | 79 | 157 |
| EXP-ARUdo.Ubq2:1:9 | 30 | 78 | 71 | 82 | 139 |
| EXP-BOUgr.Ubq1:1:6 | 38 | 58 | 250 | 43 | 63 |
| EXP-BOUgr.Ubq1:1:7 | 41 | 58 | 77 | 40 | 49 |
| EXP-BOUgr.Ubq2:1:14 | 52 | 236 | 377 | 48 | 137 |
| EXP-BOUgr.Ubq2:1:15 | 55 | 203 | 134 | 47 | 180 |
| EXP-MISsi.Ubq1:1:7 | 76 | 24 | 16 | 29 | 32 |
| EXP-SORnu.Ubq1:1:6 | 92 | 361 | 80 | 37 | 94 |
| EXP-SORnu.Ubq1:1:7 | 95 | 195 | 114 | 20 | 55 |
| EXP-SETit.Ubq1:1:10 | 99 | 132 | 85 | 50 | 63 |
| EXP-Sv.Ubq1:1:11 | 114 | 217 | 3 | 45 | 92 |
| EXP-Sv.Ubq1:1:12 | 120 | 120 | 21 | 49 | 112 |
| EXP-Zm.UbqM1:1:10 | 126 | 261 | 506 | 403 | 376 |
| EXP-Zm.UbqM1:1:12 | 132 | 775 | 362 | 253 | 247 |
| EXP-Zm.UbqM1:1:11 | 138 | 551 | 452 | 234 | 302 |
| EXP-Sb.Ubq4:1:2 | 140 | 213 | 0 | 25 | 79 |
| EXP-Sb.Ubq6:1:3 | 148 | 295 | 87 | 51 | 61 |
| EXP-Sb.Ubq7:1:2 | 150 | 423 | 229 | 274 | 90 |
| EXP-Cl.Ubq10 | 168 | 237 | 82 | 91 | 210 |

In $R_0$ corn plants, GUS expression levels in the leaf and root differed amongst the ubiquitin EXP sequences. While all of the EXP sequences demonstrated the ability to drive GUS transgene expression in stably transformed plants, each EXP sequence demonstrated a unique pattern of expression relative to the others. For example, the EXP sequences, EXP-AGRne.Ubq1:1:7 (SEQ ID NO: 1), EXP-AGRne.Ubq1:1:8 (SEQ ID NO: 5), EXP-ARUdo.Ubq1:1:8 (SEQ ID NO: 13), EXP-ARUdo.Ubq1:1:9 (SEQ ID NO: 18), EXP-ARUdo.Ubq2:1:8 (SEQ ID NO: 27), EXP-ARUdo.Ubq2:1:9 (SEQ ID NO: 30), EXP-BOUgr.Ubq1:1:6 (SEQ ID NO: 38), EXP-BOUgr.Ubq1:1:7 (SEQ ID NO: 41), EXP-BOUgr.Ubq2:1:14 (SEQ ID NO: 52), EXP-BOUgr.Ubq2:1:15 (SEQ ID NO: 55), EXP-MISsi.Ubq1:1:7 (SEQ ID NO: 76), EXP-SORnu.Ubq1:1:6 (SEQ ID NO: 92), EXP-SORnu.Ubq1:1:7 (SEQ ID NO: 95), EXP-SETit.Ubq1:1:10 (SEQ ID NO: 99), EXP-Sv.Ubq1:1:11 (SEQ ID NO: 114), EXP-Zm.UbqM1:1:12 (SEQ ID NO: 132), and EXP-Sb.Ubq7:1:2 (SEQ ID NO: 150) demonstrated lower levels of GUS expression in the root at V3 and V7 stages of development relative to EXP-Sv.Ubq1:1:12 (SEQ ID NO: 120), EXP-Zm.UbqM1:1:10 (SEQ ID NO: 126), EXP-Zm.UbqM1:1:11 (SEQ ID NO: 138), EXP-Sb.Ubq4:1:2 (SEQ ID NO: 140), and EXP-Sb.Ubq6:1:3 (SEQ ID NO: 148). Higher levels of GUS expression were observed in later stages of root development (VT) for EXP-ARUdo.Ubq1:1:8 (SEQ ID NO: 13), EXP-ARUdo.Ubq1:1:9 (SEQ ID NO: 18), EXP-BOUgr.Ubq1:1:7 (SEQ ID NO: 41), EXP-Zm.UbqM1:1:11 (SEQ ID NO: 138), and EXP-Sb.Ubq6:1:3 (SEQ ID NO: 148). Root expression driven by EXP-Zm.UbqM1:1:10 (SEQ ID NO: 140) demonstrated no expression at V3 but was high at V7 and then dropped by VT stage. Root expression driven by EXP-Zm.UbqM1:1:11 (SEQ ID NO: 150) was maintained to a similar level throughout development from stages V3, and V7 through VT. Expression of GUS driven by EXP-Cl.Ubq10 (SEQ ID NO: 168) was relatively steady from V4 to V7 stage but dropped to approximately half that of V4 and V7 at VT stage.

GUS expression levels showed dramatic differences in leaf tissue as well. The EXP sequences, EXP-Zm.UbqM1:1:10 (SEQ ID NO: 126), EXP-Zm.UbqM1:1:12 (SEQ ID NO: 132) and EXP-Zm.UbqM1:1:11 (SEQ ID NO: 138) demonstrated the highest level of GUS expression observed across all three stages of development (V3, V7 and VT). The EXP sequence, EXP-Sb.Ubq4:1:2 (SEQ ID NO: 140), showed a decline in expression from V3 to VT stages of development. The EXP sequences, EXP-ARUdo.Ubq1:1:8 (SEQ ID NO: 13) and EXP-Sb.Ubq7:1:2 (SEQ ID NO: 150) demonstrated higher levels of GUS expression in V3 and VT stage of development with a lower level of expression in the middle of growth at V7 stage. The EXP sequence, EXP-ARUdo.Ubq2:1:9 (SEQ ID NO: 30), EXP-BOUgr.Ubq1:1:7 (SEQ ID NO: 41), and EXP-MISsi.Ubq1:1:7 (SEQ ID NO: 76) maintained GUS expression over all three stages, while EXP-ARUdo.Ubq2:1:8 (SEQ ID NO: 27), EXP-BOUgr.Ubq1:1:6 (SEQ ID NO: 38), and EXP-BOUgr.Ubq2:1:15 (SEQ ID NO: 55) showed a slight decrease in expression at VT stage. Expression driven by EXP-CLUbq10 (SEQ ID NO: 168) was similar at V4 and VT stage but dropped to about half the level of V4 and VT at V7 stage.

Likewise, with respect to reproductive tissue (anther and silk) different patterns of expression were observed unique to each EXP sequence. For example, high levels of expression were observed in anther and silk for the EXP sequences EXP-ARUdo.Ubq1:1:8 (SEQ ID NO: 13), EXP-ARUdo.Ubq1:1:9 (SEQ ID NO: 18), EXP-BOUgr.Ubq2:1:14 (SEQ ID NO: 52), EXP-BOUgr.Ubq2:1:15 (SEQ ID NO: 55), EXP-SORnu.Ubq1:1:7 (SEQ ID NO: 95), EXP-Zm.UbqM1:1:10 (SEQ ID NO: 126), EXP-Zm.UbqM1:1:12 (SEQ ID NO: 132), EXP-Zm.UbqM1:1:11 (SEQ ID NO: 138), and EXP-Sb.Ubq7:1:2 (SEQ ID NO: 150). Expression driven by the EXP sequences EXP-AGRne.Ubq1:1:7 (SEQ ID NO: 1), EXP-SORnu.Ubq1:1:6 (SEQ ID NO: 92), EXP-Sv.Ubq1:1:11 (SEQ ID NO: 114), EXP-Sv.Ubq1:1:12 (SEQ ID NO: 120), EXP-Sb.Ubq4:1:2 (SEQ ID NO: 140), EXP-Sb.Ubq6:1:3 (SEQ ID NO: 148), and EXP-CLUbq10 (SEQ ID NO: 168) was high in the anther but lower in the silk relative to each EXP sequence, while expression driven by EXP-BOUgr.Ubq1:1:6 (SEQ ID NO: 38) was higher in the silk in comparison to expression in the anther.

Expression in the developing seed (21 DAP embryo and endosperm) was different among the EXP sequences. The EXP sequences, EXP-Zm.UbqM1:1:10 (SEQ ID NO: 126), EXP-Zm.UbqM1:1:12 (SEQ ID NO: 132), and EXP-Zm.UbqM1:1:11 (SEQ ID NO: 138) drove high expression of GUS in the developing seed embryo and endosperm tissue. Levels of expression in the endosperm were about two-fold or more higher than in the embryo when GUS was driven by the EXP sequences, EXP-ARUdo.Ubq1:1:8 (SEQ ID NO: 13), EXP-ARUdo.Ubq1:1:9 (SEQ ID NO: 18), EXP-ARUdo.Ubq2:1:8 (SEQ ID NO: 27), EXP-BOUgr.Ubq2:1:14 (SEQ ID NO: 52), EXP-BOUgr.Ubq2:1:15 (SEQ ID NO: 55), EXP-SORnu.Ubq1:1:6 (SEQ ID NO: 92), EXP-SORnu.Ubq1:1:7 (SEQ ID NO: 95), EXP-Sv.Ubq1:1:12 (SEQ ID NO: 120), EXP-Sb.Ubq4:1:2 (SEQ ID NO: 140), and EXP-Cl.Ubq10 (SEQ ID NO: 168). Expression of GUS was three-fold higher in the embryo than in the endosperm when driven by EXP-Sb.Ubq7:1:2 (SEQ ID NO: 150). GUS expression levels were relatively equivalent in the embryo and endosperm when driven by the EXP sequences EXP-AGRne.Ubq1:1:7 (SEQ ID NO: 1), EXP-AGRne.Ubq1:1:8 (SEQ ID NO: 5), EXP-BOUgr.Ubq1:1:6 (SEQ ID NO: 38), EXP-BOUgr.Ubq1:1:7 (SEQ ID NO: 41), EXP-MISsi.Ubq1:1:7 (SEQ ID NO: 76), EXP-SETit.Ubq1:1:10 (SEQ ID NO: 99), and EXP-Sb.Ubq6:1:3 (SEQ ID NO: 148).

Each EXP sequence demonstrated the ability to drive transgene expression in stably transformed corn plants. However, each EXP sequence had a pattern of expression for each tissue that was unique and offers an opportunity to select the EXP sequence which will best provide expression of a specific transgene depending upon the tissue expression strategy needed to achieve the desired results. This example demonstrates that EXP sequences isolated from homologous genes do not necessarily behave equivalently in the transformed plant and that expression can only be determined through empirical investigation of the properties for each EXP sequence and cannot be predicted based upon the gene homology from which the promoter was derived.

Example 6

Enhancers Derived from the Regulatory Elements

Enhancers are derived from the promoter elements provided herein, such as those presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169. The enhancer element may be comprised of one or more cis regulatory elements that, when operably linked 5' or 3' to a promoter element, or operably linked 5' or 3' to additional enhancer elements that are operably linked to a promoter, can enhance or modulate expression of a transgene, or provide expression of a transgene in a specific cell type or plant organ or at a particular time point in development or circadian rhythm. Enhancers are made by removing the TATA box or functionally similar elements and any downstream DNA sequence from the promoters that allow transcription to be initiated from the promoters provided herein as described above, including fragments thereof, in which the TATA box or functionally similar elements and DNA sequence downstream of the TATA box are removed.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements are cloned, using methods known in the art, to be operably linked to one or more copies of the enhancer element which are operably linked 5' or 3' to a promoter element, or operably linked 5' or 3' to additional enhancer elements that are operably linked to a promoter. Enhancer elements can also be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector is constructed using methods known in the art similar to the constructs described in the previous examples in which the resulting plant expression vectors contain a right border region from *A. tumefaciens*, a first expression cassette to test the regulatory or a chimeric regulatory element comprised of, a regulatory or chimeric regulatory element, operably linked to an intron derived from the HSP70 heat shock protein of *Z. mays* (I-Zm.DnaK-1:1:1 SEQ ID NO: 165) or any of the introns presented herein or any other intron, operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158) or the 3' UTR from the rice lipid transfer protein gene (T-Os.LTP-1:1:1, SEQ ID NO: 160); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by other *Agrobacterium*-mediated or particle bombardment methods known in the art. Alternatively, protoplast cells derived from corn or other genus plants are transformed using methods known in the art to perform transient assays GUS expression driven by the regulatory element comprising one or more enhancers is evaluated in stable or transient plant assays to determine the effects of the enhancer element on expression of a transgene. Modifications to one or more enhancer elements or duplication of one or more enhancer elements is performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 7

Analysis of Intron Enhancement of GUS Activity Using Plant Derived Protoplasts An intron is selected based upon experimentation and comparison with an intronless expression vector control to empirically select an intron and configuration within the vector transfer DNA (T-DNA) element arrangement for optimal expression of a transgene. For example, in the expression of an herbicide resistance gene, such as CP4, which confers tolerance to glyphosate, it is desirable to have transgene expression within the reproductive tissues as well as the vegetative tissues, to prevent the loss of yield when applying the herbicide. An intron in this instance would be selected upon its ability, when operably linked to a constitutive promoter, to enhance expression of the herbicide resistance conferring transgene, particularly within the reproductive cells and tissues of the transgenic plant and thus providing both vegetative and reproductive tolerance to the transgenic plant when sprayed with the herbicide. In most ubiquitin genes, the 5' UTR is comprised of a leader, which has an intron sequence embedded within it. The regulatory elements derived from such genes are therefore assayed using the entire 5' UTR comprising the promoter, leader, and intron. To achieve different expression profiles or to modulate the level of transgene expression, the intron from such a regulatory element may be removed or substituted with a heterologous intron.

Figure 9:
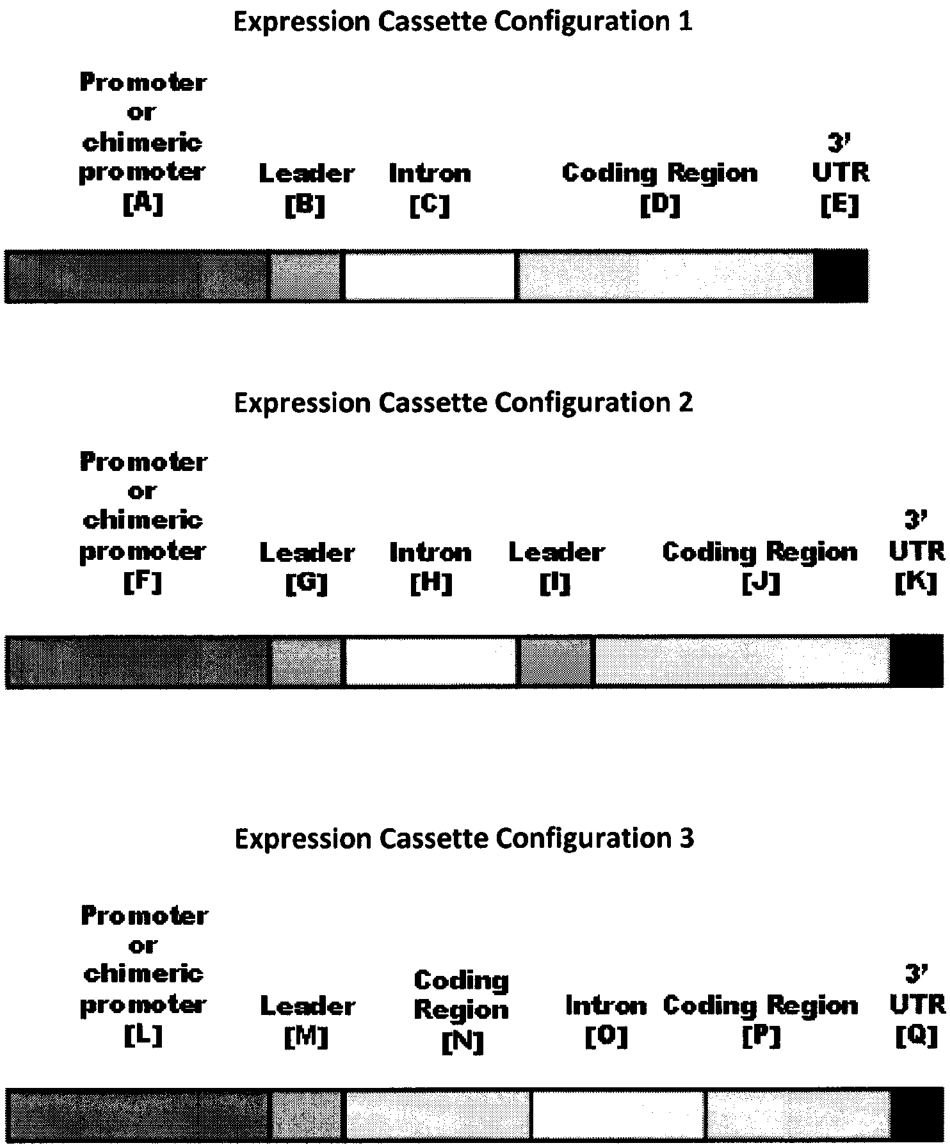
FIG. 9: Shows expression cassette configurations of the invention.

Introns presented herein as SEQ ID NOs: 4, 12, 15, 20, 26, 29, 37, 40, 48, 51, 54, 57, 59, 65, 69, 81, 91, 94 and 171 are identified using genomic DNA contigs in comparison to expressed sequence tag clusters or cDNA contigs to identify exon and intron sequences within the genomic DNA. In addition, 5' UTR or leader sequences are also used to define the intron/exon splice junction of one or more introns under conditions when the gene sequence encodes a leader sequence that is interrupted by one or more introns. Introns are cloned using methods known in the art into a plant transformation vector to be operably linked 3' to a regulatory element and leader fragment and operably linked 5' to either a second leader fragment or to coding sequences, for instance as depicted in the expression cassettes presented in FIG. 9.

Thus, for instance, a first possible expression cassette (Expression Cassette Configuration 1 in FIG. 9) is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible expression cassette (Expression Cassette Configuration 2 in FIG. 9) is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible expression cassette (Expression Cassette Configuration 3 in FIG. 9) is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Expression Cassette Configuration 3 is designed to allow splicing of the intron in such a manner as to produce a complete open reading frame without a frame shift between the first and second fragment of the coding sequence.

As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified.

The introns are assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive promoter such as the Cauliflower mosaic virus promoter, P-CaMV.35S-enh-1:1:9 (SEQ ID NO: 166), operably linked 5' to a leader element, L-CaMV.35S-1:1:15 (SEQ ID NO: 167), operably linked 5' to a test intron element (e.g. one of SEQ ID NOs: 4, 12, 15, 20, 26, 29, 37, 40, 48, 51, 54, 57, 59, 65, 69, 81, 91, 94 and 171), operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158). Protoplast cells derived from corn or other genus plant tissue are transformed with the base plant vector and Luciferase control vectors as described previously in Example 2 above, and assayed for activity. To compare the relative ability of the intron to enhance expression, GUS values are expressed as a ratio of GUS to Luciferase activity and compared with those levels imparted by a construct comprising the constitutive promoter operably linked to a known intron standard such as that as the intron derived from the HSP70 heat shock protein of *Zea mays*, I-Zm.DnaK-1:1:1 (SEQ ID NO: 165), as well as a construct comprising the constitutive promoter, but without an intron operably linked to the promoter.

For stable plant assay of the introns presented as SEQ ID NOs: 4, 12, 15, 20, 26, 29, 37, 40, 48, 51, 54, 57, 59, 65, 69, 81, 91, 94 and 171, a GUS expression plant transformation vector is constructed similar to the constructs described in the previous examples in which the resulting plant expression vectors contains a right border region from *A. tumefaciens*, a first expression cassette to test the intron comprised of a constitutive promoter such as the Cauliflower mosaic virus promoter, P-CaMV.35S-enh-1:1:9 (SEQ ID NO: 166), operably linked 5' to a leader element, L-CaMV.35S-1:1:15 (SEQ ID NO: 167), operably linked 5' to a test intron element provided herein, operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158); a second transgene selection cassette used for selection of transformed plant cells that confers resistance to glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by *Agrobacterium*-mediated methods known in the art. Single-copy or low copy number transformants are selected for comparison to single-copy or low copy number transformed plants, transformed with a plant transformation vector identical to the test vector but without the test intron to determine if the test intron provides an intron mediated enhancement effect.

Any of the introns presented as SEQ ID NOs: 4, 12, 15, 20, 26, 29, 37, 40, 48, 51, 54, 57, 59, 65, 69, 81, 91, 94 and 171 can be modified in a number of ways, such as deleting fragments within the intron sequence, which may reduce expression or duplication of fragments with the intron that may enhance expression. In addition, DNA sequences within the intron that may affect the specificity of expression to either particular cells types or tissues and organs can be duplicated or altered or deleted to affect expression and patterns of expression of the transgene. In addition, the introns provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi, or animal cells, so long as the intron provides enhancement or attenuation or specificity of expression of the transgene to which it is operably linked.

Having illustrated and described the principles of the invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:
a) a DNA sequence with at least 95 percent sequence identity to SEQ ID NO: 168 or 169 and having promoter activity;
b) a DNA sequence comprising SEQ ID NO: 168 or 169; and
c) a fragment comprising at least 200 contiguous nucleotides of SEQ ID NO: 169, wherein the fragment has promoter activity;
wherein said DNA sequence is operably linked to a heterologous transcribable DNA molecule.

2. The recombinant DNA molecule of claim 1, wherein said DNA sequence has at least 95 percent sequence identity to the DNA sequence of SEQ ID NO: 168 or 169 and has promoter activity.

3. The DNA molecule of claim 1, wherein the heterologous transcribable DNA molecule is a gene of agronomic interest.

4. The recombinant DNA molecule of claim 3, wherein the gene of agronomic interest confers herbicide tolerance in a plant.

5. The recombinant DNA molecule of claim 3, wherein the gene of agronomic interest confers pest resistance in a plant.

6. A construct comprising the recombinant DNA molecule of claim 1.

7. A transgenic plant cell comprising a recombinant DNA molecule comprising a DNA sequence selected from the group consisting of:
a) a DNA sequence with at least 95 percent sequence identity to SEQ ID NO: 168 or 169 and having promoter activity;
b) a DNA sequence comprising SEQ ID NO: 168 or 169; and
c) a fragment comprising at least 200 contiguous nucleotides of SEQ ID NO: 169, wherein the fragment has promoter activity;
wherein said DNA sequence is operably linked to a heterologous transcribable DNA molecule.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising a recombinant DNA molecule comprising a DNA sequence selected from the group consisting of:
a) a DNA sequence with at least 95 percent sequence identity to SEQ ID NO: 168 or 169 and having promoter activity;
b) a DNA sequence comprising SEQ ID NO: 168 or 169; and
c) a fragment comprising at least 200 contiguous nucleotides of SEQ ID NO: 169, wherein the fragment has promoter activity;
wherein said DNA sequence is operably linked to a heterologous transcribable DNA molecule.

11. A progeny plant of the transgenic plant of claim 10, wherein the progeny plant comprises said recombinant DNA molecule.

12. A transgenic seed of the transgenic plant of claim 10, wherein the seed comprises said recombinant DNA molecule.

13. A method of expressing a transcribable DNA molecule comprising obtaining a transgenic plant according to claim 10 and cultivating said plant, wherein the transcribable DNA molecule is expressed.

14. A method of producing a transgenic plant comprising:
a) transforming a plant cell with the recombinant DNA molecule of claim 1 to produce a transformed plant cell; and
b) regenerating a transgenic plant from the transformed plant cell.

15. The recombinant DNA molecule of claim 1, wherein said DNA sequence is selected from the group consisting of: SEQ ID NOs: 168 or 169.

16. The transgenic plant cell of claim 7, wherein said DNA sequence is selected from the group consisting of: SEQ ID NOs: 168 or 169.

17. The transgenic plant, or part thereof, of claim 10, wherein said DNA sequence is selected from the group consisting of: SEQ ID NOs: 168 or 169.

18. The recombinant DNA molecule of claim 1 wherein said fragment comprising at least 200 contiguous nucleotides of SEQ ID NO:169 having promoter activity is operably linked to SEQ ID NO: 170 and SEQ ID NO: 171.

19. The transgenic plant cell comprising a recombinant DNA molecule of claim 7 wherein said fragment comprising at least 200 contiguous nucleotides of SEQ ID NO:169 having promoter activity is operably linked to SEQ ID NO: 170 and SEQ ID NO: 171.

20. The transgenic plant, or part thereof, comprising a recombinant DNA molecule of claim 10 wherein said fragment comprising at least 200 contiguous nucleotides of SEQ ID NO:169 having promoter activity is operably linked to SEQ ID NO: 170 and SEQ ID NO: 171.

* * * * *

SEQUENCE LISTING

<160> NUMBER OF SEQ ID NOS: 171

<210> SEQ ID NO 1
<211> LENGTH: 3143
<212> TYPE: DNA
<213> ORGANISM: Agrostis nebulosa

<400> SEQUENCE: 1
ggcctcttta cgtttggcac aatttaattg aatcccggca tggcatgtta gaccggagtg 60
agccggccct tttactggta tgacactccc tctgtcttga gtgtcgctgt gccagcttgt 120
acctctgtct atgttcacag cccgtgctgt gtacctagac cctccgtttg tccacattca 180
ttttaatctc tattgtatct tgtcaaaacc taaaagccta aaacgactct gataaaggga 240
cagaaagatt atacaagagc aagtgtataa tgaaataatg taagcgagct atatgaattg 300
tcacgtgtca tatttatgtt gagacgaaga agagaaaata aacaccatgc aaatttatgg 360
cgagtgatag atggccagat gggcacaagg cctcctattt cttaaatcgg attttgtaag 420
aacgaaaaaa gggacttata agagaatagg atagaccata tatcaatgat gtagtatgca 480
tcaagatcta actattatat gagtgaattg ataaatttat tctaggtgac atggccttaa 540
cgatgaacag tacatggtta aatcaataga acaatagcca actctagcag ctctaaaaaa 600
agatatatat tcgtcgaggc actattatgc aaccacatag tcaacttcaa caccgcttga 660
gtgcgttctc atgttttttt tttcttgcaa attacgcttt tctaaaataa aataatttgg 720
atcgtgcaat tatttcactt taggtgtgcg tgactacgtg agtaacattt ttgaatctca 780
gaaaggaaat aaaagtataa tactgctgcc tactttgagg attcggcttg ttatttaaaa 840
ccgtctttaa ggtcaaatgc tcaagattca ttcaacaatt gaaacgtctc acatgattaa 900
atcatgtata aggatgctaa ggtcttgctt gacaatgttt ttctaggaat ttcatctaac 960
tttttgagtg aaactatcaa ataataattt taaaacaatt ttataagaga agctccggag 1020
ataaaaggcc atctaatcta tgttagaaga gtgaagttta ctccctctgt cccaaaaata 1080
gaattctaag tatgaaatga tttttttgtt atacaaaagg agtatatatc acaagattga 1140
tgtcagttat gcttagggca cgtacacgac gctggtgctt taggtagacg ttaatcgttg 1200
tttctgcatt ttattttatt ttgttgccac ggtgtacatt tgggtagacg tttgtcacag 1260
gcattgccac tcaaacaagc agccggcgct tggagctttt atagtttgaa aagtgacggt 1320
tttaaggatg ggtaagctga ttagtatatg taagtttagc tttttccatt gtaggttaag 1380
ccttaaggct cttacacaat tgtttcatta ttctcattct ttaagagccc atataagcgt 1440
tcatgaattg tacatatcct tagatttttt tttttgggta aagctcgagc ttctgtatct 1500
aaaagtagag aaatcagaaa aagattcatg ttttggtagt tttgatttct tgcctccata 1560
ataattttgg tttaccattt tttgtttgat tttagtttta gaagcgttta tagcaggatt 1620
taaaatccaa aactaccatt atcttcaagt gaccgtcagt gagccgttta acggcgtcga 1680
caagtccaac ggacaccaac cagtgaacca ccagcgtcga gccaagcgat gcaaacggaa 1740
cggccgagac gttgacacct ttggcgcggc acggcatgtc ggatctccct ctctggcccc 1800
ctctcgagag ttccagctcc acctccaccg gtggcggttt ccaagtccgt tccgttccgt 1860
tccgcctcct gcctgctcct ctcagacggc acgaaaccgt gacggcaccg gcagcacggg 1920
gggattcctt ttccactgct ccttcctttt cccttcctcg cccgccgcta taaatagcca 1980
gccccgtccc cagattcttt cccaacctca tctttgttcg gagcacccac acaacccgat 2040
ccccaattcc ctcgtctctc ctcgcgagcc tcgtcgaccc ccccttcaag gtacggcgat 2100
cgtcctccct ccctctctct ctctaccttc tcttctctag actagatcgg cgacccggtc 2160
catggttagg gcctgctagt tctgttcctg ttttttccat ggctgcgagg taaaatagat 2220
ctgatggcgt tatgatggtt aactcgtcat actcttgcga tctatggtcc ctttaggaca 2280
tcgatttaat ttcggatggt tcgagatcgg tgatccatgg ttagtaccct aggcagtggg 2340
gttagatccg tgctgttagg gttcgtagat ggattctgat tgctcagtaa ctgggaaacc 2400
tgggatggtt ctagctggga atcctgggat ggttctagct ggttcgcaga tgagatcgat 2460
ttcatggtct gctatatctt gtttcgttgc ctaggttccg tttaatctgt ccgtggtatg 2520
atgttagcct ttgataaggt tcgatcgtgc tagctacgtc ctgcgcagca tttaattgtc 2580
aggtcataat ttttagcatt cctgtttttg tttggtttgg ttttgtctgg ttgggctgta 2640
gatagtttca atctacctgt cggtttattt tattaaattt ggattggatc tgtatgtgtc 2700
acatatatct tcatgattaa tatggttgga attatctctt catcttttag atatatatgg 2760
ataggtatat atgttgctgt gggttttact ggtactttat tagatatatt catgcttaga 2820
tacatgaagc aacgtgctgt tacagtttaa taattcttgt ttatctaata aacaaataag 2880
gataggtata tatgttgctg atggttttac tgatacttta ttagatagta cttctttgac 2940
atgaaggaac atcctgcgac agcttaataa ttattcttca tctaataaaa agcttgcttt 3000
ttaattattt tgatatactt ggatgatgtc atgcagcagc tatgtgtgaa ttttcggccc 3060
tgtcttcata tgatgtttat ttgcttggga ctgtttcttt ggctgataac tcaccctgtt 3120
gtttggtgat ccttctgcag gtg 3143

<210> SEQ ID NO 2
<211> LENGTH: 2005
<212> TYPE: DNA
<213> ORGANISM: Agrostis nebulosa

<400> SEQUENCE: 2
ggcctcttta cgtttggcac aatttaattg aatcccggca tggcatgtta gaccggagtg 60
agccggccct tttactggta tgacactccc tctgtcttga gtgtcgctgt gccagcttgt 120
acctctgtct atgttcacag cccgtgctgt gtacctagac cctccgtttg tccacattca 180
ttttaatctc tattgtatct tgtcaaaacc taaaagccta aaacgactct gataaaggga 240
cagaaagatt atacaagagc aagtgtataa tgaaataatg taagcgagct atatgaattg 300
tcacgtgtca tatttatgtt gagacgaaga agagaaaata aacaccatgc aaatttatgg 360
cgagtgatag atggccagat gggcacaagg cctcctattt cttaaatcgg attttgtaag 420
aacgaaaaaa gggacttata agagaatagg atagaccata tatcaatgat gtagtatgca 480
tcaagatcta actattatat gagtgaattg ataaatttat tctaggtgac atggccttaa 540
cgatgaacag tacatggtta aatcaataga acaatagcca actctagcag ctctaaaaaa 600
agatatatat tcgtcgaggc actattatgc aaccacatag tcaacttcaa caccgcttga 660
gtgcgttctc atgttttttt tttcttgcaa attacgcttt tctaaaataa aataatttgg 720
atcgtgcaat tatttcactt taggtgtgcg tgactacgtg agtaacattt ttgaatctca 780
gaaaggaaat aaaagtataa tactgctgcc tactttgagg attcggcttg ttatttaaaa 840
ccgtctttaa ggtcaaatgc tcaagattca ttcaacaatt gaaacgtctc acatgattaa 900
atcatgtata aggatgctaa ggtcttgctt gacaatgttt ttctaggaat ttcatctaac 960
tttttgagtg aaactatcaa ataataattt taaaacaatt ttataagaga agctccggag 1020

-continued

```
ataaaaggcc atctaatcta tgttagaaga gtgaagttta ctccctctgt cccaaaaata   1080

gaattctaag tatgaaatga ttttttgtt atacaaaagg agtatatatc acaagattga   1140

tgtcagttat gcttagggca cgtacacgac gctggtgctt taggtagacg ttaatcgttg   1200

tttctgcatt ttattttatt ttgttgccac ggtgtacatt tgggtagacg tttgtcacag   1260

gcattgccac tcaaacaagc agccggcgct tggagctttt atagtttgaa aagtgacggt   1320

tttaaggatg ggtaagctga ttagtatatg taagtttagc tttttccatt gtaggttaag   1380

ccttaaggct cttacacaat tgtttcatta ttctcattct ttaagagccc atataagcgt   1440

tcatgaattg tacatatcct tagatttttt tttttgggta aagctcgagc ttctgtatct   1500

aaaagtagag aaatcagaaa aagattcatg ttttggtagt tttgatttct tgcctccata   1560

ataattttgg tttaccattt tttgtttgat tttagtttta gaagcgttta tagcaggatt   1620

taaaatccaa aactaccatt atcttcaagt gaccgtcagt gagccgttta acggcgtcga   1680

caagtccaac ggacaccaac cagtgaacca ccagcgtcga gccaagcgat gcaaacggaa   1740

cggccgagac gttgacacct ttggcgcggc acggcatgtc ggatctccct ctctggcccc   1800

ctctcgagag ttccagctcc acctccaccg gtggcggttt ccaagtccgt tccgttccgt   1860

tccgcctcct gcctgctcct ctcagacggc acgaaaccgt gacggcaccg gcagcacggg   1920

gggattcctt ttccactgct ccttcctttt cccttcctcg cccgccgcta taaatagcca   1980

gccccgtccc cagattcttt cccaa                                          2005


<210> SEQ ID NO 3
<211> LENGTH: 85
<212> TYPE: DNA
<213> ORGANISM: Agrostis nebulosa

<400> SEQUENCE: 3

cctcatcttt gttcggagca cccacacaac ccgatcccca attccctcgt ctctcctcgc     60

gagcctcgtc gacccccccct tcaag                                          85


<210> SEQ ID NO 4
<211> LENGTH: 1053
<212> TYPE: DNA
<213> ORGANISM: Agrostis nebulosa

<400> SEQUENCE: 4

gtacggcgat cgtcctccct ccctctctct ctctaccttc tcttctctag actagatcgg     60

cgacccggtc catggttagg gcctgctagt tctgttcctg ttttttccat ggctgcgagg    120

taaaatagat ctgatggcgt tatgatggtt aactcgtcat actcttgcga tctatggtcc    180

ctttaggaca tcgatttaat ttcggatggt tcgagatcgg tgatccatgg ttagtaccct    240

aggcagtggg gttagatccg tgctgttagg gttcgtagat ggattctgat tgctcagtaa    300

ctgggaaacc tgggatggtt ctagctggga atcctgggat ggttctagct ggttcgcaga    360

tgagatcgat ttcatggtct gctatatctt gtttcgttgc ctaggttccg tttaatctgt    420

ccgtggtatg atgttagcct ttgataaggt tcgatcgtgc tagctacgtc ctgcgcagca    480

tttaattgtc aggtcataat ttttagcatt cctgtttttg tttggtttgg ttttgtctgg    540

ttgggctgta gatagtttca atctacctgt cggtttattt tattaaattt ggattggatc    600

tgtatgtgtc acatatatct tcatgattaa tatggttgga attatctctt catcttttag    660

atatatatgg ataggtatat atgttgctgt gggttttact ggtactttat tagatatatt    720

catgcttaga tacatgaagc aacgtgctgt tacagtttaa taattcttgt ttatctaata    780
```

-continued aacaaataag gataggtata tatgttgctg atggttttac tgatacttta ttagatagta 840
cttctttgac atgaaggaac atcctgcgac agcttaataa ttattcttca tctaataaaa 900
agcttgcttt ttaattattt tgatatactt ggatgatgtc atgcagcagc tatgtgtgaa 960
ttttcggccc tgtcttcata tgatgtttat ttgcttggga ctgtttcttt ggctgataac 1020
tcaccctgtt gtttggtgat ccttctgcag gtg 1053

<210> SEQ ID NO 5
<211> LENGTH: 2137
<212> TYPE: DNA
<213> ORGANISM: Agrostis nebulosa

<400> SEQUENCE: 5
gagaagctcc ggagataaaa ggccatctaa tctatgttag aagagtgaag tttactccct 60
ctgtcccaaa aatagaattc taagtatgaa atgatttttt tgttatacaa aaggagtata 120
tatcacaaga ttgatgtcag ttatgcttag ggcacgtaca cgacgctggt gctttaggta 180
gacgttaatc gttgtttctg cattttattt tattttgttg ccacggtgta catttgggta 240
gacgtttgtc acaggcattg ccactcaaac aagcagccgg cgcttggagc ttttatagtt 300
tgaaaagtga cggttttaag gatgggtaag ctgattagta tatgtaagtt tagctttttc 360
cattgtaggt taagccttaa ggctcttaca caattgtttc attattctca ttctttaaga 420
gcccatataa gcgttcatga attgtacata tccttagatt tttttttttg ggtaaagctc 480
gagcttctgt atctaaaagt agagaaatca gaaaaagatt catgttttgg tagttttgat 540
ttcttgcctc cataataatt ttggtttacc attttttgtt tgattttagt tttagaagcg 600
tttatagcag gatttaaaat ccaaaactac cattatcttc aagtgaccgt cagtgagccg 660
tttaacggcg tcgacaagtc caacggacac caaccagtga accaccagcg tcgagccaag 720
cgatgcaaac ggaacggccg agacgttgac acctttggcg cggcacggca tgtcggatct 780
ccctctctgg ccccctctcg agagttccag ctccacctcc accggtggcg gtttccaagt 840
ccgttccgtt ccgttccgcc tcctgcctgc tcctctcaga cggcacgaaa ccgtgacggc 900
accggcagca cggggggatt ccttttccac tgctccttcc ttttcccttc ctcgcccgcc 960
gctataaata gccagccccg tccccagatt ctttcccaac ctcatctttg ttcggagcac 1020
ccacacaacc cgatccccaa ttccctcgtc tctcctcgcg agcctcgtcg accccccctt 1080
caaggtacgg cgatcgtcct ccctccctct ctctctctac cttctcttct ctagactaga 1140
tcggcgaccc ggtccatggt tagggcctgc tagttctgtt cctgtttttt ccatggctgc 1200
gaggtaaaat agatctgatg gcgttatgat ggttaactcg tcatactctt gcgatctatg 1260
gtccctttag gacatcgatt taatttcgga tggttcgaga tcggtgatcc atggttagta 1320
ccctaggcag tggggttaga tccgtgctgt tagggttcgt agatggattc tgattgctca 1380
gtaactggga aacctgggat ggttctagct gggaatcctg ggatggttct agctggttcg 1440
cagatgagat cgatttcatg gtctgctata tcttgtttcg ttgcctaggt tccgtttaat 1500
ctgtccgtgg tatgatgtta gcctttgata aggttcgatc gtgctagcta cgtcctgcgc 1560
agcatttaat tgtcaggtca taatttttag cattcctgtt tttgtttggt ttggttttgt 1620
ctggttgggc tgtagatagt ttcaatctac ctgtcggttt attttattaa atttggattg 1680
gatctgtatg tgtcacatat atcttcatga ttaatatggt tggaattatc tcttcatctt 1740
ttagatatat atggataggt atatatgttg ctgtgggttt tactggtact ttattagata 1800

-continued

```
tattcatgct tagatacatg aagcaacgtg ctgttacagt ttaataattc ttgtttatct   1860

aataaacaaa taaggatagg tatatatgtt gctgatggtt ttactgatac tttattagat   1920

agtacttctt tgacatgaag gaacatcctg cgacagctta ataattattc ttcatctaat   1980

aaaaagcttg ctttttaatt attttgatat acttggatga tgtcatgcag cagctatgtg   2040

tgaattttcg gccctgtctt catatgatgt ttatttgctt gggactgttt ctttggctga   2100

taactcaccc tgttgtttgg tgatccttct gcaggtg                            2137
```

<210> SEQ ID NO 6
<211> LENGTH: 999
<212> TYPE: DNA
<213> ORGANISM: Agrostis nebulosa

<400> SEQUENCE: 6

```
gagaagctcc ggagataaaa ggccatctaa tctatgttag aagagtgaag tttactccct     60

ctgtcccaaa aatagaattc taagtatgaa atgatttttt tgttatacaa aaggagtata    120

tatcacaaga ttgatgtcag ttatgcttag ggcacgtaca cgacgctggt gctttaggta    180

gacgttaatc gttgtttctg cattttattt tattttgttg ccacggtgta catttgggta    240

gacgtttgtc acaggcattg ccactcaaac aagcagccgg cgcttggagc ttttatagtt    300

tgaaaagtga cggttttaag gatgggtaag ctgattagta tatgtaagtt tagctttttc    360

cattgtaggt taagccttaa ggctcttaca caattgtttc attattctca ttctttaaga    420

gcccatataa gcgttcatga attgtacata tccttagatt tttttttttg ggtaaagctc    480

gagcttctgt atctaaaagt agagaaatca gaaaaagatt catgttttgg tagttttgat    540

ttcttgcctc cataataatt ttggtttacc attttttgtt tgattttagt tttagaagcg    600

tttatagcag gatttaaaat ccaaaactac cattatcttc aagtgaccgt cagtgagccg    660

tttaacggcg tcgacaagtc caacggacac caaccagtga accaccagcg tcgagccaag    720

cgatgcaaac ggaacggccg agacgttgac acctttggcg cggcacggca tgtcggatct    780

ccctctctgg ccccctctcg agagttccag ctccacctcc accggtggcg gtttccaagt    840

ccgttccgtt ccgttccgcc tcctgcctgc tcctctcaga cggcacgaaa ccgtgacggc    900

accggcagca cggggggatt ccttttccac tgctccttcc ttttcccttc ctcgcccgcc    960

gctataaata gccagccccg tccccagatt ctttcccaa                           999
```

<210> SEQ ID NO 7
<211> LENGTH: 1900
<212> TYPE: DNA
<213> ORGANISM: Agrostis nebulosa

<400> SEQUENCE: 7

```
gtagacgttt gtcacaggca ttgccactca aacaagcagc cggcgcttgg agcttttata     60

gtttgaaaag tgacggtttt aaggatgggt aagctgatta gtatatgtaa gtttagcttt    120

ttccattgta ggttaagcct taaggctctt acacaattgt ttcattattc tcattcttta    180

agagcccata taagcgttca tgaattgtac atatccttag attttttttt ttgggtaaag    240

ctcgagcttc tgtatctaaa agtagagaaa tcagaaaaag attcatgttt tggtagtttt    300

gatttcttgc ctccataata attttggttt accatttttt gtttgatttt agttttagaa    360

gcgtttatag caggatttaa aatccaaaac taccattatc ttcaagtgac cgtcagtgag    420

ccgtttaacg gcgtcgacaa gtccaacgga caccaaccag tgaaccacca gcgtcgagcc    480

aagcgatgca aacggaacgg ccgagacgtt gacacctttg gcgcggcacg gcatgtcgga    540
```

```
tctccctctc tggccccctc tcgagagttc cagctccacc tccaccggtg gcggtttcca    600

agtccgttcc gttccgttcc gcctcctgcc tgctcctctc agacggcacg aaaccgtgac    660

ggcaccggca gcacgggggg attccttttc cactgctcct tccttttccc ttcctcgccc    720

gccgctataa atagccagcc ccgtccccag attctttccc aacctcatct ttgttcggag    780

cacccacaca acccgatccc caattccctc gtctctcctc gcgagcctcg tcgacccccc    840

cttcaaggta cggcgatcgt cctccctccc tctctctctc taccttctct tctctagact    900

agatcggcga cccggtccat ggttagggcc tgctagttct gttcctgttt tttccatggc    960

tgcgaggtaa aatagatctg atggcgttat gatggttaac tcgtcatact cttgcgatct   1020

atggtccctt taggacatcg atttaatttc ggatggttcg agatcggtga tccatggtta   1080

gtaccctagg cagtggggtt agatccgtgc tgttagggtt cgtagatgga ttctgattgc   1140

tcagtaactg ggaaacctgg gatggttcta gctgggaatc ctgggatggt tctagctggt   1200

tcgcagatga gatcgatttc atggtctgct atatcttgtt tcgttgccta ggttccgttt   1260

aatctgtccg tggtatgatg ttagcctttg ataaggttcg atcgtgctag ctacgtcctg   1320

cgcagcattt aattgtcagg tcataatttt tagcattcct gtttttgttt ggtttggttt   1380

tgtctggttg ggctgtagat agtttcaatc tacctgtcgg tttattttat taaatttgga   1440

ttggatctgt atgtgtcaca tatatcttca tgattaatat ggttggaatt atctcttcat   1500

cttttagata tatatggata ggtatatatg ttgctgtggg ttttactggt actttattag   1560

atatattcat gcttagatac atgaagcaac gtgctgttac agtttaataa ttcttgttta   1620

tctaataaac aaataaggat aggtatatat gttgctgatg gttttactga tactttatta   1680

gatagtactt ctttgacatg aaggaacatc ctgcgacagc ttaataatta ttcttcatct   1740

aataaaaagc ttgcttttta attattttga tatacttgga tgatgtcatg cagcagctat   1800

gtgtgaattt tcggccctgt cttcatatga tgtttatttg cttgggactg tttctttggc   1860

tgataactca ccctgttgtt tggtgatcct tctgcaggtg                         1900
```

<210> SEQ ID NO 8
<211> LENGTH: 762
<212> TYPE: DNA
<213> ORGANISM: Agrostis nebulosa

<400> SEQUENCE: 8

```
gtagacgttt gtcacaggca ttgccactca aacaagcagc cggcgcttgg agcttttata     60

gtttgaaaag tgacggtttt aaggatgggt aagctgatta gtatatgtaa gtttagcttt    120

ttccattgta ggttaagcct taaggctctt acacaattgt ttcattattc tcattcttta    180

agagcccata taagcgttca tgaattgtac atatccttag attttttttt ttgggtaaag    240

ctcgagcttc tgtatctaaa agtagagaaa tcagaaaaag attcatgttt tggtagtttt    300

gatttcttgc ctccataata attttggttt accatttttt gtttgatttt agttttagaa    360

gcgtttatag caggatttaa aatccaaaac taccattatc ttcaagtgac cgtcagtgag    420

ccgtttaacg gcgtcgacaa gtccaacgga caccaaccag tgaaccacca gcgtcgagcc    480

aagcgatgca aacggaacgg ccgagacgtt gacacctttg gcgcggcacg gcatgtcgga    540

tctccctctc tggccccctc tcgagagttc cagctccacc tccaccggtg gcggtttcca    600

agtccgttcc gttccgttcc gcctcctgcc tgctcctctc agacggcacg aaaccgtgac    660

ggcaccggca gcacgggggg attccttttc cactgctcct tccttttccc ttcctcgccc    720
```

-continued gccgctataa atagccagcc ccgtccccag attctttccc aa 762

<210> SEQ ID NO 9
<211> LENGTH: 5068
<212> TYPE: DNA
<213> ORGANISM: Arundo donax

<400> SEQUENCE: 9
ggcctcttta cgtttggcac aatttgatcg aatccaacac ggcaagttaa catttgaaga 60
ttgaaccggg cactaatgca agtctacaac taagaactac aagaaagcat gttccttgag 120
gtacttggat gcaacctcac aattatcaaa ttaattaaca actacagtta gaattttaga 180
tcacaagaat atcacgaact gtggatacta cttcaagggc tattcttttc tgaatgttgc 240
agttggttgt tttaaacata ttacaaacta ggtgtttaaa tgccaaaaag ttcatggaaa 300
aagattaagc taatattcca tccgtccaca aaatttaaat gctaggaatc attatatttg 360
tggatagaag gagtagttag taagacctac acttaattac acattggtca ttcctggagg 420
aataatcccc catagcaagt tgttttgagt ttgactaccc aaacttgcat aaattttttc 480
ttaaaaaaag ggggagcttc accattccat caagatggcg aggctaaatg aaacgcacga 540
tgggcaaaac ggactaacgt acaaacaaca aggcaatgaa agatagggtt ttgataaata 600
tcaaatatac aaagtcaacc aaagaaaaaa gagatcccaa tggctaacct ttggatccgt 660
gtcgcaattt gtgctttagg acatacaagg tggatttctt ctttggcaaa ctctataata 720
attgggtgac ggtggcctca cggcagcctc aaagagtcgg tagcaacttt tagatctttt 780
gagctgaaac tcaattatgt agtagaatga tatttagata gatagatcga aatttggggg 840
tgtgaaaaca aagaggttct caatattgat agcaactcca acgaatggat atggaaaata 900
catgattttt tattcgagta gaaaaaggag gggaacggaa caaatctagc aatagtagcc 960
accaaagatg aggaccctgg atttcggatc caatagtggt aaggaagaaa gggccggact 1020
atccagaata aggtgaattg gtcaaggaag cggaagtctc cataaagaaa ttgtgggctc 1080
acttgatgtg agaaagaaga ccgaccaaga agcgggtttt gggggacaga ggagattggt 1140
gccaggttgc agtggcatgt atgtggggga agaggcaatg acaacggccg agagaggaga 1200
agggaatgag gtaagtattt gaagtgaaga ggtgcccata taggttaaaa aatgagctgt 1260
ggatttaaat caaaggtgtc agcgacacag gcacggaagt accctaagtt acctatgtgg 1320
gtcgcatatc acgctaagtt ccttcaccgt acaaggtgaa agtaacactg gcaatgtgcc 1380
ccagctgcaa ggcttgtcta tcaatgtggc cctacaaggc tcctggctac cccaggagct 1440
caaaacacgt ggcacatggt ggtacttcgc ccgacctcta tgctcaccgt gcacccggcc 1500
ccgaggtcaa tggctcctga gcacccgact gcatgactgg acccctgagt acccgacccc 1560
cgggacaagc tcccgtggac cttccccggg gatcaggctc acgagtactc gacctcacgt 1620
caatggctct cccgagtacc caaccttgtg tcgatagctc actaaggatc atgtgctaat 1680
ccttagcatc tcggattttg agtactaggc cattatttgc atgccatcct cttggatcta 1740
tgcggatttt caaggacctt acctaagcat caacatgcac aaacacaaac ccttcgtgaa 1800
gccatcccca actactcggg tggcaggacc ctcgacacgt gcgatgcgag ctcggacaga 1860
gctgacaaga acctcccgac ggcgcattaa atgccctggc aagggcgccc cgcctcgtcg 1920
agctctggac ttcatcaagt cacatcaaca gcaggcaggc gctccttccg cagacttcat 1980
catgagggaa tccgttaccc tctatttaca tagtgcagcg gggaatgtgg agatcaaatc 2040
tctccaatga tgtcactgtg tagcatgtat tagcacgcca acaccctgtc gcttaccacg 2100

-continued

```
aggatcagcc atgcaagcaa gagatgttgg tcgggcctcg gtggcaactg aggctatagt   2160
gacctatgac gagcaggcca tagataggcc cactggcaag cccaagaatc gctagacggg   2220
ctagatctgg acacttgtcc gcaccaagca ctaccgttgc aactgcaacc tctatatgta   2280
actatagatt cacatgttgc gacatctttg cccaatacgt attgtaccct agacagctca   2340
ccctatcttt ttcttttttt tcctctttct tcttcctcct ccttgcatgg agacgtagaa   2400
ggactcctcc cttgtgacta ttaaaggaag gacttagggc tgtgctaggg gagagaactt   2460
ttggacttgg gagagctctg cactgaacat cttcctctcc acgcttgtaa tattttccac   2520
aacaaagaat tccataaagc cggatgtagg gctattatcc ctctcgggag gcctgaacca   2580
gggtaaaaca ccactcttct caccagcgtt cgccgcatta gtctagacta gcatcttttg   2640
accctatatc gaaccatcta gggactttac gtcccctgcc tgcagtttcc cggtgacaga   2700
atgactatga tttttcgtcg attttataaa agtgaaaaca accggttgat atctatgcgc   2760
actattttcc tacatatatt tctaacttct tgcttagcca tgtcggttaa gagcaagtgg   2820
agagcactct catttcgtag aacaagtgat gaatgccgac ctgcatcatc ttacttagac   2880
ttgatcatca agtggaatcc ccattcatct taataatctc atattgagtg ccaatgcaac   2940
attgttataa tcctcttcat atgctaattc ttcaaagcta acgtagttaa atgaaggcaa   3000
aatatgcaac ttcgtcctct aagtttgctc aaaggctcat ttttaccctt taactatcaa   3060
accgattact ttcgtccctg aactttcatg tttggtccaa tttaatccct gggctgatgt   3120
atccgtccac ggtggtgtgt ccaatcagtg aataatctag ttagtgaagc cagaagtcca   3180
tagtgcccct tgctctgtca ccatatatcc agttcaaccg caccaatttg ccatctcgaa   3240
ctggttcatg ttttattcag gttggtaaat gaattttgcc aattcaatgt agttagatat   3300
ttccatgtca ttttagtaca tttaccaatt ttttatattc tggctagaaa aggagaatgg   3360
tgacgtcttt cggaagatca agatcaatta tcaagtatca gcaacagcac ctgaaggttg   3420
gagtgcatta gttgtcattg agaataatgc tagctattca ttgcactggc attagagaca   3480
gagagggcga gccagtttga catggcaaat tagcacagtc aaactggata cgtggtgacg   3540
gagggagggg cactatgaat tttggtgac ggagggaggg gcactatgaa tttttggctt   3600
tgctgacggg acacgccact atggatgaaa ttggacaaaa tacgaatatt caaggatgaa   3660
agtggtcggt ttgatagttc agggatgaaa tgtgtctttg ggcaaacttt gaggacgaag   3720
ttgcctattt tgcattaaac gaatatattt atataccca aaaaaaagaa tacacatctc   3780
cactccgagc cggcatgtgg ggtccccact agtcagccac tgtatggcgc cgactagctc   3840
aacggccacg aaccagccaa ccaccagcgc aacctaaacg gcgtaaacgt tgacggcatc   3900
tctctctcgc cccgtctcga agcttccgca ccgctcgctg gtcgctgccc ggcgccgctc   3960
gtgctggact ctttccgtgg cggcttccgc gaaattgcgt ggtggagagg agagacggaa   4020
ccgtcacggc actggattcc ttccccaccc ggcttggccg gcccctcctc gcctccataa   4080
ataggcaccc cgtcctcgcc tcctctcccc acctcatctc ctcctttccc gtgaaccgtg   4140
aacacaaccc gacccagatc ccctcttgcg agcttcgtcg atccctcctc cgcgtcaagg   4200
tacggagctt ctcctccccc ttcttctcta gatcggcgtg ttatgttgtt tccgtggttg   4260
cttggttgga tgaatcgaat gattcttagg gcctaggagg ctggttagat ctgttgcgtt   4320
ctgtttcgta gatggatttt ggtgtaagat caggtcggtt ccgctgttta acttgtgatg   4380
ctagtgtgat tttgggaggg atttgagttg ttaatctggg agttgttggg aggttctcgt   4440
```

```
aggcggattg tagatgaagt cgcccgcacg atttgcgtgg cttgttgggt agctagggtt   4500
agatctgctc ggatttttca ttgttactta ttgagagata atgtagctaa cctttacttg   4560
ttcatctatg tatctcgtat tcgtattcat ctggttcgat ggtgctagat agatgcgcct   4620
gatttgtccg atcgaattgg gtagcatccg cggcttgttt ggtagtgttc tgattgattt   4680
gtcgctctag atctgagtgg aataatatta catctcaaca tgttactaga aacttggttt   4740
atagctccgg atttacatgt ttattcttat gtaaggtttt aaatgaaaga tttatgctac   4800
tgctgctcgt tgatccttta gcatccacct gaggaacatg catgcatctg ttacttcttt   4860
tgatatatgc ttagatagtt gttagtatat actgctgttg ttcgatgatc cttcaggatg   4920
aacatgcatg atcatgttac ttgtttttat atgcttctgc tgttcgttga ttctttagta   4980
ctacctacct gatcatcttg catgtttcct gcttgttaga gattaattga ttaggcttac   5040
cttgttgcct ggtgattctt ccttgcag                                      5068
```

<210> SEQ ID NO 10
<211> LENGTH: 4114
<212> TYPE: DNA
<213> ORGANISM: Arundo donax

<400> SEQUENCE: 10

```
ggcctcttta cgtttggcac aatttgatcg aatccaacac ggcaagttaa catttgaaga     60
ttgaaccggg cactaatgca agtctacaac taagaactac aagaaagcat gttccttgag    120
gtacttggat gcaacctcac aattatcaaa ttaattaaca actacagtta gaattttaga    180
tcacaagaat atcacgaact gtggatacta cttcaagggc tattcttttc tgaatgttgc    240
agttggttgt tttaaacata ttacaaacta ggtgtttaaa tgccaaaaag ttcatggaaa    300
aagattaagc taatattcca tccgtccaca aaatttaaat gctaggaatc attatatttg    360
tggatagaag gagtagttag taagacctac acttaattac acattggtca ttcctggagg    420
aataatcccc catagcaagt tgttttgagt ttgactaccc aaacttgcat aaattttttc    480
ttaaaaaaag ggggagcttc accattccat caagatggcg aggctaaatg aaacgcacga    540
tgggcaaaac ggactaacgt acaaacaaca aggcaatgaa agatagggtt ttgataaata    600
tcaaatatac aaagtcaacc aaagaaaaaa gagatcccaa tggctaacct ttggatccgt    660
gtcgcaattt gtgctttagg acatacaagg tggatttctt ctttggcaaa ctctataata    720
attgggtgac ggtggcctca cggcagcctc aaagagtcgg tagcaacttt tagatctttt    780
gagctgaaac tcaattatgt agtagaatga tatttagata gatagatcga aatttggggg    840
tgtgaaaaca aagaggttct caatattgat agcaactcca acgaatggat atggaaaata    900
catgattttt tattcgagta gaaaaaggag gggaacggaa caaatctagc aatagtagcc    960
accaaagatg aggaccctgg atttcggatc caatagtggt aaggaagaaa gggccggact   1020
atccagaata aggtgaattg gtcaaggaag cggaagtctc cataaagaaa ttgtgggctc   1080
acttgatgtg agaaagaaga ccgaccaaga agcgggtttt gggggacaga ggagattggt   1140
gccaggttgc agtggcatgt atgtggggga agaggcaatg acaacggccg agagaggaga   1200
agggaatgag gtaagtattt gaagtgaaga ggtgcccata taggttaaaa aatgagctgt   1260
ggatttaaat caaaggtgtc agcgacacag gcacggaagt accctaagtt acctatgtgg   1320
gtcgcatatc acgctaagtt ccttcaccgt acaaggtgaa agtaacactg gcaatgtgcc   1380
ccagctgcaa ggcttgtcta tcaatgtggc cctacaaggc tcctggctac cccaggagct   1440
caaaacacgt ggcacatggt ggtacttcgc ccgacctcta tgctcaccgt gcacccggcc   1500
```

```
ccgaggtcaa tggctcctga gcacccgact gcatgactgg acccctgagt acccgacccc   1560
cgggacaagc tcccgtggac cttccccggg gatcaggctc acgagtactc gacctcacgt   1620
caatggctct cccgagtacc caaccttgtg tcgatagctc actaaggatc atgtgctaat   1680
ccttagcatc tcggattttg agtactaggc cattatttgc atgccatcct cttggatcta   1740
tgcggatttt caaggacctt acctaagcat caacatgcac aaacacaaac ccttcgtgaa   1800
gccatcccca actactcggg tggcaggacc ctcgacacgt gcgatgcgag ctcggacaga   1860
gctgacaaga acctcccgac ggcgcattaa atgccctggc aagggcgccc cgcctcgtcg   1920
agctctggac ttcatcaagt cacatcaaca gcaggcaggc gctccttccg cagacttcat   1980
catgagggaa tccgttaccc tctatttaca tagtgcagcg gggaatgtgg agatcaaatc   2040
tctccaatga tgtcactgtg tagcatgtat tagcacgcca acaccctgtc gcttaccacg   2100
aggatcagcc atgcaagcaa gagatgttgg tcgggcctcg gtggcaactg aggctatagt   2160
gacctatgac gagcaggcca tagataggcc cactggcaag cccaagaatc gctagacggg   2220
ctagatctgg acacttgtcc gcaccaagca ctaccgttgc aactgcaacc tctatatgta   2280
actatagatt cacatgttgc gacatctttg cccaatacgt attgtaccct agacagctca   2340
ccctatcttt ttcttttttt tcctctttct tcttcctcct ccttgcatgg agacgtagaa   2400
ggactcctcc cttgtgacta ttaaaggaag gacttagggc tgtgctaggg gagagaactt   2460
ttggacttgg gagagctctg cactgaacat cttcctctcc acgcttgtaa tattttccac   2520
aacaaagaat tccataaagc cggatgtagg gctattatcc ctctcgggag gcctgaacca   2580
gggtaaaaca ccactcttct caccagcgtt cgccgcatta gtctagacta gcatcttttg   2640
accctatatc gaaccatcta gggactttac gtcccctgcc tgcagtttcc cggtgacaga   2700
atgactatga tttttcgtcg attttataaa agtgaaaaca accggttgat atctatgcgc   2760
actattttcc tacatatatt tctaacttct tgcttagcca tgtcggttaa gagcaagtgg   2820
agagcactct catttcgtag aacaagtgat gaatgccgac ctgcatcatc ttacttagac   2880
ttgatcatca agtggaatcc ccattcatct taataatctc atattgagtg ccaatgcaac   2940
attgttataa tcctcttcat atgctaattc ttcaaagcta acgtagttaa atgaaggcaa   3000
aatatgcaac ttcgtcctct aagtttgctc aaaggctcat ttttaccctt taactatcaa   3060
accgattact ttcgtccctg aactttcatg tttggtccaa tttaatccct gggctgatgt   3120
atccgtccac ggtggtgtgt ccaatcagtg aataatctag ttagtgaagc cagaagtcca   3180
tagtgcccct tgctctgtca ccatatatcc agttcaaccg caccaatttg ccatctcgaa   3240
ctggttcatg ttttattcag gttggtaaat gaattttgcc aattcaatgt agttagatat   3300
ttccatgtca ttttagtaca tttaccaatt ttttatattc tggctagaaa aggagaatgg   3360
tgacgtcttt cggaagatca agatcaatta tcaagtatca gcaacagcac ctgaaggttg   3420
gagtgcatta gttgtcattg agaataatgc tagctattca ttgcactggc attagagaca   3480
gagagggcga gccagtttga catggcaaat tagcacagtc aaactggata cgtggtgacg   3540
gagggagggg cactatgaat tttggtgac ggagggaggg gcactatgaa tttttggctt   3600
tgctgacggg acacgccact atggatgaaa ttggacaaaa tacgaatatt caaggatgaa   3660
agtggtcggt ttgatagttc agggatgaaa tgtgtctttg ggcaaacttt gaggacgaag   3720
ttgcctattt tgcattaaac gaatatattt atatacccca aaaaaaagaa tacacatctc   3780
cactccgagc cggcatgtgg ggtccccact agtcagccac tgtatggcgc cgactagctc   3840
```

aacggccacg aaccagccaa ccaccagcgc aacctaaacg gcgtaaacgt tgacggcatc 3900
tctctctcgc cccgtctcga agcttccgca ccgctcgctg gtcgctgccc ggcgccgctc 3960
gtgctggact ctttccgtgg cggcttccgc gaaattgcgt ggtggagagg agagacggaa 4020
ccgtcacggc actggattcc ttccccaccc ggcttggccg gcccctcctc gcctccataa 4080
ataggcaccc cgtcctcgcc tcctctcccc acct 4114

<210> SEQ ID NO 11
<211> LENGTH: 85
<212> TYPE: DNA
<213> ORGANISM: Arundo donax

<400> SEQUENCE: 11
catctcctcc tttcccgtga accgtgaaca caacccgacc cagatcccct cttgcgagct 60
tcgtcgatcc ctcctccgcg tcaag 85

<210> SEQ ID NO 12
<211> LENGTH: 869
<212> TYPE: DNA
<213> ORGANISM: Arundo donax

<400> SEQUENCE: 12
gtacggagct tctcctcccc cttcttctct agatcggcgt gttatgttgt ttccgtggtt 60
gcttggttgg atgaatcgaa tgattcttag ggcctaggag gctggttaga tctgttgcgt 120
tctgtttcgt agatggattt tggtgtaaga tcaggtcggt tccgctgttt aacttgtgat 180
gctagtgtga tttttgggag gatttgagtt gttaatctgg gagttgttgg gaggttctcg 240
taggcggatt gtagatgaag tcgcccgcac gatttgcgtg gcttgttggg tagctagggt 300
tagatctgct cggatttttc attgttactt attgagagat aatgtagcta acctttactt 360
gttcatctat gtatctcgta ttcgtattca tctggttcga tggtgctaga tagatgcgcc 420
tgatttgtcc gatcgaattg ggtagcatcc gcggcttgtt tggtagtgtt ctgattgatt 480
tgtcgctcta gatctgagtg gaataatatt acatctcaac atgttactag aaacttggtt 540
tatagctccg gatttacatg tttattctta tgtaaggttt taaatgaaag atttatgcta 600
ctgctgctcg ttgatccttt agcatccacc tgaggaacat gcatgcatct gttacttctt 660
ttgatatatg cttagatagt tgttagtata tactgctgtt gttcgatgat ccttcaggat 720
gaacatgcat gatcatgtta cttgttttta tatgcttctg ctgttcgttg attctttagt 780
actacctacc tgatcatctt gcatgtttcc tgcttgttag agattaattg attaggctta 840
ccttgttgcc tggtgattct tccttgcag 869

<210> SEQ ID NO 13
<211> LENGTH: 2969
<212> TYPE: DNA
<213> ORGANISM: Arundo donax

<400> SEQUENCE: 13
gatcagccat gcaagcaaga gatgttggtc gggcctcggt ggcaactgag gctatagtga 60
cctatgacga gcaggccata gataggccca ctggcaagcc caagaatcgc tagacgggct 120
agatctggac acttgtccgc accaagcact accgttgcaa ctgcaacctc tatatgtaac 180
tatagattca catgttgcga catctttgcc caatacgtat tgtaccctag acagctcacc 240
ctatcttttt cttttttttc ctctttcttc ttcctcctcc ttgcatggag acgtagaagg 300
actcctccct tgtgactatt aaaggaagga cttagggctg tgctagggga gagaactttt 360

-continued

```
ggacttggga gagctctgca ctgaacatct tcctctccac gcttgtaata ttttccacaa    420
caaagaattc cataaagccg gatgtagggc tattatccct ctcgggaggc ctgaaccagg    480
gtaaaacacc actcttctca ccagcgttcg ccgcattagt ctagactagc atcttttgac    540
cctatatcga accatctagg gactttacgt cccctgcctg cagtttcccg gtgacagaat    600
gactatgatt tttcgtcgat tttataaaag tgaaaacaac cggttgatat ctatgcgcac    660
tattttccta catatatttc taacttcttg cttagccatg tcggttaaga gcaagtggag    720
agcactctca tttcgtagaa caagtgatga atgccgacct gcatcatctt acttagactt    780
gatcatcaag tggaatcccc attcatctta ataatctcat attgagtgcc aatgcaacat    840
tgttataatc ctcttcatat gctaattctt caaagctaac gtagttaaat gaaggcaaaa    900
tatgcaactt cgtcctctaa gtttgctcaa aggctcattt ttaccctta actatcaaac    960
cgattacttt cgtccctgaa ctttcatgtt tggtccaatt taatccctgg gctgatgtat   1020
ccgtccacgg tggtgtgtcc aatcagtgaa taatctagtt agtgaagcca gaagtccata   1080
gtgcccttg ctctgtcacc atatatccag ttcaaccgca ccaatttgcc atctcgaact   1140
ggttcatgtt ttattcaggt tggtaaatga attttgccaa ttcaatgtag ttagatattt   1200
ccatgtcatt ttagtacatt taccaatttt ttatattctg gctagaaaag gagaatggtg   1260
acgtctttcg gaagatcaag atcaattatc aagtatcagc aacagcacct gaaggttgga   1320
gtgcattagt tgtcattgag aataatgcta gctattcatt gcactggcat tagagacaga   1380
gagggcgagc cagtttgaca tggcaaatta gcacagtcaa actggatacg tggtgacgga   1440
gggaggggca ctatgaattt ttggtgacgg agggaggggc actatgaatt tttggctttg   1500
ctgacgggac acgccactat ggatgaaatt ggacaaaata cgaatattca aggatgaaag   1560
tggtcggttt gatagttcag ggatgaaatg tgtctttggg caaactttga ggacgaagtt   1620
gcctattttg cattaaacga atatatttat ataccccaaa aaaaagaata cacatctcca   1680
ctccgagccg gcatgtgggg tccccactag tcagccactg tatggcgccg actagctcaa   1740
cggccacgaa ccagccaacc accagcgcaa cctaaacggc gtaaacgttg acggcatctc   1800
tctctcgccc cgtctcgaag cttccgcacc gctcgctggt cgctgcccgg cgccgctcgt   1860
gctggactct ttccgtggcg gcttccgcga aattgcgtgg tggagaggag agacggaacc   1920
gtcacggcac tggattcctt ccccacccgg cttggccggc ccctcctcgc ctccataaat   1980
aggcaccccg tcctcgcctc ctctccccac ctcatctcct cctttcccgt gaaccgtgaa   2040
cacaacccga cccagatccc ctcttgcgag cttcgtcgat ccctcctccg cgtcaaggta   2100
cggagcttct cctcccccctt cttctctaga tcggcgtgtt atgttgtttc cgtggttgct   2160
tggttggatg aatcgaatga ttcttagggc ctaggaggct ggttagatct gttgcgttct   2220
gtttcgtaga tggattttgg tgtaagatca ggtcggttcc gctgtttaac ttgtgatgct   2280
agtgtgattt ttgggaggat ttgagttgtt aatctgggag ttgttgggag gttctcgtag   2340
gcggattgta gatgaagtcg cccgcacgat ttgcgtggct tgttgggtag ctagggttag   2400
atctgctcgg atttttcatt gttacttatt gagagataat gtagctaacc tttacttgtt   2460
catctatgta tctcgtattc gtattcatct ggttcgatgg tgctagatag atgcgcctga   2520
tttgtccgat cgaattgggt agcatccgcg gcttgtttgg tagtgttctg attgatttgt   2580
cgctctagat ctgagtggaa taatattaca tctcaacatg ttactagaaa cttggtttat   2640
agctccggat ttacatgttt attcttatgt aaggttttaa atgaaagatt tatgctactg   2700
```

-continued ctgctcgttg atcctttagc atccacctga ggaacatgca tgcatctgtt acttcttttg 2760
atatatgctt agatagttgt tagtatatac tgctgttgtt cgatgatcct tcaggatgaa 2820
catgcatgat catgttactt gtttttatat gcttctgctg ttcgttgatt ctttagtact 2880
acctacctga tcatcttgca tgtttcctgc ttgttagaga ttaattgatt aggcttacct 2940
tgttgcctgg tgattcttcc ttgcaggtg 2969

<210> SEQ ID NO 14
<211> LENGTH: 2012
<212> TYPE: DNA
<213> ORGANISM: Arundo donax

<400> SEQUENCE: 14
gatcagccat gcaagcaaga gatgttggtc gggcctcggt ggcaactgag gctatagtga 60
cctatgacga gcaggccata gataggccca ctggcaagcc caagaatcgc tagacgggct 120
agatctggac acttgtccgc accaagcact accgttgcaa ctgcaacctc tatatgtaac 180
tatagattca catgttgcga catctttgcc caatacgtat tgtaccctag acagctcacc 240
ctatcttttt cttttttttc ctctttcttc ttcctcctcc ttgcatggag acgtagaagg 300
actcctccct tgtgactatt aaaggaagga cttagggctg tgctagggga gagaactttt 360
ggacttggga gagctctgca ctgaacatct tcctctccac gcttgtaata ttttccacaa 420
caaagaattc cataaagccg gatgtagggc tattatccct ctcgggaggc ctgaaccagg 480
gtaaaacacc actcttctca ccagcgttcg ccgcattagt ctagactagc atcttttgac 540
cctatatcga accatctagg gactttacgt cccctgcctg cagtttcccg gtgacagaat 600
gactatgatt tttcgtcgat tttataaaag tgaaaacaac cggttgatat ctatgcgcac 660
tattttccta catatatttc taacttcttg cttagccatg tcggttaaga gcaagtggag 720
agcactctca tttcgtagaa caagtgatga atgccgacct gcatcatctt acttagactt 780
gatcatcaag tggaatcccc attcatctta ataatctcat attgagtgcc aatgcaacat 840
tgttataatc ctcttcatat gctaattctt caaagctaac gtagttaaat gaaggcaaaa 900
tatgcaactt cgtcctctaa gtttgctcaa aggctcattt ttacccttta actatcaaac 960
cgattacttt cgtccctgaa ctttcatgtt tggtccaatt taatccctgg gctgatgtat 1020
ccgtccacgg tggtgtgtcc aatcagtgaa taatctagtt agtgaagcca gaagtccata 1080
gtgccccttg ctctgtcacc atatatccag ttcaaccgca ccaatttgcc atctcgaact 1140
ggttcatgtt ttattcaggt tggtaaatga attttgccaa ttcaatgtag ttagatattt 1200
ccatgtcatt ttagtacatt taccaatttt ttatattctg gctagaaaag gagaatggtg 1260
acgtctttcg gaagatcaag atcaattatc aagtatcagc aacagcacct gaaggttgga 1320
gtgcattagt tgtcattgag aataatgcta gctattcatt gcactggcat tagagacaga 1380
gagggcgagc cagtttgaca tggcaaatta gcacagtcaa actggatacg tggtgacgga 1440
gggaggggca ctatgaattt ttggtgacgg agggaggggc actatgaatt tttggctttg 1500
ctgacgggac acgccactat ggatgaaatt ggacaaaata cgaatattca aggatgaaag 1560
tggtcggttt gatagttcag ggatgaaatg tgtctttggg caaactttga ggacgaagtt 1620
gcctattttg cattaaacga atatatttat ataccccaaa aaaaagaata cacatctcca 1680
ctccgagccg gcatgtgggg tccccactag tcagccactg tatggcgccg actagctcaa 1740
cggccacgaa ccagccaacc accagcgcaa cctaaacggc gtaaacgttg acggcatctc 1800
tctctcgccc cgtctcgaag cttccgcacc gctcgctggt cgctgcccgg cgccgctcgt 1860
gctggactct ttccgtggcg gcttccgcga aattgcgtgg tggagaggag agacggaacc 1920
gtcacggcac tggattcctt ccccacccgg cttggccggc ccctcctcgc ctccataaat 1980
aggcaccccg tcctcgcctc ctctccccac ct 2012

<210> SEQ ID NO 15
<211> LENGTH: 872
<212> TYPE: DNA
<213> ORGANISM: Arundo donax

<400> SEQUENCE: 15
gtacggagct tctcctcccc cttcttctct agatcggcgt gttatgttgt ttccgtggtt 60
gcttggttgg atgaatcgaa tgattcttag ggcctaggag gctggttaga tctgttgcgt 120
tctgtttcgt agatggattt tggtgtaaga tcaggtcggt tccgctgttt aacttgtgat 180
gctagtgtga tttttgggag gatttgagtt gttaatctgg gagttgttgg gaggttctcg 240
taggcggatt gtagatgaag tcgcccgcac gatttgcgtg gcttgttggg tagctagggt 300
tagatctgct cggatttttc attgttactt attgagagat aatgtagcta acctttactt 360
gttcatctat gtatctcgta ttcgtattca tctggttcga tggtgctaga tagatgcgcc 420
tgatttgtcc gatcgaattg ggtagcatcc gcggcttgtt tggtagtgtt ctgattgatt 480
tgtcgctcta gatctgagtg gaataatatt acatctcaac atgttactag aaacttggtt 540
tatagctccg gatttacatg tttattctta tgtaaggttt taaatgaaag atttatgcta 600
ctgctgctcg ttgatccttt agcatccacc tgaggaacat gcatgcatct gttacttctt 660
ttgatatatg cttagatagt tgttagtata tactgctgtt gttcgatgat ccttcaggat 720
gaacatgcat gatcatgtta cttgttttta tatgcttctg ctgttcgttg attctttagt 780
actacctacc tgatcatctt gcatgtttcc tgcttgttag agattaattg attaggctta 840
ccttgttgcc tggtgattct tccttgcagg tg 872

<210> SEQ ID NO 16
<211> LENGTH: 1954
<212> TYPE: DNA
<213> ORGANISM: Arundo donax

<400> SEQUENCE: 16
tgatgtatcc gtccacggtg gtgtgtccaa tcagtgaata atctagttag tgaagccaga 60
agtccatagt gccccttgct ctgtcaccat atatccagtt caaccgcacc aatttgccat 120
ctcgaactgg ttcatgtttt attcaggttg gtaaatgaat tttgccaatt caatgtagtt 180
agatatttcc atgtcatttt agtacattta ccaatttttt atattctggc tagaaaagga 240
gaatggtgac gtctttcgga agatcaagat caattatcaa gtatcagcaa cagcacctga 300
aggttggagt gcattagttg tcattgagaa taatgctagc tattcattgc actggcatta 360
gagacagaga gggcgagcca gtttgacatg gcaaattagc acagtcaaac tggatacgtg 420
gtgacggagg gaggggcact atgaattttt ggtgacggag ggaggggcac tatgaatttt 480
tggctttgct gacgggacac gccactatgg atgaaattgg acaaaatacg aatattcaag 540
gatgaaagtg gtcggtttga tagttcaggg atgaaatgtg tctttgggca aactttgagg 600
acgaagttgc ctattttgca ttaaacgaat atatttatat accccaaaaa aaagaataca 660
catctccact ccgagccggc atgtggggtc cccactagtc agccactgta tggcgccgac 720
tagctcaacg gccacgaacc agccaaccac cagcgcaacc taaacggcgt aaacgttgac 780

-continued

```
ggcatctctc tctcgccccg tctcgaagct tccgcaccgc tcgctggtcg ctgcccggcg    840

ccgctcgtgc tggactcttt ccgtggcggc ttccgcgaaa ttgcgtggtg gagaggagag    900

acggaaccgt cacggcactg gattccttcc ccacccggct tggccggccc ctcctcgcct    960

ccataaatag gcaccccgtc ctcgcctcct ctccccacct catctcctcc tttcccgtga   1020

accgtgaaca caacccgacc cagatcccct cttgcgagct tcgtcgatcc ctcctccgcg   1080

tcaaggtacg gagcttctcc tccccttct tctctagatc ggcgtgttat gttgtttccg   1140

tggttgcttg gttggatgaa tcgaatgatt cttagggcct aggaggctgg ttagatctgt   1200

tgcgttctgt ttcgtagatg gattttggtg taagatcagg tcggttccgc tgtttaactt   1260

gtgatgctag tgtgattttt gggaggattt gagttgttaa tctgggagtt gttgggaggt   1320

tctcgtaggc ggattgtaga tgaagtcgcc cgcacgattt gcgtggcttg ttgggtagct   1380

agggttagat ctgctcggat ttttcattgt tacttattga gagataatgt agctaacctt   1440

tacttgttca tctatgtatc tcgtattcgt attcatctgg ttcgatggtg ctagatagat   1500

gcgcctgatt tgtccgatcg aattgggtag catccgcggc ttgtttggta gtgttctgat   1560

tgatttgtcg ctctagatct gagtggaata atattacatc tcaacatgtt actagaaact   1620

tggtttatag ctccggattt acatgtttat tcttatgtaa ggttttaaat gaaagattta   1680

tgctactgct gctcgttgat cctttagcat ccacctgagg aacatgcatg catctgttac   1740

ttcttttgat atatgcttag atagttgtta gtatatactg ctgttgttcg atgatccttc   1800

aggatgaaca tgcatgatca tgttacttgt ttttatatgc ttctgctgtt cgttgattct   1860

ttagtactac ctacctgatc atcttgcatg tttcctgctt gttagagatt aattgattag   1920

gcttaccttg ttgcctggtg attcttcctt gcag                                1954
```

<210> SEQ ID NO 17
<211> LENGTH: 1000
<212> TYPE: DNA
<213> ORGANISM: Arundo donax

<400> SEQUENCE: 17

```
tgatgtatcc gtccacggtg gtgtgtccaa tcagtgaata atctagttag tgaagccaga     60

agtccatagt gccccttgct ctgtcaccat atatccagtt caaccgcacc aatttgccat    120

ctcgaactgg ttcatgtttt attcaggttg gtaaatgaat tttgccaatt caatgtagtt    180

agatatttcc atgtcatttt agtacattta ccaatttttt atattctggc tagaaaagga    240

gaatggtgac gtctttcgga agatcaagat caattatcaa gtatcagcaa cagcacctga    300

aggttggagt gcattagttg tcattgagaa taatgctagc tattcattgc actggcatta    360

gagacagaga gggcgagcca gtttgacatg gcaaattagc acagtcaaac tggatacgtg    420

gtgacggagg gaggggcact atgaattttt ggtgacggag ggaggggcac tatgaatttt    480

tggctttgct gacgggacac gccactatgg atgaaattgg acaaaatacg aatattcaag    540

gatgaaagtg gtcggtttga tagttcaggg atgaaatgtg tctttgggca aactttgagg    600

acgaagttgc ctattttgca ttaaacgaat atatttatat accccaaaaa aaagaataca    660

catctccact ccgagccggc atgtggggtc cccactagtc agccactgta tggcgccgac    720

tagctcaacg gccacgaacc agccaaccac cagcgcaacc taaacggcgt aaacgttgac    780

ggcatctctc tctcgccccg tctcgaagct tccgcaccgc tcgctggtcg ctgcccggcg    840

ccgctcgtgc tggactcttt ccgtggcggc ttccgcgaaa ttgcgtggtg gagaggagag    900

acggaaccgt cacggcactg gattccttcc ccacccggct tggccggccc ctcctcgcct    960
```

```
ccataaatag gcaccccgtc ctcgcctcct ctccccacct                         1000


<210> SEQ ID NO 18
<211> LENGTH: 1957
<212> TYPE: DNA
<213> ORGANISM: Arundo donax

<400> SEQUENCE: 18

tgatgtatcc gtccacggtg gtgtgtccaa tcagtgaata atctagttag tgaagccaga     60

agtccatagt gccccttgct ctgtcaccat atatccagtt caaccgcacc aatttgccat    120

ctcgaactgg ttcatgtttt attcaggttg gtaaatgaat tttgccaatt caatgtagtt    180

agatatttcc atgtcatttt agtacattta ccaatttttt atattctggc tagaaaagga    240

gaatggtgac gtctttcgga agatcaagat caattatcaa gtatcagcaa cagcacctga    300

aggttggagt gcattagttg tcattgagaa taatgctagc tattcattgc actggcatta    360

gagacagaga gggcgagcca gtttgacatg gcaaattagc acagtcaaac tggatacgtg    420

gtgacggagg gaggggcact atgaattttt ggtgacggag ggaggggcac tatgaatttt    480

tggctttgct gacgggacac gccactatgg atgaaattgg acaaaatacg aatattcaag    540

gatgaaagtg gtcggtttga tagttcaggg atgaaatgtg tctttgggca aactttgagg    600

acgaagttgc ctattttgca ttaaacgaat atatttatat accccaaaaa aaagaataca    660

catctccact ccgagccggc atgtggggtc cccactagtc agccactgta tggcgccgac    720

tagctcaacg gccacgaacc agccaaccac cagcgcaacc taaacggcgt aaacgttgac    780

ggcatctctc tctcgccccg tctcgaagct tccgcaccgc tcgctggtcg ctgcccggcg    840

ccgctcgtgc tggactcttt ccgtggcggc ttccgcgaaa ttgcgtggtg gagaggagag    900

acggaaccgt cacggcactg gattccttcc ccacccggct tggccggccc ctcctcgcct    960

ccataaatag gcaccccgtc ctcgcctcct ctccccacct catctcctcc tttcccgtga   1020

accgtgaaca caacccgacc cagatcccct cttgcgagct tcgtcgatcc ctcctccgcg   1080

tcaaggtacg gagcttctcc tccccccttct tctctagatc ggcgtgttat gttgtttccg   1140

tggttgcttg gttggatgaa tcgaatgatt cttagggcct aggaggctgg ttagatctgt   1200

tgcgttctgt ttcgtagatg gattttggtg taagatcagg tcggttccgc tgtttaactt   1260

gtgatgctag tgtgattttt gggaggattt gagttgttaa tctgggagtt gttgggaggt   1320

tctcgtaggc ggattgtaga tgaagtcgcc cgcacgattt gcgtggcttg ttgggtagct   1380

agggttagat ctgctcggat ttttcattgt tacttattga gagataatgt agctaacctt   1440

tacttgttca tctatgtatc tcgtattcgt attcatctgg ttcgatggtg ctagatagat   1500

gcgcctgatt tgtccgatcg aattgggtag catccgcggc ttgtttggta gtgttctgat   1560

tgatttgtcg ctctagatct gagtggaata atattacatc tcaacatgtt actagaaact   1620

tggtttatag ctccggattt acatgtttat tcttatgtaa ggttttaaat gaaagattta   1680

tgctactgct gctcgttgat cctttagcat ccacctgagg aacatgcatg catctgttac   1740

ttcttttgat atatgcttag atagttgtta gtatatactg ctgttgttcg atgatccttc   1800

aggatgaaca tgcatgatca tgttacttgt ttttatatgc ttctgctgtt cgttgattct   1860

ttagtactac ctacctgatc atcttgcatg tttcctgctt gttagagatt aattgattag   1920

gcttaccttg ttgcctggtg attcttcctt gcaggtg                            1957


<210> SEQ ID NO 19
```

<211> LENGTH: 1957
<212> TYPE: DNA
<213> ORGANISM: Arundo donax

<400> SEQUENCE: 19

```
tgatgtatcc gtccacggtg gtgtgtccaa tcagtgaata atctagttag tgaagccaga     60
agtccatagt gccccttgct ctgtcaccat atatccagtt caaccgcacc aatttgccat    120
ctcgaactgg ttcatgtttt attcaggttg gtaaatgaat tttgccaatt caatgtagtt    180
agatatttcc atgtcatttt agtacattta ccaatttttt atattctggc tagaaaagga    240
gaatggtgac gtctttcgga agatcaagat caattatcaa gtatcagcaa cagcacctga    300
aggttggagt gcattagttg tcattgagaa taatgctagc tattcattgc actggcatta    360
gagacagaga gggcgagcca gtttgacatg gcaaattagc acagtcaaac tggatacgtg    420
gtgacggagg gaggggcact atgaattttt ggtgacggag ggaggggcac tatgaatttt    480
tggctttgct gacgggacac gccactatgg atgaaattgg acaaaatacg aatattcaag    540
gatgaaagtg gtcggtttga tagttcaggg atgaaatgtg tctttgggca aactttgagg    600
acgaagttgc ctattttgca ttaaacgaat atatttatat accccaaaaa aaagaataca    660
catctccact ccgagccggc atgtggggtc cccactagtc agccactgta tggcgccgac    720
tagctcaacg gccacgaacc agccaaccac cagcgcaacc taaacggcgt aaacgttgac    780
ggcatctctc tctcgccccg tctcgaagct tccgcaccgc tcgctggtcg ctgcccggcg    840
ccgctcgtgc tggactcttt ccgtggcggc ttccgcgaaa ttgcgtggtg gagaggagag    900
acggaaccgt cacggcactg gattccttcc ccacccggct tggccggccc ctcctcgcct    960
ccataaatag gcaccccgtc ctcgcctcct ctccccacct catctcctcc tttcccgtga   1020
accgtgaaca caacccgacc cagatcccct cttgcgagct tcgtcgatcc ctcctccgcg   1080
tcaaggtacg gagcttctcc tccccccttct tctctagatc ggcgtgttat gttgtttccg   1140
tggttgcttg gttggatgaa tcgaatgatt cttagggcct aggaggctgg ttagatctgt   1200
tgcgttctgt ttcgtagatg gattttggtg taagatcagg tcggttccgc tgtttaactt   1260
gtgatgctag tgtgattttt gggaggattt gagttgttaa tctgggagtt gttgggaggt   1320
tctcgtaggc ggattgtaga tgaagtcgcc cgcacgattt gcgtggcttg ttgggtagct   1380
agggttagat ctgctcggat ttttcattgt tacttattga gagataatgt agctaacctt   1440
tacttgttca tctatgtata tcgtattcgt attcatctgg ttcgatggtg ctagatagat   1500
gcgcctgatt tgtccgatcg aattgggtag catccgcggc ttgtttggta gtgttctgat   1560
tgatttgtcg ctctagatct gagtggaata atattacatc tcaacatgtt actagaaact   1620
tggtttatag ctccggattt acatgtttat tcttatgtaa ggttttaaat gaaagattta   1680
tgctactgct gctcgttgat cctttagcat ccacctgagg aacatgcatg catctgttac   1740
ttcttttgat atatgcttag atagttgtta gtatatactg ctgttgttcg atgatccttc   1800
aggatgaaca tgcatgatca tgttacttgt ttttatatgc ttctgctgtt cgttgattct   1860
ttagtactac ctacctgatc atcttgcatg tttcctgctt gttagagatt aattgattag   1920
gcttaccttg ttgcctggtg attcttcctt gcaggtg                            1957
```

<210> SEQ ID NO 20
<211> LENGTH: 872
<212> TYPE: DNA
<213> ORGANISM: Arundo donax

<400> SEQUENCE: 20

-continued

```
gtacggagct tctcctcccc cttcttctct agatcggcgt gttatgttgt ttccgtggtt     60

gcttggttgg atgaatcgaa tgattcttag ggcctaggag gctggttaga tctgttgcgt    120

tctgtttcgt agatggattt tggtgtaaga tcaggtcggt tccgctgttt aacttgtgat    180

gctagtgtga tttttgggag gatttgagtt gttaatctgg gagttgttgg gaggttctcg    240

taggcggatt gtagatgaag tcgcccgcac gatttgcgtg gcttgttggg tagctagggt    300

tagatctgct cggatttttc attgttactt attgagagat aatgtagcta acctttactt    360

gttcatctat gtatatcgta ttcgtattca tctggttcga tggtgctaga tagatgcgcc    420

tgatttgtcc gatcgaattg ggtagcatcc gcggcttgtt tggtagtgtt ctgattgatt    480

tgtcgctcta gatctgagtg gaataatatt acatctcaac atgttactag aaacttggtt    540

tatagctccg gatttacatg tttattctta tgtaaggttt taaatgaaag atttatgcta    600

ctgctgctcg ttgatccttt agcatccacc tgaggaacat gcatgcatct gttacttctt    660

ttgatatatg cttagatagt tgttagtata tactgctgtt gttcgatgat ccttcaggat    720

gaacatgcat gatcatgtta cttgttttta tatgcttctg ctgttcgttg attctttagt    780

actacctacc tgatcatctt gcatgtttcc tgcttgttag agattaattg attaggctta    840

ccttgttgcc tggtgattct tccttgcagg tg                                   872


<210> SEQ ID NO 21
<211> LENGTH: 1712
<212> TYPE: DNA
<213> ORGANISM: Arundo donax

<400> SEQUENCE: 21

gtgacgtctt tcggaagatc aagatcaatt atcaagtatc agcaacagca cctgaaggtt     60

ggagtgcatt agttgtcatt gagaataatg ctagctattc attgcactgg cattagagac    120

agagagggcg agccagtttg acatggcaaa ttagcacagt caaactggat acgtggtgac    180

ggagggaggg gcactatgaa tttttggtga cggagggagg ggcactatga atttttggct    240

ttgctgacgg gacacgccac tatggatgaa attggacaaa atacgaatat tcaaggatga    300

aagtggtcgg tttgatagtt cagggatgaa atgtgtcttt gggcaaactt tgaggacgaa    360

gttgcctatt ttgcattaaa cgaatatatt tatataccc aaaaaaaaga atacacatct    420

ccactccgag ccggcatgtg gggtccccac tagtcagcca ctgtatggcg ccgactagct    480

caacggccac gaaccagcca accaccagcg caacctaaac ggcgtaaacg ttgacggcat    540

ctctctctcg ccccgtctcg aagcttccgc accgctcgct ggtcgctgcc cggcgccgct    600

cgtgctggac tctttccgtg gcggcttccg cgaaattgcg tggtggagag gagagacgga    660

accgtcacgg cactggattc cttccccacc cggcttggcc ggcccctcct cgcctccata    720

aataggcacc ccgtcctcgc ctcctctccc cacctcatct cctcctttcc cgtgaaccgt    780

gaacacaacc cgacccagat cccctcttgc gagcttcgtc gatccctcct ccgcgtcaag    840

gtacggagct tctcctcccc cttcttctct agatcggcgt gttatgttgt ttccgtggtt    900

gcttggttgg atgaatcgaa tgattcttag ggcctaggag gctggttaga tctgttgcgt    960

tctgtttcgt agatggattt tggtgtaaga tcaggtcggt tccgctgttt aacttgtgat   1020

gctagtgtga tttttgggag gatttgagtt gttaatctgg gagttgttgg gaggttctcg   1080

taggcggatt gtagatgaag tcgcccgcac gatttgcgtg gcttgttggg tagctagggt   1140

tagatctgct cggatttttc attgttactt attgagagat aatgtagcta acctttactt   1200
```

-continued gttcatctat gtatctcgta ttcgtattca tctggttcga tggtgctaga tagatgcgcc 1260
tgatttgtcc gatcgaattg ggtagcatcc gcggcttgtt tggtagtgtt ctgattgatt 1320
tgtcgctcta gatctgagtg gaataatatt acatctcaac atgttactag aaacttggtt 1380
tatagctccg gatttacatg tttattctta tgtaaggttt taaatgaaag atttatgcta 1440
ctgctgctcg ttgatccttt agcatccacc tgaggaacat gcatgcatct gttacttctt 1500
ttgatatatg cttagatagt tgttagtata tactgctgtt gttcgatgat ccttcaggat 1560
gaacatgcat gatcatgtta cttgttttta tatgcttctg ctgttcgttg attctttagt 1620
actacctacc tgatcatctt gcatgtttcc tgcttgttag agattaattg attaggctta 1680
ccttgttgcc tggtgattct tccttgcagg tg 1712

<210> SEQ ID NO 22
<211> LENGTH: 755
<212> TYPE: DNA
<213> ORGANISM: Arundo donax

<400> SEQUENCE: 22
gtgacgtctt tcggaagatc aagatcaatt atcaagtatc agcaacagca cctgaaggtt 60
ggagtgcatt agttgtcatt gagaataatg ctagctattc attgcactgg cattagagac 120
agagagggcg agccagtttg acatggcaaa ttagcacagt caaactggat acgtggtgac 180
ggagggaggg gcactatgaa tttttggtga cggagggagg ggcactatga atttttggct 240
ttgctgacgg gacacgccac tatggatgaa attggacaaa atacgaatat tcaaggatga 300
aagtggtcgg tttgatagtt cagggatgaa atgtgtcttt gggcaaactt tgaggacgaa 360
gttgcctatt ttgcattaaa cgaatatatt tatatacccc aaaaaaaaga atacacatct 420
ccactccgag ccggcatgtg gggtccccac tagtcagcca ctgtatggcg ccgactagct 480
caacggccac gaaccagcca accaccagcg caacctaaac ggcgtaaacg ttgacggcat 540
ctctctctcg ccccgtctcg aagcttccgc accgctcgct ggtcgctgcc cggcgccgct 600
cgtgctggac tctttccgtg gcggcttccg cgaaattgcg tggtggagag gagagacgga 660
accgtcacgg cactggattc cttccccacc cggcttggcc ggcccctcct cgcctccata 720
aataggcacc ccgtcctcgc ctcctctccc cacct 755

<210> SEQ ID NO 23
<211> LENGTH: 3276
<212> TYPE: DNA
<213> ORGANISM: Arundo donax

<400> SEQUENCE: 23
ggcctcttta cgtttggcac aatttgatcg aatccaacac ggcaagttag cctttgaagc 60
ttgaaccggg cactaatgca agtatataat aactgagaac tacaagaaag catattcctt 120
gaggtactta tgcaacctta caattatcaa attaattaac aactagcagt tagaatttta 180
tatcacaaga atatcatgaa ccgtggatac tacttcttaa agggctattc tttttctgaa 240
tgtcgcagtt ggttatttta accatattac aaactagggg tttaaatccc aaaaagttca 300
cggaaaggga ttaagcaagt agttagcaag actcacactt atgaccgtta gccaaattac 360
acattggtca ttccaggagg agtaatcccc catagctagt tgttttgagt ttgactaccc 420
aaacttgcat aatcgttttc ctagaggggg ggggggggtt caccattcca tcaagatgag 480
gcaaagctaa atgaaacaca cgagaggcaa aacggactga cgtgatagag tttttaataa 540
atatcaaata tgtagagtca accaaagaaa aaagatatcc caatggctaa actttggatc 600

-continued

```
tatgtcgtaa ttcgtgtttt aggacataca aggcgaattc cttctacggc aaactctaga    660
atagctgggc gacaatggcc tcacgatagc ctcaaagagt tggtagcaac tttgagatct    720
tttgatccga aactcaatta tgtagtacaa tgatatttag atagattgat tgaaagttgg    780
gggtgggggc gaaagcgaag gggatctcaa tattaataca tctatagtga atggatatag    840
aaaacacagg atttccaatt caagtagaaa taggaggaac ggaacagatc tagcaatagt    900
agccaccaaa gacgaggagg attctagatt gcaaatccaa ggtgaaagga agaaatgttg    960
aactatccag aataaggcgg attggccaag gaggcggaag tctctagaaa gaagtcattt   1020
ggctctgagg gctcacttga tgcgagaagg aagactgact gaggaatgga ttttggtgga   1080
ccgaggaaat tggtgctggg ttgcagaggc atgtatgtgg gaaaagaggc agtggcaacg   1140
atcgagagag gagaagggaa tgaggtaagt atttgaagtg aagaggagcc catataggtg   1200
aaaaataaaa ataatccatc gtggattcaa ataatcaaag ggctatgacc tttcatcaat   1260
tttagaaaag tgaaaacaac cggtttaaca cctatatgca ccattttcct acatagattt   1320
ttaacttctt acttaaccat gttgactaag agcaagtgga gagcactctc atttcataga   1380
acaagtgatg aatgccaacc tgcattatta tcttaattag actttgatca tcaagtggaa   1440
tcccatttat cttaataatc ttggcaacat tgttataatg ctacttcata tgctaattct   1500
tcaaagctaa catcgttaaa cgaatacata tctcctgtat tctaagaccc tatttagaat   1560
acagaaattt tacagaaatc agttcaattc tcgtagaatt gggaaagaaa tcctccgttc   1620
caaacgtgac ctaagccggc atggcacgac cccactcgtc aggcactgta tgtaaacgtc   1680
agcaactccg tggcaagtaa cgtcgagagg aggagcgggc ctaacggcgc cgactagctc   1740
aacggccacc aaccagccaa ccaccagcgc aaccgaaacg gcgcaaacgt tgacgtcatc   1800
tctctctctc tcgcgccccg cgtcccgaag cttccgcacc actcgctggt cgctgctagc   1860
tgggccccac cggccggccc cgttcgtgct ggactcttct tcctcgaaat tgcgtggtgg   1920
agagggagag ggggcacctc gagacggaac cgtcacggca cgggattcct tccccacccg   1980
gcccctcctc gtctccataa ataggcgccc cctcctcgcg tcctctcccc cgtctcatct   2040
cctcctgttc cgtgaaccgt gaacgcaacc cgacccccag atctctctcg cgagcatcgt   2100
cgatccctcc tccgcgtcaa ggtacggatc ttctccttcc tcccccttcc cctctgggtc   2160
ggcgtgtcgt gttgtttctc tagttgcttg gctggatgga tcgagtggtt cttagggctt   2220
agatggctgg ttagatctgt tgcgttctgt ttcgtagatg gatttttggt gtagatctgg   2280
taggttatgc tggttaactg gtgatgctcc tgcgattttt gggggatctg agttgttaat   2340
ctggtagttg tatggggttc tcgtagccgg attgtagatg aaatcgtccg cgcggtttgc   2400
gtggctcgtt ggttagctag ggttagatct gctcggattt ttcattgttc ctgattcaga   2460
gatgtagtta acctttactt gttcatcttt gtatctcgta ttcgtacctg catgtatgat   2520
ctgtttcgat ggtgctagat aggtgcgcct gatttgtccg atcgaatctg gtagcatgcg   2580
ctgtttgttt ggtagtgttc tgattgattt gtcgctctag atctgagtag aataggatta   2640
tttctcaaca tgatattaga agcttggttt atagctccgg attagcatgt atgttacatg   2700
tttattctta tgtaaggttt taaacggaag atatatgcta ctgctgctca ttgattcttt   2760
atcatccacc tgagtccatg catgcttctg ttacttcttt tgatatgtgc ttagatagct   2820
gttgatatgt actgctgctg ttagatgatc cttcaggatg aacatgcatg attctgttac   2880
ttgttttggt atgcttagat aaatcaagat acgcttctgc tgttcgttga ttctttagta   2940
```

-continued

```
ctacctacct gatcagctta gatagatcaa gatatgcttc tgctgttcgt tgattcttta   3000

gtaataccta cctgatcagc ttagatagat caagatacgc ttctgctgtt cgttgattct   3060

ctagtactac ctacctgata aacatgcatg ttttctgctt gttaaaggtt gattgcttag   3120

gctcatcttt ttcttttcgt tgattctcta gtactaccta cctgataaac atgcatgttt   3180

tctgcttgtt aaagattgat tgcttagtct catctttttc tttctctttt gtctaccgcc   3240

aggcctaacc ttgttgctgg tgactctttc ttgcag                              3276
```

<210> SEQ ID NO 24
<211> LENGTH: 2033
<212> TYPE: DNA
<213> ORGANISM: Arundo donax

<400> SEQUENCE: 24

```
ggcctcttta cgtttggcac aatttgatcg aatccaacac ggcaagttag cctttgaagc     60

ttgaaccggg cactaatgca agtatataat aactgagaac tacaagaaag catattcctt    120

gaggtactta tgcaacctta caattatcaa attaattaac aactagcagt tagaatttta    180

tatcacaaga atatcatgaa ccgtggatac tacttcttaa agggctattc tttttctgaa    240

tgtcgcagtt ggttatttta accatattac aaactagggg tttaaatccc aaaaagttca    300

cggaaaggga ttaagcaagt agttagcaag actcacactt atgaccgtta gccaaattac    360

acattggtca ttccaggagg agtaatcccc catagctagt tgttttgagt ttgactaccc    420

aaacttgcat aatcgttttc ctagaggggg gggggggtt caccattcca tcaagatgag    480

gcaaagctaa atgaaacaca cgagaggcaa aacggactga cgtgatagag tttttaataa    540

atatcaaata tgtagagtca accaaagaaa aaagatatcc caatggctaa actttggatc    600

tatgtcgtaa ttcgtgtttt aggacataca aggcgaattc cttctacggc aaactctaga    660

atagctgggc gacaatggcc tcacgatagc ctcaaagagt tggtagcaac tttgagatct    720

tttgatccga aactcaatta tgtagtacaa tgatatttag atagattgat tgaaagttgg    780

gggtgggggc gaaagcgaag gggatctcaa tattaataca tctatagtga atggatatag    840

aaaacacagg atttccaatt caagtagaaa taggaggaac ggaacagatc tagcaatagt    900

agccaccaaa gacgaggagg attctagatt gcaaatccaa ggtgaaagga agaaatgttg    960

aactatccag aataaggcgg attggccaag gaggcggaag tctctagaaa gaagtcattt   1020

ggctctgagg gctcacttga tgcgagaagg aagactgact gaggaatgga ttttggtgga   1080

ccgaggaaat tggtgctggg ttgcagaggc atgtatgtgg gaaaagaggc agtggcaacg   1140

atcgagagag gagaagggaa tgaggtaagt atttgaagtg aagaggagcc catataggtg   1200

aaaaataaaa ataatccatc gtggattcaa ataatcaaag ggctatgacc tttcatcaat   1260

tttagaaaag tgaaaacaac cggtttaaca cctatatgca ccattttcct acatagattt   1320

ttaacttctt acttaaccat gttgactaag agcaagtgga gagcactctc atttcataga   1380

acaagtgatg aatgccaacc tgcattatta tcttaattag actttgatca tcaagtggaa   1440

tcccatttat cttaataatc ttggcaacat tgttataatg ctacttcata tgctaattct   1500

tcaaagctaa catcgttaaa cgaatacata tctcctgtat tctaagaccc tatttagaat   1560

acagaaattt tacagaaatc agttcaattc tcgtagaatt gggaaagaaa tcctccgttc   1620

caaacgtgac ctaagccggc atggcacgac cccactcgtc aggcactgta tgtaaacgtc   1680

agcaactccg tggcaagtaa cgtcgagagg aggagcgggc ctaacggcgc cgactagctc   1740

aacggccacc aaccagccaa ccaccagcgc aaccgaaacg gcgcaaacgt tgacgtcatc   1800
```

tctctctctc tcgcgccccg cgtcccgaag cttccgcacc actcgctggt cgctgctagc 1860
tgggccccac cggccggccc cgttcgtgct ggactcttct tcctcgaaat tgcgtggtgg 1920
agagggagag ggggcacctc gagacggaac cgtcacggca cgggattcct tccccacccg 1980
gcccctcctc gtctccataa ataggcgccc cctcctcgcg tcctctcccc cgt 2033

<210> SEQ ID NO 25
<211> LENGTH: 88
<212> TYPE: DNA
<213> ORGANISM: Arundo donax

<400> SEQUENCE: 25
ctcatctcct cctgttccgt gaaccgtgaa cgcaacccga cccccagatc tctctcgcga 60
gcatcgtcga tccctcctcc gcgtcaag 88

<210> SEQ ID NO 26
<211> LENGTH: 1155
<212> TYPE: DNA
<213> ORGANISM: Arundo donax

<400> SEQUENCE: 26
gtacggatct tctccttcct ccccccttccc ctctgggtcg gcgtgtcgtg ttgtttctct 60
agttgcttgg ctggatggat cgagtggttc ttagggctta gatggctggt tagatctgtt 120
gcgttctgtt tcgtagatgg atttttggtg tagatctggt aggttatgct ggttaactgg 180
tgatgctcct gcgatttttg ggggatctga gttgttaatc tggtagttgt atggggttct 240
cgtagccgga ttgtagatga aatcgtccgc gcggtttgcg tggctcgttg gttagctagg 300
gttagatctg ctcggatttt tcattgttcc tgattcagag atgtagttaa cctttacttg 360
ttcatctttg tatctcgtat tcgtacctgc atgtatgatc tgtttcgatg gtgctagata 420
ggtgcgcctg atttgtccga tcgaatctgg tagcatgcgc tgtttgtttg gtagtgttct 480
gattgatttg tcgctctaga tctgagtaga ataggattat ttctcaacat gatattagaa 540
gcttggttta tagctccgga ttagcatgta tgttacatgt ttattcttat gtaaggtttt 600
aaacggaaga tatatgctac tgctgctcat tgattcttta tcatccacct gagtccatgc 660
atgcttctgt tacttctttt gatatgtgct tagatagctg ttgatatgta ctgctgctgt 720
tagatgatcc ttcaggatga acatgcatga ttctgttact tgttttggta tgcttagata 780
aatcaagata cgcttctgct gttcgttgat tctttagtac tacctacctg atcagcttag 840
atagatcaag atatgcttct gctgttcgtt gattctttag taatacctac ctgatcagct 900
tagatagatc aagatacgct tctgctgttc gttgattctc tagtactacc tacctgataa 960
acatgcatgt tttctgcttg ttaaaggttg attgcttagg ctcatctttt tcttttcgtt 1020
gattctctag tactacctac ctgataaaca tgcatgtttt ctgcttgtta aagattgatt 1080
gcttagtctc atctttttct ttctcttttg tctaccgcca ggcctaacct tgttgctggt 1140
gactctttct tgcag 1155

<210> SEQ ID NO 27
<211> LENGTH: 3250
<212> TYPE: DNA
<213> ORGANISM: Arundo donax

<400> SEQUENCE: 27
gaatccaaca cggcaagtta gcctttgaag cttgaaccgg gcactaatgc aagtatataa 60

-continued

```
taactgagaa ctacaagaaa gcatattcct tgaggtactt atgcaacctt acaattatca     120
aattaattaa caactagcag ttagaatttt atatcacaag aatatcatga accgtggata     180
ctacttctta aagggctatt ctttttctga atgtcgcagt tggttatttt aaccatatta     240
caaactaggg gtttaaatcc caaaaagttc acggaaaggg attaagcaag tagttagcaa     300
gactcacact tatgaccgtt agccaaatta cacattggtc attccaggag gagtaatccc     360
ccatagctag ttgttttgag tttgactacc caaacttgca taatcgtttt cctagagggg     420
gggggggggt tcaccattcc atcaagatga ggcaaagcta aatgaaacac acgagaggca     480
aaacggactg acgtgataga gtttttaata aatatcaaat atgtagagtc aaccaaagaa     540
aaaagatatc ccaatggcta aactttggat ctatgtcgta attcgtgttt taggacatac     600
aaggcgaatt ccttctacgg caaactctag aatagctggg cgacaatggc ctcacgatag     660
cctcaaagag ttggtagcaa ctttgagatc ttttgatccg aaactcaatt atgtagtaca     720
atgatattta gatagattga ttgaaagttg ggggtggggg cgaaagcgaa ggggatctca     780
atattaatac atctatagtg aatggatata gaaaacacag gatttccaat tcaagtagaa     840
ataggaggaa cggaacagat ctagcaatag tagccaccaa agacgaggag gattctagat     900
tgcaaatcca aggtgaaagg aagaaatgtt gaactatcca gaataaggcg gattggccaa     960
ggaggcggaa gtctctagaa agaagtcatt tggctctgag ggctcacttg atgcgagaag    1020
gaagactgac tgaggaatgg attttggtgg accgaggaaa ttggtgctgg gttgcagagg    1080
catgtatgtg ggaaaagagg cagtggcaac gatcgagaga ggagaaggga atgaggtaag    1140
tatttgaagt gaagaggagc ccatataggt gaaaaataaa aataatccat cgtggattca    1200
aataatcaaa gggctatgac ctttcatcaa ttttagaaaa gtgaaaacaa ccggtttaac    1260
acctatatgc accattttcc tacatagatt tttaacttct tacttaacca tgttgactaa    1320
gagcaagtgg agagcactct catttcatag aacaagtgat gaatgccaac ctgcattatt    1380
atcttaatta gactttgatc atcaagtgga atcccattta tcttaataat cttggcaaca    1440
ttgttataat gctacttcat atgctaattc ttcaaagcta acatcgttaa acgaatacat    1500
atctcctgta ttctaagacc ctatttagaa tacagaaatt ttacagaaat cagttcaatt    1560
ctcgtagaat tgggaaagaa atcctccgtt ccaaacgtga cctaagccgg catggcacga    1620
ccccactcgt caggcactgt atgtaaacgt cagcaactcc gtggcaagta acgtcgagag    1680
gaggagcggg cctaacggcg ccgactagct caacggccac caaccagcca accaccagcg    1740
caaccgaaac ggcgcaaacg ttgacgtcat ctctctctct ctcgcgcccc gcgtcccgaa    1800
gcttccgcac cactcgctgg tcgctgctag ctgggcccca ccggccggcc ccgttcgtgc    1860
tggactcttc ttcctcgaaa ttgcgtggtg gagagggaga gggggcacct cgagacggaa    1920
ccgtcacggc acgggattcc ttccccaccc ggcccctcct cgtctccata aataggcgcc    1980
ccctcctcgc gtcctctccc ccgtctcatc tcctcctgtt ccgtgaaccg tgaacgcaac    2040
ccgaccccca gatctctctc gcgagcatcg tcgatccctc ctccgcgtca aggtacggat    2100
cttctccttc ctccccctto ccctctgggt cggcgtgtcg tgttgtttct ctagttgctt    2160
ggctggatgg atcgagtggt tcttagggct tagatggctg gttagatctg ttgcgttctg    2220
tttcgtagat ggatttttgg tgtagatctg gtaggttatg ctggttaact ggtgatgctc    2280
ctgcgatttt tgggggatct gagttgttaa tctggtagtt gtatggggtt ctcgtagccg    2340
gattgtagat gaaatcgtcc gcgcggtttg cgtggctcgt tggttagcta gggttagatc    2400
tgctcggatt tttcattgtt cctgattcag agatgtagtt aacctttact tgttcatctt    2460
```

tgtatctcgt attcgtacct gcatgtatga tctgtttcga tggtgctaga taggtgcgcc 2520
tgatttgtcc gatcgaatct ggtagcatgc gctgtttgtt tggtagtgtt ctgattgatt 2580
tgtcgctcta gatctgagta gaataggatt atttctcaac atgatattag aagcttggtt 2640
tatagctccg gattagcatg tatgttacat gtttattctt atgtaaggtt ttaaacggaa 2700
gatatatgct actgctgctc attgattctt tatcatccac ctgagtccat gcatgcttct 2760
gttacttctt ttgatatgtg cttagatagc tgttgatatg tactgctgct gttagatgat 2820
ccttcaggat gaacatgcat gattctgtta cttgttttgg tatgcttaga taaatcaaga 2880
tacgcttctg ctgttcgttg attctttagt actacctacc tgatcagctt agatagatca 2940
agatatgctt ctgctgttcg ttgattcttt agtaatacct acctgatcag cttagataga 3000
tcaagatacg cttctgctgt tcgttgattc tctagtacta cctacctgat aaacatgcat 3060
gttttctgct tgttaaaggt tgattgctta ggctcatctt tttcttttcg ttgattctct 3120
agtactacct acctgataaa catgcatgtt ttctgcttgt taaagattga ttgcttagtc 3180
tcatcttttt ctttctcttt tgtctaccgc caggcctaac cttgttgctg gtgactcttt 3240
cttgcaggtg 3250

<210> SEQ ID NO 28
<211> LENGTH: 2004
<212> TYPE: DNA
<213> ORGANISM: Arundo donax

<400> SEQUENCE: 28
gaatccaaca cggcaagtta gcctttgaag cttgaaccgg gcactaatgc aagtatataa 60
taactgagaa ctacaagaaa gcatattcct tgaggtactt atgcaacctt acaattatca 120
aattaattaa caactagcag ttagaatttt atatcacaag aatatcatga accgtggata 180
ctacttctta aagggctatt ctttttctga atgtcgcagt tggttatttt aaccatatta 240
caaactaggg gtttaaatcc caaaaagttc acggaaaggg attaagcaag tagttagcaa 300
gactcacact tatgaccgtt agccaaatta cacattggtc attccaggag gagtaatccc 360
ccatagctag ttgttttgag tttgactacc caaacttgca taatcgtttt cctagagggg 420
gggggggggt tcaccattcc atcaagatga ggcaaagcta aatgaaacac acgagaggca 480
aaacggactg acgtgataga gtttttaata aatatcaaat atgtagagtc aaccaaagaa 540
aaaagatatc ccaatggcta aactttggat ctatgtcgta attcgtgttt taggacatac 600
aaggcgaatt ccttctacgg caaactctag aatagctggg cgacaatggc ctcacgatag 660
cctcaaagag ttggtagcaa ctttgagatc ttttgatccg aaactcaatt atgtagtaca 720
atgatattta gatagattga ttgaaagttg ggggtggggg cgaaagcgaa ggggatctca 780
atattaatac atctatagtg aatggatata gaaaacacag gatttccaat tcaagtagaa 840
ataggaggaa cggaacagat ctagcaatag tagccaccaa agacgaggag gattctagat 900
tgcaaatcca aggtgaaagg aagaaatgtt gaactatcca gaataaggcg gattggccaa 960
ggaggcggaa gtctctagaa agaagtcatt tggctctgag ggctcacttg atgcgagaag 1020
gaagactgac tgaggaatgg attttggtgg accgaggaaa ttggtgctgg gttgcagagg 1080
catgtatgtg ggaaaagagg cagtggcaac gatcgagaga ggagaaggga atgaggtaag 1140
tatttgaagt gaagaggagc ccatataggt gaaaaataaa aataatccat cgtggattca 1200
aataatcaaa gggctatgac ctttcatcaa ttttagaaaa gtgaaaacaa ccggtttaac 1260

-continued acctatatgc accattttcc tacatagatt tttaacttct tacttaacca tgttgactaa 1320
gagcaagtgg agagcactct catttcatag aacaagtgat gaatgccaac ctgcattatt 1380
atcttaatta gactttgatc atcaagtgga atcccattta tcttaataat cttggcaaca 1440
ttgttataat gctacttcat atgctaattc ttcaaagcta acatcgttaa acgaatacat 1500
atctcctgta ttctaagacc ctatttagaa tacagaaatt ttacagaaat cagttcaatt 1560
ctcgtagaat tgggaaagaa atcctccgtt ccaaacgtga cctaagccgg catggcacga 1620
ccccactcgt caggcactgt atgtaaacgt cagcaactcc gtggcaagta acgtcgagag 1680
gaggagcggg cctaacggcg ccgactagct caacggccac caaccagcca accaccagcg 1740
caaccgaaac ggcgcaaacg ttgacgtcat ctctctctct ctcgcgcccc gcgtcccgaa 1800
gcttccgcac cactcgctgg tcgctgctag ctgggcccca ccggccggcc ccgttcgtgc 1860
tggactcttc ttcctcgaaa ttgcgtggtg gagagggaga gggggcacct cgagacggaa 1920
ccgtcacggc acgggattcc ttccccaccc ggcccctcct cgtctccata aataggcgcc 1980
ccctcctcgc gtcctctccc ccgt 2004

<210> SEQ ID NO 29
<211> LENGTH: 1158
<212> TYPE: DNA
<213> ORGANISM: Arundo donax

<400> SEQUENCE: 29
gtacggatct tctccttcct ccccccttccc ctctgggtcg gcgtgtcgtg ttgtttctct 60
agttgcttgg ctggatggat cgagtggttc ttagggctta gatggctggt tagatctgtt 120
gcgttctgtt tcgtagatgg atttttggtg tagatctggt aggttatgct ggttaactgg 180
tgatgctcct gcgatttttg ggggatctga gttgttaatc tggtagttgt atggggttct 240
cgtagccgga ttgtagatga aatcgtccgc gcggtttgcg tggctcgttg gttagctagg 300
gttagatctg ctcggatttt tcattgttcc tgattcagag atgtagttaa cctttacttg 360
ttcatctttg tatctcgtat tcgtacctgc atgtatgatc tgtttcgatg gtgctagata 420
ggtgcgcctg atttgtccga tcgaatctgg tagcatgcgc tgtttgtttg gtagtgttct 480
gattgatttg tcgctctaga tctgagtaga ataggattat ttctcaacat gatattagaa 540
gcttggttta tagctccgga ttagcatgta tgttacatgt ttattcttat gtaaggtttt 600
aaacggaaga tatatgctac tgctgctcat tgattcttta tcatccacct gagtccatgc 660
atgcttctgt tacttctttt gatatgtgct tagatagctg ttgatatgta ctgctgctgt 720
tagatgatcc ttcaggatga acatgcatga ttctgttact tgttttggta tgcttagata 780
aatcaagata cgcttctgct gttcgttgat tctttagtac tacctacctg atcagcttag 840
atagatcaag atatgcttct gctgttcgtt gattctttag taatacctac ctgatcagct 900
tagatagatc aagatacgct tctgctgttc gttgattctc tagtactacc tacctgataa 960
acatgcatgt tttctgcttg ttaaaggttg attgcttagg ctcatctttt tcttttcgtt 1020
gattctctag tactacctac ctgataaaca tgcatgtttt ctgcttgtta aagattgatt 1080
gcttagtctc atctttttct ttctcttttg tctaccgcca ggcctaacct tgttgctggt 1140
gactctttct tgcaggtg 1158

<210> SEQ ID NO 30
<211> LENGTH: 2247
<212> TYPE: DNA
<213> ORGANISM: Arundo donax

<400> SEQUENCE: 30
tcacttgatg cgagaaggaa gactgactga ggaatggatt ttggtggacc gaggaaattg 60
gtgctgggtt gcagaggcat gtatgtggga aaagaggcag tggcaacgat cgagagagga 120
gaagggaatg aggtaagtat ttgaagtgaa gaggagccca tataggtgaa aaataaaaat 180
aatccatcgt ggattcaaat aatcaaaggg ctatgacctt tcatcaattt tagaaaagtg 240
aaaacaaccg gtttaacacc tatatgcacc attttcctac atagattttt aacttcttac 300
ttaaccatgt tgactaagag caagtggaga gcactctcat ttcatagaac aagtgatgaa 360
tgccaacctg cattattatc ttaattagac tttgatcatc aagtggaatc ccatttatct 420
taataatctt ggcaacattg ttataatgct acttcatatg ctaattcttc aaagctaaca 480
tcgttaaacg aatacatatc tcctgtattc taagacccta tttagaatac agaaatttta 540
cagaaatcag ttcaattctc gtagaattgg gaaagaaatc ctccgttcca aacgtgacct 600
aagccggcat ggcacgaccc cactcgtcag gcactgtatg taaacgtcag caactccgtg 660
gcaagtaacg tcgagaggag gagcgggcct aacggcgccg actagctcaa cggccaccaa 720
ccagccaacc accagcgcaa ccgaaacggc gcaaacgttg acgtcatctc tctctctctc 780
gcgccccgcg tcccgaagct tccgcaccac tcgctggtcg ctgctagctg ggccccaccg 840
gccggccccg ttcgtgctgg actcttcttc ctcgaaattg cgtggtggag agggagaggg 900
ggcacctcga gacggaaccg tcacggcacg ggattccttc cccacccggc ccctcctcgt 960
ctccataaat aggcgccccc tcctcgcgtc ctctccccg tctcatctcc tcctgttccg 1020
tgaaccgtga acgcaacccg acccccagat ctctctcgcg agcatcgtcg atccctcctc 1080
cgcgtcaagg tacggatctt ctccttcctc cccctcccc tctgggtcgg cgtgtcgtgt 1140
tgtttctcta gttgcttggc tggatggatc gagtggttct tagggcttag atggctggtt 1200
agatctgttg cgttctgttt cgtagatgga tttttggtgt agatctggta ggttatgctg 1260
gttaactggt gatgctcctg cgatttttgg gggatctgag ttgttaatct ggtagttgta 1320
tggggttctc gtagccggat tgtagatgaa atcgtccgcg cggtttgcgt ggctcgttgg 1380
ttagctaggg ttagatctgc tcggattttt cattgttcct gattcagaga tgtagttaac 1440
ctttacttgt tcatctttgt atctcgtatt cgtacctgca tgtatgatct gtttcgatgg 1500
tgctagatag gtgcgcctga tttgtccgat cgaatctggt agcatgcgct gtttgtttgg 1560
tagtgttctg attgatttgt cgctctagat ctgagtagaa taggattatt tctcaacatg 1620
atattagaag cttggtttat agctccggat tagcatgtat gttacatgtt tattcttatg 1680
taaggtttta aacggaagat atatgctact gctgctcatt gattctttat catccacctg 1740
agtccatgca tgcttctgtt acttcttttg atatgtgctt agatagctgt tgatatgtac 1800
tgctgctgtt agatgatcct tcaggatgaa catgcatgat tctgttactt gttttggtat 1860
gcttagataa atcaagatac gcttctgctg ttcgttgatt ctttagtact acctacctga 1920
tcagcttaga tagatcaaga tatgcttctg ctgttcgttg attctttagt aatacctacc 1980
tgatcagctt agatagatca agatacgctt ctgctgttcg ttgattctct agtactacct 2040
acctgataaa catgcatgtt ttctgcttgt taaaggttga ttgcttaggc tcatcttttt 2100
cttttcgttg attctctagt actacctacc tgataaacat gcatgttttc tgcttgttaa 2160
agattgattg cttagtctca tctttttctt tctcttttgt ctaccgccag gcctaacctt 2220
gttgctggtg actctttctt gcaggtg 2247

<210> SEQ ID NO 31
<211> LENGTH: 1001
<212> TYPE: DNA
<213> ORGANISM: Arundo donax

<400> SEQUENCE: 31
tcacttgatg cgagaaggaa gactgactga ggaatggatt ttggtggacc gaggaaattg 60
gtgctgggtt gcagaggcat gtatgtggga aaagaggcag tggcaacgat cgagagagga 120
gaagggaatg aggtaagtat ttgaagtgaa gaggagccca tataggtgaa aaataaaaat 180
aatccatcgt ggattcaaat aatcaaaggg ctatgacctt tcatcaattt tagaaaagtg 240
aaaacaaccg gtttaacacc tatatgcacc attttcctac atagattttt aacttcttac 300
ttaaccatgt tgactaagag caagtggaga gcactctcat ttcatagaac aagtgatgaa 360
tgccaacctg cattattatc ttaattagac tttgatcatc aagtggaatc ccatttatct 420
taataatctt ggcaacattg ttataatgct acttcatatg ctaattcttc aaagctaaca 480
tcgttaaacg aatacatatc tcctgtattc taagacccta tttagaatac agaaatttta 540
cagaaatcag ttcaattctc gtagaattgg gaaagaaatc ctccgttcca aacgtgacct 600
aagccggcat ggcacgaccc cactcgtcag gcactgtatg taaacgtcag caactccgtg 660
gcaagtaacg tcgagaggag gagcgggcct aacggcgccg actagctcaa cggccaccaa 720
ccagccaacc accagcgcaa ccgaaacggc gcaaacgttg acgtcatctc tctctctctc 780
gcgccccgcg tcccgaagct tccgcaccac tcgctggtcg ctgctagctg ggccccaccg 840
gccggccccg ttcgtgctgg actcttcttc ctcgaaattg cgtggtggag agggagaggg 900
ggcacctcga gacggaaccg tcacggcacg ggattccttc cccacccggc ccctcctcgt 960
ctccataaat aggcgccccc tcctcgcgtc ctctccccg t 1001

<210> SEQ ID NO 32
<211> LENGTH: 1942
<212> TYPE: DNA
<213> ORGANISM: Arundo donax

<400> SEQUENCE: 32
catgttgact aagagcaagt ggagagcact ctcatttcat agaacaagtg atgaatgcca 60
acctgcatta ttatcttaat tagactttga tcatcaagtg gaatcccatt tatcttaata 120
atcttggcaa cattgttata atgctacttc atatgctaat tcttcaaagc taacatcgtt 180
aaacgaatac atatctcctg tattctaaga ccctatttag aatacagaaa ttttacagaa 240
atcagttcaa ttctcgtaga attgggaaag aaatcctccg ttccaaacgt gacctaagcc 300
ggcatggcac gaccccactc gtcaggcact gtatgtaaac gtcagcaact ccgtggcaag 360
taacgtcgag aggaggagcg ggcctaacgg cgccgactag ctcaacggcc accaaccagc 420
caaccaccag cgcaaccgaa acggcgcaaa cgttgacgtc atctctctct ctctcgcgcc 480
ccgcgtcccg aagcttccgc accactcgct ggtcgctgct agctgggccc caccggccgg 540
ccccgttcgt gctggactct tcttcctcga aattgcgtgg tggagaggga gagggggcac 600
ctcgagacgg aaccgtcacg gcacgggatt ccttccccac ccggcccctc ctcgtctcca 660
taaataggcg ccccctcctc gcgtcctctc cccgtctca tctcctcctg ttccgtgaac 720
cgtgaacgca acccgacccc cagatctctc tcgcgagcat cgtcgatccc tcctccgcgt 780
caaggtacgg atcttctcct tcctccccct tcccctctgg gtcggcgtgt cgtgttgttt 840
ctctagttgc ttggctggat ggatcgagtg gttcttaggg cttagatggc tggttagatc 900
tgttgcgttc tgtttcgtag atggattttt ggtgtagatc tggtaggtta tgctggttaa 960
ctggtgatgc tcctgcgatt tttgggggat ctgagttgtt aatctggtag ttgtatgggg 1020
ttctcgtagc cggattgtag atgaaatcgt ccgcgcggtt tgcgtggctc gttggttagc 1080
tagggttaga tctgctcgga tttttcattg ttcctgattc agagatgtag ttaaccttta 1140
cttgttcatc tttgtatctc gtattcgtac ctgcatgtat gatctgtttc gatggtgcta 1200
gataggtgcg cctgatttgt ccgatcgaat ctggtagcat gcgctgtttg tttggtagtg 1260
ttctgattga tttgtcgctc tagatctgag tagaatagga ttatttctca acatgatatt 1320
agaagcttgg tttatagctc cggattagca tgtatgttac atgtttattc ttatgtaagg 1380
ttttaaacgg aagatatatg ctactgctgc tcattgattc tttatcatcc acctgagtcc 1440
atgcatgctt ctgttacttc ttttgatatg tgcttagata gctgttgata tgtactgctg 1500
ctgttagatg atccttcagg atgaacatgc atgattctgt tacttgtttt ggtatgctta 1560
gataaatcaa gatacgcttc tgctgttcgt tgattcttta gtactaccta cctgatcagc 1620
ttagatagat caagatatgc ttctgctgtt cgttgattct ttagtaatac ctacctgatc 1680
agcttagata gatcaagata cgcttctgct gttcgttgat tctctagtac tacctacctg 1740
ataaacatgc atgttttctg cttgttaaag gttgattgct taggctcatc tttttctttt 1800
cgttgattct ctagtactac ctacctgata aacatgcatg ttttctgctt gttaaagatt 1860
gattgcttag tctcatcttt ttctttctct tttgtctacc gccaggccta accttgttgc 1920
tggtgactct ttcttgcagg tg 1942

<210> SEQ ID NO 33
<211> LENGTH: 696
<212> TYPE: DNA
<213> ORGANISM: Arundo donax

<400> SEQUENCE: 33
catgttgact aagagcaagt ggagagcact ctcatttcat agaacaagtg atgaatgcca 60
acctgcatta ttatcttaat tagactttga tcatcaagtg gaatcccatt tatcttaata 120
atcttggcaa cattgttata atgctacttc atatgctaat tcttcaaagc taacatcgtt 180
aaacgaatac atatctcctg tattctaaga ccctatttag aatacagaaa ttttacagaa 240
atcagttcaa ttctcgtaga attgggaaag aaatcctccg ttccaaacgt gacctaagcc 300
ggcatggcac gaccccactc gtcaggcact gtatgtaaac gtcagcaact ccgtggcaag 360
taacgtcgag aggaggagcg ggcctaacgg cgccgactag ctcaacggcc accaaccagc 420
caaccaccag cgcaaccgaa acggcgcaaa cgttgacgtc atctctctct ctctcgcgcc 480
ccgcgtcccg aagcttccgc accactcgct ggtcgctgct agctgggccc caccggccgg 540
ccccgttcgt gctggactct tcttcctcga aattgcgtgg tggagaggga gagggggcac 600
ctcgagacgg aaccgtcacg gcacgggatt ccttccccac ccggcccctc ctcgtctcca 660
taaataggcg ccccctcctc gcgtcctctc ccccgt 696

<210> SEQ ID NO 34
<211> LENGTH: 3511
<212> TYPE: DNA
<213> ORGANISM: Bouteloua gracilis

<400> SEQUENCE: 34
gtggccagct tttgttctag ttcaacggtc ccggccttcc gtgcacctaa tactacactg 60

-continued

```
attaatctat tgcagctaac ctcaaaagaa atacacttgc agttgtctgt cccaatcaag    120
ccactagcag actctcatgt cattgatgga ggaaattaaa ttcagtcttt gacgtggatg    180
caacaactgc acagtatacc atgcatctta attagccgtt gtgtcaaagt ttgttttgct    240
gacgttttga gaaaaccaac tttgaccaac aggagatgag cgtcttgcgt ttggcacagt    300
gtaatggaat ccggcacggc aagttagact ctgtagtgtt agcggtctct ttacgtttgg    360
cacaatttaa ttgaatcccg gcatggcatg ttagaccgga gtgagccggc ccttttactg    420
gtatgacact ccctctgtct tgagtgtcgc tgtgccagct tgtacctctg tctatgttca    480
cagcccgtgc tgtgtaccta gaccctccgt ttgtccacat tcattttaat ctctattgta    540
tcttgtcaaa acctaaaagc ctaaaacgac tctgataaag ggacagaaag attatacaag    600
agcaagtgta taatgaaata atgtaagcga gctatatgaa ttgtcacgtg tcatatttat    660
gttgagacga agaagagaaa ataaacacca tgcaaattta tggcgagtga tagatggcca    720
gatgggcaca aggcctccta tttcttaaat cggattttgt aagaacgaaa aaagggactt    780
ataagagaat aggatagacc atatatcaat gatgtagtat gcatcaagat ctaactatta    840
tatgagtgaa ttgataaatt tattctaggt gacatggcct taacgatgaa cagtacgtgg    900
ttaaatcaat agaacaatag ccaactctag cggctctaaa aaaagatata tattcgtcga    960
ggcactatta tgcaaccaca tagtcaactt caacgccgct tgagtgcgtt ctcatgtttt   1020
tttttcttg caaattacgc ttttctaaaa taaaataatt tggatcgtgc aattatttca   1080
ctttaggtgt gcgtgactac gtgagtaaca attttgaatc tcagaaagga aataaaagta   1140
taatactgct acctactttg aggattcagc ttgttactta aaaccgtctt taaggtcaaa   1200
tgctcaagat tcattcaaca attgaaacgt ctcacatgat taaaccatgt ataaggatgc   1260
taaggtcttg cttgacaatg tttttctagg aatttcatct aactttttga gtgaaactat   1320
caaataataa ttttaaaaca attttataag agaagctccg gagataaaag ggcatctaat   1380
ctatgttaga agagtgaagt ttactccctc tgtcccaaaa atagaattct aagtatgaaa   1440
tgattttttt gttatacgaa aggagtatat atcacaagat tgatgtcagt tatgcttagg   1500
gcacgtacac gacgctggtg ctttaggtag acgttaatcg ttgtttctgc attttatttt   1560
attttgttgc cacggtgtac atttgggtag acgtttgtca caggcattgc cactcaaaca   1620
agcagccggc gcttggagct tttatagttt gaaaagtgac ggttttaatg atgggtaagc   1680
tgattagtat atgtaagttt agctttttcc attgtaggtt aagccttaag gctcttacac   1740
aattgtttca ttattctcat tctttaagag cccatataag cgttcatgaa ttgtacatat   1800
ccttagatgt tttttttttt gggtaaagct cgagcttctc tatctaaaag tagagaaatc   1860
agaaaaagat tcatgtttg gtagttttga tttcttgcct ccataataat tttggtttac   1920
catttttgt ttgattttag ttttagaagc gtttatagca ggatttaaaa tccaaaacta   1980
ccattatctt caagtgaccg tcagtgagcc gtttaacggc gtcgacaagt ccaacggaca   2040
ccaaccagtg aaccaccagc gtcgagccaa gcgatgcaaa cggaacggcc gagacgttga   2100
cacctttggc gcggcacggc atgtcggatc tccctctctg gccagagagt tccagctcca   2160
cctccacctc cacctccacc ggtggcggtt tccaagtccg ttccgttccg ttccgttccg   2220
ttccgttccg cctcctgcct gctcctctca gacggcacga aaccgtgacg gcaccggcag   2280
cacgggggga ttccttttcc actgctcctt cctcttccct tcctcgcccg ccgctataaa   2340
tagccagccc cgtccccaga ttctttccca acctcatctt tgttcggagc acgcacacaa   2400
cccgatcccc aattccctcg tctctcctcg cgagcctcgt cgaccccccc cttcaaggta   2460
```

cggcgatcat cctccctccc tccctctctc taccttctct tctctagact agatcggcga 2520
cccggtccat ggttagggcc tgctagttct gttcctgttt tttccatggc tgcgaggtaa 2580
aatagatctg atggcgttat gatggttaac tcgtcatact cttgcgatct atggtccctt 2640
taggacatcg atttaatttc ggatggttcg agatcggtga tccatggtta gtaccctagg 2700
cagtggggtt agatccgtgc tgttagggtt cgtagatgga ttctgattgc tcagtaactg 2760
ggaaacctgg gatggttcta gctgggaatc ctgggatggt tctagctggt tcgcagatga 2820
gatcgatttc atggtctgct atatcttgtt tcgttgccta ggttccgttt aatctgtccg 2880
tggtatgatg ttagcctttg ataaggttcg atcgtgctag ctacgtcctg cgcagcattt 2940
aattgtcagg tcataatttt tagcattcct gtttttgttt ggtttggttt tgtctggttg 3000
ggctgtagat agtttcaatc tacctgtcgg tttattttat taaatttgga ttggatctgt 3060
atgtgtcaca tatatcttca tgattaagat ggttggaatt atctcttcat cttttagata 3120
tatatggata ggtatatatg ttgctgtggg ttttactggt actttattag atatattcat 3180
gcttagatac atgaagcaac gtgctgttac agtttaataa ttcttgttta tctaataaac 3240
aaataaggat aggtatatgt tgctgatggt tttactgata ctttattaga tagtactttg 3300
acatgaagga acatcctgcg acagcttaat aattattctt catctaataa aaagcttgct 3360
ttttaattat tttaattatt ttgatatact tggatgatgt catgcagcag ctatgtgtga 3420
attttcggcc ctgtcttcat atgatgttta tttgcttggg actgtttctt tggctgataa 3480
cttaccctgt tgtttggtga tccttctgca g 3511

<210> SEQ ID NO 35
<211> LENGTH: 2371
<212> TYPE: DNA
<213> ORGANISM: Bouteloua gracilis

<400> SEQUENCE: 35
gtggccagct tttgttctag ttcaacggtc ccggccttcc gtgcacctaa tactacactg 60
attaatctat tgcagctaac ctcaaaagaa atacacttgc agttgtctgt cccaatcaag 120
ccactagcag actctcatgt cattgatgga ggaaattaaa ttcagtcttt gacgtggatg 180
caacaactgc acagtatacc atgcatctta attagccgtt gtgtcaaagt ttgttttgct 240
gacgttttga gaaaaccaac tttgaccaac aggagatgag cgtcttgcgt ttggcacagt 300
gtaatggaat ccggcacggc aagttagact ctgtagtgtt agcggtctct ttacgtttgg 360
cacaatttaa ttgaatcccg gcatggcatg ttagaccgga gtgagccggc ccttttactg 420
gtatgacact ccctctgtct tgagtgtcgc tgtgccagct tgtacctctg tctatgttca 480
cagcccgtgc tgtgtaccta gaccctccgt ttgtccacat tcattttaat ctctattgta 540
tcttgtcaaa acctaaaagc ctaaaacgac tctgataaag ggacagaaag attatacaag 600
agcaagtgta taatgaaata atgtaagcga gctatatgaa ttgtcacgtg tcatatttat 660
gttgagacga agaagagaaa ataaacacca tgcaaattta tggcgagtga tagatggcca 720
gatgggcaca aggcctccta tttcttaaat cggattttgt aagaacgaaa aaagggactt 780
ataagagaat aggatagacc atatatcaat gatgtagtat gcatcaagat ctaactatta 840
tatgagtgaa ttgataaatt tattctaggt gacatggcct taacgatgaa cagtacgtgg 900
ttaaatcaat agaacaatag ccaactctag cggctctaaa aaaagatata tattcgtcga 960
ggcactatta tgcaaccaca tagtcaactt caacgccgct tgagtgcgtt ctcatgtttt 1020

-continued

```
tttttcttg caaattacgc ttttctaaaa taaaataatt tggatcgtgc aattatttca   1080

ctttaggtgt gcgtgactac gtgagtaaca attttgaatc tcagaaagga aataaaagta   1140

taatactgct acctactttg aggattcagc ttgttactta aaaccgtctt taaggtcaaa   1200

tgctcaagat tcattcaaca attgaaacgt ctcacatgat taaaccatgt ataaggatgc   1260

taaggtcttg cttgacaatg tttttctagg aatttcatct aactttttga gtgaaactat   1320

caaataataa ttttaaaaca attttataag agaagctccg gagataaaag ggcatctaat   1380

ctatgttaga agagtgaagt ttactccctc tgtcccaaaa atagaattct aagtatgaaa   1440

tgattttttt gttatacgaa aggagtatat atcacaagat tgatgtcagt tatgcttagg   1500

gcacgtacac gacgctggtg ctttaggtag acgttaatcg ttgtttctgc attttatttt   1560

attttgttgc cacggtgtac atttgggtag acgtttgtca caggcattgc cactcaaaca   1620

agcagccggc gcttggagct tttatagttt gaaaagtgac ggttttaatg atgggtaagc   1680

tgattagtat atgtaagttt agctttttcc attgtaggtt aagccttaag gctcttacac   1740

aattgtttca ttattctcat tctttaagag cccatataag cgttcatgaa ttgtacatat   1800

ccttagatgt tttttttttt gggtaaagct cgagcttctc tatctaaaag tagagaaatc   1860

agaaaaagat tcatgttttg gtagttttga tttcttgcct ccataataat tttggtttac   1920

catttttgt ttgattttag ttttagaagc gtttatagca ggatttaaaa tccaaaacta   1980

ccattatctt caagtgaccg tcagtgagcc gtttaacggc gtcgacaagt ccaacggaca   2040

ccaaccagtg aaccaccagc gtcgagccaa gcgatgcaaa cggaacggcc gagacgttga   2100

cacctttggc gcggcacggc atgtcggatc tccctctctg gccagagagt tccagctcca   2160

cctccacctc cacctccacc ggtggcggtt tccaagtccg ttccgttccg ttccgttccg   2220

ttccgttccg cctcctgcct gctcctctca gacggcacga aaccgtgacg gcaccggcag   2280

cacgggggga ttcctttcc actgctcctt cctcttccct tcctcgcccg ccgctataaa   2340

tagccagccc cgtccccaga ttctttccca a                                 2371
```

<210> SEQ ID NO 36
<211> LENGTH: 86
<212> TYPE: DNA
<213> ORGANISM: Bouteloua gracilis

<400> SEQUENCE: 36

```
cctcatcttt gttcggagca cgcacacaac ccgatcccca attccctcgt ctctcctcgc     60

gagcctcgtc gacccccccc ttcaag                                           86
```

<210> SEQ ID NO 37
<211> LENGTH: 1054
<212> TYPE: DNA
<213> ORGANISM: Bouteloua gracilis

<400> SEQUENCE: 37

```
gtacggcgat catcctccct ccctccctct ctctaccttc tcttctctag actagatcgg     60

cgacccggtc catggttagg gcctgctagt tctgttcctg ttttttccat ggctgcgagg    120

taaaatagat ctgatggcgt tatgatggtt aactcgtcat actcttgcga tctatggtcc    180

ctttaggaca tcgatttaat ttcggatggt tcgagatcgg tgatccatgg ttagtaccct    240

aggcagtggg gttagatccg tgctgttagg gttcgtagat ggattctgat tgctcagtaa    300

ctgggaaacc tgggatggtt ctagctggga atcctgggat ggttctagct ggttcgcaga    360

tgagatcgat ttcatggtct gctatatctt gtttcgttgc ctaggttccg tttaatctgt    420
```

-continued

```
ccgtggtatg atgttagcct ttgataaggt tcgatcgtgc tagctacgtc ctgcgcagca    480

tttaattgtc aggtcataat ttttagcatt cctgtttttg tttggtttgg ttttgtctgg    540

ttgggctgta gatagtttca atctacctgt cggtttattt tattaaattt ggattggatc    600

tgtatgtgtc acatatatct tcatgattaa gatggttgga attatctctt catcttttag    660

atatatatgg ataggtatat atgttgctgt gggttttact ggtactttat tagatatatt    720

catgcttaga tacatgaagc aacgtgctgt tacagtttaa taattcttgt ttatctaata    780

aacaaataag gataggtata tgttgctgat ggttttactg atactttatt agatagtact    840

ttgacatgaa ggaacatcct gcgacagctt aataattatt cttcatctaa taaaaagctt    900

gctttttaat tattttaatt attttgatat acttggatga tgtcatgcag cagctatgtg    960

tgaattttcg gccctgtctt catatgatgt ttatttgctt gggactgttt ctttggctga   1020

taacttaccc tgttgtttgg tgatccttct gcag                               1054
```

<210> SEQ ID NO 38
<211> LENGTH: 3142
<212> TYPE: DNA
<213> ORGANISM: Bouteloua gracilis

<400> SEQUENCE: 38

```
gaatcccggc atggcatgtt agaccggagt gagccggccc ttttactggt atgacactcc     60

ctctgtcttg agtgtcgctg tgccagcttg tacctctgtc tatgttcaca gcccgtgctg    120

tgtacctaga ccctccgttt gtccacattc attttaatct ctattgtatc ttgtcaaaac    180

ctaaaagcct aaaacgactc tgataaaggg acagaaagat tatacaagag caagtgtata    240

atgaaataat gtaagcgagc tatatgaatt gtcacgtgtc atatttatgt tgagacgaag    300

aagagaaaat aaacaccatg caaatttatg gcgagtgata gatggccaga tgggcacaag    360

gcctcctatt tcttaaatcg gattttgtaa gaacgaaaaa agggacttat aagagaatag    420

gatagaccat atatcaatga tgtagtatgc atcaagatct aactattata tgagtgaatt    480

gataaattta ttctaggtga catggcctta acgatgaaca gtacgtggtt aaatcaatag    540

aacaatagcc aactctagcg gctctaaaaa aagatatata ttcgtcgagg cactattatg    600

caaccacata gtcaacttca acgccgcttg agtgcgttct catgtttttt ttttcttgca    660

aattacgctt ttctaaaata aaataatttg gatcgtgcaa ttatttcact ttaggtgtgc    720

gtgactacgt gagtaacaat tttgaatctc agaaaggaaa taaaagtata atactgctac    780

ctactttgag gattcagctt gttacttaaa accgtcttta aggtcaaatg ctcaagattc    840

attcaacaat tgaaacgtct cacatgatta aaccatgtat aaggatgcta aggtcttgct    900

tgacaatgtt tttctaggaa tttcatctaa ctttttgagt gaaactatca aataataatt    960

ttaaaacaat tttataagag aagctccgga gataaaaggg catctaatct atgttagaag   1020

agtgaagttt actccctctg tcccaaaaat agaattctaa gtatgaaatg attttttttgt   1080

tatacgaaag gagtatatat cacaagattg atgtcagtta tgcttagggc acgtacacga   1140

cgctggtgct ttaggtagac gttaatcgtt gtttctgcat tttattttat tttgttgcca   1200

cggtgtacat ttgggtagac gtttgtcaca ggcattgcca ctcaaacaag cagccggcgc   1260

ttggagcttt tatagtttga aaagtgacgg ttttaatgat gggtaagctg attagtatat   1320

gtaagtttag ctttttccat tgtaggttaa gccttaaggc tcttacacaa ttgtttcatt   1380

attctcattc tttaagagcc catataagcg ttcatgaatt gtacatatcc ttagatgttt   1440
```

-continued

```
ttttttttgg gtaaagctcg agcttctcta tctaaaagta gagaaatcag aaaaagattc   1500
atgttttggt agttttgatt tcttgcctcc ataataattt tggtttacca ttttttgttt   1560
gattttagtt ttagaagcgt ttatagcagg atttaaaatc caaaactacc attatcttca   1620
agtgaccgtc agtgagccgt ttaacggcgt cgacaagtcc aacggacacc aaccagtgaa   1680
ccaccagcgt cgagccaagc gatgcaaacg gaacggccga gacgttgaca cctttggcgc   1740
ggcacggcat gtcggatctc cctctctggc cagagagttc cagctccacc tccacctcca   1800
cctccaccgg tggcggtttc caagtccgtt ccgttccgtt ccgttccgtt ccgttccgcc   1860
tcctgcctgc tcctctcaga cggcacgaaa ccgtgacggc accggcagca cggggggatt   1920
ccttttccac tgctccttcc tcttcccttc ctcgcccgcc gctataaata gccagccccg   1980
tccccagatt ctttcccaac ctcatctttg ttcggagcac gcacacaacc cgatccccaa   2040
ttccctcgtc tctcctcgcg agcctcgtcg accccccct tcaaggtacg gcgatcatcc   2100
tccctccctc cctctctcta ccttctcttc tctagactag atcggcgacc cggtccatgg   2160
ttagggcctg ctagttctgt tcctgttttt tccatggctg cgaggtaaaa tagatctgat   2220
ggcgttatga tggttaactc gtcatactct tgcgatctat ggtcccttta ggacatcgat   2280
ttaatttcgg atggttcgag atcggtgatc catggttagt accctaggca gtggggttag   2340
atccgtgctg ttagggttcg tagatggatt ctgattgctc agtaactggg aaacctggga   2400
tggttctagc tgggaatcct gggatggttc tagctggttc gcagatgaga tcgatttcat   2460
ggtctgctat atcttgtttc gttgcctagg ttccgtttaa tctgtccgtg gtatgatgtt   2520
agcctttgat aaggttcgat cgtgctagct acgtcctgcg cagcatttaa ttgtcaggtc   2580
ataattttta gcattcctgt ttttgtttgg tttggttttg tctggttggg ctgtagatag   2640
tttcaatcta cctgtcggtt tattttatta aatttggatt ggatctgtat gtgtcacata   2700
tatcttcatg attaagatgg ttggaattat ctcttcatct tttagatata tatggatagg   2760
tatatatgtt gctgtgggtt ttactggtac tttattagat atattcatgc ttagatacat   2820
gaagcaacgt gctgttacag tttaataatt cttgtttatc taataaacaa ataaggatag   2880
gtatatgttg ctgatggttt tactgatact ttattagata gtactttgac atgaaggaac   2940
atcctgcgac agcttaataa ttattcttca tctaataaaa agcttgcttt ttaattattt   3000
taattatttt gatatacttg gatgatgtca tgcagcagct atgtgtgaat tttcggccct   3060
gtcttcatat gatgtttatt tgcttgggac tgtttctttg gctgataact taccctgttg   3120
tttggtgatc cttctgcagg tg                                             3142
```

<210> SEQ ID NO 39
<211> LENGTH: 1999
<212> TYPE: DNA
<213> ORGANISM: Bouteloua gracilis

<400> SEQUENCE: 39

```
gaatcccggc atggcatgtt agaccggagt gagccggccc ttttactggt atgacactcc     60
ctctgtcttg agtgtcgctg tgccagcttg tacctctgtc tatgttcaca gcccgtgctg    120
tgtacctaga ccctccgttt gtccacattc attttaatct ctattgtatc ttgtcaaaac    180
ctaaaagcct aaaacgactc tgataaaggg acagaaagat tatacaagag caagtgtata    240
atgaaataat gtaagcgagc tatatgaatt gtcacgtgtc atatttatgt tgagacgaag    300
aagagaaaat aaacaccatg caaatttatg gcgagtgata gatggccaga tgggcacaag    360
gcctcctatt tcttaaatcg gattttgtaa gaacgaaaaa agggacttat aagagaatag    420
```

gatagaccat atatcaatga tgtagtatgc atcaagatct aactattata tgagtgaatt 480
gataaattta ttctaggtga catggcctta acgatgaaca gtacgtggtt aaatcaatag 540
aacaatagcc aactctagcg gctctaaaaa aagatatata ttcgtcgagg cactattatg 600
caaccacata gtcaacttca acgccgcttg agtgcgttct catgtttttt ttttcttgca 660
aattacgctt ttctaaaata aaataatttg gatcgtgcaa ttatttcact ttaggtgtgc 720
gtgactacgt gagtaacaat tttgaatctc agaaaggaaa taaaagtata atactgctac 780
ctactttgag gattcagctt gttacttaaa accgtcttta aggtcaaatg ctcaagattc 840
attcaacaat tgaaacgtct cacatgatta aaccatgtat aaggatgcta aggtcttgct 900
tgacaatgtt tttctaggaa tttcatctaa ctttttgagt gaaactatca aataataatt 960
ttaaaacaat tttataagag aagctccgga gataaaaggg catctaatct atgttagaag 1020
agtgaagttt actccctctg tcccaaaaat agaattctaa gtatgaaatg atttttttgt 1080
tatacgaaag gagtatatat cacaagattg atgtcagtta tgcttagggc acgtacacga 1140
cgctggtgct ttaggtagac gttaatcgtt gtttctgcat tttattttat tttgttgcca 1200
cggtgtacat ttgggtagac gtttgtcaca ggcattgcca ctcaaacaag cagccggcgc 1260
ttggagcttt tatagtttga aaagtgacgg ttttaatgat gggtaagctg attagtatat 1320
gtaagtttag ctttttccat tgtaggttaa gccttaaggc tcttacacaa ttgtttcatt 1380
attctcattc tttaagagcc catataagcg ttcatgaatt gtacatatcc ttagatgttt 1440
tttttttggg gtaaagctcg agcttctcta tctaaaagta gagaaatcag aaaaagattc 1500
atgttttggt agttttgatt tcttgcctcc ataataattt tggtttacca ttttttgttt 1560
gattttagtt ttagaagcgt ttatagcagg atttaaaatc caaaactacc attatcttca 1620
agtgaccgtc agtgagccgt ttaacggcgt cgacaagtcc aacggacacc aaccagtgaa 1680
ccaccagcgt cgagccaagc gatgcaaacg gaacggccga gacgttgaca cctttggcgc 1740
ggcacggcat gtcggatctc cctctctggc cagagagttc cagctccacc tccacctcca 1800
cctccaccgg tggcggtttc caagtccgtt ccgttccgtt ccgttccgtt ccgttccgcc 1860
tcctgcctgc tcctctcaga cggcacgaaa ccgtgacggc accggcagca cggggggatt 1920
ccttttccac tgctccttcc tcttcccttc ctcgcccgcc gctataaata gccagccccg 1980
tccccagatt ctttcccaa 1999

<210> SEQ ID NO 40
<211> LENGTH: 1057
<212> TYPE: DNA
<213> ORGANISM: Bouteloua gracilis

<400> SEQUENCE: 40
gtacggcgat catcctccct ccctccctct ctctaccttc tcttctctag actagatcgg 60
cgacccggtc catggttagg gcctgctagt tctgttcctg ttttttccat ggctgcgagg 120
taaaatagat ctgatggcgt tatgatggtt aactcgtcat actcttgcga tctatggtcc 180
ctttaggaca tcgatttaat ttcggatggt tcgagatcgg tgatccatgg ttagtaccct 240
aggcagtggg gttagatccg tgctgttagg gttcgtagat ggattctgat tgctcagtaa 300
ctgggaaacc tgggatggtt ctagctggga atcctgggat ggttctagct ggttcgcaga 360
tgagatcgat ttcatggtct gctatatctt gtttcgttgc ctaggttccg tttaatctgt 420
ccgtggtatg atgttagcct ttgataaggt tcgatcgtgc tagctacgtc ctgcgcagca 480

-continued

```
tttaattgtc aggtcataat ttttagcatt cctgtttttg tttggtttgg ttttgtctgg    540

ttgggctgta gatagtttca atctacctgt cggtttattt tattaaattt ggattggatc    600

tgtatgtgtc acatatatct tcatgattaa gatggttgga attatctctt catcttttag    660

atatatatgg ataggtatat atgttgctgt gggttttact ggtactttat tagatatatt    720

catgcttaga tacatgaagc aacgtgctgt tacagtttaa taattcttgt ttatctaata    780

aacaaataag gataggtata tgttgctgat ggttttactg atactttatt agatagtact    840

ttgacatgaa ggaacatcct gcgacagctt aataattatt cttcatctaa taaaaagctt    900

gctttttaat tattttaatt attttgatat acttggatga tgtcatgcag cagctatgtg    960

tgaattttcg gccctgtctt catatgatgt ttatttgctt gggactgttt ctttggctga   1020

taacttaccc tgttgtttgg tgatccttct gcaggtg                            1057
```

<210> SEQ ID NO 41
<211> LENGTH: 2165
<212> TYPE: DNA
<213> ORGANISM: Bouteloua gracilis

<400> SEQUENCE: 41

```
gagaagctcc ggagataaaa gggcatctaa tctatgttag aagagtgaag tttactccct     60

ctgtcccaaa aatagaattc taagtatgaa atgatttttt tgttatacga aaggagtata    120

tatcacaaga ttgatgtcag ttatgcttag ggcacgtaca cgacgctggt gctttaggta    180

gacgttaatc gttgtttctg cattttattt tattttgttg ccacggtgta catttgggta    240

gacgtttgtc acaggcattg ccactcaaac aagcagccgg cgcttggagc ttttatagtt    300

tgaaaagtga cggttttaat gatgggtaag ctgattagta tatgtaagtt tagctttttc    360

cattgtaggt taagccttaa ggctcttaca caattgtttc attattctca ttctttaaga    420

gcccatataa gcgttcatga attgtacata tccttagatg tttttttttt tgggtaaagc    480

tcgagcttct ctatctaaaa gtagagaaat cagaaaaaga ttcatgtttt ggtagttttg    540

atttcttgcc tccataataa ttttggttta ccatttttg tttgatttta gttttagaag    600

cgtttatagc aggatttaaa atccaaaact accattatct tcaagtgacc gtcagtgagc    660

cgtttaacgg cgtcgacaag tccaacggac accaaccagt gaaccaccag cgtcgagcca    720

agcgatgcaa acggaacggc cgagacgttg acacctttgg cgcggcacgg catgtcggat    780

ctccctctct ggccagagag ttccagctcc acctccacct ccacctccac cggtggcggt    840

ttccaagtcc gttccgttcc gttccgttcc gttccgttcc gcctcctgcc tgctcctctc    900

agacggcacg aaaccgtgac ggcaccggca gcacgggggg attccttttc cactgctcct    960

tcctcttccc ttcctcgccc gccgctataa atagccagcc ccgtccccag attctttccc   1020

aacctcatct ttgttcggag cacgcacaca acccgatccc caattccctc gtctctcctc   1080

gcgagcctcg tcgacccccc ccttcaaggt acggcgatca tcctccctcc ctccctctct   1140

ctaccttctc ttctctagac tagatcggcg acccggtcca tggttagggc ctgctagttc   1200

tgttcctgtt ttttccatgg ctgcgaggta aaatagatct gatggcgtta tgatggttaa   1260

ctcgtcatac tcttgcgatc tatggtccct ttaggacatc gatttaattt cggatggttc   1320

gagatcggtg atccatggtt agtaccctag gcagtggggt tagatccgtg ctgttagggt   1380

tcgtagatgg attctgattg ctcagtaact gggaaacctg ggatggttct agctgggaat   1440

cctgggatgg ttctagctgg ttcgcagatg agatcgattt catggtctgc tatatcttgt   1500

ttcgttgcct aggttccgtt taatctgtcc gtggtatgat gttagccttt gataaggttc   1560
```

gatcgtgcta gctacgtcct gcgcagcatt taattgtcag gtcataattt ttagcattcc 1620
tgtttttgtt tggtttggtt ttgtctggtt gggctgtaga tagtttcaat ctacctgtcg 1680
gtttatttta ttaaatttgg attggatctg tatgtgtcac atatatcttc atgattaaga 1740
tggttggaat tatctcttca tcttttagat atatatggat aggtatatat gttgctgtgg 1800
gttttactgg tactttatta gatatattca tgcttagata catgaagcaa cgtgctgtta 1860
cagtttaata attcttgttt atctaataaa caaataagga taggtatatg ttgctgatgg 1920
ttttactgat actttattag atagtacttt gacatgaagg aacatcctgc gacagcttaa 1980
taattattct tcatctaata aaaagcttgc tttttaatta ttttaattat tttgatatac 2040
ttggatgatg tcatgcagca gctatgtgtg aattttcggc cctgtcttca tatgatgttt 2100
atttgcttgg gactgtttct ttggctgata acttaccctg ttgtttggtg atccttctgc 2160
aggtg 2165

<210> SEQ ID NO 42
<211> LENGTH: 1022
<212> TYPE: DNA
<213> ORGANISM: Bouteloua gracilis
<400> SEQUENCE: 42
gagaagctcc ggagataaaa gggcatctaa tctatgttag aagagtgaag tttactccct 60
ctgtcccaaa aatagaattc taagtatgaa atgatttttt tgttatacga aaggagtata 120
tatcacaaga ttgatgtcag ttatgcttag ggcacgtaca cgacgctggt gctttaggta 180
gacgttaatc gttgtttctg cattttattt tattttgttg ccacggtgta catttgggta 240
gacgtttgtc acaggcattg ccactcaaac aagcagccgg cgcttggagc ttttatagtt 300
tgaaaagtga cggttttaat gatgggtaag ctgattagta tatgtaagtt tagctttttc 360
cattgtaggt taagccttaa ggctcttaca caattgtttc attattctca ttctttaaga 420
gcccatataa gcgttcatga attgtacata tccttagatg tttttttttt tgggtaaagc 480
tcgagcttct ctatctaaaa gtagagaaat cagaaaaaga ttcatgtttt ggtagttttg 540
atttcttgcc tccataataa ttttggttta ccattttttg tttgatttta gttttagaag 600
cgtttatagc aggatttaaa atccaaaact accattatct tcaagtgacc gtcagtgagc 660
cgtttaacgg cgtcgacaag tccaacggac accaaccagt gaaccaccag cgtcgagcca 720
agcgatgcaa acggaacggc cgagacgttg acacctttgg cgcggcacgg catgtcggat 780
ctccctctct ggccagagag ttccagctcc acctccacct ccacctccac cggtggcggt 840
ttccaagtcc gttccgttcc gttccgttcc gttccgttcc gcctcctgcc tgctcctctc 900
agacggcacg aaaccgtgac ggcaccggca gcacgggggg attccttttc cactgctcct 960
tcctcttccc ttcctcgccc gccgctataa atagccagcc ccgtccccag attctttccc 1020
aa 1022

<210> SEQ ID NO 43
<211> LENGTH: 1903
<212> TYPE: DNA
<213> ORGANISM: Bouteloua gracilis
<400> SEQUENCE: 43
actcaaacaa gcagccggcg cttggagctt ttatagtttg aaaagtgacg gttttaatga 60
tgggtaagct gattagtata tgtaagttta gctttttcca ttgtaggtta agccttaagg 120
ctcttacaca attgtttcat tattctcatt ctttaagagc ccatataagc gttcatgaat 180
tgtacatatc cttagatgtt tttttttttg ggtaaagctc gagcttctct atctaaaagt 240
agagaaatca gaaaaagatt catgttttgg tagttttgat ttcttgcctc cataataatt 300
ttggtttacc attttttgtt tgattttagt tttagaagcg tttatagcag gatttaaaat 360
ccaaaactac cattatcttc aagtgaccgt cagtgagccg tttaacggcg tcgacaagtc 420
caacggacac caaccagtga accaccagcg tcgagccaag cgatgcaaac ggaacggccg 480
agacgttgac acctttggcg cggcacggca tgtcggatct ccctctctgg ccagagagtt 540
ccagctccac ctccacctcc acctccaccg gtggcggttt ccaagtccgt tccgttccgt 600
tccgttccgt tccgttccgc ctcctgcctg ctcctctcag acggcacgaa accgtgacgg 660
caccggcagc acggggggat tccttttcca ctgctccttc ctcttccctt cctcgcccgc 720
cgctataaat agccagcccc gtccccagat tctttcccaa cctcatcttt gttcggagca 780
cgcacacaac ccgatcccca attccctcgt ctctcctcgc gagcctcgtc gacccccccc 840
ttcaaggtac ggcgatcatc ctccctccct ccctctctct accttctctt ctctagacta 900
gatcggcgac ccggtccatg gttagggcct gctagttctg ttcctgtttt ttccatggct 960
gcgaggtaaa atagatctga tggcgttatg atggttaact cgtcatactc ttgcgatcta 1020
tggtcccttt aggacatcga tttaatttcg gatggttcga gatcggtgat ccatggttag 1080
taccctaggc agtggggtta gatccgtgct gttagggttc gtagatggat tctgattgct 1140
cagtaactgg gaaacctggg atggttctag ctgggaatcc tgggatggtt ctagctggtt 1200
cgcagatgag atcgatttca tggtctgcta tatcttgttt cgttgcctag gttccgttta 1260
atctgtccgt ggtatgatgt tagcctttga taaggttcga tcgtgctagc tacgtcctgc 1320
gcagcattta attgtcaggt cataattttt agcattcctg tttttgtttg gtttggtttt 1380
gtctggttgg gctgtagata gtttcaatct acctgtcggt ttattttatt aaatttggat 1440
tggatctgta tgtgtcacat atatcttcat gattaagatg gttggaatta tctcttcatc 1500
ttttagatat atatggatag gtatatatgt tgctgtgggt tttactggta ctttattaga 1560
tatattcatg cttagataca tgaagcaacg tgctgttaca gtttaataat tcttgtttat 1620
ctaataaaca aataaggata ggtatatgtt gctgatggtt ttactgatac tttattagat 1680
agtactttga catgaaggaa catcctgcga cagcttaata attattcttc atctaataaa 1740
aagcttgctt tttaattatt ttaattattt tgatatactt ggatgatgtc atgcagcagc 1800
tatgtgtgaa ttttcggccc tgtcttcata tgatgtttat ttgcttggga ctgtttcttt 1860
ggctgataac ttaccctgtt gtttggtgat ccttctgcag gtg 1903

<210> SEQ ID NO 44
<211> LENGTH: 760
<212> TYPE: DNA
<213> ORGANISM: Bouteloua gracilis

<400> SEQUENCE: 44
actcaaacaa gcagccggcg cttggagctt ttatagtttg aaaagtgacg gttttaatga 60
tgggtaagct gattagtata tgtaagttta gctttttcca ttgtaggtta agccttaagg 120
ctcttacaca attgtttcat tattctcatt ctttaagagc ccatataagc gttcatgaat 180
tgtacatatc cttagatgtt tttttttttg ggtaaagctc gagcttctct atctaaaagt 240
agagaaatca gaaaaagatt catgttttgg tagttttgat ttcttgcctc cataataatt 300
ttggtttacc attttttgtt tgattttagt tttagaagcg tttatagcag gatttaaaat 360
ccaaaactac cattatcttc aagtgaccgt cagtgagccg tttaacggcg tcgacaagtc 420
caacggacac caaccagtga accaccagcg tcgagccaag cgatgcaaac ggaacggccg 480
agacgttgac acctttggcg cggcacggca tgtcggatct ccctctctgg ccagagagtt 540
ccagctccac ctccacctcc acctccaccg gtggcggttt ccaagtccgt tccgttccgt 600
tccgttccgt tccgttccgc ctcctgcctg ctcctctcag acggcacgaa accgtgacgg 660
caccggcagc acggggggat tccttttcca ctgctccttc ctcttccctt cctcgcccgc 720
cgctataaat agccagcccc gtccccagat tctttcccaa 760

<210> SEQ ID NO 45
<211> LENGTH: 3234
<212> TYPE: DNA
<213> ORGANISM: Bouteloua gracilis

<400> SEQUENCE: 45
ggcctcttta cgtttggcac aacttagttg aatccggctt ccggcaaact atatggcaag 60
ttagacccaa gtgtgagccg gccaccgcaa gttattgtga cattatacgt aggaagcaag 120
tgtataataa gaatatgaga taatgtaagc agctatatga attatcacgt catatttatg 180
ttaagatgaa gaggagagaa taaacggtac gtaaatttat agcgagtgat agacgggcac 240
gaggcctcct agctatttcc ataaatcgga ttttgtaaga acaaaaaaga ggacttatta 300
taagagaatg tggtaagtaa gcatactccc tccgtttcaa attataagtt gttttaactt 360 ttttttata tctattttac tatacattag atataataat gtgtctagat acataataaa 420
atggatgaac aaaaaagtca aagtgactta caatttggaa cggagggagt aagttcaagc 480
catcaaggca cttctatgca accacatagt caacttgaat gccgcttgag tgccttctca 540 agttttttt ttcttgcaaa aattgtttct tttttttaa aaaagtataa tttggatcgt 600
gcaaatttct ctctaggtgt gtgtgtgact gtgtgagtaa caatttctct agttgtgcgt 660
gactgctgct tactttggag attacaatat atttctaaaa tgcttcgatt acttatttat 720
aaaccgtctc taaggccaat tgctcaagat tcattcaaca attgaaacgt ctcacatgat 780
taaatcatat aaagtttcta agtcttgttt gacaagattt ttttagattt tcatctaaat 840
tggatgaaac tatcaaacac taattttaaa aaatataaga gaagctccgg agataaaagg 900
tcgtctatgt tattataaga gtaaagtcgt ctattctctt cgtcccaaca tatataattc 960
taagcatgaa ttgctttctt tttggacaaa aggagtatgc cacaacacaa gaatgatgtc 1020
accgtcatgc ttagatcctt ttatggtaaa gcttcacctt ctataatcta acaatagaga 1080
aatcggggaa aaatcatgtt ttggttgttt ttatttctaa cctccacaat aactttggtt 1140
taccattttt tgtttgattt tagttttaga gaagcgttta taacaggacc taaaatcttt 1200
ttttgagtac acagtacaac gcagacgctc atacacgcac gcacaatgtc ctctatgaac 1260
acacgtaagg aaaccctaca ccttgagcac cttcgaagga ctgagccggc aaatctagag 1320
attctcgaag tcactattgg cacctcgtta tcaacgagaa cgtcgcttac cacttaaagc 1380
ataacaccga gaaatcccgt aacaaatcca gtaaaatacg agcacccgta ccaagttgaa 1440
tatttgaacc cgagtgggta gattccaccg caaaggacct aaccagatca tttcgcaaac 1500
aggaactaaa atcggtagag agcccagaca aaaacctttt ctaagagcaa ctccagtgaa 1560
agcccctact ttaggtataa aatgcaacac tagtggagct tctaaataaa cttctatttt 1620
tcatgccctc ctaaaattta ctcctaaaac cctagctata ggagcctcct atccatcctc 1680

-continued

```
tattttattc cactagaatt gattataaat ttagcctctt aaattttata agttgggagt   1740
cgagggtaac tagagttgct ctaaacggac cttatcttca agtgacctca gtgagcccgt   1800
ttaacggcgt cgacaagtct aatctaacgg acaccaacca gagaaccacc gccagcgccg   1860
agccaagcga cgttgacatc ttggcgcggc acggcatctc cctggcgtct ggtcccctcc   1920
cgagacttcc gctccacctc ccaccggtgg cggtttccga gtccgttccg cctcctctca   1980
cacggcacga aaccttgacg gcaccggcag cacgggggat tccgttccca cggctccttc   2040
cctttccctt cctcgcccgc tgctataaat agccagcccc atccccagct tcttccccaa   2100
cctcatcttc tcgtgttgtt cggcccaacc cgatcgatcc ccaattccct cgtcgtctct   2160
cgtcgcgagc ctcgtcgatc cccgcttcaa ggtacagcga tcgatcgatc atcctcgctc   2220
tctctacctt ctctctctta gggcgtgctg gttctgttcc tgtttttcca tggctgcgag   2280
gtacaataga ttggcgattc atggttaggg cctgctagtt ctgttcctgt ttttttttt   2340 tccatggctg cgaggcacaa tagatctgat ggcgttatga tggttaactt gtcatactct   2400
tgcgatctat ggtcccttta ggagtttagg acatcgattt aatttcggat agttcgagat   2460
ctgtgatcca tggttagtac cctaggcagt ggggttagat ccgtgctgtt atggttcgta   2520
gatggattct gattgctcag taactgggaa tcctgggatg gttctagctg gttcgcagat   2580
aagatcgatt tcatgatatg ctatatcttg tttggttgcc gtggttccgt taaatctgtc   2640
tgttatgatc ttagtctttg ataaggttcg gtcgtgctag ctacgtcctg tgcagcactt   2700
aattgtcagg tcataatttt tagcatgcct tttttttatt ggtttggttt tgtctgactg   2760
ggctgtagat agtttcaatc tttgtctgac tgggctgtag atagtttcaa tcttcctgtc   2820
tgtttatttt attaaatttg gatctgtatg tgtgtcatat atcttcatct tttagatata   2880
tcgataggta tatatgttgc tgtcgttttt tactgttcct ttatgagata tattcatgct   2940
tagatacatg aaacaacgtg ctgttacagt ttaatagttc ttgtttatct aataaacaaa   3000
taaggatagg tgctgcagtt agttttactg gtactttttt tgacatgaac ctacggctta   3060
ataattagtc ttcatcaaat aaaaagcata ttttttaatt atttcgatat acttgaatga   3120
tgtcatatgc agcatctgtg tgaatttttg gccctgtctt catatgatgt ttatttgctt   3180
gggactgttt ctttggctga taactcaccc tgttgtttgg tgatccttct gcag          3234
```

<210> SEQ ID NO 46
<211> LENGTH: 2100
<212> TYPE: DNA
<213> ORGANISM: Bouteloua gracilis

<400> SEQUENCE: 46

```
ggcctcttta cgtttggcac aacttagttg aatccggctt ccggcaaact atatggcaag     60
ttagacccaa gtgtgagccg gccaccgcaa gttattgtga cattatacgt aggaagcaag    120
tgtataataa gaatatgaga taatgtaagc agctatatga attatcacgt catatttatg    180
ttaagatgaa gaggagagaa taaacggtac gtaaatttat agcgagtgat agacgggcac    240
gaggcctcct agctatttcc ataaatcgga ttttgtaaga acaaaaaaga ggacttatta    300
taagagaatg tggtaagtaa gcatactccc tccgtttcaa attataagtt gttttaactt    360
tttttttata tctattttac tatacattag atataataat gtgtctagat acataataaa    420
atggatgaac aaaaaagtca aagtgactta caatttggaa cggagggagt aagttcaagc    480
catcaaggca cttctatgca accacatagt caacttgaat gccgcttgag tgccttctca    540
agtttttttt ttcttgcaaa aattgtttct ttttttttaa aaaagtataa tttggatcgt    600
```

-continued

```
gcaaatttct ctctaggtgt gtgtgtgact gtgtgagtaa caatttctct agttgtgcgt    660

gactgctgct tactttggag attacaatat atttctaaaa tgcttcgatt acttatttat    720

aaaccgtctc taaggccaat tgctcaagat tcattcaaca attgaaacgt ctcacatgat    780

taaatcatat aaagtttcta agtcttgttt gacaagattt ttttagattt tcatctaaat    840

tggatgaaac tatcaaacac taattttaaa aaatataaga gaagctccgg agataaaagg    900

tcgtctatgt tattataaga gtaaagtcgt ctattctctt cgtcccaaca tatataattc    960

taagcatgaa ttgctttctt tttggacaaa aggagtatgc cacaacacaa gaatgatgtc   1020

accgtcatgc ttagatcctt ttatggtaaa gcttcacctt ctataatcta acaatagaga   1080

aatcggggaa aaatcatgtt ttggttgttt ttatttctaa cctccacaat aactttggtt   1140

taccattttt tgtttgattt tagttttaga gaagcgttta taacaggacc taaaatcttt   1200

ttttgagtac acagtacaac gcagacgctc atacacgcac gcacaatgtc ctctatgaac   1260

acacgtaagg aaaccctaca ccttgagcac cttcgaagga ctgagccggc aaatctagag   1320

attctcgaag tcactattgg cacctcgtta tcaacgagaa cgtcgcttac cacttaaagc   1380

ataacaccga gaaatcccgt aacaaatcca gtaaaatacg agcacccgta ccaagttgaa   1440

tatttgaacc cgagtgggta gattccaccg caaaggacct aaccagatca tttcgcaaac   1500

aggaactaaa atcggtagag agcccagaca aaaacctttt ctaagagcaa ctccagtgaa   1560

agcccctact ttaggtataa aatgcaacac tagtggagct tctaaataaa cttctatttt   1620

tcatgccctc ctaaaattta ctcctaaaac cctagctata ggagcctcct atccatcctc   1680

tattttattc cactagaatt gattataaat ttagcctctt aaattttata agttgggagt   1740

cgagggtaac tagagttgct ctaaacggac cttatcttca agtgacctca gtgagcccgt   1800

ttaacggcgt cgacaagtct aatctaacgg acaccaacca gagaaccacc gccagcgccg   1860

agccaagcga cgttgacatc ttggcgcggc acggcatctc cctggcgtct ggtcccctcc   1920

cgagacttcc gctccacctc ccaccggtgg cggtttccga gtccgttccg cctcctctca   1980

cacggcacga aaccttgacg gcaccggcag cacgggggat tccgttccca cggctccttc   2040

cctttccctt cctcgcccgc tgctataaat agccagcccc atccccagct tcttccccaa   2100
```

<210> SEQ ID NO 47
<211> LENGTH: 91
<212> TYPE: DNA
<213> ORGANISM: Bouteloua gracilis

<400> SEQUENCE: 47

```
cctcatcttc tcgtgttgtt cggcccaacc cgatcgatcc ccaattccct cgtcgtctct     60

cgtcgcgagc ctcgtcgatc cccgcttcaa g                                    91
```

<210> SEQ ID NO 48
<211> LENGTH: 1043
<212> TYPE: DNA
<213> ORGANISM: Bouteloua gracilis

<400> SEQUENCE: 48

```
gtacagcgat cgatcgatca tcctcgctct ctctaccttc tctctcttag ggcgtgctgg     60

ttctgttcct gtttttccat ggctgcgagg tacaatagat tggcgattca tggttagggc    120

ctgctagttc tgttcctgtt ttttttttt ccatggctgc gaggcacaat agatctgatg    180

gcgttatgat ggttaacttg tcatactctt gcgatctatg gtccctttag gagtttagga    240
```

-continued

```
catcgattta atttcggata gttcgagatc tgtgatccat ggttagtacc ctaggcagtg    300

gggttagatc cgtgctgtta tggttcgtag atggattctg attgctcagt aactgggaat    360

cctgggatgg ttctagctgg ttcgcagata agatcgattt catgatatgc tatatcttgt    420

ttggttgccg tggttccgtt aaatctgtct gttatgatct tagtctttga taaggttcgg    480

tcgtgctagc tacgtcctgt gcagcactta attgtcaggt cataattttt agcatgcctt    540

tttttattg gtttggtttt gtctgactgg gctgtagata gtttcaatct ttgtctgact    600

gggctgtaga tagtttcaat cttcctgtct gtttatttta ttaaatttgg atctgtatgt    660

gtgtcatata tcttcatctt ttagatatat cgataggtat atatgttgct gtcgtttttt    720

actgttcctt tatgagatat attcatgctt agatacatga aacaacgtgc tgttacagtt    780

taatagttct tgtttatcta ataaacaaat aaggataggt gctgcagtta gttttactgg    840

tactttttt gacatgaacc tacggcttaa taattagtct tcatcaaata aaaagcatat    900

tttttaatta tttcgatata cttgaatgat gtcatatgca gcatctgtgt gaatttttgg    960

ccctgtcttc atatgatgtt tatttgcttg ggactgtttc tttggctgat aactcaccct   1020

gttgtttggt gatccttctg cag                                            1043
```

<210> SEQ ID NO 49
<211> LENGTH: 3176
<212> TYPE: DNA
<213> ORGANISM: Bouteloua gracilis

<400> SEQUENCE: 49

```
aagttagacc caagtgtgag ccggccaccg caagttattg tgacattata cgtaggaagc     60

aagtgtataa taagaatatg agataatgta agcagctata tgaattatca cgtcatattt    120

atgttaagat gaagaggaga gaataaacgg tacgtaaatt tatagcgagt gatagacggg    180

cacgaggcct cctagctatt tccataaatc ggattttgta agaacaaaaa agaggactta    240

ttataagaga atgtggtaag taagcatact ccctccgttt caaattataa gttgttttaa    300

cttttttttt atatctattt tactatacat tagatataat aatgtgtcta gatacataat    360

aaaatggatg aacaaaaaag tcaaagtgac ttacaatttg gaacggaggg agtaagttca    420

agccatcaag gcacttctat gcaaccacat agtcaacttg aatgccgctt gagtgccttc    480

tcaagttttt tttttcttgc aaaaaattgtt tctttttttt taaaaaagta taatttggat    540

cgtgcaaatt tctctctagg tgtgtgtgtg actgtgtgag taacaatttc tctagttgtg    600

cgtgactgct gcttactttg gagattacaa tatatttcta aaatgcttcg attacttatt    660

tataaaccgt ctctaaggcc aattgctcaa gattcattca acaattgaaa cgtctcacat    720

gattaaatca tataaagttt ctaagtcttg tttgacaaga tttttttaga ttttcatcta    780

aattggatga aactatcaaa cactaatttt aaaaaatata agagaagctc cggagataaa    840

aggtcgtcta tgttattata agagtaaagt cgtctattct cttcgtccca acatatataa    900

ttctaagcat gaattgcttt ctttttggac aaaaggagta tgccacaaca caagaatgat    960

gtcaccgtca tgcttagatc cttttatggt aaagcttcac cttctataat ctaacaatag   1020

agaaatcggg gaaaaatcat gttttggttg tttttatttc taacctccac aataactttg   1080

gtttaccatt ttttgtttga ttttagtttt agagaagcgt ttataacagg acctaaaatc   1140

ttttttgag tacacagtac aacgcagacg ctcatacacg cacgcacaat gtcctctatg   1200

aacacacgta aggaaaccct acaccttgag caccttcgaa ggactgagcc ggcaaatcta   1260

gagattctcg aagtcactat tggcacctcg ttatcaacga gaacgtcgct taccacttaa   1320
```

agcataacac cgagaaatcc cgtaacaaat ccagtaaaat acgagcaccc gtaccaagtt 1380
gaatatttga acccgagtgg gtagattcca ccgcaaagga cctaaccaga tcatttcgca 1440
aacaggaact aaaatcggta gagagcccag acaaaaacct tttctaagag caactccagt 1500
gaaagcccct actttaggta taaaatgcaa cactagtgga gcttctaaat aaacttctat 1560
ttttcatgcc ctcctaaaat ttactcctaa aaccctagct ataggagcct cctatccatc 1620
ctctatttta ttccactaga attgattata aatttagcct cttaaatttt ataagttggg 1680
agtcgagggt aactagagtt gctctaaacg gaccttatct tcaagtgacc tcagtgagcc 1740
cgtttaacgg cgtcgacaag tctaatctaa cggacaccaa ccagagaacc accgccagcg 1800
ccgagccaag cgacgttgac atcttggcgc ggcacggcat ctccctggcg tctggtcccc 1860
tcccgagact tccgctccac ctcccaccgg tggcggtttc cgagtccgtt ccgcctcctc 1920
tcacacggca cgaaaccttg acggcaccgg cagcacgggg gattccgttc ccacggctcc 1980
ttccctttcc cttcctcgcc cgctgctata aatagccagc cccatcccca gcttcttccc 2040
caacctcatc ttctcgtgtt gttcggccca acccgatcga tccccaattc cctcgtcgtc 2100
tctcgtcgcg agcctcgtcg atccccgctt caaggtacag cgatcgatcg atcatcctcg 2160
ctctctctac cttctctctc ttagggcgtg ctggttctgt tcctgttttt ccatggctgc 2220
gaggtacaat agattggcga ttcatggtta gggcctgcta gttctgttcc tgtttttttt 2280
ttttccatgg ctgcgaggca caatagatct gatggcgtta tgatggttaa cttgtcatac 2340
tcttgcgatc tatggtccct ttaggagttt aggacatcga tttaatttcg gatagttcga 2400
gatctgtgat ccatggttag taccctaggc agtggggtta gatccgtgct gttatggttc 2460
gtagatggat tctgattgct cagtaactgg gaatcctggg atggttctag ctggttcgca 2520
gataagatcg atttcatgat atgctatatc ttgtttggtt gccgtggttc cgttaaatct 2580
gtctgttatg atcttagtct tgataaggtt cggtcgtgct agctacgtcc tgtgcagcac 2640
ttaattgtca ggtcataatt tttagcatgc ctttttttta ttggtttggt tttgtctgac 2700
tgggctgtag atagtttcaa tctttgtctg actgggctgt agatagtttc aatcttcctg 2760
tctgtttatt ttattaaatt tggatctgta tgtgtgtcat atatcttcat cttttagata 2820
tatcgatagg tatatatgtt gctgtcgttt tttactgttc ctttatgaga tatattcatg 2880
cttagataca tgaaacaacg tgctgttaca gtttaatagt tcttgtttat ctaataaaca 2940
aataaggata ggtgctgcag ttagttttac tggtactttt tttgacatga acctacggct 3000
taataattag tcttcatcaa ataaaaagca tattttttaa ttatttcgat atacttgaat 3060
gatgtcatat gcagcatctg tgtgaatttt tggccctgtc ttcatatgat gtttatttgc 3120
ttgggactgt ttctttggct gataactcac cctgttgttt ggtgatcctt ctgcag 3176

<210> SEQ ID NO 50
<211> LENGTH: 2043
<212> TYPE: DNA
<213> ORGANISM: Bouteloua gracilis

<400> SEQUENCE: 50
aagttagacc caagtgtgag ccggccaccg caagttattg tgacattata cgtaggaagc 60
aagtgtataa taagaatatg agataatgta agcagctata tgaattatca cgtcatattt 120
atgttaagat gaagaggaga gaataaacgg tacgtaaatt tatagcgagt gatagacggg 180
cacgaggcct cctagctatt tccataaatc ggattttgta agaacaaaaa agaggactta 240

-continued ttataagaga atgtggtaag taagcatact ccctccgttt caaattataa gttgttttaa 300
cttttttttt atatctattt tactatacat tagatataat aatgtgtcta gatacataat 360
aaaatggatg aacaaaaaag tcaaagtgac ttacaatttg gaacggaggg agtaagttca 420
agccatcaag gcacttctat gcaaccacat agtcaacttg aatgccgctt gagtgccttc 480
tcaagttttt tttttcttgc aaaaattgtt tctttttttt taaaaaagta taatttggat 540
cgtgcaaatt tctctctagg tgtgtgtgtg actgtgtgag taacaatttc tctagttgtg 600
cgtgactgct gcttactttg gagattacaa tatatttcta aaatgcttcg attacttatt 660
tataaaccgt ctctaaggcc aattgctcaa gattcattca acaattgaaa cgtctcacat 720
gattaaatca tataaagttt ctaagtcttg tttgacaaga ttttttttaga ttttcatcta 780 aattggatga aactatcaaa cactaatttt aaaaaaatata agagaagctc cggagataaa 840
aggtcgtcta tgttattata agagtaaagt cgtctattct cttcgtccca acatatataa 900
ttctaagcat gaattgcttt ctttttggac aaaaggagta tgccacaaca caagaatgat 960
gtcaccgtca tgcttagatc cttttatggt aaagcttcac cttctataat ctaacaatag 1020
agaaatcggg gaaaaatcat gttttggttg tttttatttc taacctccac aataactttg 1080
gtttaccatt ttttgtttga ttttagtttt agagaagcgt ttataacagg acctaaaatc 1140
tttttttgag tacacagtac aacgcagacg ctcatacacg cacgcacaat gtcctctatg 1200
aacacacgta aggaaaccct acaccttgag caccttcgaa ggactgagcc ggcaaatcta 1260
gagattctcg aagtcactat tggcacctcg ttatcaacga gaacgtcgct taccacttaa 1320
agcataacac cgagaaatcc cgtaacaaat ccagtaaaat acgagcaccc gtaccaagtt 1380
gaatatttga acccgagtgg gtagattcca ccgcaaagga cctaaccaga tcatttcgca 1440
aacaggaact aaaatcggta gagagcccag acaaaaacct tttctaagag caactccagt 1500
gaaagcccct actttaggta taaaatgcaa cactagtgga gcttctaaat aaacttctat 1560
ttttcatgcc ctcctaaaat ttactcctaa aaccctagct ataggagcct cctatccatc 1620
ctctatttta ttccactaga attgattata aatttagcct cttaaatttt ataagttggg 1680
agtcgagggt aactagagtt gctctaaacg gaccttatct tcaagtgacc tcagtgagcc 1740
cgtttaacgg cgtcgacaag tctaatctaa cggacaccaa ccagagaacc accgccagcg 1800
ccgagccaag cgacgttgac atcttggcgc ggcacggcat ctccctggcg tctggtcccc 1860
tcccgagact tccgctccac ctcccaccgg tggcggtttc cgagtccgtt ccgcctcctc 1920
tcacacggca cgaaaccttg acggcaccgg cagcacgggg gattccgttc ccacggctcc 1980
ttccctttcc cttcctcgcc cgctgctata aatagccagc cccatcccca gcttcttccc 2040
caa 2043

<210> SEQ ID NO 51
<211> LENGTH: 1042
<212> TYPE: DNA
<213> ORGANISM: Bouteloua gracilis

<400> SEQUENCE: 51
gtacagcgat cgatcgatca tcctcgctct ctctaccttc tctctcttag ggcgtgctgg 60
ttctgttcct gtttttccat ggctgcgagg tacaatagat tggcgattca tggttagggc 120
ctgctagttc tgttcctgtt ttttttttt ccatggctgc gaggcacaat agatctgatg 180
gcgttatgat ggttaacttg tcatactctt gcgatctatg gtccctttag gagtttagga 240
catcgattta atttcggata gttcgagatc tgtgatccat ggttagtacc ctaggcagtg 300
gggttagatc cgtgctgtta tggttcgtag atggattctg attgctcagt aactgggaat 360
cctgggatgg ttctagctgg ttcgcagata agatcgattt catgatatgc tatatcttgt 420
ttggttgccg tggttccgtt aaatctgtct gttatgatct tagtcttgat aaggttcggt 480
cgtgctagct acgtcctgtg cagcacttaa ttgtcaggtc ataattttta gcatgccttt 540
tttttattgg tttggttttg tctgactggg ctgtagatag tttcaatctt tgtctgactg 600
ggctgtagat agtttcaatc ttcctgtctg tttattttat taaatttgga tctgtatgtg 660
tgtcatatat cttcatcttt tagatatatc gataggtata tatgttgctg tcgtttttta 720
ctgttccttt atgagatata ttcatgctta gatacatgaa acaacgtgct gttacagttt 780
aatagttctt gtttatctaa taaacaaata aggataggtg ctgcagttag ttttactggt 840 acttttttttg acatgaacct acggcttaat aattagtctt catcaaataa aaagcatatt 900
ttttaattat ttcgatatac ttgaatgatg tcatatgcag catctgtgtg aatttttggc 960
cctgtcttca tatgatgttt atttgcttgg gactgtttct ttggctgata actcaccctg 1020
ttgtttggtg atccttctgc ag 1042

<210> SEQ ID NO 52
<211> LENGTH: 3139
<212> TYPE: DNA
<213> ORGANISM: Bouteloua gracilis

<400> SEQUENCE: 52
gacattatac gtaggaagca agtgtataat aagaatatga gataatgtaa gcagctatat 60
gaattatcac gtcatattta tgttaagatg aagaggagag aataaacggt acgtaaattt 120
atagcgagtg atagacgggc acgaggcctc ctagctattt ccataaatcg gattttgtaa 180
gaacaaaaaa gaggacttat tataagagaa tgtggtaagt aagcatactc cctccgtttc 240
aaattataag ttgttttaac ttttttttta tatctatttt actatacatt agatataata 300
atgtgtctag atacataata aaatggatga acaaaaaagt caaagtgact tacaatttgg 360
aacggaggga gtaagttcaa gccatcaagg cacttctatg caaccacata gtcaacttga 420
atgccgcttg agtgccttct caagtttttt ttttcttgca aaaattgttt cttttttttt 480
aaaaaagtat aatttggatc gtgcaaattt ctctctaggt gtgtgtgtga ctgtgtgagt 540
aacaatttct ctagttgtgc gtgactgctg cttactttgg agattacaat atatttctaa 600
aatgcttcga ttacttattt ataaaccgtc tctaaggcca attgctcaag attcattcaa 660
caattgaaac gtctcacatg attaaatcat ataaagtttc taagtcttgt ttgacaagat 720
ttttttagat tttcatctaa attggatgaa actatcaaac actaatttta aaaaatataa 780
gagaagctcc ggagataaaa ggtcgtctat gttattataa gagtaaagtc gtctattctc 840
ttcgtcccaa catatataat tctaagcatg aattgctttc tttttggaca aaaggagtat 900
gccacaacac aagaatgatg tcaccgtcat gcttagatcc ttttatggta aagcttcacc 960
ttctataatc taacaataga gaaatcgggg aaaaatcatg ttttggttgt ttttatttct 1020
aacctccaca ataactttgg tttaccattt tttgtttgat tttagtttta gagaagcgtt 1080
tataacagga cctaaaatct ttttttgagt acacagtaca acgcagacgc tcatacacgc 1140
acgcacaatg tcctctatga acacacgtaa ggaaacccta caccttgagc accttcgaag 1200
gactgagccg gcaaatctag agattctcga agtcactatt ggcacctcgt tatcaacgag 1260
aacgtcgctt accacttaaa gcataacacc gagaaatccc gtaacaaatc cagtaaaata 1320

-continued

```
cgagcacccg taccaagttg aatatttgaa cccgagtggg tagattccac cgcaaaggac   1380

ctaaccagat catttcgcaa acaggaacta aaatcggtag agagcccaga caaaaacctt   1440

ttctaagagc aactccagtg aaagccccta ctttaggtat aaaatgcaac actagtggag   1500

cttctaaata aacttctatt tttcatgccc tcctaaaatt tactcctaaa accctagcta   1560

taggagcctc ctatccatcc tctattttat tccactagaa ttgattataa atttagcctc   1620

ttaaatttta taagttggga gtcgagggta actagagttg ctctaaacgg accttatctt   1680

caagtgacct cagtgagccc gtttaacggc gtcgacaagt ctaatctaac ggacaccaac   1740

cagagaacca ccgccagcgc cgagccaagc gacgttgaca tcttggcgcg gcacggcatc   1800

tccctggcgt ctggtcccct cccgagactt ccgctccacc tcccaccggt ggcggtttcc   1860

gagtccgttc cgcctcctct cacacggcac gaaaccttga cggcaccggc agcacggggg   1920

attccgttcc cacggctcct tccctttccc ttcctcgccc gctgctataa atagccagcc   1980

ccatccccag cttcttcccc aacctcatct tctcgtgttg ttcggcccaa cccgatcgat   2040

ccccaattcc ctcgtcgtct ctcgtcgcga gcctcgtcga tccccgcttc aaggtacagc   2100

gatcgatcga tcatcctcgc tctctctacc ttctctctct tagggcgtgc tggttctgtt   2160

cctgtttttc catggctgcg aggtacaata gattggcgat tcatggttag ggcctgctag   2220

ttctgttcct gttttttttt tttccatggc tgcgaggcac aatagatctg atggcgttat   2280

gatggttaac ttgtcatact cttgcgatct atggtccctt taggagttta ggacatcgat   2340

ttaatttcgg atagttcgag atctgtgatc catggttagt accctaggca gtggggttag   2400

atccgtgctg ttatggttcg tagatggatt ctgattgctc agtaactggg aatcctggga   2460

tggttctagc tggttcgcag ataagatcga tttcatgata tgctatatct tgtttggttg   2520

ccgtggttcc gttaaatctg tctgttatga tcttagtctt tgataaggtt cggtcgtgct   2580

agctacgtcc tgtgcagcac ttaattgtca ggtcataatt tttagcatgc cttttttttta   2640

ttggtttggt tttgtctgac tgggctgtag atagtttcaa tctttgtctg actgggctgt   2700

agatagtttc aatcttcctg tctgtttatt ttattaaatt tggatctgta tgtgtgtcat   2760

atatcttcat cttttagata tatcgatagg tatatatgtt gctgtcgttt tttactgttc   2820

ctttatgaga tatattcatg cttagataca tgaaacaacg tgctgttaca gtttaatagt   2880

tcttgtttat ctaataaaca aataaggata ggtgctgcag ttagttttac tggtactttt   2940

tttgacatga acctacggct taataattag tcttcatcaa ataaaaagca tattttttaa   3000

ttatttcgat atacttgaat gatgtcatat gcagcatctg tgtgaatttt tggccctgtc   3060

ttcatatgat gtttatttgc ttgggactgt ttctttggct gataactcac cctgttgttt   3120

ggtgatcctt ctgcaggtg                                                3139
```

<210> SEQ ID NO 53
<211> LENGTH: 2002
<212> TYPE: DNA
<213> ORGANISM: Bouteloua gracilis

<400> SEQUENCE: 53

```
gacattatac gtaggaagca agtgtataat aagaatatga gataatgtaa gcagctatat     60

gaattatcac gtcatattta tgttaagatg aagaggagag aataaacggt acgtaaattt    120

atagcgagtg atagacgggc acgaggcctc ctagctattt ccataaatcg gattttgtaa    180

gaacaaaaaa gaggacttat tataagagaa tgtggtaagt aagcatactc cctccgtttc    240

aaattataag ttgttttaac ttttttttta tatctatttt actatacatt agatataata    300
```

-continued

```
atgtgtctag atacataata aaatggatga acaaaaaagt caaagtgact tacaatttgg    360

aacggaggga gtaagttcaa gccatcaagg cacttctatg caaccacata gtcaacttga    420

atgccgcttg agtgccttct caagtttttt ttttcttgca aaaattgttt cttttttttt    480

aaaaaagtat aatttggatc gtgcaaattt ctctctaggt gtgtgtgtga ctgtgtgagt    540

aacaatttct ctagttgtgc gtgactgctg cttactttgg agattacaat atatttctaa    600

aatgcttcga ttacttattt ataaaccgtc tctaaggcca attgctcaag attcattcaa    660

caattgaaac gtctcacatg attaaatcat ataaagtttc taagtcttgt ttgacaagat    720

tttttagat tttcatctaa attggatgaa actatcaaac actaatttta aaaaatataa    780

gagaagctcc ggagataaaa ggtcgtctat gttattataa gagtaaagtc gtctattctc    840

ttcgtcccaa catatataat tctaagcatg aattgctttc tttttggaca aaaggagtat    900

gccacaacac aagaatgatg tcaccgtcat gcttagatcc ttttatggta aagcttcacc    960

ttctataatc taacaataga gaaatcgggg aaaaatcatg ttttggttgt ttttatttct   1020

aacctccaca ataactttgg tttaccattt tttgtttgat tttagtttta gagaagcgtt   1080

tataacagga cctaaaatct ttttttgagt acacagtaca acgcagacgc tcatacacgc   1140

acgcacaatg tcctctatga acacacgtaa ggaaacccta caccttgagc accttcgaag   1200

gactgagccg gcaaatctag agattctcga agtcactatt ggcacctcgt tatcaacgag   1260

aacgtcgctt accacttaaa gcataacacc gagaaatccc gtaacaaatc cagtaaaata   1320

cgagcacccg taccaagttg aatatttgaa cccgagtggg tagattccac cgcaaaggac   1380

ctaaccagat catttcgcaa acaggaacta aaatcggtag agagcccaga caaaaacctt   1440

ttctaagagc aactccagtg aaagccccta ctttaggtat aaaatgcaac actagtggag   1500

cttctaaata aacttctatt tttcatgccc tcctaaaatt tactcctaaa accctagcta   1560

taggagcctc ctatccatcc tctattttat tccactagaa ttgattataa atttagcctc   1620

ttaaatttta taagttggga gtcgagggta actagagttg ctctaaacgg accttatctt   1680

caagtgacct cagtgagccc gtttaacggc gtcgacaagt ctaatctaac ggacaccaac   1740

cagagaacca ccgccagcgc cgagccaagc gacgttgaca tcttggcgcg gcacggcatc   1800

tccctggcgt ctggtcccct cccgagactt ccgctccacc tcccaccggt ggcggtttcc   1860

gagtccgttc cgcctcctct cacacggcac gaaaccttga cggcaccggc agcacggggg   1920

attccgttcc cacggctcct tccctttccc ttcctcgccc gctgctataa atagccagcc   1980

ccatccccag cttcttcccc aa                                            2002
```

<210> SEQ ID NO 54
<211> LENGTH: 1046
<212> TYPE: DNA
<213> ORGANISM: Bouteloua gracilis

<400> SEQUENCE: 54

```
gtacagcgat cgatcgatca tcctcgctct ctctaccttc tctctcttag ggcgtgctgg     60

ttctgttcct gtttttccat ggctgcgagg tacaatagat tggcgattca tggttagggc    120

ctgctagttc tgttcctgtt ttttttttt ccatggctgc gaggcacaat agatctgatg    180

gcgttatgat ggttaacttg tcatactctt gcgatctatg gtccctttag gagtttagga    240

catcgattta atttcggata gttcgagatc tgtgatccat ggttagtacc ctaggcagtg    300

gggttagatc cgtgctgtta tggttcgtag atggattctg attgctcagt aactgggaat    360
```

-continued

```
cctgggatgg ttctagctgg ttcgcagata agatcgattt catgatatgc tatatcttgt    420

ttggttgccg tggttccgtt aaatctgtct gttatgatct tagtctttga taaggttcgg    480

tcgtgctagc tacgtcctgt gcagcactta attgtcaggt cataattttt agcatgcctt    540

tttttattg gtttggtttt gtctgactgg gctgtagata gtttcaatct ttgtctgact     600

gggctgtaga tagtttcaat cttcctgtct gtttatttta ttaaatttgg atctgtatgt    660

gtgtcatata tcttcatctt ttagatatat cgataggtat atatgttgct gtcgtttttt    720

actgttcctt tatgagatat attcatgctt agatacatga aacaacgtgc tgttacagtt    780

taatagttct tgtttatcta ataaacaaat aaggataggt gctgcagtta gttttactgg    840

tacttttttt gacatgaacc tacggcttaa taattagtct tcatcaaata aaaagcatat    900

tttttaatta tttcgatata cttgaatgat gtcatatgca gcatctgtgt gaatttttgg    960

ccctgtcttc atatgatgtt tatttgcttg ggactgtttc tttggctgat aactcaccct   1020

gttgtttggt gatccttctg caggtg                                        1046
```

```
<210> SEQ ID NO 55
<211> LENGTH: 2160
<212> TYPE: DNA
<213> ORGANISM: Bouteloua gracilis

<400> SEQUENCE: 55

gagaaatcgg ggaaaaatca tgttttggtt gtttttattt ctaacctcca caataacttt     60

ggtttaccat tttttgtttg attttagttt tagagaagcg tttataacag gacctaaaat    120

cttttttga gtacacagta caacgcagac gctcatacac gcacgcacaa tgtcctctat     180

gaacacacgt aaggaaaccc tacaccttga gcaccttcga aggactgagc cggcaaatct    240

agagattctc gaagtcacta ttggcacctc gttatcaacg agaacgtcgc ttaccactta    300

aagcataaca ccgagaaatc ccgtaacaaa tccagtaaaa tacgagcacc cgtaccaagt    360

tgaatatttg aacccgagtg ggtagattcc accgcaaagg acctaaccag atcatttcgc    420

aaacaggaac taaaatcggt agagagccca gacaaaaacc ttttctaaga gcaactccag    480

tgaaagcccc tactttaggt ataaaatgca acactagtgg agcttctaaa taaacttcta    540

tttttcatgc cctcctaaaa tttactccta aaaccctagc tataggagcc tcctatccat    600

cctctatttt attccactag aattgattat aaatttagcc tcttaaattt tataagttgg    660

gagtcgaggg taactagagt tgctctaaac ggaccttatc ttcaagtgac ctcagtgagc    720

ccgtttaacg gcgtcgacaa gtctaatcta acggacacca accagagaac caccgccagc    780

gccgagccaa gcgacgttga catcttggcg cggcacggca tctccctggc gtctggtccc    840

ctcccgagac ttccgctcca cctcccaccg gtggcggttt ccgagtccgt tccgcctcct    900

ctcacacggc acgaaacctt gacggcaccg gcagcacggg ggattccgtt cccacggctc    960

cttccctttc ccttcctcgc ccgctgctat aaatagccag ccccatcccc agcttcttcc   1020

ccaacctcat cttctcgtgt tgttcggccc aacccgatcg atccccaatt ccctcgtcgt   1080

ctctcgtcgc gagcctcgtc gatccccgct tcaaggtaca gcgatcgatc gatcatcctc   1140

gctctctcta ccttctctct cttagggcgt gctggttctg ttcctgtttt tccatggctg   1200

cgaggtacaa tagattggcg attcatggtt agggcctgct agttctgttc ctgttttttt   1260

ttttccatgg ctgcgaggca caatagatct gatggcgtta tgatggttaa cttgtcatac   1320

tcttgcgatc tatggtccct ttaggagttt aggacatcga tttaatttcg gatagttcga   1380

gatctgtgat ccatggttag taccctaggc agtggggtta gatccgtgct gttatggttc   1440
```

gtagatggat tctgattgct cagtaactgg gaatcctggg atggttctag ctggttcgca 1500
gataagatcg atttcatgat atgctatatc ttgtttggtt gccgtggttc cgttaaatct 1560
gtctgttatg atcttagtct ttgataaggt tcggtcgtgc tagctacgtc ctgtgcagca 1620
cttaattgtc aggtcataat ttttagcatg cctttttttt attggtttgg ttttgtctga 1680
ctgggctgta gatagtttca atctttgtct gactgggctg tagatagttt caatcttcct 1740
gtctgtttat tttattaaat ttggatctgt atgtgtgtca tatatcttca tcttttagat 1800
atatcgatag gtatatatgt tgctgtcgtt ttttactgtt cctttatgag atatattcat 1860
gcttagatac atgaaacaac gtgctgttac agtttaatag ttcttgttta tctaataaac 1920
aaataaggat aggtgctgca gttagtttta ctggtacttt ttttgacatg aacctacggc 1980
ttaataatta gtcttcatca aataaaaagc atattttta attatttcga tatacttgaa 2040
tgatgtcata tgcagcatct gtgtgaattt ttggccctgt cttcatatga tgtttatttg 2100
cttgggactg tttctttggc tgataactca ccctgttgtt tggtgatcct tctgcaggtg 2160

<210> SEQ ID NO 56
<211> LENGTH: 1024
<212> TYPE: DNA
<213> ORGANISM: Bouteloua gracilis

<400> SEQUENCE: 56
gagaaatcgg ggaaaaatca tgttttggtt gtttttattt ctaacctcca caataacttt 60
ggtttaccat tttttgtttg attttagttt tagagaagcg tttataacag gacctaaaat 120 cttttttga gtacacagta caacgcagac gctcatacac gcacgcacaa tgtcctctat 180
gaacacacgt aaggaaaccc tacaccttga gcaccttcga aggactgagc cggcaaatct 240
agagattctc gaagtcacta ttggcacctc gttatcaacg agaacgtcgc ttaccactta 300
aagcataaca ccgagaaatc ccgtaacaaa tccagtaaaa tacgagcacc cgtaccaagt 360
tgaatatttg aacccgagtg ggtagattcc accgcaaagg acctaaccag atcatttcgc 420
aaacaggaac taaaatcggt agagagccca gacaaaaacc ttttctaaga gcaactccag 480
tgaaagcccc tactttaggt ataaaatgca acactagtgg agcttctaaa taaacttcta 540
tttttcatgc cctcctaaaa tttactccta aaaccctagc tataggagcc tcctatccat 600
cctctatttt attccactag aattgattat aaatttagcc tcttaaattt tataagttgg 660
gagtcgaggg taactagagt tgctctaaac ggaccttatc ttcaagtgac ctcagtgagc 720
ccgtttaacg gcgtcgacaa gtctaatcta acggacacca accagagaac caccgccagc 780
gccgagccaa gcgacgttga catcttggcg cggcacggca tctccctggc gtctggtccc 840
ctcccgagac ttccgctcca cctcccaccg gtggcggttt ccgagtccgt tccgcctcct 900
ctcacacggc acgaaacctt gacggcaccg gcagcacggg ggattccgtt cccacggctc 960
cttccctttc ccttcctcgc ccgctgctat aaatagccag ccccatcccc agcttcttcc 1020
ccaa 1024

<210> SEQ ID NO 57
<211> LENGTH: 1045
<212> TYPE: DNA
<213> ORGANISM: Bouteloua gracilis

<400> SEQUENCE: 57
gtacagcgat cgatcgatca tcctcgctct ctctaccttc tctctcttag ggcgtgctgg 60

-continued

```
ttctgttcct gtttttccat ggctgcgagg tacaatagat tggcgattca tggttagggc    120

ctgctagttc tgttcctgtt ttttttttc catggctgcg aggcacaata gatctgatgg    180

cgttatgatg gttaacttgt catactcttg cgatctatgg tccctttagg agtttaggac    240

atcgatttaa tttcggatag ttcgagatct gtgatccatg gttagtaccc taggcagtgg    300

ggttagatcc gtgctgttat ggttcgtaga tggattctga ttgctcagta actgggaatc    360

ctgggatggt tctagctggt tcgcagataa gatcgatttc atgatatgct atatcttgtt    420

tggttgccgt ggttccgtta aatctgtctg ttatgatctt agtctttgat aaggttcggt    480

cgtgctagct acgtcctgtg cagcacttaa ttgtcaggtc ataattttta gcatgccttt    540

tttttattgg tttggttttg tctgactggg ctgtagatag tttcaatctt tgtctgactg    600

ggctgtagat agtttcaatc ttcctgtctg tttattttat taaatttgga tctgtatgtg    660

tgtcatatat cttcatcttt tagatatatc gataggtata tatgttgctg tcgtttttta    720

ctgttccttt atgagatata ttcatgctta gatacatgaa acaacgtgct gttacagttt    780

aatagttctt gtttatctaa taaacaaata aggataggtg ctgcagttag ttttactggt    840

acttttttg acatgaacct acggcttaat aattagtctt catcaaataa aaagcatatt    900

ttttaattat ttcgatatac ttgaatgatg tcatatgcag catctgtgtg aatttttggc    960

cctgtcttca tatgatgttt atttgcttgg gactgtttct ttggctgata actcaccctg   1020

ttgtttggtg atccttctgc aggtg                                         1045
```

<210> SEQ ID NO 58
<211> LENGTH: 2160
<212> TYPE: DNA
<213> ORGANISM: Bouteloua gracilis

<400> SEQUENCE: 58

```
gagaaatcgg ggaaaaatca tgttttggtt gtttttattt ctaacctcca caataacttt     60

ggtttaccat tttttgtttg attttagttt tagagaagcg tttataacag gacctaaaat    120

cttttttga gtacacagta caacgcagac gctcatacac gcacgcacaa tgtcctctat    180

gaacacacgt aaggaaaccc tacaccttga gcaccttcga aggactgagc cggcaaatct    240

agagattctc gaagtcacta ttggcacctc gttatcaacg agaacgtcgc ttaccactta    300

aagcataaca ccgagaaatc ccgtaacaaa tccagtaaaa tacgagcacc cgtaccaagt    360

tgaatatttg aacccgagtg ggtagattcc accgcaaagg acctaaccag atcatttcgc    420

aaacaggaac taaaatcggt agagagccca gacaaaaacc ttttctaaga gcaactccag    480

tgaaagcccc tactttaggt ataaaatgca acactagtgg agcttctaaa taaacttcta    540

tttttcatgc cctcctaaaa tttactccta aaaccctagc tataggagcc tcctatccat    600

cctctatttt attccactag aattgattat aaatttagcc tcttaaattt tataagttgg    660

gagtcgaggg taactagagt tgctctaaac ggaccttatc ttcaagtgac ctcagtgagc    720

ccgtttaacg gcgtcgacaa gtctaatcta acggacacca accagagaac caccgccagc    780

gccgagccaa gcgacgttga catcttggcg cggcacggca tctccctggc gtctggtccc    840

ctcccgagac ttccgctcca cctcccaccg gtggcggttt ccgagtccgt tccgcctcct    900

ctcacacggc acgaaacctt gacggcaccg gcagcacggg ggattccgtt cccacggctc    960

cttccctttc ccttcctcgc ccgctgctat aaatagccag ccccatcccc agcttcttcc   1020

ccaacctcat cttctcgtgt tgttcggccc aacccgatcg atccccaatt ccctcgtcgt   1080

ctctcgtcgc gagcctcgtc gatccccgct tcaaggtaca gcgatcgatc gatcatcctc   1140
```

-continued gctctctcta ccttctctct cttagggcgt gctggttctg ttcctgtttt tccatggctg 1200
cgaggtacaa tagattggcg attcatggtt agggcctgct agttctgttc ctgttttttt 1260
tttttccatg gctgcgaggc acaatagatc tgatggcgtt atgatggtta acttgtcata 1320
ctcttgcgat ctatggtccc tttaggagtt taggacatcg atttaatttc ggatagttcg 1380
agatctgtga tccatggtta gtaccctagg cagtggggtt agatccgtgc tgttatggtt 1440
cgtagatgga ttctgattgc tcagtaactg ggaatcctgg gatggttcta gctggttcgc 1500
agataagatc gatttcatga tatgctatat cttgtttggt tgccgtggtt ccgttaaatc 1560
tgtctgttat gatcttagtc ttgataaggt tcggtcgtgc tagctacgtc ctgtgcagca 1620
cttaattgtc aggtcataat tttagcatg cctttttttt attggtttgg ttttgtctga 1680
ctgggctgta gatagtttca atctttgtct gactgggctg tagatagttt caatcttcct 1740
gtctgtttat tttattaaat ttggatctgt atgtgtgtca tatatcttca tcttttagat 1800
atatcgatag gtatatatgt tgctgtcgtt ttttactgtt cctttatgag atatattcat 1860
gcttagatac atgaaacaac gtgctgttac agtttaatag ttcttgttta tctaataaac 1920
aaataaggat aggtgctgca gttagtttta ctggtacttt ttttgacatg aacctacggc 1980
ttaataatta gtcttcatca aataaaaagc atatttttta attatttcga tatacttgaa 2040
tgatgtcata tgcagcatct gtgtgaattt ttggccctgt cttcatatga tgtttatttg 2100
cttgggactg tttctttggc tgataactca ccctgttgtt tggtgatcct tctgcaggtg 2160

<210> SEQ ID NO 59
<211> LENGTH: 1045
<212> TYPE: DNA
<213> ORGANISM: Bouteloua gracilis

<400> SEQUENCE: 59
gtacagcgat cgatcgatca tcctcgctct ctctaccttc tctctcttag ggcgtgctgg 60
ttctgttcct gtttttccat ggctgcgagg tacaatagat tggcgattca tggttagggc 120
ctgctagttc tgttcctgtt tttttttttt ccatggctgc gaggcacaat agatctgatg 180
gcgttatgat ggttaacttg tcatactctt gcgatctatg gtccctttag gagtttagga 240
catcgattta atttcggata gttcgagatc tgtgatccat ggttagtacc ctaggcagtg 300
gggttagatc cgtgctgtta tggttcgtag atggattctg attgctcagt aactgggaat 360
cctgggatgg ttctagctgg ttcgcagata agatcgattt catgatatgc tatatcttgt 420
ttggttgccg tggttccgtt aaatctgtct gttatgatct tagtcttgat aaggttcggt 480
cgtgctagct acgtcctgtg cagcacttaa ttgtcaggtc ataattttta gcatgccttt 540
tttttattgg tttggttttg tctgactggg ctgtagatag tttcaatctt tgtctgactg 600
ggctgtagat agtttcaatc ttcctgtctg tttattttat taaatttgga tctgtatgtg 660
tgtcatatat cttcatcttt tagatatatc gataggtata tatgttgctg tcgtttttta 720
ctgttccttt atgagatata ttcatgctta gatacatgaa acaacgtgct gttacagttt 780
aatagttctt gtttatctaa taaacaaata aggataggtg ctgcagttag ttttactggt 840
actttttttg acatgaacct acggcttaat aattagtctt catcaaataa aaagcatatt 900
ttttaattat ttcgatatac ttgaatgatg tcatatgcag catctgtgtg aatttttggc 960
cctgtcttca tatgatgttt atttgcttgg gactgtttct ttggctgata actcaccctg 1020
ttgtttggtg atccttctgc aggtg 1045

<210> SEQ ID NO 60
<211> LENGTH: 1885
<212> TYPE: DNA
<213> ORGANISM: Bouteloua gracilis

<400> SEQUENCE: 60
caacgagaac gtcgcttacc acttaaagca taacaccgag aaatcccgta acaaatccag 60
taaaatacga gcacccgtac caagttgaat atttgaaccc gagtgggtag attccaccgc 120
aaaggaccta accagatcat ttcgcaaaca ggaactaaaa tcggtagaga gcccagacaa 180 aaacctttc taagagcaac tccagtgaaa gcccctactt taggtataaa atgcaacact 240
agtggagctt ctaaataaac ttctattttt catgccctcc taaaatttac tcctaaaacc 300
ctagctatag gagcctccta tccatcctct attttattcc actagaattg attataaatt 360
tagcctctta aattttataa gttgggagtc gagggtaact agagttgctc taaacggacc 420
ttatcttcaa gtgacctcag tgagcccgtt taacggcgtc gacaagtcta atctaacgga 480
caccaaccag agaaccaccg ccagcgccga gccaagcgac gttgacatct tggcgcggca 540
cggcatctcc ctggcgtctg gtcccctccc gagacttccg ctccacctcc caccggtggc 600
ggtttccgag tccgttccgc ctcctctcac acggcacgaa accttgacgg caccggcagc 660
acgggggatt ccgttcccac ggctccttcc ctttcccttc ctcgcccgct gctataaata 720
gccagcccca tccccagctt cttccccaac ctcatcttct cgtgttgttc ggcccaaccc 780
gatcgatccc caattccctc gtcgtctctc gtcgcgagcc tcgtcgatcc ccgcttcaag 840
gtacagcgat cgatcgatca tcctcgctct ctctaccttc tctctcttag ggcgtgctgg 900
ttctgttcct gtttttccat ggctgcgagg tacaatagat tggcgattca tggttagggc 960
ctgctagttc tgttcctgtt ttttttttt ccatggctgc gaggcacaat agatctgatg 1020
gcgttatgat ggttaacttg tcatactctt gcgatctatg gtccctttag gagtttagga 1080
catcgattta atttcggata gttcgagatc tgtgatccat ggttagtacc ctaggcagtg 1140
gggttagatc cgtgctgtta tggttcgtag atggattctg attgctcagt aactgggaat 1200
cctgggatgg ttctagctgg ttcgcagata agatcgattt catgatatgc tatatcttgt 1260
ttggttgccg tggttccgtt aaatctgtct gttatgatct tagtcttgat aaggttcggt 1320
cgtgctagct acgtcctgtg cagcacttaa ttgtcaggtc ataattttta gcatgccttt 1380
tttttattgg tttggttttg tctgactggg ctgtagatag tttcaatctt tgtctgactg 1440
ggctgtagat agtttcaatc ttcctgtctg tttattttat taaatttgga tctgtatgtg 1500
tgtcatatat cttcatcttt tagatatatc gataggtata tatgttgctg tcgtttttta 1560
ctgttccttt atgagatata ttcatgctta gatacatgaa acaacgtgct gttacagttt 1620
aatagttctt gtttatctaa taaacaaata aggataggtg ctgcagttag ttttactggt 1680 acttttttg acatgaacct acggcttaat aattagtctt catcaaataa aaagcatatt 1740
ttttaattat ttcgatatac ttgaatgatg tcatatgcag catctgtgtg aatttttggc 1800
cctgtcttca tatgatgttt atttgcttgg gactgtttct ttggctgata actcaccctg 1860
ttgtttggtg atccttctgc aggtg 1885

<210> SEQ ID NO 61
<211> LENGTH: 749
<212> TYPE: DNA
<213> ORGANISM: Bouteloua gracilis

<400> SEQUENCE: 61

-continued

```
caacgagaac gtcgcttacc acttaaagca taacaccgag aaatcccgta acaaatccag      60
taaaatacga gcacccgtac caagttgaat atttgaaccc gagtgggtag attccaccgc     120
aaaggaccta accagatcat ttcgcaaaca ggaactaaaa tcggtagaga gcccagacaa     180
aaacctttc taagagcaac tccagtgaaa gcccctactt taggtataaa atgcaacact      240
agtggagctt ctaaataaac ttctattttt catgccctcc taaaatttac tcctaaaacc     300
ctagctatag gagcctccta tccatcctct attttattcc actagaattg attataaatt     360
tagcctctta aattttataa gttgggagtc gagggtaact agagttgctc taaacggacc     420
ttatcttcaa gtgacctcag tgagcccgtt taacggcgtc gacaagtcta atctaacgga     480
caccaaccag agaaccaccg ccagcgccga gccaagcgac gttgacatct tggcgcggca     540
cggcatctcc ctggcgtctg gtcccctccc gagacttccg ctccacctcc caccggtggc     600
ggtttccgag tccgttccgc ctcctctcac acggcacgaa accttgacgg caccggcagc     660
acgggggatt ccgttcccac ggctccttcc ctttcccttc ctcgcccgct gctataaata     720
gccagcccca tccccagctt cttccccaa                                       749
```

<210> SEQ ID NO 62
<211> LENGTH: 6813
<212> TYPE: DNA
<213> ORGANISM: Miscanthus sinesis

<400> SEQUENCE: 62

```
agcagactcg cattatcgat gggggaaatg aaattcagcg tttgacgtgg atgcaacaac      60
tgcactgcac aggatatctt agccgttgtg tcgaagtttg ctttgctaac gttttgagaa     120
aaccagcttt gaccaacacg agacgagcgc cttacgtttg gcacaatgta atgtagcccg     180
gcacggcaag ttagactagt atattgtgtt agccggcctc tttacgtttg gcacagttta     240
attgaatccg gcatggcaag ttagactgga gtgtgagccg gtcattgcaa agttattatg     300
acatatatat aagagcacaa gtgtataata agataatgta agcaaggcag caagctatat     360
gaattgtcac gttatattta tgttgagatg ttgagatgaa gaagagaaaa taaacagcct     420
ataaattcat agcgagtgat agacgggcac aaggcctcct atttcttaaa ccgaattttg     480
taagaacaaa aaaaaggact tataggagaa tgggatagac catatatcaa cgggaaaggt     540
acacgttgct cgagtgtttt aggcgttctg ctcactcgat cctgtagctg tccgatctgc     600
ggcgtcaaca cggcgcgcaa caagcggtgg cgggcccctc ggtagccgcg gtcggaccgg     660
acgatggcct atggcgaccc gcggcctggg cgtggcctgt gcgtgcatgc gccataggtc     720
ccggtgcatg gtgcaggcgg caggtgcatg tgcatggagt aggctttggt gctggtgcag     780
gctttggtca ggtgcaggag gggtaggttg cgcaggtgag aggtgaggtg catgctgacc     840
cgtcacatca ccttactcct agcccctaag tcttgcatgt atgcagattt attcttttag     900
cagcgacaga ttcagcagcg agagaccggc taccgtagca ttttcatttt tatttgataa     960
ttagtattta attatggact aattaggttc aaaatattcg tctcgcgatt tccaaccaaa    1020
ctgtgcaatt agttttttc gtctacattt aatgctctat acacgtatca caagattcaa     1080
cgtgatggct actgtagcac tttttgaaaa aactttttgc aactaaacaa ggcctgaggt    1140
atcgtttaaa tttaggtaca aaaaatataa gggtgtcaca tcgaatgtta cacgagatat    1200
catatgtgag tgttcggata gtaataataa aataaattac acaagtcctt agtaatccac    1260
gagacgaatt tattgagtct aattaatcag tcattagcac atggtgcatt catgcatctg    1320
```

-continued

```
catattattt tgtgttgctt ggttgaaagt tggatttcaa attgagttga atttgcattt   1380
tgaaattgct ttggaaaaat tagaaaaaaa gaaaaaaaat gaatttccct ccctcctttc   1440
tcatttccct gctttcggcc cctctgtgta gaactattcg agttctcagg tcgagtgctc   1500
gaatcatcta gcttctcttt tttgaggaga gccagagagc cagattcaga atagccagcc   1560
tcctttttag gagagagctc atccccttt atagttgaag gcagcgacga agccagcggg   1620
gggctacccg tgctccagcc tccctacggc catgatttac atggaacccg ggcttagctc   1680
gggctaccgc catgaggagg aagaagaaga taaggagggg ctagaggaag aagaagagga   1740
agctagccct ggcttcgtcg attcctggct tcgtcgctgg ttgaagggga tgggctctta   1800
caagtcagag aaagagagag aatgtatacg tgtgctatct agtcttgttg cccacgctgt   1860
caggtacgag acggttgtcg gcgcccacaa tactgtttat gtccagatgc atgtggcagg   1920
ctctaccgtg ttcgcctgtt atggcaaatg tcggcgcata caatactatt tgggttctga   1980
cacgcctgaa aggttgcata gtgcctatct ggcatggcct ggtggcaccg tccggcatgt   2040
gcgcaggata tgccagggta cggtccttgg tattacggtt tgacttgagc gccttacctt   2100
atctgctccg cctgatcccc gggctcttac cgagcgggcg tccccggtcg gtcgttccca   2160
gtcggccccg actgtgtcgg tcggggaaga gctgcaagca gaggtccggc gtatccccga   2220
tcgaaaaagg aagtcggagt cagactatgt ctccacctta gccaggcctt ccggtcgggg   2280
atcggatcat tctcccggcc tgtcattagg tatctgggtc ggcccgagag gtgtgcgttg   2340
tcgctacgct gtctgctggg ccgagtttct gttgggaagc gggtccattg gggaccccgg   2400
gtttatgaac ccgacacgtg gtcactatgc tgcatactcc ctatacagcc gctgaccagt   2460
acgctggttc accgcgtcgc ccgcgcggga cggaatggga tgtcacgacc cgctgaacgc   2520
cggggcatgg catcagcggc gaacaggcac ccggcgtgga gctgtccgtg tcaccatcta   2580
cagtgttgac gggacccgca taaaaggaga aaaaaggccc gacggtcctg gaagccttcc   2640
tctccttagc tcttctccct ctttctctct gtgtaacctg ctcttcccct tcgtctataa   2700
aaagggaagt aggacgtccc aggaagagaa gggcggttca ccactctaca tggctataga   2760
cataaaaaca cacgccttgg gagcacactc acatcagaga cttgggacct atccctctct   2820
cgctcgtttg taacccctac tacaaacttt tagtgctagt aacacgagca gcagcgacga   2880
actagacgta aggactttct gcccgaacca gtataaacat cgtgtcatct aagcacacca   2940
tacgagccag acgcgcaata ctagaaattt actagtcggt aactcgaaac accgacatct   3000
agctaatctt tttgttttat ttggtttccc tttgaaatct tctaatttag ctttcataga   3060
aataatctag gtattttta ttttatatgt tctatctgtt tgcattaatt ttgatcattt   3120
gatctgaatg ctgtggtcac gagaatcgag tgtttcatgg ccttaaaaca ctcgattatg   3180
ccatctgacc cgttttcaac cattctagtg tttctgagct atatcaatgg tgcagcatgt   3240
tagtatacat atctaactat tactccgtat atgagtgagt tgttaaattt attccaggtg   3300
aaatggcatt aacgatagcc aataggcggc taaattaata gccatactct aacagctcta   3360
aaaaacatat attcatcgag gcacctttat gcaaccacat agtcaacttc aacgtcgctt   3420
gcgtgcgttc tcaagtttc tttcttgcaa attacatttt ttttaaaaaa aagtataatt   3480
tgtatcgtgc gattttttct ctctaggtgt gcgtgactgt gggagtaaca attttgaatc   3540
tcaagaagga aataaaagaa taatactgct gcctactttg aggatttcag tattttctc   3600
taaaatgttt tggtgtgata tctaaaccgt ctttaaagcc aattgctcaa gattcattca   3660
acaattgaaa cgtctcacat gactaaatga tataaggttg ctaaggtctt tcttgataag   3720
```

```
cttttttatg aatttcatct aaattttcga gtgaaactat taaatactaa ggttgctaag   3780
tgtcattctc gctcgagaag tctaacgctt taaactttaa ccaaatatat acaagaaaat   3840
attaatattt atagtacata attagtatca ttagatagat cgttgaatct attttcataa   3900
caaacttatt tgaagaaaca aatgttgttc atatatttct atatacgaat accatagcga   3960
cacttatttt agaatgtagg gagtactccc tttgtgccgc tttgagtgtc gctttggcag   4020
ctagtaccta tgtccacctt cacagcttgt gcctagtacc tagactcttt ctctgtccac   4080
attcatttaa tctctgttgt accttgttcg gagataaaac gactctgata aagggacgag   4140
gaagtagtat gttagaggag tgaagtctac tccctttgcc gcaaaaaggt aatcctaagt   4200
gtgaattgta ttctttttttg accaaaggaa tatacaacaa gaatgatgtc atcatcatgc   4260
ttcgatcctt ttttttggta aagcttgagc ttctgtaaaa atagagaaat catgggaaaa   4320
atcacgtttt ggtggttttg atttctagcc tccacaataa ctttggtttt actatttttt   4380
gtttgatttt agtttcagaa gtccactttt gtacgtgctc gtagagccta aacaaaaggc   4440
tttccaaaac gaccttatct tcgagtgttg taaaaaaaat gagcccgttt aacggcgtcg   4500
acaagtctaa cggacaccaa ccagcgaacc accagcgccg agccaagcga agcagactgc   4560
agacggcacg gccgagacgt tgacaccttg gcgcggcaac ggcatctctc tggccccctc   4620
tcgagagttc cgctccacct ccgcatccac ctccacctcc acctccaccg gtggcggttt   4680
ccaagtccgt cccgttccgc cacctgctcc tctcacacgg cacgaaaccg tcacggcacc   4740
ggcagcacag cacgggggat tcctttccca ccgctccgtc cctttctctt cctcgcccgc   4800
ccgttataaa tagccagccc catccctcgt ctctcgtgtt gttcggagcg cacacacaac   4860
ccgatcccca atcaatcgat ccccgcttca aggtacggcg atcctcctcc ctctctctct   4920
accttctctt ctctacacta gatcggcggt ccatggttag ggcctgctag ttccgttcct   4980
gtttttccat ggctgcgagg tacaatagat ctgatggcgt tatgatggtt aacttgtcat   5040
gcttttgcga tttatagtcc ctttagatag ttcgagatcg gtgatccatg gttagtaccc   5100
taggctgtgg agtcgggtta gatccgcgct gttagggttc gtatatggag gcgagctgtt   5160
ctgattgtta acttgctggg aatcctggga tggttctagc tgttccgcag atgagatcga   5220
tttcatgatc tgctgtatct atccgtggta tgatgttagc ctttgatatg gttcgatcgt   5280
gctagctacg tcctgtgcac ttaattgtca ggtcataatt tttactatac ttttttttttg   5340
gtttggtttg gtttcgtctg atttggctgt cgttctagat cagagtagaa actgtttcaa   5400
actacctgtt ggatttatta aggtagcgtt tggttcctgg tatcgaatca tacacgcacc   5460
agtgcatctt ggatagccag ctggggccca cctgtccaac cgtttggttg ccggatcgaa   5520
cgagtccatt caagaccgaa ccatgcagag caatcgaata ttctcttgtg acgctgtatc   5580
atccagttcg gcaaaaaaca ccgaatgccg ccatacagga caccgtactg agcgtctgca   5640
actctgcatc ccgctcactg ctcacatctc cgcttgccgc ctcacccatc cgactcagac   5700
cagagccaca cggattactg ctgctggtgt gtgtattaac aaaagatcca tttgaccgga   5760
gcacatgcag cttggatgga aaaaatttat tatattcgtc agtgctgcat atgtactcat   5820
acttgcatga tggttttatt tattcgacct catcagtcct ggcactatgg aaagtcattg   5880
tagtatagat tttttaatat aatataaatc attggtgact tatcttgctt aattttattt   5940
tcttattatg aaatatcgtt gcattcataa tagcaaattt gtgcaaatat atagaatcta   6000
cgtgaaattc ttggttggac caatacaaca aacccctcaa acattctctt gtactgaacc   6060
```

ataccattcc gtacaaccat ccaaacaaaa atcatgtatc atcatgtaca tgtaaccaaa 6120
caattaacac gcaccatcct attcagactt gtctcatcca taatctatcc atccaggatg 6180
atccatccca ttcatctata tacacccaat caaacgctac ctaaaatttg gatctgtatg 6240
tgtcacatat atcttaataa gatggatgga aatatctctt tatcttttag atatggatag 6300
gtatatatgt tgctgtgggt ttgttagtta tatatatacg tgcttacata cgtgaagaaa 6360
cctgctgcta cagtttaata attcttgttc atctcaacaa ataacgatag gcgtatatgt 6420
tgctgtgttt tttactggta ctttgttaga tatatacatg cttacataca tgaagaacac 6480
atgctacagt tcaaaaattc ttgttcatct cataaacaaa aaggaggtgt atatgttgct 6540
gtgggtttta ctggtacttt attagatata tacatgctta catagatgaa gcaacatgct 6600
gctatggtgt ttaataatta ttgtttatct aataaacaaa catgcttttt aattatcttg 6660
atatgtttgg atgatggcat atgcagcagc tatgtgtgga ttttaaatac ccagcatcat 6720
gagcatgcat gaccctgcct tagtatgcag ttatttgctt gagactgttt cttttgttga 6780
tactcatcct ttagttcggt cactcttctg cag 6813

<210> SEQ ID NO 63
<211> LENGTH: 5359
<212> TYPE: DNA
<213> ORGANISM: Miscanthus sinesis

<400> SEQUENCE: 63
agcagactcg cattatcgat gggggaaatg aaattcagcg tttgacgtgg atgcaacaac 60
tgcactgcac aggatatctt agccgttgtg tcgaagtttg ctttgctaac gttttgagaa 120
aaccagcttt gaccaacacg agacgagcgc cttacgtttg gcacaatgta atgtagcccg 180
gcacggcaag ttagactagt atattgtgtt agccggcctc tttacgtttg gcacagttta 240
attgaatccg gcatggcaag ttagactgga gtgtgagccg gtcattgcaa agttattatg 300
acatatatat aagagcacaa gtgtataata agataatgta agcaaggcag caagctatat 360
gaattgtcac gttatattta tgttgagatg ttgagatgaa gaagagaaaa taaacagcct 420
ataaattcat agcgagtgat agacgggcac aaggcctcct atttcttaaa ccgaattttg 480
taagaacaaa aaaaaggact tataggagaa tgggatagac catatatcaa cgggaaaggt 540
acacgttgct cgagtgtttt aggcgttctg ctcactcgat cctgtagctg tccgatctgc 600
ggcgtcaaca cggcgcgcaa caagcggtgg cgggcccctc ggtagccgcg gtcggaccgg 660
acgatggcct atggcgaccc gcggcctggg cgtggcctgt gcgtgcatgc gccataggtc 720
ccggtgcatg gtgcaggcgg caggtgcatg tgcatggagt aggctttggt gctggtgcag 780
gctttggtca ggtgcaggag gggtaggttg cgcaggtgag aggtgaggtg catgctgacc 840
cgtcacatca ccttactcct agcccctaag tcttgcatgt atgcagattt attcttttag 900
cagcgacaga ttcagcagcg agagaccggc taccgtagca ttttcatttt tatttgataa 960
ttagtattta attatggact aattaggttc aaaatattcg tctcgcgatt tccaaccaaa 1020
ctgtgcaatt agtttttttc gtctacattt aatgctctat acacgtatca caagattcaa 1080
cgtgatggct actgtagcac tttttgaaaa aactttttgc aactaaacaa ggcctgaggt 1140
atcgtttaaa tttaggtaca aaaaatataa gggtgtcaca tcgaatgtta cacgagatat 1200
catatgtgag tgttcggata gtaataataa aataaattac acaagtcctt agtaatccac 1260
gagacgaatt tattgagtct aattaatcag tcattagcac atggtgcatt catgcatctg 1320
catattattt tgtgttgctt ggttgaaagt tggatttcaa attgagttga atttgcattt 1380
tgaaattgct ttggaaaaat tagaaaaaaa gaaaaaaaat gaatttccct ccctcctttc 1440
tcatttccct gctttcggcc cctctgtgta gaactattcg agttctcagg tcgagtgctc 1500
gaatcatcta gcttctcttt tttgaggaga gccagagagc cagattcaga atagccagcc 1560
tcctttttag gagagagctc atcccctttt atagttgaag gcagcgacga agccagcggg 1620
gggctacccg tgctccagcc tccctacggc catgatttac atggaacccg ggcttagctc 1680
gggctaccgc catgaggagg aagaagaaga taaggagggg ctagaggaag aagaagagga 1740
agctagccct ggcttcgtcg attcctggct tcgtcgctgg ttgaagggga tgggctctta 1800
caagtcagag aaagagagag aatgtatacg tgtgctatct agtcttgttg cccacgctgt 1860
caggtacgag acggttgtcg gcgcccacaa tactgtttat gtccagatgc atgtggcagg 1920
ctctaccgtg ttcgcctgtt atggcaaatg tcggcgcata caatactatt tgggttctga 1980
cacgcctgaa aggttgcata gtgcctatct ggcatggcct ggtggcaccg tccggcatgt 2040
gcgcaggata tgccagggta cggtccttgg tattacggtt tgacttgagc gccttacctt 2100
atctgctccg cctgatcccc gggctcttac cgagcgggcg tccccggtcg gtcgttccca 2160
gtcggccccg actgtgtcgg tcggggaaga gctgcaagca gaggtccggc gtatccccga 2220
tcgaaaaagg aagtcggagt cagactatgt ctccacctta gccaggcctt ccggtcgggg 2280
atcggatcat tctcccggcc tgtcattagg tatctgggtc ggcccgagag gtgtgcgttg 2340
tcgctacgct gtctgctggg ccgagtttct gttgggaagc gggtccattg gggaccccgg 2400
gtttatgaac ccgacacgtg gtcactatgc tgcatactcc ctatacagcc gctgaccagt 2460
acgctggttc accgcgtcgc ccgcgcggga cggaatggga tgtcacgacc cgctgaacgc 2520
cggggcatgg catcagcggc gaacaggcac ccggcgtgga gctgtccgtg tcaccatcta 2580
cagtgttgac gggacccgca taaaaggaga aaaaaggccc gacggtcctg gaagccttcc 2640
tctccttagc tcttctccct ctttctctct gtgtaacctg ctcttcccct tcgtctataa 2700
aaagggaagt aggacgtccc aggaagagaa gggcggttca ccactctaca tggctataga 2760
cataaaaaca cacgccttgg gagcacactc acatcagaga cttgggacct atccctctct 2820
cgctcgtttg taacccctac tacaaacttt tagtgctagt aacacgagca gcagcgacga 2880
actagacgta aggactttct gcccgaacca gtataaacat cgtgtcatct aagcacacca 2940
tacgagccag acgcgcaata ctagaaattt actagtcggt aactcgaaac accgacatct 3000
agctaatctt tttgttttat ttggtttccc tttgaaatct tctaatttag ctttcataga 3060
aataatctag gtatttttta ttttatatgt tctatctgtt tgcattaatt ttgatcattt 3120
gatctgaatg ctgtggtcac gagaatcgag tgtttcatgg ccttaaaaca ctcgattatg 3180
ccatctgacc cgttttcaac cattctagtg tttctgagct atatcaatgg tgcagcatgt 3240
tagtatacat atctaactat tactccgtat atgagtgagt tgttaaattt attccaggtg 3300
aaatggcatt aacgatagcc aataggcggc taaattaata gccatactct aacagctcta 3360
aaaaacatat attcatcgag gcacctttat gcaaccacat agtcaacttc aacgtcgctt 3420
gcgtgcgttc tcaagttttc tttcttgcaa attacatttt ttttaaaaaa aagtataatt 3480
tgtatcgtgc gatttttttct ctctaggtgt gcgtgactgt gggagtaaca attttgaatc 3540
tcaagaagga aataaaagaa taatactgct gcctactttg aggatttcag tatttttctc 3600
taaaatgttt tggtgtgata tctaaaccgt ctttaaagcc aattgctcaa gattcattca 3660
acaattgaaa cgtctcacat gactaaatga tataaggttg ctaaggtctt tcttgataag 3720

```
cttttttatg aatttcatct aaattttcga gtgaaactat taaatactaa ggttgctaag   3780
tgtcattctc gctcgagaag tctaacgctt taaactttaa ccaaatatat acaagaaaat   3840
attaatattt atagtacata attagtatca ttagatagat cgttgaatct attttcataa   3900
caaacttatt tgaagaaaca aatgttgttc atatatttct atatacgaat accatagcga   3960
cacttatttt agaatgtagg gagtactccc tttgtgccgc tttgagtgtc gctttggcag   4020
ctagtaccta tgtccacctt cacagcttgt gcctagtacc tagactcttt ctctgtccac   4080
attcatttaa tctctgttgt accttgttcg gagataaaac gactctgata aagggacgag   4140
gaagtagtat gttagaggag tgaagtctac tccctttgcc gcaaaaaggt aatcctaagt   4200
gtgaattgta ttcttttttg accaaaggaa tatacaacaa gaatgatgtc atcatcatgc   4260
ttcgatcctt ttttttggta aagcttgagc ttctgtaaaa atagagaaat catgggaaaa   4320
atcacgtttt ggtggttttg atttctagcc tccacaataa ctttggtttt actatttttt   4380
gtttgatttt agtttcagaa gtccactttt gtacgtgctc gtagagccta aacaaaaggc   4440
tttccaaaac gaccttatct tcgagtgttg taaaaaaaat gagcccgttt aacggcgtcg   4500
acaagtctaa cggacaccaa ccagcgaacc accagcgccg agccaagcga agcagactgc   4560
agacggcacg gccgagacgt tgacaccttg gcgcggcaac ggcatctctc tggccccctc   4620
tcgagagttc cgctccacct ccgcatccac ctccacctcc acctccaccg gtggcggttt   4680
ccaagtccgt cccgttccgc cacctgctcc tctcacacgg cacgaaaccg tcacggcacc   4740
ggcagcacag cacgggggat tcctttccca ccgctccgtc cctttctctt cctcgcccgc   4800
ccgttataaa tagccagccc catccctcgt ctctcgtgtt gttcggagcg cacacacaac   4860
ccgatcccca atcaatcgat ccccgcttca aggtacggcg atcctcctcc ctctctctct   4920
accttctctt ctctacacta gatcggcggt ccatggttag ggcctgctag ttccgttcct   4980
gtttttccat ggctgcgagg tacaatagat ctgatggcgt tatgatggtt aacttgtcat   5040
gcttttgcga tttatagtcc ctttagatag ttcgagatcg gtgatccatg gttagtaccc   5100
taggctgtgg agtcgggtta gatccgcgct gttagggttc gtatatggag gcgagctgtt   5160
ctgattgtta acttgctggg aatcctggga tggttctagc tgttccgcag atgagatcga   5220
tttcatgatc tgctgtatct atccgtggta tgatgttagc ctttgatatg gttcgatcgt   5280
gctagctacg tcctgtgcac ttaattgtca ggtcataatt tttactatac ttttttttg   5340
gtttggtttg gtttcgtct                                                5359
```

<210> SEQ ID NO 64
<211> LENGTH: 63
<212> TYPE: DNA
<213> ORGANISM: Miscanthus sinesis

<400> SEQUENCE: 64

```
gatttggctg tcgttctaga tcagagtaga aactgtttca aactacctgt tggatttatt     60
aag                                                                  63
```

<210> SEQ ID NO 65
<211> LENGTH: 1391
<212> TYPE: DNA
<213> ORGANISM: Miscanthus sinesis

<400> SEQUENCE: 65

```
gtagcgtttg gttcctggta tcgaatcata cacgcaccag tgcatcttgg atagccagct     60
ggggcccacc tgtccaaccg tttggttgcc ggatcgaacg agtccattca agaccgaacc    120
```

atgcagagca atcgaatatt ctcttgtgac gctgtatcat ccagttcggc aaaaaacacc 180
gaatgccgcc atacaggaca ccgtactgag cgtctgcaac tctgcatccc gctcactgct 240
cacatctccg cttgccgcct cacccatccg actcagacca gagccacacg gattactgct 300
gctggtgtgt gtattaacaa aagatccatt tgaccggagc acatgcagct tggatggaaa 360
aaatttatta tattcgtcag tgctgcatat gtactcatac ttgcatgatg gttttattta 420
ttcgacctca tcagtcctgg cactatggaa agtcattgta gtatagattt tttaatataa 480
tataaatcat tggtgactta tcttgcttaa ttttattttc ttattatgaa atatcgttgc 540
attcataata gcaaatttgt gcaaatatat agaatctacg tgaaattctt ggttggacca 600
atacaacaaa cccctcaaac attctcttgt actgaaccat accattccgt acaaccatcc 660
aaacaaaaat catgtatcat catgtacatg taaccaaaca attaacacgc accatcctat 720
tcagacttgt ctcatccata atctatccat ccaggatgat ccatcccatt catctatata 780
cacccaatca aacgctacct aaaatttgga tctgtatgtg tcacatatat cttaataaga 840
tggatggaaa tatctcttta tcttttagat atggataggt atatatgttg ctgtgggttt 900
gttagttata tatatacgtg cttacatacg tgaagaaacc tgctgctaca gtttaataat 960
tcttgttcat ctcaacaaat aacgataggc gtatatgttg ctgtgttttt tactggtact 1020
ttgttagata tatacatgct tacatacatg aagaacacat gctacagttc aaaaaattctt 1080 gttcatctca taaacaaaaa ggaggtgtat atgttgctgt gggttttact ggtactttat 1140
tagatatata catgcttaca tagatgaagc aacatgctgc tatggtgttt aataattatt 1200
gtttatctaa taaacaaaca tgctttttaa ttatcttgat atgtttggat gatggcatat 1260
gcagcagcta tgtgtggatt ttaaataccc agcatcatga gcatgcatga ccctgcctta 1320
gtatgcagtt atttgcttga gactgtttct tttgttgata ctcatccttt agttcggtca 1380
ctcttctgca g 1391

<210> SEQ ID NO 66
<211> LENGTH: 4402
<212> TYPE: DNA
<213> ORGANISM: Miscanthus sinesis

<400> SEQUENCE: 66
cacgtggtca ctatgctgca tactccctat acagccgctg accagtacgc tggttcaccg 60
cgtcgcccgc gcgggacgga atgggatgtc acgacccgct gaacgccggg gcatggcatc 120
agcggcgaac aggcacccgg cgtggagctg tccgtgtcac catctacagt gttgacggga 180
cccgcataaa aggagaaaaa aggcccgacg gtcctggaag ccttcctctc cttagctctt 240
ctccctcttt ctctctgtgt aacctgctct tccccttcgt ctataaaaag ggaagtagga 300
cgtcccagga agagaagggc ggttcaccac tctacatggc tatagacata aaaacacacg 360
ccttgggagc acactcacat cagagacttg ggacctatcc ctctctcgct cgtttgtaac 420
ccctactaca aacttttagt gctagtaaca cgagcagcag cgacgaacta gacgtaagga 480
ctttctgccc gaaccagtat aaacatcgtg tcatctaagc acaccatacg agccagacgc 540
gcaatactag aaatttacta gtcggtaact cgaaacaccg acatctagct aatctttttg 600
ttttatttgg tttccctttg aaatcttcta atttagcttt catagaaata atctaggtat 660
tttttatttt atatgttcta tctgtttgca ttaattttga tcatttgatc tgaatgctgt 720
ggtcacgaga atcgagtgtt tcatggcctt aaaacactcg attatgccat ctgacccgtt 780

-continued

```
ttcaaccatt ctagtgtttc tgagctatat caatggtgca gcatgttagt atacatatct    840
aactattact ccgtatatga gtgagttgtt aaatttattc caggtgaaat ggcattaacg    900
atagccaata ggcggctaaa ttaatagcca tactctaaca gctctaaaaa acatatattc    960
atcgaggcac ctttatgcaa ccacatagtc aacttcaacg tcgcttgcgt gcgttctcaa   1020
gttttctttc ttgcaaatta catttttttt aaaaaaaagt ataatttgta tcgtgcgatt   1080
ttttctctct aggtgtgcgt gactgtggga gtaacaattt tgaatctcaa gaaggaaata   1140
aaagaataat actgctgcct actttgagga tttcagtatt tttctctaaa atgttttggt   1200
gtgatatcta aaccgtcttt aaagccaatt gctcaagatt cattcaacaa ttgaaacgtc   1260
tcacatgact aaatgatata aggttgctaa ggtctttctt gataagcttt tttatgaatt   1320
tcatctaaat tttcgagtga aactattaaa tactaaggtt gctaagtgtc attctcgctc   1380
gagaagtcta acgctttaaa ctttaaccaa atatatacaa gaaaatatta atatttatag   1440
tacataatta gtatcattag atagatcgtt gaatctattt tcataacaaa cttatttgaa   1500
gaaacaaatg ttgttcatat atttctatat acgaatacca tagcgacact tattttagaa   1560
tgtagggagt actccctttg tgccgctttg agtgtcgctt tggcagctag tacctatgtc   1620
caccttcaca gcttgtgcct agtacctaga ctctttctct gtccacattc atttaatctc   1680
tgttgtacct tgttcggaga taaaacgact ctgataaagg gacgaggaag tagtatgtta   1740
gaggagtgaa gtctactccc tttgccgcaa aaaggtaatc ctaagtgtga attgtattct   1800
tttttgacca aaggaatata caacaagaat gatgtcatca tcatgcttcg atcctttttt   1860
ttggtaaagc ttgagcttct gtaaaaatag agaaatcatg ggaaaaatca cgttttggtg   1920
gttttgattt ctagcctcca caataacttt ggttttacta ttttttgttt gattttagtt   1980
tcagaagtcc acttttgtac gtgctcgtag agcctaaaca aaaggctttc caaaacgacc   2040
ttatcttcga gtgttgtaaa aaaaatgagc ccgtttaacg gcgtcgacaa gtctaacgga   2100
caccaaccag cgaaccacca gcgccgagcc aagcgaagca gactgcagac ggcacggccg   2160
agacgttgac accttggcgc ggcaacggca tctctctggc cccctctcga gagttccgct   2220
ccacctccgc atccacctcc acctccacct ccaccggtgg cggtttccaa gtccgtcccg   2280
ttccgccacc tgctcctctc acacggcacg aaaccgtcac ggcaccggca gcacagcacg   2340
ggggattcct ttcccaccgc tccgtccctt tctcttcctc gcccgcccgt tataaatagc   2400
cagccccatc cctcgtctct cgtgttgttc ggagcgcaca cacaacccga tccccaatca   2460
atcgatcccc gcttcaaggt acggcgatcc tcctccctct ctctctacct tctcttctct   2520
acactagatc ggcggtccat ggttagggcc tgctagttcc gttcctgttt ttccatggct   2580
gcgaggtaca atagatctga tggcgttatg atggttaact tgtcatgctt ttgcgattta   2640
tagtcccttt agatagttcg agatcggtga tccatggtta gtaccctagg ctgtggagtc   2700
gggttagatc cgcgctgtta gggttcgtat atggaggcga gctgttctga ttgttaactt   2760
gctgggaatc ctgggatggt tctagctgtt ccgcagatga gatcgatttc atgatctgct   2820
gtatctatcc gtggtatgat gttagccttt gatatggttc gatcgtgcta gctacgtcct   2880
gtgcacttaa ttgtcaggtc ataattttta ctatactttt tttttggttt ggtttggttt   2940
cgtctgattt ggctgtcgtt ctagatcaga gtagaaactg tttcaaacta cctgttggat   3000
ttattaaggt agcgtttggt tcctggtatc gaatcataca cgcaccagtg catcttggat   3060
agccagctgg ggcccacctg tccaaccgtt tggttgccgg atcgaacgag tccattcaag   3120
accgaaccat gcagagcaat cgaatattct cttgtgacgc tgtatcatcc agttcggcaa   3180
```

aaaacaccga atgccgccat acaggacacc gtactgagcg tctgcaactc tgcatcccgc 3240
tcactgctca catctccgct tgccgcctca cccatccgac tcagaccaga gccacacgga 3300
ttactgctgc tggtgtgtgt attaacaaaa gatccatttg accggagcac atgcagcttg 3360
gatggaaaaa atttattata ttcgtcagtg ctgcatatgt actcatactt gcatgatggt 3420
tttatttatt cgacctcatc agtcctggca ctatggaaag tcattgtagt atagattttt 3480
taatataata taaatcattg gtgacttatc ttgcttaatt ttattttctt attatgaaat 3540
atcgttgcat tcataatagc aaatttgtgc aaatatatag aatctacgtg aaattcttgg 3600
ttggaccaat acaacaaacc cctcaaacat tctcttgtac tgaaccatac cattccgtac 3660
aaccatccaa acaaaaatca tgtatcatca tgtacatgta accaaacaat taacacgcac 3720
catcctattc agacttgtct catccataat ctatccatcc aggatgatcc atcccattca 3780
tctatataca cccaatcaaa cgctacctaa aatttggatc tgtatgtgtc acatatatct 3840
taataagatg gatggaaata tctctttatc ttttagatat ggataggtat atatgttgct 3900
gtgggtttgt tagttatata tatacgtgct tacatacgtg aagaaacctg ctgctacagt 3960
ttaataattc ttgttcatct caacaaataa cgataggcgt atatgttgct gtgtttttta 4020
ctggtacttt gttagatata tacatgctta catacatgaa gaacacatgc tacagttcaa 4080
aaattcttgt tcatctcata aacaaaaagg aggtgtatat gttgctgtgg gttttactgg 4140
tactttatta gatatataca tgcttacata gatgaagcaa catgctgcta tggtgtttaa 4200
taattattgt ttatctaata aacaaacatg ctttttaatt atcttgatat gtttggatga 4260
tggcatatgc agcagctatg tgtggatttt aaatacccag catcatgagc atgcatgacc 4320
ctgccttagt atgcagttat ttgcttgaga ctgtttcttt tgttgatact catcctttag 4380
ttcggtcact cttctgcagg tg 4402

<210> SEQ ID NO 67
<211> LENGTH: 2423
<212> TYPE: DNA
<213> ORGANISM: Miscanthus sinesis

<400> SEQUENCE: 67
cacgtggtca ctatgctgca tactccctat acagccgctg accagtacgc tggttcaccg 60
cgtcgcccgc gcgggacgga atgggatgtc acgacccgct gaacgccggg gcatggcatc 120
agcggcgaac aggcacccgg cgtggagctg tccgtgtcac catctacagt gttgacggga 180
cccgcataaa aggagaaaaa aggcccgacg gtcctggaag ccttcctctc cttagctctt 240
ctccctcttt ctctctgtgt aacctgctct tccccttcgt ctataaaaag ggaagtagga 300
cgtcccagga agagaagggc ggttcaccac tctacatggc tatagacata aaaacacacg 360
ccttgggagc acactcacat cagagacttg ggacctatcc ctctctcgct cgtttgtaac 420
ccctactaca aacttttagt gctagtaaca cgagcagcag cgacgaacta gacgtaagga 480
ctttctgccc gaaccagtat aaacatcgtg tcatctaagc acaccatacg agccagacgc 540
gcaatactag aaatttacta gtcggtaact cgaaacaccg acatctagct aatctttttg 600
ttttatttgg tttccctttg aaatcttcta atttagcttt catagaaata atctaggtat 660
tttttatttt atatgttcta tctgtttgca ttaattttga tcatttgatc tgaatgctgt 720
ggtcacgaga atcgagtgtt tcatggcctt aaaacactcg attatgccat ctgacccgtt 780
ttcaaccatt ctagtgtttc tgagctatat caatggtgca gcatgttagt atacatatct 840

```
aactattact ccgtatatga gtgagttgtt aaatttattc caggtgaaat ggcattaacg    900
atagccaata ggcggctaaa ttaatagcca tactctaaca gctctaaaaa acatatattc    960
atcgaggcac ctttatgcaa ccacatagtc aacttcaacg tcgcttgcgt gcgttctcaa   1020
gttttctttc ttgcaaatta cattttttt aaaaaaaagt ataatttgta tcgtgcgatt   1080
ttttctctct aggtgtgcgt gactgtggga gtaacaattt tgaatctcaa gaaggaaata   1140
aaagaataat actgctgcct actttgagga tttcagtatt tttctctaaa atgttttggt   1200
gtgatatcta aaccgtcttt aaagccaatt gctcaagatt cattcaacaa ttgaaacgtc   1260
tcacatgact aaatgatata aggttgctaa ggtctttctt gataagcttt tttatgaatt   1320
tcatctaaat tttcgagtga aactattaaa tactaaggtt gctaagtgtc attctcgctc   1380
gagaagtcta acgctttaaa ctttaaccaa atatatacaa gaaaatatta atatttatag   1440
tacataatta gtatcattag atagatcgtt gaatctattt tcataacaaa cttatttgaa   1500
gaaacaaatg ttgttcatat atttctatat acgaatacca tagcgacact tattttagaa   1560
tgtagggagt actccctttg tgccgctttg agtgtcgctt tggcagctag tacctatgtc   1620
caccttcaca gcttgtgcct agtacctaga ctctttctct gtccacattc atttaatctc   1680
tgttgtacct tgttcggaga taaaacgact ctgataaagg gacgaggaag tagtatgtta   1740
gaggagtgaa gtctactccc tttgccgcaa aaaggtaatc ctaagtgtga attgtattct   1800
tttttgacca aaggaatata caacaagaat gatgtcatca tcatgcttcg atcctttttt   1860
ttggtaaagc ttgagcttct gtaaaaatag agaaatcatg ggaaaaatca cgttttggtg   1920
gttttgattt ctagcctcca caataacttt ggttttacta ttttttgttt gattttagtt   1980
tcagaagtcc acttttgtac gtgctcgtag agcctaaaca aaaggctttc caaaacgacc   2040
ttatcttcga gtgttgtaaa aaaaatgagc ccgtttaacg gcgtcgacaa gtctaacgga   2100
caccaaccag cgaaccacca gcgccgagcc aagcgaagca gactgcagac ggcacggccg   2160
agacgttgac accttggcgc ggcaacggca tctctctggc cccctctcga gagttccgct   2220
ccacctccgc atccacctcc acctccacct ccaccggtgg cggtttccaa gtccgtcccg   2280
ttccgccacc tgctcctctc acacggcacg aaaccgtcac ggcaccggca gcacagcacg   2340
ggggattcct ttcccaccgc tccgtccctt tctcttcctc gcccgcccgt tataaatagc   2400
cagccccatc cctcgtctct cgt                                           2423
```

<210> SEQ ID NO 68
<211> LENGTH: 55
<212> TYPE: DNA
<213> ORGANISM: Miscanthus sinesis

<400> SEQUENCE: 68

```
gttgttcgga gcgcacacac aacccgatcc ccaatcaatc gatccccgct tcaag          55
```

<210> SEQ ID NO 69
<211> LENGTH: 1924
<212> TYPE: DNA
<213> ORGANISM: Miscanthus sinesis

<400> SEQUENCE: 69

```
gtacggcgat cctcctccct ctctctctac cttctcttct ctacactaga tcggcggtcc     60
atggttaggg cctgctagtt ccgttcctgt ttttccatgg ctgcgaggta caatagatct    120
gatggcgtta tgatggttaa cttgtcatgc ttttgcgatt tatagtccct ttagatagtt    180
cgagatcggt gatccatggt tagtacccta ggctgtggag tcgggttaga tccgcgctgt    240
```

```
tagggttcgt atatggaggc gagctgttct gattgttaac ttgctgggaa tcctgggatg    300

gttctagctg ttccgcagat gagatcgatt tcatgatctg ctgtatctat ccgtggtatg    360

atgttagcct ttgatatggt tcgatcgtgc tagctacgtc ctgtgcactt aattgtcagg    420

tcataatttt tactatactt tttttttggt ttggtttggt ttcgtctgat ttggctgtcg    480

ttctagatca gagtagaaac tgtttcaaac tacctgttgg atttattaag gtagcgtttg    540

gttcctggta tcgaatcata cacgcaccag tgcatcttgg atagccagct ggggcccacc    600

tgtccaaccg tttggttgcc ggatcgaacg agtccattca agaccgaacc atgcagagca    660

atcgaatatt ctcttgtgac gctgtatcat ccagttcggc aaaaaacacc gaatgccgcc    720

atacaggaca ccgtactgag cgtctgcaac tctgcatccc gctcactgct cacatctccg    780

cttgccgcct cacccatccg actcagacca gagccacacg gattactgct gctggtgtgt    840

gtattaacaa aagatccatt tgaccggagc acatgcagct tggatggaaa aaatttatta    900

tattcgtcag tgctgcatat gtactcatac ttgcatgatg gttttattta ttcgacctca    960

tcagtcctgg cactatggaa agtcattgta gtatagattt tttaatataa tataaatcat   1020

tggtgactta tcttgcttaa ttttattttc ttattatgaa atatcgttgc attcataata   1080

gcaaatttgt gcaaatatat agaatctacg tgaaattctt ggttggacca atacaacaaa   1140

cccctcaaac attctcttgt actgaaccat accattccgt acaaccatcc aaacaaaaat   1200

catgtatcat catgtacatg taaccaaaca attaacacgc accatcctat tcagacttgt   1260

ctcatccata atctatccat ccaggatgat ccatcccatt catctatata cacccaatca   1320

aacgctacct aaaatttgga tctgtatgtg tcacatatat cttaataaga tggatggaaa   1380

tatctcttta tcttttagat atggataggt atatatgttg ctgtgggttt gttagttata   1440

tatatacgtg cttacatacg tgaagaaacc tgctgctaca gtttaataat tcttgttcat   1500

ctcaacaaat aacgataggc gtatatgttg ctgtgttttt tactggtact ttgttagata   1560

tatacatgct tacatacatg aagaacacat gctacagttc aaaaattctt gttcatctca   1620

taaacaaaaa ggaggtgtat atgttgctgt gggttttact ggtactttat tagatatata   1680

catgcttaca tagatgaagc aacatgctgc tatggtgttt aataattatt gtttatctaa   1740

taaacaaaca tgctttttaa ttatcttgat atgtttggat gatggcatat gcagcagcta   1800

tgtgtggatt ttaaataccc agcatcatga gcatgcatga ccctgcctta gtatgcagtt   1860

atttgcttga gactgtttct tttgttgata ctcatccttt agttcggtca ctcttctgca   1920

ggtg                                                                1924
```

<210> SEQ ID NO 70
<211> LENGTH: 3426
<212> TYPE: DNA
<213> ORGANISM: Miscanthus sinesis

<400> SEQUENCE: 70

```
gcaaccacat agtcaacttc aacgtcgctt gcgtgcgttc tcaagttttc tttcttgcaa     60

attacatttt ttttaaaaaa aagtataatt tgtatcgtgc gatttttttct ctctaggtgt    120

gcgtgactgt gggagtaaca attttgaatc tcaagaagga aataaaagaa taatactgct    180

gcctactttg aggatttcag tatttttctc taaaatgttt tggtgtgata tctaaaccgt    240

ctttaaagcc aattgctcaa gattcattca acaattgaaa cgtctcacat gactaaatga    300

tataaggttg ctaaggtctt tcttgataag cttttttatg aatttcatct aaattttcga    360
```

-continued

```
gtgaaactat taaatactaa ggttgctaag tgtcattctc gctcgagaag tctaacgctt    420
taaactttaa ccaaatatat acaagaaaat attaatattt atagtacata attagtatca    480
ttagatagat cgttgaatct attttcataa caaacttatt tgaagaaaca aatgttgttc    540
atatatttct atatacgaat accatagcga cacttatttt agaatgtagg gagtactccc    600
tttgtgccgc tttgagtgtc gctttggcag ctagtaccta tgtccacctt cacagcttgt    660
gcctagtacc tagactcttt ctctgtccac attcatttaa tctctgttgt accttgttcg    720
gagataaaac gactctgata aagggacgag gaagtagtat gttagaggag tgaagtctac    780
tccctttgcc gcaaaaaggt aatcctaagt gtgaattgta ttcttttttg accaaaggaa    840
tatacaacaa gaatgatgtc atcatcatgc ttcgatcctt tttttggta aagcttgagc    900
ttctgtaaaa atagagaaat catgggaaaa atcacgtttt ggtggttttg atttctagcc    960
tccacaataa ctttggtttt actatttttt gtttgatttt agtttcagaa gtccactttt   1020
gtacgtgctc gtagagccta aacaaaaggc tttccaaaac gaccttatct tcgagtgttg   1080
taaaaaaaat gagcccgttt aacggcgtcg acaagtctaa cggacaccaa ccagcgaacc   1140
accagcgccg agccaagcga agcagactgc agacggcacg gccgagacgt tgacaccttg   1200
gcgcggcaac ggcatctctc tggcccccctc tcgagagttc cgctccacct ccgcatccac   1260
ctccacctcc acctccaccg gtggcggttt ccaagtccgt cccgttccgc cacctgctcc   1320
tctcacacgg cacgaaaccg tcacggcacc ggcagcacag cacgggggat tcctttccca   1380
ccgctccgtc cctttctctt cctcgcccgc ccgttataaa tagccagccc catccctcgt   1440
ctctcgtgtt gttcggagcg cacacacaac ccgatcccca atcaatcgat ccccgcttca   1500
aggtacggcg atcctcctcc ctctctctct accttctctt ctctacacta gatcggcggt   1560
ccatggttag ggcctgctag ttccgttcct gtttttccat ggctgcgagg tacaatagat   1620
ctgatggcgt tatgatggtt aacttgtcat gcttttgcga tttatagtcc ctttagatag   1680
ttcgagatcg gtgatccatg gttagtaccc taggctgtgg agtcgggtta gatccgcgct   1740
gttagggttc gtatatggag gcgagctgtt ctgattgtta acttgctggg aatcctggga   1800
tggttctagc tgttccgcag atgagatcga tttcatgatc tgctgtatct atccgtggta   1860
tgatgttagc ctttgatatg gttcgatcgt gctagctacg tcctgtgcac ttaattgtca   1920
ggtcataatt tttactatac ttttttttg gtttggtttg gtttcgtctg atttggctgt   1980
cgttctagat cagagtagaa actgtttcaa actacctgtt ggatttatta aggtagcgtt   2040
tggttcctgg tatcgaatca tacacgcacc agtgcatctt ggatagccag ctggggccca   2100
cctgtccaac cgtttggttg ccggatcgaa cgagtccatt caagaccgaa ccatgcagag   2160
caatcgaata ttctcttgtg acgctgtatc atccagttcg gcaaaaaaca ccgaatgccg   2220
ccatacagga caccgtactg agcgtctgca actctgcatc ccgctcactg ctcacatctc   2280
cgcttgccgc ctcacccatc cgactcagac cagagccaca cggattactg ctgctggtgt   2340
gtgtattaac aaaagatcca tttgaccgga gcacatgcag cttggatgga aaaaatttat   2400
tatattcgtc agtgctgcat atgtactcat acttgcatga tggttttatt tattcgacct   2460
catcagtcct ggcactatgg aaagtcattg tagtatagat tttttaatat aatataaatc   2520
attggtgact tatcttgctt aattttattt tcttattatg aaatatcgtt gcattcataa   2580
tagcaaattt gtgcaaatat atagaatcta cgtgaaattc ttggttggac caatacaaca   2640
aacccctcaa acattctctt gtactgaacc ataccattcc gtacaaccat ccaaacaaaa   2700
atcatgtatc atcatgtaca tgtaaccaaa caattaacac gcaccatcct attcagactt   2760
```

-continued gtctcatcca taatctatcc atccaggatg atccatccca ttcatctata tacacccaat 2820
caaacgctac ctaaaatttg gatctgtatg tgtcacatat atcttaataa gatggatgga 2880
aatatctctt tatcttttag atatggatag gtatatatgt tgctgtgggt ttgttagtta 2940
tatatatacg tgcttacata cgtgaagaaa cctgctgcta cagtttaata attcttgttc 3000
atctcaacaa ataacgatag gcgtatatgt tgctgtgttt tttactggta ctttgttaga 3060
tatatacatg cttacataca tgaagaacac atgctacagt tcaaaaattc ttgttcatct 3120
cataaacaaa aaggaggtgt atatgttgct gtgggtttta ctggtacttt attagatata 3180
tacatgctta catagatgaa gcaacatgct gctatggtgt ttaataatta ttgtttatct 3240
aataaacaaa catgcttttt aattatcttg atatgtttgg atgatggcat atgcagcagc 3300
tatgtgtgga ttttaaatac ccagcatcat gagcatgcat gaccctgcct tagtatgcag 3360
ttatttgctt gagactgttt cttttgttga tactcatcct ttagttcggt cactcttctg 3420
caggtg 3426

<210> SEQ ID NO 71
<211> LENGTH: 1447
<212> TYPE: DNA
<213> ORGANISM: Miscanthus sinesis

<400> SEQUENCE: 71
gcaaccacat agtcaacttc aacgtcgctt gcgtgcgttc tcaagttttc tttcttgcaa 60
attacatttt ttttaaaaaa aagtataatt tgtatcgtgc gattttttct ctctaggtgt 120
gcgtgactgt gggagtaaca attttgaatc tcaagaagga aataaaagaa taatactgct 180
gcctactttg aggatttcag tatttttctc taaaatgttt tggtgtgata tctaaaccgt 240
ctttaaagcc aattgctcaa gattcattca acaattgaaa cgtctcacat gactaaatga 300
tataaggttg ctaaggtctt tcttgataag cttttttatg aatttcatct aaattttcga 360
gtgaaactat taaatactaa ggttgctaag tgtcattctc gctcgagaag tctaacgctt 420
taaactttaa ccaaatatat acaagaaaat attaatattt atagtacata attagtatca 480
ttagatagat cgttgaatct attttcataa caaacttatt tgaagaaaca aatgttgttc 540
atatatttct atatacgaat accatagcga cacttatttt agaatgtagg gagtactccc 600
tttgtgccgc tttgagtgtc gctttggcag ctagtaccta tgtccacctt cacagcttgt 660
gcctagtacc tagactcttt ctctgtccac attcatttaa tctctgttgt accttgttcg 720
gagataaaac gactctgata aagggacgag gaagtagtat gttagaggag tgaagtctac 780
tccctttgcc gcaaaaaggt aatcctaagt gtgaattgta ttcttttttg accaaaggaa 840
tatacaacaa gaatgatgtc atcatcatgc ttcgatcctt ttttttggta aagcttgagc 900
ttctgtaaaa atagagaaat catgggaaaa atcacgtttt ggtggttttg atttctagcc 960
tccacaataa ctttggtttt actatttttt gtttgatttt agtttcagaa gtccactttt 1020
gtacgtgctc gtagagccta aacaaaaggc tttccaaaac gaccttatct tcgagtgttg 1080
taaaaaaaat gagcccgttt aacggcgtcg acaagtctaa cggacaccaa ccagcgaacc 1140
accagcgccg agccaagcga agcagactgc agacggcacg gccgagacgt tgacaccttg 1200
gcgcggcaac ggcatctctc tggccccctc tcgagagttc cgctccacct ccgcatccac 1260
ctccacctcc acctccaccg gtggcggttt ccaagtccgt cccgttccgc cacctgctcc 1320
tctcacacgg cacgaaaccg tcacggcacc ggcagcacag cacgggggat tcctttccca 1380
ccgctccgtc cctttctctt cctcgcccgc ccgttataaa tagccagccc catccctcgt 1440
ctctcgt 1447

<210> SEQ ID NO 72
<211> LENGTH: 2878
<212> TYPE: DNA
<213> ORGANISM: Miscanthus sinesis

<400> SEQUENCE: 72
ctatatacga ataccatagc gacacttatt ttagaatgta gggagtactc cctttgtgcc 60
gctttgagtg tcgctttggc agctagtacc tatgtccacc ttcacagctt gtgcctagta 120
cctagactct ttctctgtcc acattcattt aatctctgtt gtaccttgtt cggagataaa 180
acgactctga taaagggacg aggaagtagt atgttagagg agtgaagtct actccctttg 240
ccgcaaaaag gtaatcctaa gtgtgaattg tattcttttt tgaccaaagg aatatacaac 300
aagaatgatg tcatcatcat gcttcgatcc tttttttgg taaagcttga gcttctgtaa 360
aaatagagaa atcatgggaa aaatcacgtt ttggtggttt tgatttctag cctccacaat 420
aactttggtt ttactatttt ttgtttgatt ttagtttcag aagtccactt ttgtacgtgc 480
tcgtagagcc taaacaaaag gctttccaaa acgaccttat cttcgagtgt tgtaaaaaaa 540
atgagcccgt ttaacggcgt cgacaagtct aacggacacc aaccagcgaa ccaccagcgc 600
cgagccaagc gaagcagact gcagacggca cggccgagac gttgacacct tggcgcggca 660
acggcatctc tctggccccc tctcgagagt tccgctccac ctccgcatcc acctccacct 720
ccacctccac cggtggcggt ttccaagtcc gtcccgttcc gccacctgct cctctcacac 780
ggcacgaaac cgtcacggca ccggcagcac agcacggggg attcctttcc caccgctccg 840
tccctttctc ttcctcgccc gcccgttata aatagccagc cccatccctc gtctctcgtg 900
ttgttcggag cgcacacaca acccgatccc caatcaatcg atccccgctt caaggtacgg 960
cgatcctcct ccctctctct ctaccttctc ttctctacac tagatcggcg gtccatggtt 1020
agggcctgct agttccgttc ctgtttttcc atggctgcga ggtacaatag atctgatggc 1080
gttatgatgg ttaacttgtc atgcttttgc gatttatagt ccctttagat agttcgagat 1140
cggtgatcca tggttagtac cctaggctgt ggagtcgggt tagatccgcg ctgttagggt 1200
tcgtatatgg aggcgagctg ttctgattgt taacttgctg ggaatcctgg gatggttcta 1260
gctgttccgc agatgagatc gatttcatga tctgctgtat ctatccgtgg tatgatgtta 1320
gcctttgata tggttcgatc gtgctagcta cgtcctgtgc acttaattgt caggtcataa 1380
tttttactat actttttttt tggtttggtt tggtttcgtc tgatttggct gtcgttctag 1440
atcagagtag aaactgtttc aaactacctg ttggatttat taaggtagcg tttggttcct 1500
ggtatcgaat catacacgca ccagtgcatc ttggatagcc agctggggcc cacctgtcca 1560
accgtttggt tgccggatcg aacgagtcca ttcaagaccg aaccatgcag agcaatcgaa 1620
tattctcttg tgacgctgta tcatccagtt cggcaaaaaa caccgaatgc cgccatacag 1680
gacaccgtac tgagcgtctg caactctgca tcccgctcac tgctcacatc tccgcttgcc 1740
gcctcaccca tccgactcag accagagcca cacggattac tgctgctggt gtgtgtatta 1800
acaaaagatc catttgaccg gagcacatgc agcttggatg gaaaaaattt attatattcg 1860
tcagtgctgc atatgtactc atacttgcat gatggtttta tttattcgac ctcatcagtc 1920
ctggcactat ggaaagtcat tgtagtatag attttttaat ataatataaa tcattggtga 1980
cttatcttgc ttaattttat tttcttatta tgaaatatcg ttgcattcat aatagcaaat 2040
ttgtgcaaat atatagaatc tacgtgaaat tcttggttgg accaatacaa caaacccctc 2100
aaacattctc ttgtactgaa ccataccatt ccgtacaacc atccaaacaa aaatcatgta 2160
tcatcatgta catgtaacca aacaattaac acgcaccatc ctattcagac ttgtctcatc 2220
cataatctat ccatccagga tgatccatcc cattcatcta tatacaccca atcaaacgct 2280
acctaaaatt tggatctgta tgtgtcacat atatcttaat aagatggatg gaaatatctc 2340
tttatctttt agatatggat aggtatatat gttgctgtgg gtttgttagt tatatatata 2400
cgtgcttaca tacgtgaaga aacctgctgc tacagtttaa taattcttgt tcatctcaac 2460
aaataacgat aggcgtatat gttgctgtgt tttttactgg tactttgtta gatatataca 2520
tgcttacata catgaagaac acatgctaca gttcaaaaat tcttgttcat ctcataaaca 2580
aaaaggaggt gtatatgttg ctgtgggttt tactggtact ttattagata tatacatgct 2640
tacatagatg aagcaacatg ctgctatggt gtttaataat tattgtttat ctaataaaca 2700
aacatgcttt ttaattatct tgatatgttt ggatgatggc atatgcagca gctatgtgtg 2760
gattttaaat acccagcatc atgagcatgc atgaccctgc cttagtatgc agttatttgc 2820
ttgagactgt ttcttttgtt gatactcatc ctttagttcg gtcactcttc tgcaggtg 2878

<210> SEQ ID NO 73
<211> LENGTH: 899
<212> TYPE: DNA
<213> ORGANISM: Miscanthus sinesis

<400> SEQUENCE: 73
ctatatacga ataccatagc gacacttatt ttagaatgta gggagtactc cctttgtgcc 60
gctttgagtg tcgctttggc agctagtacc tatgtccacc ttcacagctt gtgcctagta 120
cctagactct ttctctgtcc acattcattt aatctctgtt gtaccttgtt cggagataaa 180
acgactctga taaagggacg aggaagtagt atgttagagg agtgaagtct actccctttg 240
ccgcaaaaag gtaatcctaa gtgtgaattg tattcttttt tgaccaaagg aatatacaac 300
aagaatgatg tcatcatcat gcttcgatcc tttttttgg taaagcttga gcttctgtaa 360
aaatagagaa atcatgggaa aaatcacgtt ttggtggttt tgatttctag cctccacaat 420
aactttggtt ttactatttt ttgtttgatt ttagtttcag aagtccactt ttgtacgtgc 480
tcgtagagcc taaacaaaag gctttccaaa acgaccttat cttcgagtgt tgtaaaaaaa 540
atgagcccgt ttaacggcgt cgacaagtct aacggacacc aaccagcgaa ccaccagcgc 600
cgagccaagc gaagcagact gcagacggca cggccgagac gttgacacct tggcgcggca 660
acggcatctc tctggccccc tctcgagagt tccgctccac ctccgcatcc acctccacct 720
ccacctccac cggtggcggt ttccaagtcc gtcccgttcc gccacctgct cctctcacac 780
ggcacgaaac cgtcacggca ccggcagcac agcacggggg attcctttcc caccgctccg 840
tccctttctc ttcctcgccc gcccgttata aatagccagc cccatccctc gtctctcgt 899

<210> SEQ ID NO 74
<211> LENGTH: 2670
<212> TYPE: DNA
<213> ORGANISM: Miscanthus sinesis

<400> SEQUENCE: 74
gtatgttaga ggagtgaagt ctactccctt tgccgcaaaa aggtaatcct aagtgtgaat 60
tgtattcttt tttgaccaaa ggaatataca acaagaatga tgtcatcatc atgcttcgat 120

-continued

```
cctttttttt ggtaaagctt gagcttctgt aaaaatagag aaatcatggg aaaaatcacg    180
ttttggtggt tttgatttct agcctccaca ataactttgg ttttactatt ttttgtttga    240
ttttagtttc agaagtccac ttttgtacgt gctcgtagag cctaaacaaa aggctttcca    300
aaacgacctt atcttcgagt gttgtaaaaa aaatgagccc gtttaacggc gtcgacaagt    360
ctaacggaca ccaaccagcg aaccaccagc gccgagccaa gcgaagcaga ctgcagacgg    420
cacggccgag acgttgacac cttggcgcgg caacggcatc tctctggccc cctctcgaga    480
gttccgctcc acctccgcat ccacctccac ctccacctcc accggtggcg gtttccaagt    540
ccgtcccgtt ccgccacctg ctcctctcac acggcacgaa accgtcacgg caccggcagc    600
acagcacggg ggattccttt cccaccgctc cgtccctttc tcttcctcgc ccgcccgtta    660
taaatagcca gccccatccc tcgtctctcg tgttgttcgg agcgcacaca caacccgatc    720
cccaatcaat cgatccccgc ttcaaggtac ggcgatcctc ctccctctct ctctaccttc    780
tcttctctac actagatcgg cggtccatgg ttagggcctg ctagttccgt tcctgttttt    840
ccatggctgc gaggtacaat agatctgatg gcgttatgat ggttaacttg tcatgctttt    900
gcgatttata gtccctttag atagttcgag atcggtgatc catggttagt accctaggct    960
gtggagtcgg gttagatccg cgctgttagg gttcgtatat ggaggcgagc tgttctgatt   1020
gttaacttgc tgggaatcct gggatggttc tagctgttcc gcagatgaga tcgatttcat   1080
gatctgctgt atctatccgt ggtatgatgt tagcctttga tatggttcga tcgtgctagc   1140
tacgtcctgt gcacttaatt gtcaggtcat aatttttact atactttttt tttggtttgg   1200
tttggtttcg tctgatttgg ctgtcgttct agatcagagt agaaactgtt tcaaactacc   1260
tgttggattt attaaggtag cgtttggttc ctggtatcga atcatacacg caccagtgca   1320
tcttggatag ccagctgggg cccacctgtc caaccgtttg gttgccggat cgaacgagtc   1380
cattcaagac cgaaccatgc agagcaatcg aatattctct tgtgacgctg tatcatccag   1440
ttcggcaaaa aacaccgaat gccgccatac aggacaccgt actgagcgtc tgcaactctg   1500
catcccgctc actgctcaca tctccgcttg ccgcctcacc catccgactc agaccagagc   1560
cacacggatt actgctgctg gtgtgtgtat taacaaaaga tccatttgac cggagcacat   1620
gcagcttgga tggaaaaaat ttattatatt cgtcagtgct gcatatgtac tcatacttgc   1680
atgatggttt tatttattcg acctcatcag tcctggcact atggaaagtc attgtagtat   1740
agatttttta atataatata aatcattggt gacttatctt gcttaatttt attttcttat   1800
tatgaaatat cgttgcattc ataatagcaa atttgtgcaa atatatagaa tctacgtgaa   1860
attcttggtt ggaccaatac aacaaacccc tcaaacattc tcttgtactg aaccatacca   1920
ttccgtacaa ccatccaaac aaaaatcatg tatcatcatg tacatgtaac caaacaatta   1980
acacgcacca tcctattcag acttgtctca tccataatct atccatccag gatgatccat   2040
cccattcatc tatatacacc caatcaaacg ctacctaaaa tttggatctg tatgtgtcac   2100
atatatctta ataagatgga tggaaatatc tctttatctt ttagatatgg ataggtatat   2160
atgttgctgt gggtttgtta gttatatata tacgtgctta catacgtgaa gaaacctgct   2220
gctacagttt aataattctt gttcatctca acaaataacg ataggcgtat atgttgctgt   2280
gtttttttact ggtactttgt tagatatata catgcttaca tacatgaaga acacatgcta   2340
cagttcaaaa attcttgttc atctcataaa caaaaaggag gtgtatatgt tgctgtgggt   2400
tttactggta ctttattaga tatatacatg cttacataga tgaagcaaca tgctgctatg   2460
gtgtttaata attattgttt atctaataaa caaacatgct ttttaattat cttgatatgt   2520
```

ttggatgatg gcatatgcag cagctatgtg tggattttaa atacccagca tcatgagcat 2580
gcatgaccct gccttagtat gcagttattt gcttgagact gtttcttttg ttgatactca 2640
tcctttagtt cggtcactct tctgcaggtg 2670

<210> SEQ ID NO 75
<211> LENGTH: 691
<212> TYPE: DNA
<213> ORGANISM: Miscanthus sinesis

<400> SEQUENCE: 75
gtatgttaga ggagtgaagt ctactccctt tgccgcaaaa aggtaatcct aagtgtgaat 60
tgtattcttt tttgaccaaa ggaatataca acaagaatga tgtcatcatc atgcttcgat 120
cctttttttt ggtaaagctt gagcttctgt aaaaatagag aaatcatggg aaaaatcacg 180
ttttggtggt tttgatttct agcctccaca ataactttgg ttttactatt ttttgtttga 240
ttttagtttc agaagtccac ttttgtacgt gctcgtagag cctaaacaaa aggctttcca 300
aaacgacctt atcttcgagt gttgtaaaaa aaatgagccc gtttaacggc gtcgacaagt 360
ctaacggaca ccaaccagcg aaccaccagc gccgagccaa gcgaagcaga ctgcagacgg 420
cacggccgag acgttgacac cttggcgcgg caacggcatc tctctggccc cctctcgaga 480
gttccgctcc acctccgcat ccacctccac ctccacctcc accggtggcg gtttccaagt 540
ccgtcccgtt ccgccacctg ctcctctcac acggcacgaa accgtcacgg caccggcagc 600
acagcacggg ggattccttt cccaccgctc cgtccctttc tcttcctcgc ccgcccgtta 660
taaatagcca gccccatccc tcgtctctcg t 691

<210> SEQ ID NO 76
<211> LENGTH: 2485
<212> TYPE: DNA
<213> ORGANISM: Miscanthus sinesis

<400> SEQUENCE: 76
gtggttttga tttctagcct ccacaataac tttggtttta ctattttttg tttgatttta 60
gtttcagaag tccacttttg tacgtgctcg tagagcctaa acaaaaggct ttccaaaacg 120
accttatctt cgagtgttgt aaaaaaaatg agcccgttta acggcgtcga caagtctaac 180
ggacaccaac cagcgaacca ccagcgccga gccaagcgaa gcagactgca gacggcacgg 240
ccgagacgtt gacaccttgg cgcggcaacg gcatctctct ggccccctct cgagagttcc 300
gctccacctc cgcatccacc tccacctcca cctccaccgg tggcggtttc caagtccgtc 360
ccgttccgcc acctgctcct ctcacacggc acgaaaccgt cacggcaccg gcagcacagc 420
acgggggatt cctttcccac cgctccgtcc ctttctcttc ctcgcccgcc cgttataaat 480
agccagcccc atccctcgtc tctcgtgttg ttcggagcgc acacacaacc cgatccccaa 540
tcaatcgatc cccgcttcaa ggtacggcga tcctcctccc tctctctcta ccttctcttc 600
tctacactag atcggcggtc catggttagg gcctgctagt tccgttcctg tttttccatg 660
gctgcgaggt acaatagatc tgatggcgtt atgatggtta acttgtcatg cttttgcgat 720
ttatagtccc tttagatagt tcgagatcgg tgatccatgg ttagtaccct aggctgtgga 780
gtcgggttag atccgcgctg ttagggttcg tatatggagg cgagctgttc tgattgttaa 840
cttgctggga atcctgggat ggttctagct gttccgcaga tgagatcgat ttcatgatct 900
gctgtatcta tccgtggtat gatgttagcc tttgatatgg ttcgatcgtg ctagctacgt 960

-continued cctgtgcact taattgtcag gtcataattt ttactatact tttttttgg tttggtttgg 1020 tttcgtctga tttggctgtc gttctagatc agagtagaaa ctgtttcaaa ctacctgttg 1080
gatttattaa ggtagcgttt ggttcctggt atcgaatcat acacgcacca gtgcatcttg 1140
gatagccagc tggggcccac ctgtccaacc gtttggttgc cggatcgaac gagtccattc 1200
aagaccgaac catgcagagc aatcgaatat tctcttgtga cgctgtatca tccagttcgg 1260
caaaaaacac cgaatgccgc catacaggac accgtactga gcgtctgcaa ctctgcatcc 1320
cgctcactgc tcacatctcc gcttgccgcc tcacccatcc gactcagacc agagccacac 1380
ggattactgc tgctggtgtg tgtattaaca aaagatccat ttgaccggag cacatgcagc 1440
ttggatggaa aaaatttatt atattcgtca gtgctgcata tgtactcata cttgcatgat 1500
ggttttattt attcgacctc atcagtcctg gcactatgga aagtcattgt agtatagatt 1560
ttttaatata atataaatca ttggtgactt atcttgctta attttatttt cttattatga 1620
aatatcgttg cattcataat agcaaatttg tgcaaatata tagaatctac gtgaaattct 1680
tggttggacc aatacaacaa acccctcaaa cattctcttg tactgaacca taccattccg 1740
tacaaccatc caaacaaaaa tcatgtatca tcatgtacat gtaaccaaac aattaacacg 1800
caccatccta ttcagacttg tctcatccat aatctatcca tccaggatga tccatcccat 1860
tcatctatat acacccaatc aaacgctacc taaaatttgg atctgtatgt gtcacatata 1920
tcttaataag atggatggaa atatctcttt atcttttaga tatggatagg tatatatgtt 1980
gctgtgggtt tgttagttat atatatacgt gcttacatac gtgaagaaac ctgctgctac 2040
agtttaataa ttcttgttca tctcaacaaa taacgatagg cgtatatgtt gctgtgtttt 2100
ttactggtac tttgttagat atatacatgc ttacatacat gaagaacaca tgctacagtt 2160
caaaaattct tgttcatctc ataaacaaaa aggaggtgta tatgttgctg tgggttttac 2220
tggtacttta ttagatatat acatgcttac atagatgaag caacatgctg ctatggtgtt 2280
taataattat tgtttatcta ataaacaaac atgcttttta attatcttga tatgtttgga 2340
tgatggcata tgcagcagct atgtgtggat tttaaatacc cagcatcatg agcatgcatg 2400
accctgcctt agtatgcagt tatttgcttg agactgtttc ttttgttgat actcatcctt 2460
tagttcggtc actcttctgc aggtg 2485

<210> SEQ ID NO 77
<211> LENGTH: 506
<212> TYPE: DNA
<213> ORGANISM: Miscanthus sinesis

<400> SEQUENCE: 77
gtggttttga tttctagcct ccacaataac tttggtttta ctatttttg tttgatttta 60 gtttcagaag tccacttttg tacgtgctcg tagagcctaa acaaaaggct ttccaaaacg 120
accttatctt cgagtgttgt aaaaaaaatg agcccgttta acggcgtcga caagtctaac 180
ggacaccaac cagcgaacca ccagcgccga gccaagcgaa gcagactgca gacggcacgg 240
ccgagacgtt gacaccttgg cgcggcaacg gcatctctct ggccccctct cgagagttcc 300
gctccacctc cgcatccacc tccacctcca cctccaccgg tggcggtttc caagtccgtc 360
ccgttccgcc acctgctcct ctcacacggc acgaaaccgt cacggcaccg gcagcacagc 420
acgggggatt cctttcccac cgctccgtcc ctttctcttc ctcgcccgcc cgttataaat 480
agccagcccc atccctcgtc tctcgt 506

<210> SEQ ID NO 78
<211> LENGTH: 4079
<212> TYPE: DNA
<213> ORGANISM: Schizachyium scoparium

<400> SEQUENCE: 78
ctctatgcct gtgtcattgt gccagcccct acctctgtca atgttcaaga tccaaataag 60
agaatgggat agaccatata ttaatggtgt agtatgcatc aagatctgaa tattatatga 120
gtgaattgat aaatttattc taggtgacat ggccttaacg atggccagta cgtggttaaa 180
tcaatgaatc aatagccata ctctaatagc tctaaaaaag gatatatatt tgtcgaggca 240
ctattatgca accacatagt caacttcaaa gccgcttgag tgcgttctaa aaaaaaaatt 300
tcttgtaaat tacgcttttc tcaaaaaaat tggatcatgc atttatttca ctctaggtgt 360
gcgtgactac gtgaataaca attttgaatc tcagcaagga aataaaagta taataccgct 420
gtctactttg aagatcacaa tatctttctc ttagaatgtt tctgtttgtt atttaaaacc 480
atcgttatta aggtcaaatg atcaagattc attcaacaat tgaaacttct cacatgatta 540
catcatatat aaggttgcta aggtcttgct tgacaaggta tctctagtaa catctagttt 600
ttttgagtga aataataaaa ttttaaagca atgttacaag agaagctctg gagataaaag 660
ttagaagggt gaagtttact ccctctatcc caaagatgta attctaagaa tgacttaaat 720
tttttataca aaaggagtat atatcacaag attgatgtca tcgttatgct taggccacgt 780
acacgacgct ggcgcttatg tggacgttaa tcggtaattc ttcattttat tttattttgt 840
tgtcaccgcg tacatttggg ttaggcgttt gttaaaggca ttgccactca aacaagcagc 900
cgcgtttgga gcttttatag tttgaaaagt gacggttgta aagatgagta agctgattat 960
tagtagagta aattataatt atcatacaac aactctcaaa gtgggtgcac gttagtccaa 1020
catcttataa tttatccaac tcaatacaac aactatatag gtgggtgcat gttggtccaa 1080
catcttctaa tttgtttaat ttgatacgag aacttgtctt attggtacat atatgatcca 1140
aagcattgta acaacgtgtt tatgtatact cttaatcatg gtcatcagaa gctaacacac 1200
acgctcatgc catccatatc attcaacttt tgaatcgttt actatacaat attatttcta 1260
aatttggctg taaagatggc attgatttca taaatatgaa aaataccaaa ttgcacattt 1320
tctttctata ttataatatt gttttcatct attttcaccc cgtaaccttt aatttggtca 1380
tttagggctc actaaaactg atatgtgggt tgtgcatcgc ataagaatca agaacccaga 1440
agtaattttc aatactaaga aacaacaaaa tttggttttt ttttgtttgg tttcgattat 1500
agccgaacta accaaattta agaaagcttt ttatatttgg ccacataaga aatgatatca 1560
tttaatattg taactgattc aagctgagta atagatgaga tgagtgtgtt aggatgtgta 1620
gcttccgatg atagagaatt agagtgtaca aagacgcatc gttacaatat ttggacctta 1680
tatgcaccaa tgtgtcaagt ctcgcttcaa attaactata ttaaaagatg ttggatcaac 1740
atgcactcac ttagatatca gtcgtattaa attgaacaaa ttacaagata ttggactatg 1800
cacccactca aatagttgtt atatagtgaa tacagtttac tcttagtagt atatgtaagt 1860
tcagcctttt ctattgtagg ttaagcctta attaaggctc ttacacaatt gtttcattat 1920
tcgcgttcga agcagcttct tcgtagattt tgcgagggaa ggctgcctcg gttttgcctt 1980
ccctagcact catgtgagag cctctggcaa taggtcttct catttttatt cacattcttt 2040
aagagcccat ataagcgttc atgacttgta tatactctta gatctttttt tgtgggtaaa 2100
gctcaagcta atctaaaaat agagaaatca ggaacaaaga atcatgtttt ggtggttttg 2160
atttctagcc tccacaataa ttttagttta cctttttttg tttgatttta attttagaag 2220
ggtttatagc aggacttaaa atccaaaatg accattatct tcgagtaata acccgtttaa 2280
cggcgtcgac aagtctaacg gacaccaacc catgaaccac cagcgccgag ccaagaactg 2340
aaggtcgaga cgttgacacc tttggcgcga cacggcatgt tggcatctcc ctctctggcc 2400
ccctctcgag aattccgctc caccgcctca accggagacg gtttccaaag ttgtgcttag 2460
atgctcaaaa gttggtgaaa tcatttttat ttggcaattt gtgtccaact atagactaat 2520
taggctcaaa agatttgtct cgtaaagtac attcaaactg tgtaattagt tattttattt 2580
atctacattt aatactctat gaatgcgtca agagatttga tgtgacttta atgtgacgga 2640
caatctgaaa cttttacgca acttgcatat aaacagagcc caagtccgtt ccgttccgtt 2700
ccgcttcctc ctcccagacg gcacgaaacc gtgacggcac cggcagcacg ggattccctt 2760
tcccaccgct ccttcctttt cccttcatcg cccgcagcta taaatagcca cccccgtccg 2820
caacttcttt ccccaacctc atcttttgtt cggagcacgc acacaatccg atcgatcccc 2880
aatcccctcg tctctcctcg cgagcctcgt cgatccgcca ttcaaggtac ggcgatcatc 2940
ctccctccct ctctacctgc tcttctgtag atcggcgacc ccatccatgg ttagggcctg 3000
ctagttctgt tcctgttttt tttccatggc tgcgaggtag aatagatctg atggcgttat 3060
gatggttaat ttgtcatact cttgcggtct atgggtccct ttaggtcatc aatttaattt 3120
tgggtggttg agatcggtga tccatggtta gtaccctagt cagtggggtt ggatccgtgc 3180
tattagggtt cgtagatgga ttctgatggc tcagtaactg ggaatcctag gatggttcca 3240
tctggtttgc agatgagaac gatttcatca tctgctatat cttgtttcgt tgcgtaggtt 3300
ctgtttaaac taatccgtgg tatgatgtta gcctttgata aggttgattt catcatctgc 3360
tatatcttgt ttcgttgcgt aggttctgtt taaactaatc cgtggtatga tgttagcctt 3420
tgataaggtt tgattgtgct agctacgtcc tgtgcagcag ttaattgtca ggtcatacgt 3480
cataattttt agcatgtctg tttttgtttg atttcgttgt ctgattaggc tgtagatagt 3540
ttcgatctac ctgtcggttt attttattaa aatttggatc cgtatgtgtg tcacatatat 3600
cttcatgatt aagatggagt tatatgggta ggttatacat gtggctgtgg atcatgatta 3660
agatggattg aagtatctct ttatctttta gttaggatag attattatat atgttgctgt 3720
tgattttatt ggttctttat tatatatatt catgcttata tacataaaag caatgtgcta 3780
ttacagttta atagttcttg attatctaat aaacaaataa ggataggtat atttgttgct 3840
gttggtttta ctggtactct attagatagt actttgacat gaagcaacat cctgctatgg 3900
attaataatt attcttcgtc taataaaaag catggttttt aattattttg atttgatata 3960
cttggatgat gtcatatgca gcagctattt gtgaattttt cggccgtatc ttcatattgc 4020
ttgggactgt ttctttggtt gataactcac cctgttgttt ggtgatcctt ctgcaggtg 4079

<210> SEQ ID NO 79
<211> LENGTH: 2831
<212> TYPE: DNA
<213> ORGANISM: Schizachyium scoparium

<400> SEQUENCE: 79
ctctatgcct gtgtcattgt gccagcccct acctctgtca atgttcaaga tccaaataag 60
agaatgggat agaccatata ttaatggtgt agtatgcatc aagatctgaa tattatatga 120
gtgaattgat aaatttattc taggtgacat ggccttaacg atggccagta cgtggttaaa 180
tcaatgaatc aatagccata ctctaatagc tctaaaaaag gatatatatt tgtcgaggca 240

-continued

```
ctattatgca accacatagt caacttcaaa gccgcttgag tgcgttctaa aaaaaaaatt    300
tcttgtaaat tacgcttttc tcaaaaaaat tggatcatgc atttatttca ctctaggtgt    360
gcgtgactac gtgaataaca attttgaatc tcagcaagga aataaaagta taataccgct    420
gtctactttg aagatcacaa tatctttctc ttagaatgtt tctgtttgtt atttaaaacc    480
atcgttatta aggtcaaatg atcaagattc attcaacaat tgaaacttct cacatgatta    540
catcatatat aaggttgcta aggtcttgct tgacaaggta tctctagtaa catctagttt    600
ttttgagtga aataataaaa ttttaaagca atgttacaag agaagctctg gagataaaag    660
ttagaagggt gaagtttact ccctctatcc caaagatgta attctaagaa tgacttaaat    720
tttttataca aaaggagtat atatcacaag attgatgtca tcgttatgct taggccacgt    780
acacgacgct ggcgcttatg tggacgttaa tcggtaattc ttcattttat tttattttgt    840
tgtcaccgcg tacatttggg ttaggcgttt gttaaaggca ttgccactca aacaagcagc    900
cgcgtttgga gcttttatag tttgaaaagt gacggttgta aagatgagta agctgattat    960
tagtagagta aattataatt atcatacaac aactctcaaa gtgggtgcac gttagtccaa   1020
catcttataa tttatccaac tcaatacaac aactatatag gtgggtgcat gttggtccaa   1080
catcttctaa tttgtttaat ttgatacgag aacttgtctt attggtacat atatgatcca   1140
aagcattgta acaacgtgtt tatgtatact cttaatcatg gtcatcagaa gctaacacac   1200
acgctcatgc catccatatc attcaacttt tgaatcgttt actatacaat attatttcta   1260
aatttggctg taaagatggc attgatttca taaatatgaa aaataccaaa ttgcacattt   1320
tctttctata ttataatatt gttttcatct attttcaccc cgtaaccttt aatttggtca   1380
tttagggctc actaaaactg atatgtgggt tgtgcatcgc ataagaatca agaacccaga   1440
agtaattttc aatactaaga aacaacaaaa tttggttttt ttttgtttgg tttcgattat   1500
agccgaacta accaaattta agaaagcttt ttatatttgg ccacataaga aatgatatca   1560
tttaatattg taactgattc aagctgagta atagatgaga tgagtgtgtt aggatgtgta   1620
gcttccgatg atagagaatt agagtgtaca aagacgcatc gttacaatat ttggacctta   1680
tatgcaccaa tgtgtcaagt ctcgcttcaa attaactata ttaaaagatg ttggatcaac   1740
atgcactcac ttagatatca gtcgtattaa attgaacaaa ttacaagata ttggactatg   1800
cacccactca aatagttgtt atatagtgaa tacagtttac tcttagtagt atatgtaagt   1860
tcagcctttt ctattgtagg ttaagcctta attaaggctc ttacacaatt gtttcattat   1920
tcgcgttcga agcagcttct tcgtagattt tgcgagggaa ggctgcctcg gttttgcctt   1980
ccctagcact catgtgagag cctctggcaa taggtcttct catttttatt cacattcttt   2040
aagagcccat ataagcgttc atgacttgta tatactctta gatctttttt tgtgggtaaa   2100
gctcaagcta atctaaaaat agagaaatca ggaacaaaga atcatgtttt ggtggttttg   2160
atttctagcc tccacaataa ttttagttta ccttttttttg tttgatttta attttagaag   2220
ggtttatagc aggacttaaa atccaaaatg accattatct tcgagtaata acccgtttaa   2280
cggcgtcgac aagtctaacg gacaccaacc catgaaccac cagcgccgag ccaagaactg   2340
aaggtcgaga cgttgacacc tttggcgcga cacggcatgt tggcatctcc ctctctggcc   2400
ccctctcgag aattccgctc caccgcctca accggagacg gtttccaaag ttgtgcttag   2460
atgctcaaaa gttggtgaaa tcatttttat ttggcaattt gtgtccaact atagactaat   2520
taggctcaaa agatttgtct cgtaaagtac attcaaactg tgtaattagt tattttattt   2580
```

atctacattt aatactctat gaatgcgtca agagatttga tgtgacttta atgtgacgga 2640
caatctgaaa cttttacgca acttgcatat aaacagagcc caagtccgtt ccgttccgtt 2700
ccgcttcctc ctcccagacg gcacgaaacc gtgacggcac cggcagcacg gggattcctt 2760
tcccaccgct ccttcctttt cccttcatcg cccgcagcta taaatagcca cccccgtccg 2820
caacttcttt c 2831

<210> SEQ ID NO 80
<211> LENGTH: 95
<212> TYPE: DNA
<213> ORGANISM: Schizachyium scoparium

<400> SEQUENCE: 80
cccaacctca tcttttgttc ggagcacgca cacaatccga tcgatcccca atcccctcgt 60
ctctcctcgc gagcctcgtc gatccgccat tcaag 95

<210> SEQ ID NO 81
<211> LENGTH: 1153
<212> TYPE: DNA
<213> ORGANISM: Schizachyium scoparium

<400> SEQUENCE: 81
gtacggcgat catcctccct ccctctctac ctgctcttct gtagatcggc gaccccatcc 60
atggttaggg cctgctagtt ctgttcctgt ttttttttcca tggctgcgag gtagaataga 120
tctgatggcg ttatgatggt taatttgtca tactcttgcg gtctatgggt ccctttaggt 180
catcaattta attttgggtg gttgagatcg gtgatccatg gttagtaccc tagtcagtgg 240
ggttggatcc gtgctattag ggttcgtaga tggattctga tggctcagta actgggaatc 300
ctaggatggt tccatctggt ttgcagatga gaacgatttc atcatctgct atatcttgtt 360
tcgttgcgta ggttctgttt aaactaatcc gtggtatgat gttagccttt gataaggttg 420
atttcatcat ctgctatatc ttgtttcgtt gcgtaggttc tgtttaaact aatccgtggt 480
atgatgttag cctttgataa ggtttgattg tgctagctac gtcctgtgca gcagttaatt 540
gtcaggtcat acgtcataat ttttagcatg tctgtttttg tttgatttcg ttgtctgatt 600
aggctgtaga tagtttcgat ctacctgtcg gtttatttta ttaaaatttg gatccgtatg 660
tgtgtcacat atatcttcat gattaagatg gagttatatg ggtaggttat acatgtggct 720
gtggatcatg attaagatgg attgaagtat ctctttatct tttagttagg atagattatt 780
atatatgttg ctgttgattt tattggttct ttattatata tattcatgct tatatacata 840
aaagcaatgt gctattacag tttaatagtt cttgattatc taataaacaa ataaggatag 900
gtatatttgt tgctgttggt tttactggta ctctattaga tagtactttg acatgaagca 960
acatcctgct atggattaat aattattctt cgtctaataa aaagcatggt ttttaattat 1020
tttgatttga tatacttgga tgatgtcata tgcagcagct atttgtgaat ttttcggccg 1080
tatcttcata ttgcttggga ctgtttcttt ggttgataac tcaccctgtt gtttggtgat 1140
ccttctgcag gtg 1153

<210> SEQ ID NO 82
<211> LENGTH: 3281
<212> TYPE: DNA
<213> ORGANISM: Schizachyium scoparium

<400> SEQUENCE: 82
gtggacgtta atcggtaatt cttcatttta ttttattttg ttgtcaccgc gtacatttgg 60

-continued

```
gttaggcgtt tgttaaaggc attgccactc aaacaagcag ccgcgtttgg agcttttata    120
gtttgaaaag tgacggttgt aaagatgagt aagctgatta ttagtagagt aaattataat    180
tatcatacaa caactctcaa agtgggtgca cgttagtcca acatcttata atttatccaa    240
ctcaatacaa caactatata ggtgggtgca tgttggtcca acatcttcta atttgtttaa    300
tttgatacga gaacttgtct tattggtaca tatatgatcc aaagcattgt aacaacgtgt    360
ttatgtatac tcttaatcat ggtcatcaga agctaacaca cacgctcatg ccatccatat    420
cattcaactt ttgaatcgtt tactatacaa tattatttct aaatttggct gtaaagatgg    480
cattgatttc ataaatatga aaaataccaa attgcacatt ttctttctat attataatat    540
tgttttcatc tattttcacc ccgtaacctt taatttggtc atttagggct cactaaaact    600
gatatgtggg ttgtgcatcg cataagaatc aagaacccag aagtaatttt caatactaag    660
aaacaacaaa atttggtttt tttttgtttg gtttcgatta tagccgaact aaccaaattt    720
aagaaagctt tttatatttg gccacataag aaatgatatc atttaatatt gtaactgatt    780
caagctgagt aatagatgag atgagtgtgt taggatgtgt agcttccgat gatagagaat    840
tagagtgtac aaagacgcat cgttacaata tttggacctt atatgcacca atgtgtcaag    900
tctcgcttca aattaactat attaaaagat gttggatcaa catgcactca cttagatatc    960
agtcgtatta aattgaacaa attacaagat attggactat gcacccactc aaatagttgt   1020
tatatagtga atacagttta ctcttagtag tatatgtaag ttcagccttt tctattgtag   1080
gttaagcctt aattaaggct cttacacaat tgtttcatta ttcgcgttcg aagcagcttc   1140
ttcgtagatt ttgcgaggga aggctgcctc ggttttgcct tccctagcac tcatgtgaga   1200
gcctctggca ataggtcttc tcatttttat tcacattctt taagagccca tataagcgtt   1260
catgacttgt atatactctt agatcttttt tttgtgggta aagctcaagc taatctaaaa   1320
atagagaaat caggaacaaa gaatcatgtt ttggtggttt tgatttctag cctccacaat   1380
aattttagtt taccttttttt tgtttgattt taattttaga agggtttata gcaggactta   1440
aaatccaaaa tgaccattat cttcgagtaa taacccgttt aacggcgtcg acaagtctaa   1500
cggacaccaa cccatgaacc accagcgccg agccaagaac tgaaggtcga gacgttgaca   1560
cctttggcgc gacacggcat gttggcatct ccctctctgg ccccctctcg agaattccgc   1620
tccaccgcct caaccggaga cggtttccaa agttgtgctt agatgctcaa aagttggtga   1680
aatcattttt atttggcaat ttgtgtccaa ctatagacta attaggctca aaagatttgt   1740
ctcgtaaagt acattcaaac tgtgtaatta gttattttat ttatctacat ttaatactct   1800
atgaatgcgt caagagattt gatgtgactt taatgtgacg gacaatctga aacttttacg   1860
caacttgcat ataaacagag cccaagtccg ttccgttccg ttccgcttcc tcctcccaga   1920
cggcacgaaa ccgtgacggc accggcagca cggggattcc tttcccaccg ctccttcctt   1980
ttcccttcat cgcccgcagc tataaatagc cacccccgtc cgcaacttct ttccccaacc   2040
tcatcttttg ttcggagcac gcacacaatc cgatcgatcc ccaatcccct cgtctctcct   2100
cgcgagcctc gtcgatccgc cattcaaggt acggcgatca tcctccctcc ctctctacct   2160
gctcttctgt agatcggcga ccccatccat ggttagggcc tgctagttct gttcctgttt   2220
tttttccatg gctgcgaggt agaatagatc tgatggcgtt atgatggtta atttgtcata   2280
ctcttgcggt ctatgggtcc ctttaggtca tcaatttaat tttgggtggt tgagatcggt   2340
gatccatggt tagtacccta gtcagtgggg ttggatccgt gctattaggg ttcgtagatg   2400
```

-continued

```
gattctgatg gctcagtaac tgggaatcct aggatggttc catctggttt gcagatgaga   2460

acgatttcat catctgctat atcttgtttc gttgcgtagg ttctgtttaa actaatccgt   2520

ggtatgatgt tagcctttga taaggttgat ttcatcatct gctatatctt gtttcgttgc   2580

gtaggttctg tttaaactaa tccgtggtat gatgttagcc tttgataagg tttgattgtg   2640

ctagctacgt cctgtgcagc agttaattgt caggtcatac gtcataattt ttagcatgtc   2700

tgtttttgtt tgatttcgtt gtctgattag gctgtagata gtttcgatct acctgtcggt   2760

ttattttatt aaaatttgga tccgtatgtg tgtcacatat atcttcatga ttaagatgga   2820

gttatatggg taggttatac atgtggctgt ggatcatgat taagatggat tgaagtatct   2880

ctttatcttt tagttaggat agattattat atatgttgct gttgatttta ttggttcttt   2940

attatatata ttcatgctta tatacataaa agcaatgtgc tattacagtt taatagttct   3000

tgattatcta ataaacaaat aaggataggt atatttgttg ctgttggttt tactggtact   3060

ctattagata gtactttgac atgaagcaac atcctgctat ggattaataa ttattcttcg   3120

tctaataaaa agcatggttt ttaattattt tgatttgata tacttggatg atgtcatatg   3180

cagcagctat ttgtgaattt ttcggccgta tcttcatatt gcttgggact gtttctttgg   3240

ttgataactc accctgttgt ttggtgatcc ttctgcaggt g                       3281
```

<210> SEQ ID NO 83
<211> LENGTH: 2033
<212> TYPE: DNA
<213> ORGANISM: Schizachyium scoparium

<400> SEQUENCE: 83

```
gtggacgtta atcggtaatt cttcatttta ttttattttg ttgtcaccgc gtacatttgg     60

gttaggcgtt tgttaaaggc attgccactc aaacaagcag ccgcgtttgg agcttttata    120

gtttgaaaag tgacggttgt aaagatgagt aagctgatta ttagtagagt aaattataat    180

tatcatacaa caactctcaa agtgggtgca cgttagtcca acatcttata atttatccaa    240

ctcaatacaa caactatata ggtgggtgca tgttggtcca acatcttcta atttgtttaa    300

tttgatacga gaacttgtct tattggtaca tatatgatcc aaagcattgt aacaacgtgt    360

ttatgtatac tcttaatcat ggtcatcaga agctaacaca cacgctcatg ccatccatat    420

cattcaactt ttgaatcgtt tactatacaa tattatttct aaatttggct gtaaagatgg    480

cattgatttc ataaatatga aaaataccaa attgcacatt ttctttctat attataatat    540

tgttttcatc tattttcacc ccgtaacctt taatttggtc atttagggct cactaaaact    600

gatatgtggg ttgtgcatcg cataagaatc aagaacccag aagtaatttt caatactaag    660

aaacaacaaa atttggtttt tttttgtttg gtttcgatta tagccgaact aaccaaattt    720

aagaaagctt tttatatttg gccacataag aaatgatatc atttaatatt gtaactgatt    780

caagctgagt aatagatgag atgagtgtgt taggatgtgt agcttccgat gatagagaat    840

tagagtgtac aaagacgcat cgttacaata tttggacctt atatgcacca atgtgtcaag    900

tctcgcttca aattaactat attaaaagat gttggatcaa catgcactca cttagatatc    960

agtcgtatta aattgaacaa attacaagat attggactat gcacccactc aaatagttgt   1020

tatatagtga atacagttta ctcttagtag tatatgtaag ttcagccttt tctattgtag   1080

gttaagcctt aattaaggct cttacacaat tgtttcatta ttcgcgttcg aagcagcttc   1140

ttcgtagatt ttgcgaggga aggctgcctc ggttttgcct tccctagcac tcatgtgaga   1200

gcctctggca ataggtcttc tcatttttat tcacattctt taagagccca tataagcgtt   1260
```

catgacttgt atatactctt agatcttttt tttgtgggta aagctcaagc taatctaaaa 1320
atagagaaat caggaacaaa gaatcatgtt ttggtggttt tgatttctag cctccacaat 1380
aattttagtt taccttttttt tgtttgattt taattttaga agggtttata gcaggactta 1440
aaatccaaaa tgaccattat cttcgagtaa taacccgttt aacggcgtcg acaagtctaa 1500
cggacaccaa cccatgaacc accagcgccg agccaagaac tgaaggtcga gacgttgaca 1560
cctttggcgc gacacggcat gttggcatct ccctctctgg ccccctctcg agaattccgc 1620
tccaccgcct caaccggaga cggtttccaa agttgtgctt agatgctcaa aagttggtga 1680
aatcattttt atttggcaat ttgtgtccaa ctatagacta attaggctca aaagatttgt 1740
ctcgtaaagt acattcaaac tgtgtaatta gttattttat ttatctacat ttaatactct 1800
atgaatgcgt caagagattt gatgtgactt taatgtgacg gacaatctga aacttttacg 1860
caacttgcat ataaacagag cccaagtccg ttccgttccg ttccgcttcc tcctcccaga 1920
cggcacgaaa ccgtgacggc accggcagca cggggattcc tttcccaccg ctccttcctt 1980
ttcccttcat cgcccgcagc tataaatagc cacccccgtc cgcaacttct ttc 2033

<210> SEQ ID NO 84
<211> LENGTH: 2294
<212> TYPE: DNA
<213> ORGANISM: Schizachyium scoparium

<400> SEQUENCE: 84
gatattggac tatgcaccca ctcaaatagt tgttatatag tgaatacagt ttactcttag 60
tagtatatgt aagttcagcc ttttctattg taggttaagc cttaattaag gctcttacac 120
aattgtttca ttattcgcgt tcgaagcagc ttcttcgtag attttgcgag ggaaggctgc 180
ctcggttttg ccttccctag cactcatgtg agagcctctg gcaataggtc ttctcatttt 240
tattcacatt ctttaagagc ccatataagc gttcatgact tgtatatact cttagatctt 300 tttttgtgg gtaaagctca agctaatcta aaaatagaga aatcaggaac aaagaatcat 360
gttttggtgg ttttgatttc tagcctccac aataatttta gtttaccttt ttttgtttga 420
ttttaatttt agaagggttt atagcaggac ttaaaatcca aaatgaccat tatcttcgag 480
taataacccg tttaacggcg tcgacaagtc taacggacac caacccatga accaccagcg 540
ccgagccaag aactgaaggt cgagacgttg acacctttgg cgcgacacgg catgttggca 600
tctccctctc tggccccctc tcgagaattc cgctccaccg cctcaaccgg agacggtttc 660
caaagttgtg cttagatgct caaaagttgg tgaaatcatt tttatttggc aatttgtgtc 720
caactataga ctaattaggc tcaaaagatt tgtctcgtaa agtacattca aactgtgtaa 780
ttagttattt tatttatcta catttaatac tctatgaatg cgtcaagaga tttgatgtga 840
ctttaatgtg acggacaatc tgaaactttt acgcaacttg catataaaca gagcccaagt 900
ccgttccgtt ccgttccgct tcctcctccc agacggcacg aaaccgtgac ggcaccggca 960
gcacggggat tcctttccca ccgctccttc cttttccctt catcgcccgc agctataaat 1020
agccaccccc gtccgcaact tctttcccca acctcatctt ttgttcggag cacgcacaca 1080
atccgatcga tccccaatcc cctcgtctct cctcgcgagc ctcgtcgatc cgccattcaa 1140
ggtacggcga tcatcctccc tccctctcta cctgctcttc tgtagatcgg cgaccccatc 1200
catggttagg gcctgctagt tctgttcctg ttttttttcc atggctgcga ggtagaatag 1260
atctgatggc gttatgatgg ttaatttgtc atactcttgc ggtctatggg tccctttagg 1320

-continued tcatcaattt aattttgggt ggttgagatc ggtgatccat ggttagtacc ctagtcagtg 1380
gggttggatc cgtgctatta gggttcgtag atggattctg atggctcagt aactgggaat 1440
cctaggatgg ttccatctgg tttgcagatg agaacgattt catcatctgc tatatcttgt 1500
ttcgttgcgt aggttctgtt taaactaatc cgtggtatga tgttagcctt tgataaggtt 1560
gatttcatca tctgctatat cttgtttcgt tgcgtaggtt ctgtttaaac taatccgtgg 1620
tatgatgtta gcctttgata aggtttgatt gtgctagcta cgtcctgtgc agcagttaat 1680
tgtcaggtca tacgtcataa tttttagcat gtctgttttt gtttgatttc gttgtctgat 1740
taggctgtag atagtttcga tctacctgtc ggtttatttt attaaaattt ggatccgtat 1800
gtgtgtcaca tatatcttca tgattaagat ggagttatat gggtaggtta tacatgtggc 1860
tgtggatcat gattaagatg gattgaagta tctctttatc ttttagttag gatagattat 1920
tatatatgtt gctgttgatt ttattggttc tttattatat atattcatgc ttatatacat 1980
aaaagcaatg tgctattaca gtttaatagt tcttgattat ctaataaaca aataaggata 2040
ggtatatttg ttgctgttgg ttttactggt actctattag atagtacttt gacatgaagc 2100
aacatcctgc tatggattaa taattattct tcgtctaata aaaagcatgg tttttaatta 2160
ttttgatttg atatacttgg atgatgtcat atgcagcagc tatttgtgaa tttttcggcc 2220
gtatcttcat attgcttggg actgtttctt tggttgataa ctcaccctgt tgtttggtga 2280
tccttctgca ggtg 2294

<210> SEQ ID NO 85
<211> LENGTH: 1046
<212> TYPE: DNA
<213> ORGANISM: Schizachyium scoparium

<400> SEQUENCE: 85
gatattggac tatgcaccca ctcaaatagt tgttatatag tgaatacagt ttactcttag 60
tagtatatgt aagttcagcc ttttctattg taggttaagc cttaattaag gctcttacac 120
aattgtttca ttattcgcgt tcgaagcagc ttcttcgtag attttgcgag ggaaggctgc 180
ctcggttttg ccttccctag cactcatgtg agagcctctg gcaataggtc ttctcatttt 240
tattcacatt ctttaagagc ccatataagc gttcatgact tgtatatact cttagatctt 300
ttttttgtgg gtaaagctca agctaatcta aaaatagaga aatcaggaac aaagaatcat 360
gttttggtgg ttttgatttc tagcctccac aataatttta gtttaccttt ttttgtttga 420
ttttaatttt agaagggttt atagcaggac ttaaaatcca aaatgaccat tatcttcgag 480
taataacccg tttaacggcg tcgacaagtc taacggacac caacccatga accaccagcg 540
ccgagccaag aactgaaggt cgagacgttg acacctttgg cgcgacacgg catgttggca 600
tctccctctc tggccccctc tcgagaattc cgctccaccg cctcaaccgg agacggtttc 660
caaagttgtg cttagatgct caaaagttgg tgaaatcatt tttatttggc aatttgtgtc 720
caactataga ctaattaggc tcaaaagatt tgtctcgtaa agtacattca aactgtgtaa 780
ttagttattt tatttatcta catttaatac tctatgaatg cgtcaagaga tttgatgtga 840
ctttaatgtg acggacaatc tgaaactttt acgcaacttg catataaaca gagcccaagt 900
ccgttccgtt ccgttccgct tcctcctccc agacggcacg aaaccgtgac ggcaccggca 960
gcacggggat tcctttccca ccgctccttc cttttccctt catcgcccgc agctataaat 1020
agccaccccc gtccgcaact tctttc 1046

<210> SEQ ID NO 86
<211> LENGTH: 1795
<212> TYPE: DNA
<213> ORGANISM: Schizachyium scoparium

<400> SEQUENCE: 86
gtcgacaagt ctaacggaca ccaacccatg aaccaccagc gccgagccaa gaactgaagg 60
tcgagacgtt gacacctttg gcgcgacacg gcatgttggc atctccctct ctggcccccct 120 ctcgagaatt ccgctccacc gcctcaaccg gagacggttt ccaaagttgt gcttagatgc 180
tcaaaagttg gtgaaatcat ttttatttgg caatttgtgt ccaactatag actaattagg 240
ctcaaaagat ttgtctcgta aagtacattc aaactgtgta attagttatt ttatttatct 300
acatttaata ctctatgaat gcgtcaagag atttgatgtg actttaatgt gacggacaat 360
ctgaaacttt tacgcaactt gcatataaac agagcccaag tccgttccgt tccgttccgc 420
ttcctcctcc cagacggcac gaaaccgtga cggcaccggc agcacgggga ttcctttccc 480
accgctcctt ccttttccct tcatcgcccg cagctataaa tagccacccc cgtccgcaac 540
ttctttcccc aacctcatct tttgttcgga gcacgcacac aatccgatcg atccccaatc 600
ccctcgtctc tcctcgcgag cctcgtcgat ccgccattca aggtacggcg atcatcctcc 660
ctccctctct acctgctctt ctgtagatcg gcgaccccat ccatggttag ggcctgctag 720
ttctgttcct gtttttttc catggctgcg aggtagaata gatctgatgg cgttatgatg 780
gttaatttgt catactcttg cggtctatgg gtccctttag gtcatcaatt taattttggg 840
tggttgagat cggtgatcca tggttagtac cctagtcagt ggggttggat ccgtgctatt 900
agggttcgta gatggattct gatggctcag taactgggaa tcctaggatg gttccatctg 960
gtttgcagat gagaacgatt tcatcatctg ctatatcttg tttcgttgcg taggttctgt 1020
ttaaactaat ccgtggtatg atgttagcct ttgataaggt tgatttcatc atctgctata 1080
tcttgtttcg ttgcgtaggt tctgtttaaa ctaatccgtg gtatgatgtt agcctttgat 1140
aaggtttgat tgtgctagct acgtcctgtg cagcagttaa ttgtcaggtc atacgtcata 1200
atttttagca tgtctgtttt tgtttgattt cgttgtctga ttaggctgta gatagtttcg 1260
atctacctgt cggtttattt tattaaaatt tggatccgta tgtgtgtcac atatatcttc 1320
atgattaaga tggagttata tgggtaggtt atacatgtgg ctgtggatca tgattaagat 1380
ggattgaagt atctctttat cttttagtta ggatagatta ttatatatgt tgctgttgat 1440
tttattggtt ctttattata tatattcatg cttatataca taaaagcaat gtgctattac 1500
agtttaatag ttcttgatta tctaataaac aaataaggat aggtatattt gttgctgttg 1560
gttttactgg tactctatta gatagtactt tgacatgaag caacatcctg ctatggatta 1620
ataattattc ttcgtctaat aaaaagcatg gtttttaatt attttgattt gatatacttg 1680
gatgatgtca tatgcagcag ctatttgtga atttttcggc cgtatcttca tattgcttgg 1740
gactgtttct ttggttgata actcaccctg ttgtttggtg atccttctgc aggtg 1795

<210> SEQ ID NO 87
<211> LENGTH: 547
<212> TYPE: DNA
<213> ORGANISM: Schizachyium scoparium

<400> SEQUENCE: 87
gtcgacaagt ctaacggaca ccaacccatg aaccaccagc gccgagccaa gaactgaagg 60
tcgagacgtt gacacctttg gcgcgacacg gcatgttggc atctccctct ctggcccccct 120

```
ctcgagaatt ccgctccacc gcctcaaccg gagacggttt ccaaagttgt gcttagatgc    180

tcaaaagttg gtgaaatcat ttttatttgg caatttgtgt ccaactatag actaattagg    240

ctcaaaagat ttgtctcgta aagtacattc aaactgtgta attagttatt ttatttatct    300

acatttaata ctctatgaat gcgtcaagag atttgatgtg actttaatgt gacggacaat    360

ctgaaacttt tacgcaactt gcatataaac agagcccaag tccgttccgt tccgttccgc    420

ttcctcctcc cagacggcac gaaaccgtga cggcaccggc agcacgggga ttcctttccc    480

accgctcctt ccttttccct tcatcgcccg cagctataaa tagccacccc cgtccgcaac    540

ttctttc                                                              547
```

<210> SEQ ID NO 88
<211> LENGTH: 3357
<212> TYPE: DNA
<213> ORGANISM: Sorghastrum nutans

<400> SEQUENCE: 88

```
gtggccagct tttgttctag ttcaacggtc cgggccttcc gggaacctaa tgcactaatt     60

gattattatt aatctactat tgcagctaac ctcaaaagaa atgctctgca gttagttgtc    120

cgtcccaatc aatccaccag cagactcaca ttattgatgg aggaaattaa attcagcctt    180

tgacgtggat gcaacaactg cacaagatac catctacttt gcttaatttg ctgatgtttt    240

gagaaaatta aaccagcttt gaccaacaca tgagatgggc gccttacgtt tggcacaatg    300

taatgtagtc cggcacggca agttagactc tgtgtgtagt gttatattag ccggcctctt    360

taggtttggc acaatttaat tgaatccggc atggcaagtt agactgcagt gtgagccggt    420

caccgcaagt taggatataa tatacaagag caagtataca ataaagtgac attagcgtaa    480

agttatatga catatggaat ataagagaaa atacggagta tataataagg tgaactgtat    540

agcgatcaaa tttatgctaa gcgaagaaaa gagaagataa ataggttgaa aacttatagt    600

gagctttggc tcataatcta aataattatg agagagtggg atcgaccaca tattcatttt    660

gtagtacgta ctctctccgt tttttataag ttgctttgat ttttttttat atcaattttg    720

ctatacatct aaacataata ggaatatcaa gttcatgaag gtcgtgattt gcactaaata    780

tgttccctta ttagatagac gagttgttta gttttattgt agatgatata gcgcttgcat    840

atagcatgtg aaccggctaa attattagcc atacacgact ataaaaaatg acattccttt    900

gaggaacttt tatgcaacca aatagtcaac ttcaatgttg ctagagcggg ctttaagcca    960

aaagcagctg ctgctttgtt tccgagagaa gggacattct agttgatagc aaaacaaata   1020

cgtagcagtt gtagcgagtg tgtgagtaat aatttttctc tagtgtgtac gagtatgcga   1080

gtaataattt taaatctcta gaaggaagaa aaataatatt gctacctact ttgaggatat   1140

caatacettt ctctaaaatg ttttggtgaa gccatcttta aagctaattg ttcaagattc   1200

aaccattggg acgtctcaaa tgattagatc ctataatact cctacgtact aaattataag   1260

tcgttttgat tttattggta catacatttt gctatgtgtt tagatataat aatatgtcta   1320

gatacattgg atgaaccgaa aaaatcgaaa cgacttataa tttggatcga aaggagtatt   1380

tgctaaagtc cttttcgaag ttccggctct aaatttttgg ataaaatttt atgaaatact   1440

atcttaagaa gtaatttgac tagagaagct tgaagagtat aatctcttaa ttttgtgcta   1500

caggagtgaa gccaacgtcg tatttagatc tagatgctgt caggtagtga ggacggaggg   1560

agtattggat aaagtcattc caagatctta gaaaattaaa gtatattaag tttgattaaa   1620

tttatatgac aagtaataac attcatgatg ccaattaagt atcattagat tcttcatcaa   1680
```

ctatattttc atagtatact tatttaatgt tataaatttt tataattttt tttataattt 1740
tagctaaact cgagatcgat tcttataatt aaaaataaac tgaaaaaaaa tcacatgttc 1800
aagtgacagg aggagccagt ttaacggcgt cgacaagtct aacggacacc aaccagcgaa 1860
ccaccagcgc cgagccaatc ccaagcgaag ccgactgcag acggccgaga cgttgacacc 1920
tttggcgcgg catccatctc tccggccccc tcttgagagt tccgccccac cggcggcggt 1980
ttccaagtcc gttccgcccg ccttcgcggt tggacttgtt ccggtggcgc ctggcggatc 2040
gcgtggcgga gcggagacga cgaggtgagc cgtgggcgtt cctcctcctg ctcctctcac 2100
acggcacgga acggaaccgt gacggcaccg ggcagcacgg gcgggattcc ttccccacct 2160
ctccttcggt cctccctcca tcataaatag ccaccccccct cccaccttct ttccccacct 2220
cgtctcccct cgtgttattc ggagcacaga cacaccccga tccccaatcc tctcctcgcg 2280
agcctcgtcg atccccgctt caaggtacgg cgatcatcct ccctccctaa ctccaatccg 2340
tggttagggc ctgctagatc gtcctccctc cctacctgcg atccgtggtt cgcgcctgct 2400
agttctgttt cctgtttgtc gatggctgcg aggtataata gatctgatgg cgtgcggtgt 2460
gacggttaaa ttcacatgct cttgcgattt atacgcgaat cgatctggga ttgctcgaga 2520
tcggtgatcc atggttagaa ccctaggcgg tggagtcggg ttaaatccgt gctgttaggg 2580
ttcgtaggtg gatgcgacct gttctggttg tttacttgtc agtatttagg aatcctacta 2640
ggatggttct agctggttcg cagatgagat cgatttcatg atctgctata tctttcgttg 2700
cctaagtttc gtttaatctg tccgtggtat gatgttagcc tttgatatgc ttcgatcgtg 2760
ctagctacct cctgtgcact aaattatcag ctcgtaattt ttagcatgcc cttttttttt 2820
tgggtattgt tcgattgagg tgtcgttcta gatcagagta ggaagactgt ttcaaactac 2880
ctgctggatt tattaaattt ggatctgtat gagtatcaca tatatctcca taatttagat 2940
ggatggaaat atcccttttt cttttagata ctgtttggta tagattttgc tgtgggtttt 3000
actggtactt agatactctt cgtttagata tggatatgtt tacatgcaga tacatgaagc 3060
aacatgctgc tacagtttaa tatggatagg tgtatatgtt gttgtgggtc ctttacttac 3120
atgcttagat acatgaagca acatgctgct acgtttaata attattgttt atctgatctg 3180
atttaaacaa acatgctttt taattgtcct gaaatgcttg gatgatggca tatgcagcag 3240
ctatgtgtgg attttaaata cccagcatga gcatgcatga ccctaactta gtatgctgtt 3300
tatttgcttg acttttcttt tgttgatact caccctttttg tttgttgact cttgcag 3357

<210> SEQ ID NO 89
<211> LENGTH: 2218
<212> TYPE: DNA
<213> ORGANISM: Sorghastrum nutans

<400> SEQUENCE: 89
gtggccagct tttgttctag ttcaacggtc cgggccttcc gggaacctaa tgcactaatt 60
gattattatt aatctactat tgcagctaac ctcaaaagaa atgctctgca gttagttgtc 120
cgtcccaatc aatccaccag cagactcaca ttattgatgg aggaaattaa attcagcctt 180
tgacgtggat gcaacaactg cacaagatac catctacttt gcttaatttg ctgatgtttt 240
gagaaaatta aaccagcttt gaccaacaca tgagatgggc gccttacgtt tggcacaatg 300
taatgtagtc cggcacggca agttagactc tgtgtgtagt gttatattag ccggcctctt 360
taggtttggc acaatttaat tgaatccggc atggcaagtt agactgcagt gtgagccggt 420
caccgcaagt taggatataa tatacaagag caagtataca ataaagtgac attagcgtaa 480
agttatatga catatggaat ataagagaaa atacggagta tataataagg tgaactgtat 540
agcgatcaaa tttatgctaa gcgaagaaaa gagaagataa ataggttgaa aacttatagt 600
gagctttggc tcataatcta aataattatg agagagtggg atcgaccaca tattcatttt 660
gtagtacgta ctctctccgt tttttataag ttgctttgat ttttttttat atcaattttg 720
ctatacatct aaacataata ggaatatcaa gttcatgaag gtcgtgattt gcactaaata 780
tgttccctta ttagatagac gagttgttta gttttattgt agatgatata gcgcttgcat 840
atagcatgtg aaccggctaa attattagcc atacacgact ataaaaaatg acattccttt 900
gaggaacttt tatgcaacca aatagtcaac ttcaatgttg ctagagcggg ctttaagcca 960
aaagcagctg ctgctttgtt tccgagagaa gggacattct agttgatagc aaaacaaata 1020
cgtagcagtt gtagcgagtg tgtgagtaat aatttttctc tagtgtgtac gagtatgcga 1080
gtaataattt taaatctcta gaaggaagaa aaataatatt gctacctact ttgaggatat 1140
caataccttt ctctaaaatg ttttggtgaa gccatcttta aagctaattg ttcaagattc 1200
aaccattggg acgtctcaaa tgattagatc ctataatact cctacgtact aaattataag 1260
tcgttttgat tttattggta catacatttt gctatgtgtt tagatataat aatatgtcta 1320
gatacattgg atgaaccgaa aaaatcgaaa cgacttataa tttggatcga aaggagtatt 1380
tgctaaagtc cttttcgaag ttccggctct aaatttttgg ataaaatttt atgaaatact 1440
atcttaagaa gtaatttgac tagagaagct tgaagagtat aatctcttaa ttttgtgcta 1500
caggagtgaa gccaacgtcg tatttagatc tagatgctgt caggtagtga ggacggaggg 1560
agtattggat aaagtcattc caagatctta gaaaattaaa gtatattaag tttgattaaa 1620
tttatatgac aagtaataac attcatgatg ccaattaagt atcattagat tcttcatcaa 1680
ctatattttc atagtatact tatttaatgt tataaatttt tataattttt tttataattt 1740
tagctaaact cgagatcgat tcttataatt aaaaataaac tgaaaaaaaa tcacatgttc 1800
aagtgacagg aggagccagt ttaacggcgt cgacaagtct aacggacacc aaccagcgaa 1860
ccaccagcgc cgagccaatc ccaagcgaag ccgactgcag acggccgaga cgttgacacc 1920
tttggcgcgg catccatctc tccggccccc tcttgagagt tccgccccac cggcggcggt 1980
ttccaagtcc gttccgcccg ccttcgcggt tggacttgtt ccggtggcgc ctggcggatc 2040
gcgtggcgga gcggagacga cgaggtgagc cgtgggcgtt cctcctcctg ctcctctcac 2100
acggcacgga acggaaccgt gacggcaccg ggcagcacgg gcgggattcc ttccccacct 2160
ctccttcggt cctccctcca tcataaatag ccaccccccct cccaccttct ttccccac 2218

<210> SEQ ID NO 90
<211> LENGTH: 86
<212> TYPE: DNA
<213> ORGANISM: Sorghastrum nutans

<400> SEQUENCE: 90
ctcgtctccc ctcgtgttat tcggagcaca gacacacccc gatccccaat cctctcctcg 60
cgagcctcgt cgatccccgc ttcaag 86

<210> SEQ ID NO 91
<211> LENGTH: 1053
<212> TYPE: DNA
<213> ORGANISM: Sorghastrum nutans

<400> SEQUENCE: 91

-continued

```
gtacggcgat catcctccct ccctaactcc aatccgtggt tagggcctgc tagatcgtcc      60

tccctcccta cctgcgatcc gtggttcgcg cctgctagtt ctgtttcctg tttgtcgatg     120

gctgcgaggt ataatagatc tgatggcgtg cggtgtgacg gttaaattca catgctcttg     180

cgatttatac gcgaatcgat ctgggattgc tcgagatcgg tgatccatgg ttagaaccct     240

aggcggtgga gtcgggttaa atccgtgctg ttagggttcg taggtggatg cgacctgttc     300

tggttgttta cttgtcagta tttaggaatc ctactaggat ggttctagct ggttcgcaga     360

tgagatcgat ttcatgatct gctatatctt tcgttgccta agtttcgttt aatctgtccg     420

tggtatgatg ttagcctttg atatgcttcg atcgtgctag ctacctcctg tgcactaaat     480

tatcagctcg taatttttag catgcccttt ttttttgggg tattgttcga ttgaggtgtc     540

gttctagatc agagtaggaa gactgtttca aactacctgc tggatttatt aaatttggat     600

ctgtatgagt atcacatata tctccataat ttagatggat ggaaatatcc ctttttcttt     660

tagatactgt ttggtataga ttttgctgtg ggttttactg gtacttagat actcttcgtt     720

tagatatgga tatgtttaca tgcagataca tgaagcaaca tgctgctaca gtttaatatg     780

gataggtgta tatgttgttg tgggtccttt acttacatgc ttagatacat gaagcaacat     840

gctgctacgt ttaataatta ttgtttatct gatctgattt aaacaaacat gctttttaat     900

tgtcctgaaa tgcttggatg atggcatatg cagcagctat gtgtggattt taaataccca     960

gcatgagcat gcatgaccct aacttagtat gctgtttatt tgcttgactt ttcttttgtt    1020

gatactcacc cttttgtttg ttgactcttg cag                                 1053
```

<210> SEQ ID NO 92
<211> LENGTH: 3106
<212> TYPE: DNA
<213> ORGANISM: Sorghastrum nutans

<400> SEQUENCE: 92

```
agctttgacc aacacatgag atgggcgcct tacgtttggc acaatgtaat gtagtccggc      60

acggcaagtt agactctgtg tgtagtgtta tattagccgg cctctttagg tttggcacaa     120

tttaattgaa tccggcatgg caagttagac tgcagtgtga gccggtcacc gcaagttagg     180

atataatata caagagcaag tatacaataa agtgacatta gcgtaaagtt atatgacata     240

tggaatataa gagaaaatac ggagtatata ataaggtgaa ctgtatagcg atcaaattta     300

tgctaagcga agaaaagaga agataaatag gttgaaaact tatagtgagc tttggctcat     360

aatctaaata attatgagag agtgggatcg accacatatt cattttgtag tacgtactct     420

ctccgttttt tataagttgc tttgattttt ttttatatca attttgctat acatctaaac     480

ataataggaa tatcaagttc atgaaggtcg tgatttgcac taaatatgtt cccttattag     540

atagacgagt tgtttagttt tattgtagat gatatagcgc ttgcatatag catgtgaacc     600

ggctaaatta ttagccatac acgactataa aaaatgacat tcctttgagg aacttttatg     660

caaccaaata gtcaacttca atgttgctag agcgggcttt aagccaaaag cagctgctgc     720

tttgtttccg agagaaggga cattctagtt gatagcaaaa caaatacgta gcagttgtag     780

cgagtgtgtg agtaataatt tttctctagt gtgtacgagt atgcgagtaa taattttaaa     840

tctctagaag gaagaaaaat aatattgcta cctactttga ggatatcaat acctttctct     900

aaaatgtttt ggtgaagcca tctttaaagc taattgttca agattcaacc attgggacgt     960

ctcaaatgat tagatcctat aatactccta cgtactaaat tataagtcgt tttgatttta    1020
```

```
ttggtacata cattttgcta tgtgtttaga tataataata tgtctagata cattggatga   1080
accgaaaaaa tcgaaacgac ttataatttg gatcgaaagg agtatttgct aaagtccttt   1140
tcgaagttcc ggctctaaat ttttggataa aattttatga aatactatct taagaagtaa   1200
tttgactaga gaagcttgaa gagtataatc tcttaatttt gtgctacagg agtgaagcca   1260
acgtcgtatt tagatctaga tgctgtcagg tagtgaggac ggagggagta ttggataaag   1320
tcattccaag atcttagaaa attaaagtat attaagtttg attaaattta tatgacaagt   1380
aataacattc atgatgccaa ttaagtatca ttagattctt catcaactat attttcatag   1440
tatacttatt taatgttata aatttttata atttttttta taattttagc taaactcgag   1500
atcgattctt ataattaaaa ataaactgaa aaaaaatcac atgttcaagt gacaggagga   1560
gccagtttaa cggcgtcgac aagtctaacg gacaccaacc agcgaaccac cagcgccgag   1620
ccaatcccaa gcgaagccga ctgcagacgg ccgagacgtt gacacctttg gcgcggcatc   1680
catctctccg gccccctctt gagagttccg ccccaccggc ggcggtttcc aagtccgttc   1740
cgcccgcctt cgcggttgga cttgttccgg tggcgcctgg cggatcgcgt ggcggagcgg   1800
agacgacgag gtgagccgtg ggcgttcctc ctcctgctcc tctcacacgg cacggaacgg   1860
aaccgtgacg gcaccgggca gcacgggcgg gattccttcc ccacctctcc ttcggtcctc   1920
cctccatcat aaatagccac ccccctccca ccttctttcc ccacctcgtc tcccctcgtg   1980
ttattcggag cacagacaca ccccgatccc caatcctctc ctcgcgagcc tcgtcgatcc   2040
ccgcttcaag gtacggcgat catcctccct ccctaactcc aatccgtggt tagggcctgc   2100
tagatcgtcc tccctcccta cctgcgatcc gtggttcgcg cctgctagtt ctgtttcctg   2160
tttgtcgatg gctgcgaggt ataatagatc tgatggcgtg cggtgtgacg gttaaattca   2220
catgctcttg cgatttatac gcgaatcgat ctgggattgc tcgagatcgg tgatccatgg   2280
ttagaaccct aggcggtgga gtcgggttaa atccgtgctg ttagggttcg taggtggatg   2340
cgacctgttc tggttgttta cttgtcagta tttaggaatc ctactaggat ggttctagct   2400
ggttcgcaga tgagatcgat ttcatgatct gctatatctt tcgttgccta agtttcgttt   2460
aatctgtccg tggtatgatg ttagcctttg atatgcttcg atcgtgctag ctacctcctg   2520
tgcactaaat tatcagctcg taatttttag catgcccttt tttttttggg tattgttcga   2580
ttgaggtgtc gttctagatc agagtaggaa gactgtttca aactacctgc tggatttatt   2640
aaatttggat ctgtatgagt atcacatata tctccataat ttagatggat ggaaatatcc   2700
ctttttcttt tagatactgt ttggtataga ttttgctgtg ggttttactg gtacttagat   2760
actcttcgtt tagatatgga tatgtttaca tgcagataca tgaagcaaca tgctgctaca   2820
gtttaatatg gataggtgta tatgttgttg tgggtccttt acttacatgc ttagatacat   2880
gaagcaacat gctgctacgt ttaataatta ttgtttatct gatctgattt aaacaaacat   2940
gctttttaat tgtcctgaaa tgcttggatg atggcatatg cagcagctat gtgtggattt   3000
taaataccca gcatgagcat gcatgaccct aacttagtat gctgtttatt tgcttgactt   3060
ttcttttgtt gatactcacc cttttgtttg ttgactcttg caggtg                  3106
```

<210> SEQ ID NO 93
<211> LENGTH: 1964
<212> TYPE: DNA
<213> ORGANISM: Sorghastrum nutans

<400> SEQUENCE: 93

```
agctttgacc aacacatgag atgggcgcct tacgtttggc acaatgtaat gtagtccggc     60
```

```
acggcaagtt agactctgtg tgtagtgtta tattagccgg cctctttagg tttggcacaa    120
tttaattgaa tccggcatgg caagttagac tgcagtgtga gccggtcacc gcaagttagg    180
atataatata caagagcaag tatacaataa agtgacatta gcgtaaagtt atatgacata    240
tggaatataa gagaaaatac ggagtatata ataaggtgaa ctgtatagcg atcaaattta    300
tgctaagcga agaaaagaga agataaatag gttgaaaact tatagtgagc tttggctcat    360
aatctaaata attatgagag agtgggatcg accacatatt cattttgtag tacgtactct    420
ctccgttttt tataagttgc tttgattttt ttttatatca attttgctat acatctaaac    480
ataataggaa tatcaagttc atgaaggtcg tgatttgcac taaatatgtt cccttattag    540
atagacgagt tgtttagttt tattgtagat gatatagcgc ttgcatatag catgtgaacc    600
ggctaaatta ttagccatac acgactataa aaaatgacat tcctttgagg aacttttatg    660
caaccaaata gtcaacttca atgttgctag agcgggcttt aagccaaaag cagctgctgc    720
tttgtttccg agagaaggga cattctagtt gatagcaaaa caaatacgta gcagttgtag    780
cgagtgtgtg agtaataatt tttctctagt gtgtacgagt atgcgagtaa taattttaaa    840
tctctagaag gaagaaaaat aatattgcta cctactttga ggatatcaat acctttctct    900
aaaatgtttt ggtgaagcca tctttaaagc taattgttca agattcaacc attgggacgt    960
ctcaaatgat tagatcctat aatactccta cgtactaaat tataagtcgt tttgatttta   1020
ttggtacata cattttgcta tgtgtttaga tataataata tgtctagata cattggatga   1080
accgaaaaaa tcgaaacgac ttataatttg gatcgaaagg agtatttgct aaagtccttt   1140
tcgaagttcc ggctctaaat ttttggataa aattttatga aatactatct taagaagtaa   1200
tttgactaga gaagcttgaa gagtataatc tcttaatttt gtgctacagg agtgaagcca   1260
acgtcgtatt tagatctaga tgctgtcagg tagtgaggac ggagggagta ttggataaag   1320
tcattccaag atcttagaaa attaaagtat attaagtttg attaaattta tatgacaagt   1380
aataacattc atgatgccaa ttaagtatca ttagattctt catcaactat attttcatag   1440
tatacttatt taatgttata aatttttata attttttttta taattttagc taaactcgag   1500
atcgattctt ataattaaaa ataaactgaa aaaaaatcac atgttcaagt gacaggagga   1560
gccagtttaa cggcgtcgac aagtctaacg gacaccaacc agcgaaccac cagcgccgag   1620
ccaatcccaa gcgaagccga ctgcagacgg ccgagacgtt gacacctttg gcgcggcatc   1680
catctctccg gccccctctt gagagttccg ccccaccggc ggcggtttcc aagtccgttc   1740
cgcccgcctt cgcggttgga cttgttccgg tggcgcctgg cggatcgcgt ggcggagcgg   1800
agacgacgag gtgagccgtg ggcgttcctc ctcctgctcc tctcacacgg cacggaacgg   1860
aaccgtgacg gcaccgggca gcacgggcgg gattccttcc ccacctctcc ttcggtcctc   1920
cctccatcat aaatagccac ccccctccca ccttctttcc ccac                    1964
```

<210> SEQ ID NO 94
<211> LENGTH: 1056
<212> TYPE: DNA
<213> ORGANISM: Sorghastrum nutans

<400> SEQUENCE: 94

```
gtacggcgat catcctccct ccctaactcc aatccgtggt tagggcctgc tagatcgtcc     60
tccctcccta cctgcgatcc gtggttcgcg cctgctagtt ctgtttcctg tttgtcgatg    120
gctgcgaggt ataatagatc tgatggcgtg cggtgtgacg gttaaattca catgctcttg    180
```

cgatttatac gcgaatcgat ctgggattgc tcgagatcgg tgatccatgg ttagaaccct 240
aggcggtgga gtcgggttaa atccgtgctg ttagggttcg taggtggatg cgacctgttc 300
tggttgttta cttgtcagta tttaggaatc ctactaggat ggttctagct ggttcgcaga 360
tgagatcgat ttcatgatct gctatatctt tcgttgccta agtttcgttt aatctgtccg 420
tggtatgatg ttagcctttg atatgcttcg atcgtgctag ctacctcctg tgcactaaat 480
tatcagctcg taatttttag catgcccttt ttttttgggg tattgttcga ttgaggtgtc 540
gttctagatc agagtaggaa gactgtttca aactacctgc tggatttatt aaatttggat 600
ctgtatgagt atcacatata tctccataat ttagatggat ggaaatatcc ctttttcttt 660
tagatactgt ttggtataga ttttgctgtg ggttttactg gtacttagat actcttcgtt 720
tagatatgga tatgtttaca tgcagataca tgaagcaaca tgctgctaca gtttaatatg 780
gataggtgta tatgttgttg tgggtccttt acttacatgc ttagatacat gaagcaacat 840
gctgctacgt ttaataatta ttgtttatct gatctgattt aaacaaacat gctttttaat 900
tgtcctgaaa tgcttggatg atggcatatg cagcagctat gtgtggattt taaataccca 960
gcatgagcat gcatgaccct aacttagtat gctgtttatt tgcttgactt ttcttttgtt 1020
gatactcacc cttttgtttg ttgactcttg caggtg 1056

<210> SEQ ID NO 95
<211> LENGTH: 2165
<212> TYPE: DNA
<213> ORGANISM: Sorghastrum nutans

<400> SEQUENCE: 95
gattcaacca ttgggacgtc tcaaatgatt agatcctata atactcctac gtactaaatt 60
ataagtcgtt ttgattttat tggtacatac attttgctat gtgtttagat ataataatat 120
gtctagatac attggatgaa ccgaaaaaat cgaaacgact tataatttgg atcgaaagga 180
gtatttgcta aagtcctttt cgaagttccg gctctaaatt tttggataaa attttatgaa 240
atactatctt aagaagtaat ttgactagag aagcttgaag agtataatct cttaattttg 300
tgctacagga gtgaagccaa cgtcgtattt agatctagat gctgtcaggt agtgaggacg 360
gagggagtat tggataaagt cattccaaga tcttagaaaa ttaaagtata ttaagtttga 420
ttaaatttat atgacaagta ataacattca tgatgccaat taagtatcat tagattcttc 480
atcaactata ttttcatagt atacttattt aatgttataa atttttataa ttttttttat 540
aattttagct aaactcgaga tcgattctta taattaaaaa taaactgaaa aaaaatcaca 600
tgttcaagtg acaggaggag ccagtttaac ggcgtcgaca agtctaacgg acaccaacca 660
gcgaaccacc agcgccgagc caatcccaag cgaagccgac tgcagacggc cgagacgttg 720
acacctttgg cgcggcatcc atctctccgg ccccctcttg agagttccgc cccaccggcg 780
gcggtttcca agtccgttcc gcccgccttc gcggttggac ttgttccggt ggcgcctggc 840
ggatcgcgtg gcggagcgga gacgacgagg tgagccgtgg gcgttcctcc tcctgctcct 900
ctcacacggc acggaacgga accgtgacgg caccgggcag cacgggcggg attccttccc 960
cacctctcct tcggtcctcc ctccatcata aatagccacc cccctcccac cttctttccc 1020
cacctcgtct cccctcgtgt tattcggagc acagacacac cccgatcccc aatcctctcc 1080
tcgcgagcct cgtcgatccc cgcttcaagg tacggcgatc atcctccctc cctaactcca 1140
atccgtggtt agggcctgct agatcgtcct ccctccctac ctgcgatccg tggttcgcgc 1200
ctgctagttc tgtttcctgt ttgtcgatgg ctgcgaggta taatagatct gatggcgtgc 1260

-continued ggtgtgacgg ttaaattcac atgctcttgc gatttatacg cgaatcgatc tgggattgct 1320
cgagatcggt gatccatggt tagaacccta ggcggtggag tcgggttaaa tccgtgctgt 1380
tagggttcgt aggtggatgc gacctgttct ggttgtttac ttgtcagtat ttaggaatcc 1440
tactaggatg gttctagctg gttcgcagat gagatcgatt tcatgatctg ctatatcttt 1500
cgttgcctaa gtttcgttta atctgtccgt ggtatgatgt tagcctttga tatgcttcga 1560
tcgtgctagc tacctcctgt gcactaaatt atcagctcgt aatttttagc atgccctttt 1620 tttttgggt attgttcgat tgaggtgtcg ttctagatca gagtaggaag actgtttcaa 1680
actacctgct ggatttatta aatttggatc tgtatgagta tcacatatat ctccataatt 1740
tagatggatg gaaatatccc tttttctttt agatactgtt tggtatagat tttgctgtgg 1800
gttttactgg tacttagata ctcttcgttt agatatggat atgtttacat gcagatacat 1860
gaagcaacat gctgctacag tttaatatgg ataggtgtat atgttgttgt gggtccttta 1920
cttacatgct tagatacatg aagcaacatg ctgctacgtt taataattat tgtttatctg 1980
atctgattta aacaaacatg ctttttaatt gtcctgaaat gcttggatga tggcatatgc 2040
agcagctatg tgtggatttt aaatacccag catgagcatg catgacccta acttagtatg 2100
ctgtttattt gcttgacttt tcttttgttg atactcaccc ttttgtttgt tgactcttgc 2160
aggtg 2165

<210> SEQ ID NO 96
<211> LENGTH: 1023
<212> TYPE: DNA
<213> ORGANISM: Sorghastrum nutans

<400> SEQUENCE: 96
gattcaacca ttgggacgtc tcaaatgatt agatcctata atactcctac gtactaaatt 60
ataagtcgtt ttgattttat tggtacatac attttgctat gtgtttagat ataataatat 120
gtctagatac attggatgaa ccgaaaaaat cgaaacgact tataatttgg atcgaaagga 180
gtatttgcta aagtcctttt cgaagttccg gctctaaatt tttggataaa attttatgaa 240
atactatctt aagaagtaat ttgactagag aagcttgaag agtataatct cttaattttg 300
tgctacagga gtgaagccaa cgtcgtattt agatctagat gctgtcaggt agtgaggacg 360
gagggagtat tggataaagt cattccaaga tcttagaaaa ttaaagtata ttaagtttga 420
ttaaatttat atgacaagta ataacattca tgatgccaat taagtatcat tagattcttc 480
atcaactata ttttcatagt atacttattt aatgttataa atttttataa ttttttttat 540
aattttagct aaactcgaga tcgattctta taattaaaaa taaactgaaa aaaaatcaca 600
tgttcaagtg acaggaggag ccagtttaac ggcgtcgaca agtctaacgg acaccaacca 660
gcgaaccacc agcgccgagc caatcccaag cgaagccgac tgcagacggc cgagacgttg 720
acacctttgg cgcggcatcc atctctccgg ccccctcttg agagttccgc cccaccggcg 780
gcggtttcca agtccgttcc gcccgccttc gcggttggac ttgttccggt ggcgcctggc 840
ggatcgcgtg gcggagcgga gacgacgagg tgagccgtgg gcgttcctcc tcctgctcct 900
ctcacacggc acggaacgga accgtgacgg caccgggcag cacgggcggg attccttccc 960
cacctctcct tcggtcctcc ctccatcata aatagccacc cccctcccac cttctttccc 1020
cac 1023

<210> SEQ ID NO 97

<211> LENGTH: 1866
<212> TYPE: DNA
<213> ORGANISM: Sorghastrum nutans

<400> SEQUENCE: 97
gtgctacagg agtgaagcca acgtcgtatt tagatctaga tgctgtcagg tagtgaggac 60
ggagggagta ttggataaag tcattccaag atcttagaaa attaaagtat attaagtttg 120
attaaattta tatgacaagt aataacattc atgatgccaa ttaagtatca ttagattctt 180
catcaactat attttcatag tatacttatt taatgttata aatttttata attttttta 240 taattttagc taaactcgag atcgattctt ataattaaaa ataaactgaa aaaaaatcac 300
atgttcaagt gacaggagga gccagtttaa cggcgtcgac aagtctaacg gacaccaacc 360
agcgaaccac cagcgccgag ccaatcccaa gcgaagccga ctgcagacgg ccgagacgtt 420
gacacctttg gcgcggcatc catctctccg gccccctctt gagagttccg ccccaccggc 480
ggcggtttcc aagtccgttc cgcccgcctt cgcggttgga cttgttccgg tggcgcctgg 540
cggatcgcgt ggcggagcgg agacgacgag gtgagccgtg ggcgttcctc ctcctgctcc 600
tctcacacgg cacggaacgg aaccgtgacg gcaccgggca gcacgggcgg gattccttcc 660
ccacctctcc ttcggtcctc cctccatcat aaatagccac ccccctccca ccttctttcc 720
ccacctcgtc tcccctcgtg ttattcggag cacagacaca ccccgatccc caatcctctc 780
ctcgcgagcc tcgtcgatcc ccgcttcaag gtacggcgat catcctccct ccctaactcc 840
aatccgtggt tagggcctgc tagatcgtcc tccctcccta cctgcgatcc gtggttcgcg 900
cctgctagtt ctgtttcctg tttgtcgatg gctgcgaggt ataatagatc tgatggcgtg 960
cggtgtgacg gttaaattca catgctcttg cgatttatac gcgaatcgat ctgggattgc 1020
tcgagatcgg tgatccatgg ttagaaccct aggcggtgga gtcgggttaa atccgtgctg 1080
ttagggttcg taggtggatg cgacctgttc tggttgttta cttgtcagta tttaggaatc 1140
ctactaggat ggttctagct ggttcgcaga tgagatcgat ttcatgatct gctatatctt 1200
tcgttgccta agtttcgttt aatctgtccg tggtatgatg ttagcctttg atatgcttcg 1260
atcgtgctag ctacctcctg tgcactaaat tatcagctcg taatttttag catgcccttt 1320
ttttttgggg tattgttcga ttgaggtgtc gttctagatc agagtaggaa gactgtttca 1380
aactacctgc tggatttatt aaatttggat ctgtatgagt atcacatata tctccataat 1440
ttagatggat ggaaatatcc ctttttcttt tagatactgt ttggtataga ttttgctgtg 1500
ggttttactg gtacttagat actcttcgtt tagatatgga tatgtttaca tgcagataca 1560
tgaagcaaca tgctgctaca gtttaatatg gataggtgta tatgttgttg tgggtccttt 1620
acttacatgc ttagatacat gaagcaacat gctgctacgt ttaataatta ttgtttatct 1680
gatctgattt aaacaaacat gctttttaat tgtcctgaaa tgcttggatg atggcatatg 1740
cagcagctat gtgtggattt taaataccca gcatgagcat gcatgaccct aacttagtat 1800
gctgtttatt tgcttgactt ttcttttgtt gatactcacc cttttgtttg ttgactcttg 1860
caggtg 1866

<210> SEQ ID NO 98
<211> LENGTH: 724
<212> TYPE: DNA
<213> ORGANISM: Sorghastrum nutans

<400> SEQUENCE: 98
gtgctacagg agtgaagcca acgtcgtatt tagatctaga tgctgtcagg tagtgaggac 60
ggagggagta ttggataaag tcattccaag atcttagaaa attaaagtat attaagtttg 120
attaaattta tatgacaagt aataacattc atgatgccaa ttaagtatca ttagattctt 180
catcaactat attttcatag tatacttatt taatgttata aatttttata atttttttta 240
taattttagc taaactcgag atcgattctt ataattaaaa ataaactgaa aaaaaatcac 300
atgttcaagt gacaggagga gccagtttaa cggcgtcgac aagtctaacg gacaccaacc 360
agcgaaccac cagcgccgag ccaatcccaa gcgaagccga ctgcagacgg ccgagacgtt 420
gacacctttg gcgcggcatc catctctccg gccccctctt gagagttccg ccccaccggc 480
ggcggtttcc aagtccgttc cgcccgcctt cgcggttgga cttgttccgg tggcgcctgg 540
cggatcgcgt ggcggagcgg agacgacgag gtgagccgtg ggcgttcctc ctcctgctcc 600
tctcacacgg cacggaacgg aaccgtgacg gcaccgggca gcacgggcgg gattccttcc 660
ccacctctcc ttcggtcctc cctccatcat aaatagccac ccccctccca ccttctttcc 720
ccac 724

<210> SEQ ID NO 99
<211> LENGTH: 2625
<212> TYPE: DNA
<213> ORGANISM: Setaria italica

<400> SEQUENCE: 99
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380

-continued

```
acgcggagga gtcgtgcgtg gtccaacacg gccggcgggc tgggctgcga ccttaaccag   1440

caaggcacgc cacgacccgc cccgccctcg aggcataaat accctcccat cccgttgccg   1500

caagactcag atcagattcc gatccccagt tcttccccaa tcaccttgtg gtctctcgtg   1560

tcgcggttcc cagggacgcc tccggctcgt cgctcgacag cgatctccgc cccagcaagg   1620

tatagattca gttccttgct ccgatcccaa tctggttgag atgttgctcc gatgcgactt   1680

gattatgtca tatatctgcg gtttgcaccg atctgaagcc tagggtttct cgagcgaccc   1740

agttatttgc aatttgcgat ttgctcgttt gttgcgcagc gtagtttatg tttggagtaa   1800

tcgaggattt gtatgcggcg tcggcgctac ctgcttaatc acgccatgtg acgcggttac   1860

ttgcagaggc tgggttctgt tatgtcgtga tctaagaatc tagattaggc tcagtcgttc   1920

ttgctgtcga ctagtttgtt ttgatatcca tgtagtacaa gttacttaaa atttaggtcc   1980

aatatatttt gcatgctttt ggcctgttat tcttgccaac aagttgtcct ggtaaaaagt   2040

agatgtgaaa gtcacgtatt gggacaaatt gatggtttag tgctatagtt ctatagttct   2100

gtgatacatc tatctgattt tttttggtct attggtgcct aacttatctg aaaatcatgg   2160

aacatgaggc tagtttgatc atggtttagt tcattgtgat taataatgta tgatttagta   2220

gctattttgg tgatcgtgtc attttatttg tgaatggaat cattgtatgt aaatgaagct   2280

agttcagggg ttacgatgta gctggctttg tattctaaag gctgctatta ttcatccatc   2340

gatttcacct atatgtaatc cagagctttt gatgtgaaat ttgtctgatc cttcactagg   2400

aaggacagaa cattgttaat attttggcac atctgtctta ttctcatcct ttgtttgaac   2460

atgttagcct gttcaaacag atactgttgt aatgtcctag ttatataggt acatatgtgt   2520

tctctattga gtttatggac ttttgtgtgt gaagttatat ttcattttgc tcaaaactca   2580

tgtttgcaag ctttctgaca ttattctatt gttctgaaac agggt                   2625
```

<210> SEQ ID NO 100
<211> LENGTH: 1492
<212> TYPE: DNA
<213> ORGANISM: Setaria italica

<400> SEQUENCE: 100

```
actgccgcga cacgcctcac tggcgggagg gctccgagcg ctctctcccc ggcggccggc     60

ggagcagcga tctggattgg agagaataga ggaaagagag ggaaaaggag agagatagcg    120

caaagagctg aaaagataag gttgtgcggg ctgtggtgat tagaggacca ctaatccctc    180

catctcctaa tgacgcggtg cccaagacca gtgccgcggc acaccagcgt ctaagtgaac    240

ttccgctaac cttccggtca ttgcgcctga aagatgtcat gtggcgaggc ccccctctca    300

gtagattgcc aactgcctac cgtgccactc ttccatgcat gattgctccc gtctatcccg    360

tttctcacaa cagatagaca acagtaagca tcactaaagc aagcatgtgt agaaccttaa    420

aaaaaggctt atactaccag tatactatca accagcatgc cgtttttgaa gtatccagga    480

ttagaagctt ctactgcgct tttatattat agctgtggac ccgtggtaac ctttctcttt    540

tggcgcttgc ttaatctcgg ccgtgctggt ccatgcttag gcactaggca gagatagagc    600

cgggggtgaa tggggctaaa gctcagctgc tcgaggggcc gtgggctggt ttccactagc    660

ctacagctgt gccacgtgcg gccgcgcaag ccgaagcaag cacgctgagc cgttggacag    720

cttgtcataa tgccattacg tggattacac gtaactggcc ctgtaactac tcgttcggcc    780

atcatcaaac gacgacgtcc gctaggcgac gacacgggta atgcacgcag ccacccaggc    840

gcgcgcgcta gcggagcacg gtcaggtgac acgggcgtcg tgacgcttcc gagttgaagg    900
```

ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cc 1492

<210> SEQ ID NO 101
<211> LENGTH: 127
<212> TYPE: DNA
<213> ORGANISM: Setaria italica

<400> SEQUENCE: 101
cgttgccgca agactcagat cagattccga tccccagttc ttccccaatc accttgtggt 60
ctctcgtgtc gcggttccca gggacgcctc cggctcgtcg ctcgacagcg atctccgccc 120
cagcaag 127

<210> SEQ ID NO 102
<211> LENGTH: 1006
<212> TYPE: DNA
<213> ORGANISM: Setaria italica

<400> SEQUENCE: 102
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa cagggt 1006

<210> SEQ ID NO 103

<211> LENGTH: 2625
<212> TYPE: DNA
<213> ORGANISM: Setaria italica

<400> SEQUENCE: 103
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920
ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040
agatgtgaaa gtcacgtatt gggacaaatt gatggtttag tgctatagtt ctatagttct 2100
gtgatacatc tatctgattt tttttggtct attggtgcct aacttatctg aaaatcatgg 2160
aacatgaggc tagtttgatc atggtttagt tcattgtgat taataatgta tgatttagta 2220

-continued

```
gctattttgg tgatcgtgtc attttatttg tgaatggaat cattgtatgt aaatgaagct   2280

agttcagggg ttacgatgta gctggctttg tattctaaag gctgctatta ttcatccatc   2340

gatttcacct atatgtaatc cagagctttt gatgtgaaat ttgtctgatc cttcactagg   2400

aaggacagaa cattgttaat attttggcac atctgtctta ttctcatcct ttgtttgaac   2460

atgttagcct gttcaaacag atactgttgt aatgtcctag ttatataggt acatatgtgt   2520

tctctattga gtttatggac ttttgtgtgt gaagttatat ttcattttgc tcaaaactca   2580

tgtttgcaag ctttctgaca ttattctatt gttctgaaac aggtg                    2625
```

<210> SEQ ID NO 104
<211> LENGTH: 1492
<212> TYPE: DNA
<213> ORGANISM: Setaria italica

<400> SEQUENCE: 104

```
actgccgcga cacgcctcac tggcgggagg gctccgagcg ctctctcccc ggcggccggc     60

ggagcagcga tctggattgg agagaataga ggaaagagag ggaaaaggag agagatagcg    120

caaagagctg aaaagataag gttgtgcggg ctgtggtgat tagaggacca ctaatccctc    180

catctcctaa tgacgcggtg cccaagacca gtgccgcggc acaccagcgt ctaagtgaac    240

ttccgctaac cttccggtca ttgcgcctga aagatgtcat gtggcgaggc ccccctctca    300

gtagattgcc aactgcctac cgtgccactc ttccatgcat gattgctccc gtctatcccg    360

tttctcacaa cagatagaca acagtaagca tcactaaagc aagcatgtgt agaaccttaa    420

aaaaaggctt atactaccag tatactatca accagcatgc cgtttttgaa gtatccagga    480

ttagaagctt ctactgcgct tttatattat agctgtggac ctgtggtaac ctttctcttt    540

tggcgcttgc ttaatctcgg ccgtgctggt ccatgcttag gcactaggca gagatagagc    600

cgggggtgaa tggggctaaa gctcagctgc tcgaggggcc gtgggctggt ttccactagc    660

ctacagctgt gccacgtgcg gccgcgcaag ccgaagcaag cacgctgagc cgttggacag    720

cttgtcataa tgccattacg tggattacac gtaactggcc ctgtaactac tcgttcggcc    780

atcatcaaac gacgacgtcc gctaggcgac gacacgggta atgcacgcag ccacccaggc    840

gcgcgcgcta gcggagcacg gtcaggtgac acgggcgtcg tgacgcttcc gagttgaagg    900

ggttaacgcc agaaacagtg tttggccagg gtatgaacat aacaaaaaat attcacacga    960

aagaatggaa gtatggagct gctactgtgt aaatgccaag caggaaactc acgcccgcta   1020

acatccaacg gccaacagct cgacgtgccg gtcagcagag catcggaaca ctggtgattg   1080

gtggagccgg cagtatgcgc cccagcacgg ccgaggtggt ggtggcccgt ggccctgctg   1140

tctgcgcggc tcgggacaac ttgaaactgg gccaccgcct cgtcgcaact cgcaacccgt   1200

tggcggaaga aaggaatggc tcgtaggggc ccgggtagaa tcgaagaatg ttgcgctggg   1260

cttcgattca cataacatgg gcctgaagct ctaaaacgac ggcccggtcg ccgcgcgatg   1320

gaaagagacc ggatcctcct cgtgaattct ggaaggccac acgagagcga cccaccaccg   1380

acgcggagga gtcgtgcgtg gtccaacacg gccggcgggc tgggctgcga ccttaaccag   1440

caaggcacgc cacgacccgc cccgccctcg aggcataaat accctcccat cc           1492
```

<210> SEQ ID NO 105
<211> LENGTH: 1006
<212> TYPE: DNA
<213> ORGANISM: Setaria italica

<400> SEQUENCE: 105
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa caggtg 1006

<210> SEQ ID NO 106
<211> LENGTH: 2167
<212> TYPE: DNA
<213> ORGANISM: Setaria italica

<400> SEQUENCE: 106
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac acgtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agcatcggaa cactggtgat tggtggagcc ggcagtatgc gccccagcac ggccgaggtg 660
gtggtggccc gtggccctgc tgtctgcgcg gctcgggaca acttgaaact gggccaccgc 720
ctcgtcgcaa ctcgcaaccc gttggcggaa gaaaggaatg gctcgtaggg gcccgggtag 780
aatcgaagaa tgttgcgctg ggcttcgatt cacataacat gggcctgaag ctctaaaacg 840
acggcccggt cgccgcgcga tggaaagaga ccggatcctc ctcgtgaatt ctggaaggcc 900
acacgagagc gacccaccac cgacgcggag gagtcgtgcg tggtccaaca cggccggcgg 960
gctgggctgc gaccttaacc agcaaggcac gccacgaccc gccccgccct cgaggcataa 1020
ataccctccc atcccgttgc cgcaagactc agatcagatt ccgatcccca gttcttcccc 1080
aatcaccttg tggtctctcg tgtcgcggtt cccagggacg cctccggctc gtcgctcgac 1140
agcgatctcc gccccagcaa ggtatagatt cagttccttg ctccgatccc aatctggttg 1200
agatgttgct ccgatgcgac ttgattatgt catatatctg cggtttgcac cgatctgaag 1260
cctagggttt ctcgagcgac ccagttattt gcaatttgcg atttgctcgt ttgttgcgca 1320
gcgtagttta tgtttggagt aatcgaggat ttgtatgcgg cgtcggcgct acctgcttaa 1380
tcacgccatg tgacgcggtt acttgcagag gctgggttct gttatgtcgt gatctaagaa 1440
tctagattag gctcagtcgt tcttgctgtc gactagtttg ttttgatatc catgtagtac 1500
aagttactta aaatttaggt ccaatatatt ttgcatgctt ttggcctgtt attcttgcca 1560
acaagttgtc ctggtaaaaa gtagatgtga aagtcacgta ttgggacaaa ttgatggttt 1620
agtgctatag ttctatagtt ctgtgataca tctatctgat tttttttggt ctattggtgc 1680
ctaacttatc tgaaaatcat ggaacatgag gctagtttga tcatggttta gttcattgtg 1740
attaataatg tatgatttag tagctatttt ggtgatcgtg tcattttatt tgtgaatgga 1800
atcattgtat gtaaatgaag ctagttcagg ggttacgatg tagctggctt tgtattctaa 1860
aggctgctat tattcatcca tcgatttcac ctatatgtaa tccagagctt ttgatgtgaa 1920
atttgtctga tccttcacta ggaaggacag aacattgtta atattttggc acatctgtct 1980
tattctcatc ctttgtttga acatgttagc ctgttcaaac agatactgtt gtaatgtcct 2040
agttatatag gtacatatgt gttctctatt gagtttatgg acttttgtgt gtgaagttat 2100
atttcatttt gctcaaaact catgtttgca agctttctga cattattcta ttgttctgaa 2160
acaggtg 2167

<210> SEQ ID NO 107
<211> LENGTH: 1034
<212> TYPE: DNA
<213> ORGANISM: Setaria italica

<400> SEQUENCE: 107
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac acgtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agcatcggaa cactggtgat tggtggagcc ggcagtatgc gccccagcac ggccgaggtg 660
gtggtggccc gtggccctgc tgtctgcgcg gctcgggaca acttgaaact gggccaccgc 720
ctcgtcgcaa ctcgcaaccc gttggcggaa gaaaggaatg gctcgtaggg gcccgggtag 780
aatcgaagaa tgttgcgctg ggcttcgatt cacataacat gggcctgaag ctctaaaacg 840
acggcccggt cgccgcgcga tggaaagaga ccggatcctc ctcgtgaatt ctggaaggcc 900
acacgagagc gacccaccac cgacgcggag gagtcgtgcg tggtccaaca cggccggcgg 960

-continued gctgggctgc gaccttaacc agcaaggcac gccacgaccc gccccgccct cgaggcataa 1020
ataccctccc atcc 1034

<210> SEQ ID NO 108
<211> LENGTH: 1813
<212> TYPE: DNA
<213> ORGANISM: Setaria italica

<400> SEQUENCE: 108
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag gtg 1813

<210> SEQ ID NO 109
<211> LENGTH: 680
<212> TYPE: DNA
<213> ORGANISM: Setaria italica

<400> SEQUENCE: 109
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc 680

<210> SEQ ID NO 110
<211> LENGTH: 2634
<212> TYPE: DNA
<213> ORGANISM: Setaria viridis

<400> SEQUENCE: 110
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320

-continued ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcccgttgcc 1500
gcaagactca gatcagattc cgatccccag ttcttcccca atcaccttgt ggtctctcgt 1560
gtcgcggttc ccagggacgc ctccggctcg tcgctcgaca gcgatctccg ccccagcaag 1620
gtatagattc agttccttgc tccgatccca atctggttga gatgttgctc cgatgcgact 1680
tgattatgtc atatatctgc ggtttgcacc gatctgaagc ctagggtttc tcgagcgacc 1740
cagttgtttg caatttgcga tttgctcgtt tgttgcgcat cgtagtttat gtttggagta 1800
atcgaggatt tgtatgcggc gtcggcgcta cctgcttaat cacgccatgt gacgcggtta 1860
cttgcagagg ctgggttagt gggttctgtt atgtcgtgat ctaagaatct agattaggct 1920
cagtcgttct tgctgtcgac tagtttgttt tgatatccat gtagtacaag ttacttaaaa 1980
tttaggtcca atatatttg catgcttttg gcctgttatt cttgccaaca agttgtcctg 2040
gtaaaaagta gatgtgaaag tcacgtattg ggacaaattg atggttaagt gctatagttc 2100
tatagttctg tgatacatct atctgatttt ttttggtcta ttggtgccta acttatctga 2160
aaatcatgga acatgaggct agtttgatca tggtttagtt cattgtgatt aataatgtat 2220
gatttagtag ctattttggt gatcgtgtca ttttatttgt gaatggaatc attgtatgta 2280
aatgaagcta gttcaggggt tatgatgtag ctggctttgt attctaaagg ctgctattat 2340
tcatccatcg atttcaccta tatgtaatcc agagctttcg atgtgaaatt tgtctgatcc 2400
ttcactagga aggacagaac attgttaata ttttggcaca tctgtcttat tctcatcctt 2460
tgtttgaaca tgttagcctg ttcaaacaga tactgttgta atgtcctagt tatataggta 2520
catatgtgtt ctctattgag tttatggact tttgtgtgtg aagttatatt tcattttgct 2580
caaaactcat gtttgcaagc tttctgacat tattctattg ttctgaaaca ggtg 2634

<210> SEQ ID NO 111
<211> LENGTH: 1493
<212> TYPE: DNA
<213> ORGANISM: Setaria viridis

<400> SEQUENCE: 111
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcc 1493

<210> SEQ ID NO 112
<211> LENGTH: 127
<212> TYPE: DNA
<213> ORGANISM: Setaria viridis

<400> SEQUENCE: 112
cgttgccgca agactcagat cagattccga tccccagttc ttccccaatc accttgtggt 60
ctctcgtgtc gcggttccca gggacgcctc cggctcgtcg ctcgacagcg atctccgccc 120
cagcaag 127

<210> SEQ ID NO 113
<211> LENGTH: 1014
<212> TYPE: DNA
<213> ORGANISM: Setaria viridis

<400> SEQUENCE: 113
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttgtttg caatttgcga tttgctcgtt tgttgcgcat cgtagtttat gtttggagta 180
atcgaggatt tgtatgcggc gtcggcgcta cctgcttaat cacgccatgt gacgcggtta 240
cttgcagagg ctgggttagt gggttctgtt atgtcgtgat ctaagaatct agattaggct 300
cagtcgttct tgctgtcgac tagtttgttt tgatatccat gtagtacaag ttacttaaaa 360
tttaggtcca atatatttg catgcttttg gcctgttatt cttgccaaca agttgtcctg 420
gtaaaaagta gatgtgaaag tcacgtattg ggacaaattg atggttaagt gctatagttc 480
tatagttctg tgatacatct atctgatttt ttttggtcta ttggtgccta acttatctga 540
aaatcatgga acatgaggct agtttgatca tggtttagtt cattgtgatt aataatgtat 600
gatttagtag ctattttggt gatcgtgtca ttttatttgt gaatggaatc attgtatgta 660
aatgaagcta gttcaggggt tatgatgtag ctggctttgt attctaaagg ctgctattat 720
tcatccatcg atttcaccta tatgtaatcc agagctttcg atgtgaaatt tgtctgatcc 780
ttcactagga aggacagaac attgttaata ttttggcaca tctgtcttat tctcatcctt 840
tgtttgaaca tgttagcctg ttcaaacaga tactgttgta atgtcctagt tatataggta 900
catatgtgtt ctctattgag tttatggact tttgtgtgtg aagttatatt tcattttgct 960
caaaactcat gtttgcaagc tttctgacat tattctattg ttctgaaaca ggtg 1014

<210> SEQ ID NO 114
<211> LENGTH: 2634
<212> TYPE: DNA
<213> ORGANISM: Setaria viridis

<400> SEQUENCE: 114
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcccgttgcc 1500
gcaagactca gatcagattc cgatccccag ttcttcccca atcaccttgt ggtctctcgt 1560
gtcgcggttc ccagggacgc ctccggctcg tcgctcgaca gcgatctccg ccccagcaag 1620
gtatagattc agttccttgc tccgatccca atctggttga gatgttgctc cgatgcgact 1680
tgattatgtc atatatctgc ggtttgcacc gatctgaagc ctagggtttc tcgagcgacc 1740
cagttgtttg caatttgcga tttgctcgtt tgttgcgcat cgtagtttat gtttggagta 1800
atcgaggatt tgtatgcggc gtcggcgcta cctgcttaat cacgccatgt gacgcggtta 1860
cttgcagagg ctgggttagt gggttctgtt atgtcgtgat ctaagaatct agattaggct 1920
cagtcgttct tgctgtcgac tagtttgttt tgatatccat gtagtacaag ttacttaaaa 1980
tttaggtcca atatattttg catgcttttg gcctgttatt cttgccaaca agttgtcctg 2040
gtaaaaagta gatgtgaaag tcacgtattg ggacaaattg atggttaagt gctatagttc 2100
tatagttctg tgatacatct atctgatttt ttttggtcta ttggtgccta acttatctga 2160

```
aaatcatgga acatgaggct agtttgatca tggtttagtt cattgtgatt aataatgtat   2220

gatttagtag ctattttggt gatcgtgtca ttttatttgt gaatggaatc attgtatgta   2280

aatgaagcta gttcaggggt tatgatgtag ctggctttgt attctaaagg ctgctattat   2340

tcatccatcg atttcaccta tatgtaatcc agagctttcg atgtgaaatt tgtctgatcc   2400

ttcactagga aggacagaac attgttaata ttttggcaca tctgtcttat tctcatcctt   2460

tgtttgaaca tgttagcctg ttcaaacaga tactgttgta atgtcctagt tatataggta   2520

catatgtgtt ctctattgag tttatggact tttgtgtgtg aagttatatt tcattttgct   2580

caaaactcat gtttgcaagc tttctgacat tattctattg ttctgaaaca gggt         2634
```

<210> SEQ ID NO 115
<211> LENGTH: 1014
<212> TYPE: DNA
<213> ORGANISM: Setaria viridis

<400> SEQUENCE: 115

```
gtatagattc agttccttgc tccgatccca atctggttga gatgttgctc cgatgcgact     60

tgattatgtc atatatctgc ggtttgcacc gatctgaagc ctagggtttc tcgagcgacc    120

cagttgtttg caatttgcga tttgctcgtt tgttgcgcat cgtagtttat gtttggagta    180

atcgaggatt tgtatgcggc gtcggcgcta cctgcttaat cacgccatgt gacgcggtta    240

cttgcagagg ctgggttagt gggttctgtt atgtcgtgat ctaagaatct agattaggct    300

cagtcgttct tgctgtcgac tagtttgttt tgatatccat gtagtacaag ttacttaaaa    360

tttaggtcca atatattttg catgcttttg gcctgttatt cttgccaaca agttgtcctg    420

gtaaaaagta gatgtgaaag tcacgtattg ggacaaattg atggttaagt gctatagttc    480

tatagttctg tgatacatct atctgatttt ttttggtcta ttggtgccta acttatctga    540

aaatcatgga acatgaggct agtttgatca tggtttagtt cattgtgatt aataatgtat    600

gatttagtag ctattttggt gatcgtgtca ttttatttgt gaatggaatc attgtatgta    660

aatgaagcta gttcaggggt tatgatgtag ctggctttgt attctaaagg ctgctattat    720

tcatccatcg atttcaccta tatgtaatcc agagctttcg atgtgaaatt tgtctgatcc    780

ttcactagga aggacagaac attgttaata ttttggcaca tctgtcttat tctcatcctt    840

tgtttgaaca tgttagcctg ttcaaacaga tactgttgta atgtcctagt tatataggta    900

catatgtgtt ctctattgag tttatggact tttgtgtgtg aagttatatt tcattttgct    960

caaaactcat gtttgcaagc tttctgacat tattctattg ttctgaaaca gggt         1014
```

<210> SEQ ID NO 116
<211> LENGTH: 2176
<212> TYPE: DNA
<213> ORGANISM: Setaria viridis

<400> SEQUENCE: 116

```
gccgtttttg aagtatccag gattagaagc ttctactgcg cttttatatt atagctgtgg     60

acctgtggta acctttctct tttggcgctt gcttaatctc ggccgtgctg gtccatgctt    120

aggcactagg cagagataga gccgggggtg aatggggcta aagctcagct gctcgagggg    180

ccgtgggctg gtttccacta gcctacagct gtgccacgtg cggccgcgca agccgaagca    240

agcacgctga gccgttggac agcttgtcat aatgccatta cgtggattac aggtaactgg    300

ccctgtaact actcgttcgg ccatcatcaa acgacgacgt ccgctaggcg acgacacggg    360
```

taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agacatcgga acactggtga ttggtggagc cggcagtatg cgccccagca cggccgaggt 660
ggtggtggcc cgtggccctg ctgtctgcgc ggctcgggac aacttgaaac tgggccaccg 720
cctcgtcgca actcgcaacc cgttggcgga agaaaggaat ggctcgtagg ggcccgggta 780
gaatccaaga atgttgcgct gggcttcgat tcacataaca tgggcctgaa gctctaaaac 840
gacggcccgg tcaccgggcg atggaaagag accggatcct cctcgtgaat tctggaaggc 900
cacacgagag cgacccacca ccgacgcgga ggagtcgtgc gtggtccaac acggccggcg 960
ggctgggctg cgaccttaac cagcaaggca cgccacgacc cgcctcgccc tcgaggcata 1020
aataccctcc catcccgttg ccgcaagact cagatcagat tccgatcccc agttcttccc 1080
caatcacctt gtggtctctc gtgtcgcggt tcccagggac gcctccggct cgtcgctcga 1140
cagcgatctc cgccccagca aggtatagat tcagttcctt gctccgatcc caatctggtt 1200
gagatgttgc tccgatgcga cttgattatg tcatatatct gcggtttgca ccgatctgaa 1260
gcctagggtt tctcgagcga cccagttgtt tgcaatttgc gatttgctcg tttgttgcgc 1320
atcgtagttt atgtttggag taatcgagga tttgtatgcg gcgtcggcgc tacctgctta 1380
atcacgccat gtgacgcggt tacttgcaga ggctgggtta gtgggttctg ttatgtcgtg 1440
atctaagaat ctagattagg ctcagtcgtt cttgctgtcg actagtttgt tttgatatcc 1500
atgtagtaca agttacttaa aatttaggtc caatatattt tgcatgcttt tggcctgtta 1560
ttcttgccaa caagttgtcc tggtaaaaag tagatgtgaa agtcacgtat tgggacaaat 1620
tgatggttaa gtgctatagt tctatagttc tgtgatacat ctatctgatt ttttttggtc 1680
tattggtgcc taacttatct gaaaatcatg gaacatgagg ctagtttgat catggtttag 1740
ttcattgtga ttaataatgt atgatttagt agctattttg gtgatcgtgt cattttattt 1800
gtgaatggaa tcattgtatg taaatgaagc tagttcaggg gttatgatgt agctggcttt 1860
gtattctaaa ggctgctatt attcatccat cgatttcacc tatatgtaat ccagagcttt 1920
cgatgtgaaa tttgtctgat ccttcactag gaaggacaga acattgttaa tattttggca 1980
catctgtctt attctcatcc tttgtttgaa catgttagcc tgttcaaaca gatactgttg 2040
taatgtccta gttatatagg tacatatgtg ttctctattg agtttatgga cttttgtgtg 2100
tgaagttata tttcattttg ctcaaaactc atgtttgcaa gctttctgac attattctat 2160
tgttctgaaa caggtg 2176

<210> SEQ ID NO 117
<211> LENGTH: 1035
<212> TYPE: DNA
<213> ORGANISM: Setaria viridis

<400> SEQUENCE: 117
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac aggtaactgg 300

```
ccctgtaact actcgttcgg ccatcatcaa acgacgacgt ccgctaggcg acgacacggg    360

taatgcacgc agccacccag gcgcgcgcgc tagcggagca cggtcaggtg acacgggcgt    420

cgtgacgctt ccgagttgaa ggggttaacg ccagaaacag tgtttggcca gggtatgaac    480

ataacaaaaa atattcacac gaaagaatgg aagtatggag ctgctactgt gtaaatgcca    540

agcaggaaac tcacgcccgc taacatccaa cggccaacag ctcgacgtgc cggtcagcag    600

agacatcgga acactggtga ttggtggagc cggcagtatg cgccccagca cggccgaggt    660

ggtggtggcc cgtggccctg ctgtctgcgc ggctcgggac aacttgaaac tgggccaccg    720

cctcgtcgca actcgcaacc cgttggcgga agaaaggaat ggctcgtagg ggcccgggta    780

gaatccaaga atgttgcgct gggcttcgat tcacataaca tgggcctgaa gctctaaaac    840

gacggcccgg tcaccgggcg atggaaagag accggatcct cctcgtgaat tctggaaggc    900

cacacgagag cgacccacca ccgacgcgga ggagtcgtgc gtggtccaac acggccggcg    960

ggctgggctg cgaccttaac cagcaaggca cgccacgacc cgcctcgccc tcgaggcata   1020

aataccctcc catcc                                                    1035
```

<210> SEQ ID NO 118
<211> LENGTH: 1822
<212> TYPE: DNA
<213> ORGANISM: Setaria viridis

<400> SEQUENCE: 118

```
cacgggtaat gcacgcagcc acccaggcgc gcgcgctagc ggagcacggt caggtgacac     60

gggcgtcgtg acgcttccga gttgaagggg ttaacgccag aaacagtgtt tggccagggt    120

atgaacataa caaaaaatat tcacacgaaa gaatggaagt atggagctgc tactgtgtaa    180

atgccaagca ggaaactcac gcccgctaac atccaacggc caacagctcg acgtgccggt    240

cagcagagac atcggaacac tggtgattgg tggagccggc agtatgcgcc ccagcacggc    300

cgaggtggtg gtggcccgtg gccctgctgt ctgcgcggct cgggacaact tgaaactggg    360

ccaccgcctc gtcgcaactc gcaacccgtt ggcggaagaa aggaatggct cgtaggggcc    420

cgggtagaat ccaagaatgt tgcgctgggc ttcgattcac ataacatggg cctgaagctc    480

taaaacgacg gcccggtcac cgggcgatgg aaagagaccg gatcctcctc gtgaattctg    540

gaaggccaca cgagagcgac ccaccaccga cgcggaggag tcgtgcgtgg tccaacacgg    600

ccggcgggct gggctgcgac cttaaccagc aaggcacgcc acgacccgcc tcgccctcga    660

ggcataaata ccctcccatc ccgttgccgc aagactcaga tcagattccg atccccagtt    720

cttccccaat caccttgtgg tctctcgtgt cgcggttccc agggacgcct ccggctcgtc    780

gctcgacagc gatctccgcc ccagcaaggt atagattcag ttccttgctc cgatcccaat    840

ctggttgaga tgttgctccg atgcgacttg attatgtcat atatctgcgg tttgcaccga    900

tctgaagcct agggtttctc gagcgaccca gttgtttgca atttgcgatt tgctcgtttg    960

ttgcgcatcg tagtttatgt ttggagtaat cgaggatttg tatgcggcgt cggcgctacc   1020

tgcttaatca cgccatgtga cgcggttact tgcagaggct gggttagtgg gttctgttat   1080

gtcgtgatct aagaatctag attaggctca gtcgttcttg ctgtcgacta gtttgttttg   1140

atatccatgt agtacaagtt acttaaaatt taggtccaat atattttgca tgcttttggc   1200

ctgttattct tgccaacaag ttgtcctggt aaaaagtaga tgtgaaagtc acgtattggg   1260

acaaattgat ggttaagtgc tatagttcta tagttctgtg atacatctat ctgatttttt   1320
```

-continued ttggtctatt ggtgcctaac ttatctgaaa atcatggaac atgaggctag tttgatcatg 1380
gtttagttca ttgtgattaa taatgtatga tttagtagct attttggtga tcgtgtcatt 1440
ttatttgtga atggaatcat tgtatgtaaa tgaagctagt tcaggggtta tgatgtagct 1500
ggctttgtat tctaaaggct gctattattc atccatcgat ttcacctata tgtaatccag 1560
agctttcgat gtgaaatttg tctgatcctt cactaggaag gacagaacat tgttaatatt 1620
ttggcacatc tgtcttattc tcatcctttg tttgaacatg ttagcctgtt caaacagata 1680
ctgttgtaat gtcctagtta tataggtaca tatgtgttct ctattgagtt tatggacttt 1740
tgtgtgtgaa gttatatttc attttgctca aaactcatgt ttgcaagctt tctgacatta 1800
ttctattgtt ctgaaacagg tg 1822

<210> SEQ ID NO 119
<211> LENGTH: 681
<212> TYPE: DNA
<213> ORGANISM: Setaria viridis

<400> SEQUENCE: 119
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctc gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc c 681

<210> SEQ ID NO 120
<211> LENGTH: 1822
<212> TYPE: DNA
<213> ORGANISM: Setaria viridis

<400> SEQUENCE: 120
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660

-continued ggcataaata ccctcccatc ccgttgccgc aagactcaga tcagattccg atccccagtt 720
cttccccaat caccttgtgg tctctcgtgt cgcggttccc agggacgcct ccggctcgtc 780
gctcgacagc gatctccgcc ccagcaaggt atagattcag ttccttgctc cgatcccaat 840
ctggttgaga tgttgctccg atgcgacttg attatgtcat atatctgcgg tttgcaccga 900
tctgaagcct agggtttctc gagcgaccca gttgtttgca atttgcgatt tgctcgtttg 960
ttgcgcatcg tagtttatgt ttggagtaat cgaggatttg tatgcggcgt cggcgctacc 1020
tgcttaatca cgccatgtga cgcggttact tgcagaggct gggttagtgg gttctgttat 1080
gtcgtgatct aagaatctag attaggctca gtcgttcttg ctgtcgacta gtttgttttg 1140
atatccatgt agtacaagtt acttaaaatt taggtccaat atattttgca tgcttttggc 1200
ctgttattct tgccaacaag ttgtcctggt aaaaagtaga tgtgaaagtc acgtattggg 1260
acaaattgat ggttaagtgc tatagttcta tagttctgtg atacatctat ctgatttttt 1320
ttggtctatt ggtgcctaac ttatctgaaa atcatggaac atgaggctag tttgatcatg 1380
gtttagttca ttgtgattaa taatgtatga tttagtagct attttggtga tcgtgtcatt 1440
ttatttgtga atggaatcat tgtatgtaaa tgaagctagt tcaggggtta tgatgtagct 1500
ggctttgtat tctaaaggct gctattattc atccatcgat ttcacctata tgtaatccag 1560
agctttcgat gtgaaatttg tctgatcctt cactaggaag gacagaacat tgttaatatt 1620
ttggcacatc tgtcttattc tcatcctttg tttgaacatg ttagcctgtt caaacagata 1680
ctgttgtaat gtcctagtta tataggtaca tatgtgttct ctattgagtt tatggacttt 1740
tgtgtgtgaa gttatatttc attttgctca aaactcatgt ttgcaagctt tctgacatta 1800
ttctattgtt ctgaaacagg gt 1822

<210> SEQ ID NO 121
<211> LENGTH: 681
<212> TYPE: DNA
<213> ORGANISM: Setaria viridis

<400> SEQUENCE: 121
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc c 681

<210> SEQ ID NO 122
<211> LENGTH: 1925
<212> TYPE: DNA
<213> ORGANISM: Zea mays subsp. Mexicana

<400> SEQUENCE: 122
gtcgtgcccc tctctagaga taatgagcat tgcatgtcta agttataaaa aattaccaca 60 tattttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag tttttttattt 420 aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc aacctcgtgt tcgttcggag cgcgcacaca cacaaccaga tctcccccaa 900
atccacccgt cggcacctcc gcttcaaggt acgccgctca tcctcctccc cccccctctct 960 ctaccttctc tagatcggcg tttcggtcca tggttagggc ccggtagttc tacttctgtt 1020
catgtttgtg ttagatccgt gtttgtgtta gatccgtgct gctagatttc gtacacggat 1080
gcgacctgta catcagacat gttctgattg ctaacttgcc agtgtttctc tttggggaat 1140
cctgggatgg ctctagccgt tccgcagacg ggatcgattt catgaatttt ttttgtttcg 1200
ttgcataggg tttggtttgc ccttttcctt tatttcaata tatgccgtgc acttgtttgt 1260
cgggtcatct tttcatgttt tttttggctt ggttgtgatg atgtggtctg gttgggcggt 1320
cgttctagat cggagtagaa tactgtttca aactacctgg tggatttatt aaaggatctg 1380
tatgtatgtg ccatacatct tcatagttac gagtttaaga tgatggatgg aaatatcgat 1440
ctaggatagg tatacatgtt gatgcgggtt ttactgatgc atatacagag atgctttttt 1500
ttcgcttggt tgtgatgatg tggtctggtc gggcggtcgt tctagatcgg agtagaatac 1560
tgtttcaaac tacctggtgg atttattaat tttggatctg tatgtgtgtc atacatcttc 1620
atagttacga gtttaagatc gatggaaata tcgatctagg ataggtatac atgttgatgt 1680
gggttttact gatgcatata catggcatat gcagcatcta ttcatatgct ctaaccttga 1740
gtacctatct attataataa acaagtatgt tttataatta ttttgatctt gatatacttg 1800
gatgatggca tatgcagcag ctatatgtgg atttttttag ccctgccttc atacgctatt 1860
tatttgcttg gtactgtttc ttttgtcgat gctcaccctg ttgtttggtg atacttctgc 1920
aggtc 1925

<210> SEQ ID NO 123
<211> LENGTH: 850
<212> TYPE: DNA
<213> ORGANISM: Zea mays subsp. Mexicana

<400> SEQUENCE: 123
gtcgtgcccc tctctagaga taatgagcat tgcatgtcta agttataaaa aattaccaca 60 tattttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag ttttttattt 420
aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc 850

<210> SEQ ID NO 124
<211> LENGTH: 78
<212> TYPE: DNA
<213> ORGANISM: Zea mays subsp. Mexicana

<400> SEQUENCE: 124
aacctcgtgt tcgttcggag cgcgcacaca cacaaccaga tctcccccaa atccacccgt 60
cggcacctcc gcttcaag 78

<210> SEQ ID NO 125
<211> LENGTH: 997
<212> TYPE: DNA
<213> ORGANISM: Zea mays subsp. Mexicana

<400> SEQUENCE: 125
gtacgccgct catcctcctc cccccctct ctctaccttc tctagatcgg cgtttcggtc 60
catggttagg gcccggtagt tctacttctg ttcatgtttg tgttagatcc gtgtttgtgt 120
tagatccgtg ctgctagatt tcgtacacgg atgcgacctg tacatcagac atgttctgat 180
tgctaacttg ccagtgtttc tctttgggga atcctgggat ggctctagcc gttccgcaga 240
cgggatcgat ttcatgaatt ttttttgttt cgttgcatag ggtttggttt gcccttttcc 300
tttatttcaa tatatgccgt gcacttgttt gtcgggtcat cttttcatgt ttttttggc 360 ttggttgtga tgatgtggtc tggttgggcg gtcgttctag atcggagtag aatactgttt 420
caaactacct ggtggattta ttaaaggatc tgtatgtatg tgccatacat cttcatagtt 480
acgagtttaa gatgatggat ggaaatatcg atctaggata ggtatacatg ttgatgcggg 540
ttttactgat gcatatacag agatgctttt ttttcgcttg gttgtgatga tgtggtctgg 600
tcgggcggtc gttctagatc ggagtagaat actgtttcaa actacctggt ggatttatta 660
attttggatc tgtatgtgtg tcatacatct tcatagttac gagtttaaga tcgatggaaa 720
tatcgatcta ggataggtat acatgttgat gtgggtttta ctgatgcata tacatggcat 780
atgcagcatc tattcatatg ctctaacctt gagtacctat ctattataat aaacaagtat 840
gttttataat tattttgatc ttgatatact tggatgatgg catatgcagc agctatatgt 900
ggattttttt agccctgcct tcatacgcta tttatttgct tggtactgtt tcttttgtcg 960
atgctcaccc tgttgtttgg tgatacttct gcaggtc 997

<210> SEQ ID NO 126
<211> LENGTH: 1925
<212> TYPE: DNA
<213> ORGANISM: Zea mays subsp. Mexicana

<400> SEQUENCE: 126
gtcgtgcccc tctctagaga taatgagcat tgcatgtcta agttataaaa aattaccaca 60
tatttttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag tttttttattt 420 aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc aacctcgtgt tcgttcggag cgcgcacaca cacaaccaga tctcccccaa 900
atccacccgt cggcacctcc gcttcaaggt acgccgctca tcctcctccc ccccctctct 960
ctaccttctc tagatcggcg tttcggtcca tggttagggc ccggtagttc tacttctgtt 1020
catgtttgtg ttagatccgt gtttgtgtta gatccgtgct gctagatttc gtacacggat 1080
gcgacctgta catcagacat gttctgattg ctaacttgcc agtgtttctc tttggggaat 1140
cctgggatgg ctctagccgt tccgcagacg ggatcgattt catgaatttt ttttgtttcg 1200
ttgcataggg tttggtttgc ccttttcctt tatttcaata tatgccgtgc acttgtttgt 1260
cgggtcatct tttcatgttt tttttggctt ggttgtgatg atgtggtctg gttgggcggt 1320
cgttctagat cggagtagaa tactgtttca aactacctgg tggatttatt aaaggatctg 1380
tatgtatgtg ccatacatct tcatagttac gagtttaaga tgatggatgg aaatatcgat 1440
ctaggatagg tatacatgtt gatgcgggtt ttactgatgc atatacagag atgctttttt 1500
ttcgcttggt tgtgatgatg tggtctggtc gggcggtcgt tctagatcgg agtagaatac 1560
tgtttcaaac tacctggtgg atttattaat tttggatctg tatgtgtgtc atacatcttc 1620
atagttacga gtttaagatc gatggaaata tcgatctagg ataggtatac atgttgatgt 1680
gggttttact gatgcatata catggcatat gcagcatcta ttcatatgct ctaaccttga 1740
gtacctatct attataataa acaagtatgt tttataatta ttttgatctt gatatacttg 1800
gatgatggca tatgcagcag ctatatgtgg attttttttag ccctgccttc atacgctatt 1860
tatttgcttg gtactgtttc ttttgtcgat gctcaccctg ttgtttggtg atacttctgc 1920
agggt 1925

<210> SEQ ID NO 127
<211> LENGTH: 997

<212> TYPE: DNA
<213> ORGANISM: Zea mays subsp. Mexicana

<400> SEQUENCE: 127
gtacgccgct catcctcctc ccccccctct ctctaccttc tctagatcgg cgtttcggtc 60
catggttagg gcccggtagt tctacttctg ttcatgtttg tgttagatcc gtgtttgtgt 120
tagatccgtg ctgctagatt tcgtacacgg atgcgacctg tacatcagac atgttctgat 180
tgctaacttg ccagtgtttc tctttgggga atcctgggat ggctctagcc gttccgcaga 240
cgggatcgat ttcatgaatt ttttttgttt cgttgcatag ggtttggttt gccctttttcc 300
tttatttcaa tatatgccgt gcacttgttt gtcgggtcat cttttcatgt ttttttggc 360
ttggttgtga tgatgtggtc tggttgggcg gtcgttctag atcggagtag aatactgttt 420
caaactacct ggtggattta ttaaaggatc tgtatgtatg tgccatacat cttcatagtt 480
acgagtttaa gatgatggat ggaaatatcg atctaggata ggtatacatg ttgatgcggg 540
ttttactgat gcatatacag agatgctttt ttttcgcttg gttgtgatga tgtggtctgg 600
tcgggcggtc gttctagatc ggagtagaat actgtttcaa actacctggt ggatttatta 660
attttggatc tgtatgtgtg tcatacatct tcatagttac gagtttaaga tcgatggaaa 720
tatcgatcta ggataggtat acatgttgat gtgggtttta ctgatgcata tacatggcat 780
atgcagcatc tattcatatg ctctaacctt gagtacctat ctattataat aaacaagtat 840
gttttataat tattttgatc ttgatatact tggatgatgg catatgcagc agctatatgt 900
ggattttttt agccctgcct tcatacgcta tttatttgct tggtactgtt tcttttgtcg 960
atgctcaccc tgttgtttgg tgatacttct gcagggt 997

<210> SEQ ID NO 128
<211> LENGTH: 1974
<212> TYPE: DNA
<213> ORGANISM: Zea mays subsp. Mexicana

<400> SEQUENCE: 128
gtcgtgcccc tctctagaga taaagagcat tgcatgtcta agttataaaa aattaccaca 60
tatttttttt gtcacacttg tttgaagtgc agtttatcta tctttataca tatatttaaa 120
ctttactcta cgaataatat aatctatagt actacaataa tatcagtgtt ttagagaatc 180
atataaatga acagttagac atggtctaaa ggacaattga gtattttgac aacaggactc 240
tacagtttta tctttttagt gtgcatgtgt tctccttttt tttttgcaaa tagcttcacc 300
tatataatac ttcatccatt ttattagtac atccatttag ggtttagggt taatggtttt 360
tatagactaa ttttttttagt acatctattt tattctattt tagcctctaa attaagaaaa 420
ctaaaactct attttagttt ttttatttaa taatttagat ataaaataga ataaaataaa 480
gtgactaaaa attaaacaaa taccctttaa gaaattaaaa aaactaagga aacatttttc 540
ttgtttcgag tagataatgc cagcctgtta aacgccgtcg acgagtctaa cggacaccaa 600
ccagcgaacc agcagcgtcg cgtcgggcca agcgaagcag acggcacggc atctctgtcg 660
ctgcctctgg acccctctcg agagttccgc tccaccgttg gacttgctcc gctgtcggca 720
tccagaaatt gcgtggcgga gcggcagacg tgagccggca cggcaggcgg cctcctcctc 780
ctctcacggc accggcagct acgggggatt cctttcccac cgctccttcg ctttcccttc 840
ctcgcccgcc gtaataaata gacacccccct ccacaccttc tttccccaac ctcgtgttgt 900
tcggagcgca cacacacaca accagatctc ccccaaatcc acccgtcggc acctccgctt 960

-continued

```
caaggtacgc cgctcatcct cccccccccc tctctacctt ctctagatcg gcgttccggt   1020

ccatggttag ggcccggtag ttctacttct gttcatgttt gtgttagatc cgtgtttgtg   1080

ttagatccgt gctgctagcg ttcgtacacg gatgcgacct gtacgtcaga cacgttctga   1140

ttgctaactt gccagtgttt ctctttgggg aatcctggga tggctctagc cgttccgcag   1200

acgggatcga tttcatgatt ttttttgttt cgttgcatag ggtttggttt gcccttttcc   1260

tttatttcaa tatatgccgt gcacttgttt gtcgggtcat cttttcatgc ttttttttgt   1320

cttggttgtg atgatgtggt ctggttgggc ggtcgttcta gatcggagaa gaattctgtt   1380

tcaaactacc tggtggattt attaattttg gatctgtatg tgtgtgccat acatattcat   1440

agttacgaat tgaagatgat ggatggaaat atcgatctag gataggtata catgttgatg   1500

cgggttttac tgatgcatat acagagatgc tttttgttcg cttggttgtg atgatgtggt   1560

ctggttgggc ggtcgttcat tcgttctaga tcggagtaga atactgtttc aaactacctg   1620

gtgtatttat taattttgga actgtatgtg tgtgtcatac atcttcatag ttacgagttt   1680

aagatggatg gaaatatcga tctaggatag gtatacatgt tgatgtgggt tttactgatg   1740

catatacatg atggcatatg cagcatctat tcatatgctc taaccttgag tacctatcta   1800

ttataataaa caagtatgtt ttataattat tttgatcttg atatacttgg atgatggcat   1860

atgcagcagc tatatgtgga ttttttttagc cctgccttca tacgctattt atttgcttgg   1920

tactgtttct tttgtcgatg ctcaccctgt tgtttggtga tacttctgca ggtc         1974
```

<210> SEQ ID NO 129
<211> LENGTH: 887
<212> TYPE: DNA
<213> ORGANISM: Zea mays subsp. Mexicana

<400> SEQUENCE: 129

```
gtcgtgcccc tctctagaga taaagagcat tgcatgtcta agttataaaa aattaccaca     60

tatttttttt gtcacacttg tttgaagtgc agtttatcta tctttataca tatatttaaa    120

ctttactcta cgaataatat aatctatagt actacaataa tatcagtgtt ttagagaatc    180

atataaatga acagttagac atggtctaaa ggacaattga gtattttgac aacaggactc    240

tacagtttta tctttttagt gtgcatgtgt tctccttttt tttttgcaaa tagcttcacc    300

tatataatac ttcatccatt ttattagtac atccatttag ggtttagggt taatggtttt    360

tatagactaa ttttttttagt acatctattt tattctattt tagcctctaa attaagaaaa    420

ctaaaactct attttagttt ttttatttaa taatttagat ataaaataga ataaaataaa    480

gtgactaaaa attaaacaaa taccctttaa gaaattaaaa aaactaagga aacatttttc    540

ttgtttcgag tagataatgc cagcctgtta aacgccgtcg acgagtctaa cggacaccaa    600

ccagcgaacc agcagcgtcg cgtcgggcca agcgaagcag acggcacggc atctctgtcg    660

ctgcctctgg acccctctcg agagttccgc tccaccgttg gacttgctcc gctgtcggca    720

tccagaaatt gcgtggcgga gcggcagacg tgagccggca cggcaggcgg cctcctcctc    780

ctctcacggc accggcagct acgggggatt cctttcccac cgctccttcg ctttcccttc    840

ctcgcccgcc gtaataaata gacacccccct ccacaccttc tttcccc                 887
```

<210> SEQ ID NO 130
<211> LENGTH: 77
<212> TYPE: DNA
<213> ORGANISM: Zea mays subsp. Mexicana

<400> SEQUENCE: 130
aacctcgtgt tgttcggagc gcacacacac acaaccagat ctcccccaaa tccacccgtc 60
ggcacctccg cttcaag 77

<210> SEQ ID NO 131
<211> LENGTH: 1010
<212> TYPE: DNA
<213> ORGANISM: Zea mays subsp. Mexicana

<400> SEQUENCE: 131
gtacgccgct catcctcccc ccccccctctc taccttctct agatcggcgt tccggtccat 60
ggttagggcc cggtagttct acttctgttc atgtttgtgt tagatccgtg tttgtgttag 120
atccgtgctg ctagcgttcg tacacggatg cgacctgtac gtcagacacg ttctgattgc 180
taacttgcca gtgtttctct ttggggaatc ctgggatggc tctagccgtt ccgcagacgg 240
gatcgatttc atgatttttt ttgtttcgtt gcatagggtt tggtttgccc ttttccttta 300
tttcaatata tgccgtgcac ttgtttgtcg ggtcatcttt tcatgctttt ttttgtcttg 360
gttgtgatga tgtggtctgg ttgggcggtc gttctagatc ggagaagaat tctgtttcaa 420
actacctggt ggatttatta attttggatc tgtatgtgtg tgccatacat attcatagtt 480
acgaattgaa gatgatggat ggaaatatcg atctaggata ggtatacatg ttgatgcggg 540
ttttactgat gcatatacag agatgctttt tgttcgcttg gttgtgatga tgtggtctgg 600
ttgggcggtc gttcattcgt tctagatcgg agtagaatac tgtttcaaac tacctggtgt 660
atttattaat tttggaactg tatgtgtgtg tcatacatct tcatagttac gagtttaaga 720
tggatggaaa tatcgatcta ggataggtat acatgttgat gtgggtttta ctgatgcata 780
tacatgatgg catatgcagc atctattcat atgctctaac cttgagtacc tatctattat 840
aataaacaag tatgttttat aattattttg atcttgatat acttggatga tggcatatgc 900
agcagctata tgtggatttt tttagccctg ccttcatacg ctatttattt gcttggtact 960
gtttcttttg tcgatgctca ccctgttgtt tggtgatact tctgcaggtc 1010

<210> SEQ ID NO 132
<211> LENGTH: 1974
<212> TYPE: DNA
<213> ORGANISM: Zea mays subsp. Mexicana

<400> SEQUENCE: 132
gtcgtgcccc tctctagaga taaagagcat tgcatgtcta agttataaaa aattaccaca 60
tatttttttt gtcacacttg tttgaagtgc agtttatcta tctttataca tatatttaaa 120
ctttactcta cgaataatat aatctatagt actacaataa tatcagtgtt ttagagaatc 180
atataaatga acagttagac atggtctaaa ggacaattga gtattttgac aacaggactc 240
tacagtttta tctttttagt gtgcatgtgt tctccttttt tttttgcaaa tagcttcacc 300
tatataatac ttcatccatt ttattagtac atccatttag ggtttagggt taatggtttt 360
tatagactaa tttttttagt acatctattt tattctattt tagcctctaa attaagaaaa 420
ctaaaactct attttagttt ttttatttaa taatttagat ataaaataga ataaaataaa 480
gtgactaaaa attaaacaaa taccctttaa gaaattaaaa aaactaagga aacatttttc 540
ttgtttcgag tagataatgc cagcctgtta aacgccgtcg acgagtctaa cggacaccaa 600
ccagcgaacc agcagcgtcg cgtcgggcca agcgaagcag acggcacggc atctctgtcg 660
ctgcctctgg acccctctcg agagttccgc tccaccgttg gacttgctcc gctgtcggca 720

-continued

```
tccagaaatt gcgtggcgga gcggcagacg tgagccggca cggcaggcgg cctcctcctc    780
ctctcacggc accggcagct acgggggatt cctttcccac cgctccttcg ctttcccttc    840
ctcgcccgcc gtaataaata gacaccccct ccacaccttc tttccccaac ctcgtgttgt    900
tcggagcgca cacacacaca accagatctc ccccaaatcc acccgtcggc acctccgctt    960
caaggtacgc cgctcatcct cccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgacct gtacgtcaga cacgttctga   1140
ttgctaactt gccagtgttt ctctttgggg aatcctggga tggctctagc cgttccgcag   1200
acgggatcga tttcatgatt ttttttgttt cgttgcatag ggtttggttt gccctttcc    1260
tttatttcaa tatatgccgt gcacttgttt gtcgggtcat cttttcatgc ttttttttgt   1320
cttggttgtg atgatgtggt ctggttgggc ggtcgttcta gatcggagaa gaattctgtt   1380
tcaaactacc tggtggattt attaatttg gatctgtatg tgtgtgccat acatattcat    1440
agttacgaat tgaagatgat ggatggaaat atcgatctag gataggtata catgttgatg   1500
cgggttttac tgatgcatat acagagatgc tttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga ttttttagc cctgccttca tacgctattt atttgcttgg    1920
tactgtttct tttgtcgatg ctcaccctgt tgtttggtga tacttctgca gggt         1974
```

<210> SEQ ID NO 133
<211> LENGTH: 1010
<212> TYPE: DNA
<213> ORGANISM: Zea mays subsp. Mexicana

<400> SEQUENCE: 133

```
gtacgccgct catcctcccc ccccctctc taccttctct agatcggcgt tccggtccat      60
ggttagggcc cggtagttct acttctgttc atgtttgtgt tagatccgtg tttgtgttag    120
atccgtgctg ctagcgttcg tacacggatg cgacctgtac gtcagacacg ttctgattgc    180
taacttgcca gtgtttctct ttggggaatc ctgggatggc tctagccgtt ccgcagacgg    240
gatcgatttc atgatttttt ttgtttcgtt gcatagggtt tggtttgccc ttttccttta    300
tttcaatata tgccgtgcac ttgtttgtcg ggtcatcttt tcatgctttt ttttgtcttg    360
gttgtgatga tgtggtctgg ttgggcggtc gttctagatc ggagaagaat tctgtttcaa    420
actacctggt ggatttatta attttggatc tgtatgtgtg tgccatacat attcatagtt    480
acgaattgaa gatgatggat ggaaatatcg atctaggata ggtatacatg ttgatgcggg    540
ttttactgat gcatatacag agatgctttt tgttcgcttg gttgtgatga tgtggtctgg    600
ttgggcggtc gttcattcgt tctagatcgg agtagaatac tgtttcaaac tacctggtgt    660
atttattaat tttggaactg tatgtgtgtg tcatacatct tcatagttac gagtttaaga    720
tggatggaaa tatcgatcta ggataggtat acatgttgat gtgggtttta ctgatgcata    780
tacatgatgg catatgcagc atctattcat atgctctaac cttgagtacc tatctattat    840
aataaacaag tatgttttat aattattttg atcttgatat acttggatga tggcatatgc    900
```

agcagctata tgtggatttt tttagccctg ccttcatacg ctatttattt gcttggtact 960
gtttcttttg tcgatgctca ccctgttgtt tggtgatact tctgcagggt 1010

<210> SEQ ID NO 134
<211> LENGTH: 2008
<212> TYPE: DNA
<213> ORGANISM: Zea mays subsp. Mexicana

<400> SEQUENCE: 134
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gtttttttg caaatagctt gacctatata 300
atacttcatc cattttatta gtacatccat ttaggattta gggttgatgg tttctataga 360
ctaattttta gtacatccat tttattcttt ttagtctcta aatttttaa aactaaaact 420 ctattttagt tttttattta ataatttaga tataaaatga aataaaataa attgactaca 480
aataaaacaa atacccttta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacaccccct ccacaccctc tttccccaac ctcgtgttcg ttcggagcgc 900
acacacacgc aaccagatct cccccaaatc cagccgtcgg cacctccgct tcaaggtacg 960
ccgctcatcc tcccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc tttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggattttt 1920 agccctgcct tcatacgcta tttatttgct tggtactgtt tcttttgtcc gatgctcacc 1980
ctgttgttgg gtgatacttc tgcaggtc 2008

<210> SEQ ID NO 135
<211> LENGTH: 877
<212> TYPE: DNA
<213> ORGANISM: Zea mays subsp. Mexicana

<400> SEQUENCE: 135
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccottta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacaccccct ccacaccctc tttcccc 877

<210> SEQ ID NO 136
<211> LENGTH: 78
<212> TYPE: DNA
<213> ORGANISM: Zea mays subsp. Mexicana

<400> SEQUENCE: 136
aacctcgtgt tcgttcggag cgcacacaca cgcaaccaga tctcccccaa atccagccgt 60
cggcacctcc gcttcaag 78

<210> SEQ ID NO 137
<211> LENGTH: 1053
<212> TYPE: DNA
<213> ORGANISM: Zea mays subsp. Mexicana

<400> SEQUENCE: 137
gtacgccgct catcctcccc cccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600
catatacaga gatgctttt ttcgcttggt tgtgatgatg tggtctggtt gggcggtcgt 660
tctagatcgg agtagaatac tgtttcaaac tacctggtgg atttattaat tttgtatctt 720
tatgtgtgtg ccatacatct tcatagttac gagtttaaga tgatggatgg aaatattgat 780
ctaggatagg tatacatgtt gatgtgggtt ttactgatgc atatacatga tggcatatgc 840
ggcatctatt catatgctct aaccttgagt acctatctat tataataaac aagtatgttt 900
tataattatt ttgatcttga tatacttgga tgatggcata tgcagcagct atatgtggat 960
tttttagccc tgccttcata cgctatttat ttgcttggta ctgtttcttt tgtccgatgc 1020
tcaccctgtt gttgggtgat acttctgcag gtc 1053

<210> SEQ ID NO 138
<211> LENGTH: 2008
<212> TYPE: DNA
<213> ORGANISM: Zea mays subsp. Mexicana

<400> SEQUENCE: 138
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccctta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacacccct ccacaccctc tttccccaac ctcgtgttcg ttcggagcgc 900
acacacacgc aaccagatct cccccaaatc cagccgtcgg cacctccgct tcaaggtacg 960
ccgctcatcc tcccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc ttttttcgc ttggttgtga tgatgtggtc tggttgggcg gtcgttctag 1620

-continued atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgttgg gtgatacttc tgcagggt 2008

<210> SEQ ID NO 139
<211> LENGTH: 1053
<212> TYPE: DNA
<213> ORGANISM: Zea mays subsp. Mexicana

<400> SEQUENCE: 139
gtacgccgct catcctcccc cccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600
catatacaga gatgcttttt ttcgcttggt tgtgatgatg tggtctggtt gggcggtcgt 660
tctagatcgg agtagaatac tgtttcaaac tacctggtgg atttattaat tttgtatctt 720
tatgtgtgtg ccatacatct tcatagttac gagtttaaga tgatggatgg aaatattgat 780
ctaggatagg tatacatgtt gatgtgggtt ttactgatgc atatacatga tggcatatgc 840
ggcatctatt catatgctct aaccttgagt acctatctat tataataaac aagtatgttt 900
tataattatt ttgatcttga tatacttgga tgatggcata tgcagcagct atatgtggat 960
tttttagccc tgccttcata cgctatttat ttgcttggta ctgtttcttt tgtccgatgc 1020
tcaccctgtt gttgggtgat acttctgcag ggt 1053

<210> SEQ ID NO 140
<211> LENGTH: 1635
<212> TYPE: DNA
<213> ORGANISM: Sorghum bicolor

<400> SEQUENCE: 140
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga cgtaaccctc cgttgcccac 420
gataaaagct ccaccccga ccccggcccc ccgatttccc ctacggacca gtctcccccc 480
gatcgcaatc gcgaattcgt cgcaccatcg gcacgcagac gaacgaagca aggctctccc 540
catcggctcg tcaaggtatg cgttccctag atttgttccc ttcctctctc ggtttgtcta 600
tatatatgca tgtatggtcg attcccgatc tcgtcgattc tcggtttcgc cttccgtacg 660
aagattcgtt tagattgttc atatgttctg ttgtgttacc agattgatcg gatcaacttg 720
atccagttat cttcgctcct ccgattagat ccgtttctat ttcagtatat atatactagt 780
atagtatcta gggttcacac tgttgaccga ctggttactt ggaattgatc cgtgctgagt 840
tcagttgttg ccgtccataa aggcccgtgc tattgtctgt tctgaaacga aatcctgtag 900
atttcttagg gttagtgttc aattcatcaa aaggttgatt agtgaattat caaatttgag 960
agggttaaat cattctcatc atgttgtctc gaatgtaatc ccaaagatat tatagactgt 1020
gtttcgattt gatggattga tttgtgtatc atctaaatca acaaggctaa gtcatcagtt 1080
catagaatca tgtttaggtt tccgttcaat agactagttt tatcaatata taaaattata 1140
agaagggtag ggtaaatcac gttgcctcaa atgccatcct gtatggtttg gtttcaattc 1200
aattagtttg gttgattagg gtatgctctg gattaagatg gttaaatctt ccctagcatc 1260
ttccctgcct atccttactt gatccgtttc ggatatgttg gaagtacagc gagcttattt 1320
catgttgata gtgacccctt tcagattata ctattgaata ttgtatgttt gccacttctg 1380
tatgttgaat tatcctgcta aattagcaat ggaattagca tattggcaat tggtatgcat 1440
ggacctaatc aggacggatg tggttatgtt agtttcaatt cattgtcaat tcattgttca 1500
cctgcgttag atatatatga tgatttttac gtgtagttca tagttcttga gttttggatc 1560
tttcttatct gatatatgct ttcctgtgcc tgtgctttat tgtgtcttac catgcgattt 1620
ttgtctatgc aggtc 1635

<210> SEQ ID NO 141
<211> LENGTH: 401
<212> TYPE: DNA
<213> ORGANISM: Sorghum bicolor

<400> SEQUENCE: 141
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga c 401

<210> SEQ ID NO 142
<211> LENGTH: 154
<212> TYPE: DNA
<213> ORGANISM: Sorghum bicolor

<400> SEQUENCE: 142
gtaaccctcc gttgcccacg ataaaagctc cacccccgac cccggccccc cgatttcccc 60
tacggaccag tctccccccg atcgcaatcg cgaattcgtc gcaccatcgg cacgcagacg 120
aacgaagcaa ggctctcccc atcggctcgt caag 154

<210> SEQ ID NO 143
<211> LENGTH: 1080
<212> TYPE: DNA
<213> ORGANISM: Sorghum bicolor

<400> SEQUENCE: 143
gtatgcgttc cctagatttg ttcccttcct ctctcggttt gtctatatat atgcatgtat 60
ggtcgattcc cgatctcgtc gattctcggt ttcgccttcc gtacgaagat tcgtttagat 120
tgttcatatg ttctgttgtg ttaccagatt gatcggatca acttgatcca gttatcttcg 180
ctcctccgat tagatccgtt tctatttcag tatatatata ctagtatagt atctagggtt 240
cacactgttg accgactggt tacttggaat tgatccgtgc tgagttcagt tgttgccgtc 300
cataaaggcc cgtgctattg tctgttctga aacgaaatcc tgtagatttc ttagggttag 360
tgttcaattc atcaaaaggt tgattagtga attatcaaat ttgagagggt taaatcattc 420
tcatcatgtt gtctcgaatg taatcccaaa gatattatag actgtgtttc gatttgatgg 480
attgatttgt gtatcatcta aatcaacaag gctaagtcat cagttcatag aatcatgttt 540
aggtttccgt tcaatagact agttttatca atatataaaa ttataagaag ggtagggtaa 600
atcacgttgc ctcaaatgcc atcctgtatg gtttggtttc aattcaatta gtttggttga 660
ttagggtatg ctctggatta agatggttaa atcttcccta gcatcttccc tgcctatcct 720
tacttgatcc gtttcggata tgttggaagt acagcgagct tatttcatgt tgatagtgac 780
ccctttcaga ttatactatt gaatattgta tgtttgccac ttctgtatgt tgaattatcc 840
tgctaaatta gcaatggaat tagcatattg gcaattggta tgcatggacc taatcaggac 900
ggatgtggtt atgttagttt caattcattg tcaattcatt gttcacctgc gttagatata 960
tatgatgatt tttacgtgta gttcatagtt cttgagtttt ggatctttct tatctgatat 1020
atgctttcct gtgcctgtgc tttattgtgt cttaccatgc gatttttgtc tatgcaggtc 1080

<210> SEQ ID NO 144
<211> LENGTH: 2067
<212> TYPE: DNA
<213> ORGANISM: Sorghum bicolor

<400> SEQUENCE: 144
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480 ccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840

```
atccaggcaa ggcgcagagc ctcagaccag attccgatca atcacccata agctcccccc    900
aaatctgttc ctcgtctccc gtctcgcggt ttcctacttc cctcggacgc ctccggcaag    960
tcgctcgacc gcgcgattcc gcccgctcaa ggtatcaact cggttcacca ctccaatcta   1020
cgtctgattt agatgttact tccatctatg tctaatttag atgttactcc gatgcgattg   1080
gattatgttt atgcggtttg cactgctctg gaaactggaa tctagggttt cgagtgattt   1140
gatcgatcgc gatctgtgat ttcgttgcgc cttgtgtatg cttggagtga tctaggcttg   1200
tatatgcggc atcgcgatct gacgcggttg ctttgtagag gctgggggtc taggctgtga   1260
ttttagaatc aaataaagct gttccttacc gtagatgttt cctacatgtt ctgtccagta   1320
ctccagtgct atattcacat tgtttgaggc ttgagttttg tcgatcagtg gtcatgagaa   1380
aaatatatct catgatttta gaggcaccta ttgggaaagg tagatggttc cgttttacat   1440
gttttataga ccttgtggca tggctccttt gttctatggg tgctttattt tcctgaataa   1500
cagtaatgcg agactggtct atgggtgctt tgaccagtaa tgcgagacta gttatttgat   1560
catggtgcag ttcctagtga ttacgaacaa caatttggta gctcagttca ttcagcattg   1620
gtttctacga tccttatcat tttacttctg aatgaattta tttatttaag atattacagt   1680
gcaataaact gctgtataat atcagtaaca aactgctatt actagtaaat gcctagattc   1740
ataataattc attattctac ttgaaaatga tcttaggcct ttttatgcgg tcctacgcat   1800
ccttccacag gacttgctgt ttgtttgttt tttgtaatcc ctcgctggga cgcagaatgg   1860
ttcatctgtg ctaataattt ttttgcatat ataagtttat agttctcatt attcatgtgg   1920
ctatggtagc ctgtaaaatc tattgtaata acatattagt cagccataca tctgttccaa   1980
cttgctcaat tgcaaatcat atctccactt aaagcacatg tttgcaagct ttctgacaag   2040
tttctttgtg tttgattgaa acaggtg                                       2067
```

<210> SEQ ID NO 145
<211> LENGTH: 855
<212> TYPE: DNA
<213> ORGANISM: Sorghum bicolor

<400> SEQUENCE: 145

```
cattaaaagt cattatgtgc atgcgtcgta actaacatgg atatgttgct gcactatctc     60
ctcgcactag ctgcgcatga taaagccaca agccaaaatt aattattatg ggtgagaata    120
aatacgtacc agcaccggcc atagaaaaag tacattatta aaggtctaat ttggaaacag    180
tctgaaaacg acgtgcgctg cagaggtaaa tgtaattttc ggcactaaaa ccattatcaa    240
ctaattcatt caataacagt tatttagaaa atgtatagct cgctctaaaa aaacagttta    300
gaaaaacagt caaaataatt cgaccaacaa acagttaata aggttcatta aatatataat    360
gcacggtgct atttgatctt ttaaaggaaa aagaggaata gtcgtgggcg ccaggcggga    420
attggggcgc gggagtctgc cggacgacgc gttccgtccg aacggccgga cccgacgagg    480
ccccccgcc gccccacgtc gcagaaccgt ccgtgggtgg taatctggcc gggtacacca    540
gccgtcccct tgggcggcct cacagcactg ggctcacacg tgagttttgt tctgggcttc    600
ggatcgcacc atatgggcct cggcatcaga aagacggggc ccgtctggga tagaagagac    660
aggaacctcc tcgtggattc cagaagccag ccacgagcga ccaccgacgc ggaggatact    720
cgtcgtccaa gtccaacacg gcgggcgggc gggcggacgc gtgggctggg ctaactgcct    780
aaccttaacc tccaaggcac gccaaggccc gcttctccca cccgacataa atatcccccc    840
```

-continued atccaggcaa ggcgc 855

<210> SEQ ID NO 146
<211> LENGTH: 136
<212> TYPE: DNA
<213> ORGANISM: Sorghum bicolor

<400> SEQUENCE: 146
agagcctcag accagattcc gatcaatcac ccataagctc cccccaaatc tgttcctcgt 60
ctcccgtctc gcggtttcct acttccctcg gacgcctccg gcaagtcgct cgaccgcgcg 120
attccgcccg ctcaag 136

<210> SEQ ID NO 147
<211> LENGTH: 1076
<212> TYPE: DNA
<213> ORGANISM: Sorghum bicolor

<400> SEQUENCE: 147
gtatcaactc ggttcaccac tccaatctac gtctgattta gatgttactt ccatctatgt 60
ctaatttaga tgttactccg atgcgattgg attatgttta tgcggtttgc actgctctgg 120
aaactggaat ctagggtttc gagtgatttg atcgatcgcg atctgtgatt tcgttgcgcc 180
ttgtgtatgc ttggagtgat ctaggcttgt atatgcggca tcgcgatctg acgcggttgc 240
tttgtagagg ctgggggtct aggctgtgat tttagaatca aataaagctg ttccttaccg 300
tagatgtttc ctacatgttc tgtccagtac tccagtgcta tattcacatt gtttgaggct 360
tgagttttgt cgatcagtgg tcatgagaaa aatatatctc atgattttag aggcacctat 420
tgggaaaggt agatggttcc gttttacatg ttttatagac cttgtggcat ggctcctttg 480
ttctatgggt gctttatttt cctgaataac agtaatgcga gactggtcta tgggtgcttt 540
gaccagtaat gcgagactag ttatttgatc atggtgcagt tcctagtgat tacgaacaac 600
aatttggtag ctcagttcat tcagcattgg tttctacgat ccttatcatt ttacttctga 660
atgaatttat ttatttaaga tattacagtg caataaactg ctgtataata tcagtaacaa 720
actgctatta ctagtaaatg cctagattca taataattca ttattctact tgaaaatgat 780
cttaggcctt tttatgcggt cctacgcatc cttccacagg acttgctgtt tgtttgtttt 840
ttgtaatccc tcgctgggac gcagaatggt tcatctgtgc taataatttt tttgcatata 900
taagtttata gttctcatta ttcatgtggc tatggtagcc tgtaaaatct attgtaataa 960
catattagtc agccatacat ctgttccaac ttgctcaatt gcaaatcata tctccactta 1020
aagcacatgt ttgcaagctt tctgacaagt ttctttgtgt ttgattgaaa caggtg 1076

<210> SEQ ID NO 148
<211> LENGTH: 2067
<212> TYPE: DNA
<213> ORGANISM: Sorghum bicolor

<400> SEQUENCE: 148
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480
cccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840
atccaggcaa ggcgcagagc ctcagaccag attccgatca atcacccata agctcccccc 900
aaatctgttc ctcgtctccc gtctcgcggt ttcctacttc cctcggacgc ctccggcaag 960
tcgctcgacc gcgcgattcc gcccgctcaa ggtatcaact cggttcacca ctccaatcta 1020
cgtctgattt agatgttact tccatctatg tctaatttag atgttactcc gatgcgattg 1080
gattatgttt atgcggtttg cactgctctg gaaactggaa tctagggttt cgagtgattt 1140
gatcgatcgc gatctgtgat ttcgttgcgc cttgtgtatg cttggagtga tctaggcttg 1200
tatatgcggc atcgcgatct gacgcggttg ctttgtagag gctgggggtc taggctgtga 1260
ttttagaatc aaataaagct gttccttacc gtagatgttt cctacatgtt ctgtccagta 1320
ctccagtgct atattcacat tgtttgaggc ttgagttttg tcgatcagtg gtcatgagaa 1380
aaatatatct catgatttta gaggcaccta ttgggaaagg tagatggttc cgttttacat 1440
gttttataga ccttgtggca tggctccttt gttctatggg tgctttattt tcctgaataa 1500
cagtaatgcg agactggtct atgggtgctt tgaccagtaa tgcgagacta gttatttgat 1560
catggtgcag ttcctagtga ttacgaacaa caatttggta gctcagttca ttcagcattg 1620
gtttctacga tccttatcat tttacttctg aatgaattta tttatttaag atattacagt 1680
gcaataaact gctgtataat atcagtaaca aactgctatt actagtaaat gcctagattc 1740
ataataattc attattctac ttgaaaatga tcttaggcct ttttatgcgg tcctacgcat 1800
ccttccacag gacttgctgt ttgtttgttt tttgtaatcc ctcgctggga cgcagaatgg 1860
ttcatctgtg ctaataattt ttttgcatat ataagtttat agttctcatt attcatgtgg 1920
ctatggtagc ctgtaaaatc tattgtaata acatattagt cagccataca tctgttccaa 1980
cttgctcaat tgcaaatcat atctccactt aaagcacatg tttgcaagct ttctgacaag 2040
tttctttgtg tttgattgaa acagggt 2067

<210> SEQ ID NO 149
<211> LENGTH: 1076
<212> TYPE: DNA
<213> ORGANISM: Sorghum bicolor

<400> SEQUENCE: 149
gtatcaactc ggttcaccac tccaatctac gtctgattta gatgttactt ccatctatgt 60
ctaatttaga tgttactccg atgcgattgg attatgttta tgcggtttgc actgctctgg 120
aaactggaat ctagggtttc gagtgatttg atcgatcgcg atctgtgatt tcgttgcgcc 180
ttgtgtatgc ttggagtgat ctaggcttgt atatgcggca tcgcgatctg acgcggttgc 240
tttgtagagg ctgggggtct aggctgtgat tttagaatca aataaagctg ttccttaccg 300
tagatgtttc ctacatgttc tgtccagtac tccagtgcta tattcacatt gtttgaggct 360

-continued

```
tgagttttgt cgatcagtgg tcatgagaaa aatatatctc atgattttag aggcacctat    420

tgggaaaggt agatggttcc gttttacatg ttttatagac cttgtggcat ggctcctttg    480

ttctatgggt gctttatttt cctgaataac agtaatgcga gactggtcta tgggtgcttt    540

gaccagtaat gcgagactag ttatttgatc atggtgcagt tcctagtgat tacgaacaac    600

aatttggtag ctcagttcat tcagcattgg tttctacgat ccttatcatt ttacttctga    660

atgaatttat ttatttaaga tattacagtg caataaactg ctgtataata tcagtaacaa    720

actgctatta ctagtaaatg cctagattca taataattca ttattctact tgaaaatgat    780

cttaggcctt tttatgcggt cctacgcatc cttccacagg acttgctgtt tgtttgtttt    840

ttgtaatccc tcgctgggac gcagaatggt tcatctgtgc taataatttt tttgcatata    900

taagtttata gttctcatta ttcatgtggc tatggtagcc tgtaaaatct attgtaataa    960

catattagtc agccatacat ctgttccaac ttgctcaatt gcaaatcata tctccactta   1020

aagcacatgt ttgcaagctt tctgacaagt ttctttgtgt ttgattgaaa cagggt       1076
```

<210> SEQ ID NO 150
<211> LENGTH: 2003
<212> TYPE: DNA
<213> ORGANISM: Sorghum bicolor

<400> SEQUENCE: 150

```
agaagtaaaa aaaaagttcg tttcagaatc ataaaggtaa gttaaaaaaa gaccatacaa     60

aaaagaggta tttaatgata aactataatc cagaatttgt taggatagta tataagaata    120

agaccttgtt tagtttcaaa aaaatttgca aaattttcca gattcctcgt cacatcaaat    180

ctttagaggt atgcatggag tattaaatat agacaagacc taaataagaa aacatgaaat    240

gttcacgaaa aaaatcaagc caatgcatga tcgaagcaaa cggtatagta acggtgttaa    300

cctgatccat tgatctttgt aatctttaac ggccacctac cgcgggcagc aaacggcgtc    360

cccctcctcg atatctccgc ggcggcctct ggctttttcc gcggaattgc gcggtgggga    420

cggattccac gagaccgcaa cgcaaccgcc tctcgccgct gggccccaca ccgctcggtg    480

ccgtagcccg tagcctcacg ggattctttc tccctcctcc cccgtgtata aattggcttc    540

atcccctccc tgcctcatcc atccaaatcc cactccccaa tcccatcccg tcggagaaat    600

tcatcgaagc gaagcgaagc gaatcctccc gatcctctca aggtacgcga gttttcgaat    660

cccctccaga cccctcgtat gctttccctg ttcgttttcg tcgtagcgtt tgattaggta    720

tgctttccct gttcgtgttc gtcgtagggt tcgattaggt cgtgtgaggc catggcctgc    780

tgtgataaat ttatttgttg ttatatcgga tctgtagtcg atttgggggt cgtggtgtag    840

atccgcgggc tgtgatgaag ttatttggtg tgattgtgct cgcgtgattc tgcgcgttga    900

gctcgagtag atctgatggt tggacgaccg attggttcgt tggctggctg cgctaaggtt    960

gggctgggct catgttgcgt tcgctgttgc gcgtgattcc gcggatggac ttgcgcttga   1020

ttgccgccag atcacgttac gattatgtga tttcgtttgg aactttttag atttgtagct   1080

tctgcttatt atatgacaga tgcgcctact gctcatatgc ctgtggtaaa taatggatgg   1140

ctgtgggtca aactagttga ttgtcgagtc atgtatcata tacaggtgta tagacttgcg   1200

tctaattgtt tgcatgttgc agttatatga tttgttttag attgtttgtt ccactcatct   1260

aggctgtaaa agggacacta cttattagct tgttgtttaa tctttttatt agtagattat   1320

attggtaatg ttttactaat tattattatg ttatatgtga cttctgctca tgcctgatta   1380

taatcataga tcactgtagt tgattgttga atcatgtgtc aaatacccgt atacataaca   1440
```

ctacacattt gcttagttgt ttccttaact catgcaaatt gaacaccatg tatgatttgc 1500
atggtgctgt aatgttaaat actacagtcc tgttggtact tgtttagtaa gaatctgctt 1560
catacaacta tatgctatgc ctgatgataa tcatatatct ttgtgtaatt aataattagt 1620
tgactgttga ataatgtatc gagtacatac catggcacaa ttgcttagtc acttccttaa 1680
ccatgcatat tgaactgacc ccttcatgtt ctgctgaatt gttctattct gattagacca 1740
tacatcatgt attgcaatct ttatttgcaa ttgtaatgta atggttcggt tctcaaatgt 1800
taaatgctat agttgtgcta ctttctaatg ttaaatgcta tagctgtgct acttgtaaga 1860
tctgcttcat agtttagtta aattaggatg atgagctttg atgctgtaac tttgtttgat 1920
tatgttcata gttgatcagt ttttgttaga ctcacagtaa cttatggtct cactcttctt 1980
ctggtctttg atgtttgcag cgg 2003

<210> SEQ ID NO 151
<211> LENGTH: 565
<212> TYPE: DNA
<213> ORGANISM: Sorghum bicolor

<400> SEQUENCE: 151
agaagtaaaa aaaaagttcg tttcagaatc ataaaggtaa gttaaaaaaa gaccatacaa 60
aaaagaggta tttaatgata aactataatc cagaatttgt taggatagta tataagaata 120
agaccttgtt tagtttcaaa aaaatttgca aaattttcca gattcctcgt cacatcaaat 180
ctttagaggt atgcatggag tattaaatat agacaagacc taaataagaa aacatgaaat 240
gttcacgaaa aaaatcaagc caatgcatga tcgaagcaaa cggtatagta acggtgttaa 300
cctgatccat tgatctttgt aatctttaac ggccacctac cgcgggcagc aaacggcgtc 360
cccctcctcg atatctccgc ggcggcctct ggctttttcc gcggaattgc gcggtgggga 420
cggattccac gagaccgcaa cgcaaccgcc tctcgccgct gggcccccaca ccgctcggtg 480 ccgtagcccg tagcctcacg ggattctttc tccctcctcc cccgtgtata aattggcttc 540
atcccctccc tgcctcatcc atcca 565

<210> SEQ ID NO 152
<211> LENGTH: 77
<212> TYPE: DNA
<213> ORGANISM: Sorghum bicolor

<400> SEQUENCE: 152
aatcccactc cccaatccca tcccgtcgga gaaattcatc gaagcgaagc gaagcgaatc 60
ctcccgatcc tctcaag 77

<210> SEQ ID NO 153
<211> LENGTH: 1361
<212> TYPE: DNA
<213> ORGANISM: Sorghum bicolor

<400> SEQUENCE: 153
gtacgcgagt tttcgaatcc cctccagacc cctcgtatgc tttccctgtt cgttttcgtc 60
gtagcgtttg attaggtatg ctttccctgt tcgtgttcgt cgtagggttc gattaggtcg 120
tgtgaggcca tggcctgctg tgataaattt atttgttgtt atatcggatc tgtagtcgat 180
ttgggggtcg tggtgtagat ccgcgggctg tgatgaagtt atttggtgtg attgtgctcg 240
cgtgattctg cgcgttgagc tcgagtagat ctgatggttg gacgaccgat tggttcgttg 300
gctggctgcg ctaaggttgg gctgggctca tgttgcgttc gctgttgcgc gtgattccgc 360
ggatggactt gcgcttgatt gccgccagat cacgttacga ttatgtgatt tcgtttggaa 420
ctttttagat ttgtagcttc tgcttattat atgacagatg cgcctactgc tcatatgcct 480
gtggtaaata atggatggct gtgggtcaaa ctagttgatt gtcgagtcat gtatcatata 540
caggtgtata gacttgcgtc taattgtttg catgttgcag ttatatgatt tgttttagat 600
tgtttgttcc actcatctag gctgtaaaag ggacactact tattagcttg ttgtttaatc 660
tttttattag tagattatat tggtaatgtt ttactaatta ttattatgtt atatgtgact 720
tctgctcatg cctgattata atcatagatc actgtagttg attgttgaat catgtgtcaa 780
atacccgtat acataacact acacatttgc ttagttgttt ccttaactca tgcaaattga 840
acaccatgta tgatttgcat ggtgctgtaa tgttaaatac tacagtcctg ttggtacttg 900
tttagtaaga atctgcttca tacaactata tgctatgcct gatgataatc atatatcttt 960
gtgtaattaa taattagttg actgttgaat aatgtatcga gtacatacca tggcacaatt 1020
gcttagtcac ttccttaacc atgcatattg aactgacccc ttcatgttct gctgaattgt 1080
tctattctga ttagaccata catcatgtat tgcaatcttt atttgcaatt gtaatgtaat 1140
ggttcggttc tcaaatgtta aatgctatag ttgtgctact ttctaatgtt aaatgctata 1200
gctgtgctac ttgtaagatc tgcttcatag tttagttaaa ttaggatgat gagctttgat 1260
gctgtaactt tgtttgatta tgttcatagt tgatcagttt ttgttagact cacagtaact 1320
tatggtctca ctcttcttct ggtctttgat gtttgcagcg g 1361

<210> SEQ ID NO 154
<211> LENGTH: 1812
<212> TYPE: DNA
<213> ORGANISM: Artificial sequence
<220> FEATURE:
<223> OTHER INFORMATION: Codon optimized coding sequence.

<400> SEQUENCE: 154
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtatc accgtttgtg tgaacaacga actgaactgg 420
cagactatcc cgccgggaat ggtgattacc gacgaaaacg gcaagaaaaa gcagtcttac 480
ttccatgatt tctttaacta tgccggaatc catcgcagcg taatgctcta caccacgccg 540
aacacctggg tggacgatat caccgtggtg acgcatgtcg cgcaagactg taaccacgcg 600
tctgttgact ggcaggtggt ggccaatggt gatgtcagcg ttgaactgcg tgatgcggat 660
caacaggtgg ttgcaactgg acaaggcact agcgggactt tgcaagtggt gaatccgcac 720
ctctggcaac cgggtgaagg ttatctctat gaactgtgcg tcacagccaa aagccagaca 780
gagtgtgata tctacccgct tcgcgtcggc atccggtcag tggcagtgaa gggcgaacag 840
ttcctgatta accacaaacc gttctacttt actggctttg gtcgtcatga agatgcggac 900
ttgcgtggca aaggattcga taacgtgctg atggtgcacg accacgcatt aatggactgg 960
attggggcca actcctaccg tacctcgcat taccettacg ctgaagagat gctcgactgg 1020
gcagatgaac atggcatcgt ggtgattgat gaaactgctg ctgtcggctt taacctctct 1080
ttaggcattg gtttcgaagc gggcaacaag ccgaaagaac tgtacagcga agaggcagtc 1140
aacggggaaa ctcagcaagc gcacttacag gcgattaaag agctgatagc gcgtgacaaa 1200
aaccacccaa gcgtggtgat gtggagtatt gccaacgaac cggatacccg tccgcaaggt 1260
gcacgggaat atttcgcgcc actggcggaa gcaacgcgta aactcgaccc gacgcgtccg 1320
atcacctgcg tcaatgtaat gttctgcgac gctcacaccg ataccatcag cgatctcttt 1380
gatgtgctgt gcctgaaccg ttattacgga tggtatgtcc aaagcggcga tttggaaacg 1440
gcagagaagg tactggaaaa agaacttctg gcctggcagg agaaactgca tcagccgatt 1500
atcatcaccg aatacggcgt ggatacgtta gccgggctgc actcaatgta caccgacatg 1560
tggagtgaag agtatcagtg tgcatggctg gatatgtatc accgcgtctt tgatcgcgtc 1620
agcgccgtcg tcggtgaaca ggtatggaat ttcgccgatt ttgcgacctc gcaaggcata 1680
ttgcgcgttg gcggtaacaa gaaagggatc ttcactcgcg accgcaaacc gaagtcggcg 1740
gcttttctgc tgcaaaaacg ctggactggc atgaacttcg gtgaaaaacc gcagcaggga 1800
ggcaaacaat ga 1812

<210> SEQ ID NO 155
<211> LENGTH: 2001
<212> TYPE: DNA
<213> ORGANISM: Artificial sequence
<220> FEATURE:
<223> OTHER INFORMATION: Chimeric coding sequence with processable intron.

<400> SEQUENCE: 155
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtaag tttctgcttc tacctttgat atatatataa 420
taattatcat taattagtag taatataata tttcaaatat ttttttcaaa ataaaagaat 480
gtagtatata gcaattgctt ttctgtagtt tataagtgtg tatattttaa tttataactt 540
ttctaatata tgaccaaaat ttgttgatgt gcaggtatca ccgtttgtgt gaacaacgaa 600
ctgaactggc agactatccc gccgggaatg gtgattaccg acgaaaacgg caagaaaaag 660
cagtcttact tccatgattt ctttaactat gccggaatcc atcgcagcgt aatgctctac 720
accacgccga acacctgggt ggacgatatc accgtggtga cgcatgtcgc gcaagactgt 780
aaccacgcgt ctgttgactg gcaggtggtg gccaatggtg atgtcagcgt tgaactgcgt 840
gatgcggatc aacaggtggt tgcaactgga caaggcacta gcgggacttt gcaagtggtg 900
aatccgcacc tctggcaacc gggtgaaggt tatctctatg aactgtgcgt cacagccaaa 960
agccagacag agtgtgatat ctacccgctt cgcgtcggca tccggtcagt ggcagtgaag 1020
ggcgaacagt tcctgattaa ccacaaaccg ttctacttta ctggctttgg tcgtcatgaa 1080
gatgcggact tgcgtggcaa aggattcgat aacgtgctga tggtgcacga ccacgcatta 1140
atggactgga ttggggccaa ctcctaccgt acctcgcatt acccttacgc tgaagagatg 1200

```
ctcgactggg cagatgaaca tggcatcgtg gtgattgatg aaactgctgc tgtcggcttt   1260
aacctctctt taggcattgg tttcgaagcg ggcaacaagc cgaaagaact gtacagcgaa   1320
gaggcagtca acggggaaac tcagcaagcg cacttacagg cgattaaaga gctgatagcg   1380
cgtgacaaaa accacccaag cgtggtgatg tggagtattg ccaacgaacc ggatacccgt   1440
ccgcaaggtg cacgggaata tttcgcgcca ctggcggaag caacgcgtaa actcgacccg   1500
acgcgtccga tcacctgcgt caatgtaatg ttctgcgacg ctcacaccga taccatcagc   1560
gatctctttg atgtgctgtg cctgaaccgt tattacggat ggtatgtcca aagcggcgat   1620
ttggaaacgg cagagaaggt actggaaaaa gaacttctgg cctggcagga gaaactgcat   1680
cagccgatta tcatcaccga atacggcgtg gatacgttag ccgggctgca ctcaatgtac   1740
accgacatgt ggagtgaaga gtatcagtgt gcatggctgg atatgtatca ccgcgtcttt   1800
gatcgcgtca gcgccgtcgt cggtgaacag gtatggaatt tcgccgattt tgcgacctcg   1860
caaggcatat tgcgcgttgg cggtaacaag aaagggatct tcactcgcga ccgcaaaccg   1920
aagtcggcgg cttttctgct gcaaaaacgc tggactggca tgaacttcgg tgaaaaaccg   1980
cagcagggag gcaaacaatg a                                             2001
```

<210> SEQ ID NO 156
<211> LENGTH: 1653
<212> TYPE: DNA
<213> ORGANISM: Artificial sequence
<220> FEATURE:
<223> OTHER INFORMATION: Codon optimized coding sequence.

<400> SEQUENCE: 156

```
atggaagacg ccaaaaacat aaagaaaggc ccggcgccat tctatcctct agaggatgga     60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggccctt ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttt tacgatccct tcaggattac    840
aaaattcaaa gtgcgttgct agtaccaacc ctattttcat tcttcgccaa aagcactctg    900
attgacaaat acgatttatc taatttacac gaaattgctt ctgggggcgc acctctttcg    960
aaagaagtcg gggaagcggt tgcaaaacgc ttccatcttc cagggatacg acaaggatat   1020
gggctcactg agactacatc agctattctg attacacccg agggggatga taaaccgggc   1080
gcggtcggta aagttgttcc atttttttgaa gcgaaggttg tggatctgga taccgggaaa   1140
acgctgggcg ttaatcagag aggcgaatta tgtgtcagag gacctatgat tatgtccggt   1200
```

tatgtaaaca atccggaagc gaccaacgcc ttgattgaca aggatggatg gctacattct 1260
ggagacatag cttactggga cgaagacgaa cacttcttca tagttgaccg cttgaagtct 1320
ttaattaaat acaaaggata tcaggtggcc cccgctgaat tggaatcgat attgttacaa 1380
caccccaaca tcttcgacgc gggcgtggca ggtcttcccg acgatgacgc cggtgaactt 1440
cccgccgccg ttgttgtttt ggagcacgga aagacgatga cggaaaaaga gatcgtggat 1500
tacgtcgcca gtcaagtaac aaccgcgaaa aagttgcgcg gaggagttgt gtttgtggac 1560
gaagtaccga aaggtcttac cggaaaactc gacgcaagaa aaatcagaga gatcctcata 1620
aaggccaaga agggcggaaa gtccaaattg taa 1653

<210> SEQ ID NO 157
<211> LENGTH: 936
<212> TYPE: DNA
<213> ORGANISM: Artificial sequence
<220> FEATURE:
<223> OTHER INFORMATION: Codon optimized coding sequence.

<400> SEQUENCE: 157
atggcttcca aggtgtacga ccccgagcaa cgcaaacgca tgatcactgg gcctcagtgg 60
tgggctcgct gcaagcaaat gaacgtgctg gactccttca tcaactacta tgattccgag 120
aagcacgccg agaacgccgt gatttttctg catggtaacg ctgcctccag ctacctgtgg 180
aggcacgtcg tgcctcacat cgagcccgtg gctagatgca tcatccctga tctgatcgga 240
atgggtaagt ccggcaagag cgggaatggc tcatatcgcc tcctggatca ctacaagtac 300
ctcaccgctt ggttcgagct gctgaacctt ccaaagaaaa tcatctttgt gggccacgac 360 tgggggggctt gtctggcctt tcactactcc tacgagcacc aagacaagat caaggccatc 420
gtccatgctg agagtgtcgt ggacgtgatc gagtcctggg acgagtggcc tgacatcgag 480
gaggatatcg ccctgatcaa gagcgaagag ggcgagaaaa tggtgcttga gaataacttc 540
ttcgtcgaga ccatgctccc aagcaagatc atgcggaaac tggagcctga ggagttcgct 600
gcctacctgg agccattcaa ggagaagggc gaggttagac ggcctaccct ctcctggcct 660
cgcgagatcc ctctcgttaa gggaggcaag cccgacgtcg tccagattgt ccgcaactac 720
aacgcctacc ttcgggccag cgacgatctg cctaagatgt tcatcgagtc cgaccctggg 780
ttcttttcca acgctattgt cgagggagct aagaagttcc ctaacaccga gttcgtgaag 840
gtgaagggcc tccacttcag ccaggaggac gctccagatg aaatgggtaa gtacatcaag 900
agcttcgtgg agcgcgtgct gaagaacgag cagtaa 936

<210> SEQ ID NO 158
<211> LENGTH: 253
<212> TYPE: DNA
<213> ORGANISM: Agrobacterium tumefaciens

<400> SEQUENCE: 158
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 159
<211> LENGTH: 210

<212> TYPE: DNA
<213> ORGANISM: Triticum aestivum

<400> SEQUENCE: 159
ctgcatgcgt ttggacgtat gctcattcag gttggagcca atttggttga tgtgtgtgcg 60
agttcttgcg agtctgatga gacatctctg tattgtgttt ctttccccag tgttttctgt 120
acttgtgtaa tcggctaatc gccaacagat tcggcgatga ataaatgaga aataaattgt 180
tctgattttg agtgcaaaaa aaaaggaatt 210

<210> SEQ ID NO 160
<211> LENGTH: 300
<212> TYPE: DNA
<213> ORGANISM: Oryza sativa

<400> SEQUENCE: 160
attaatcgat cctccgatcc cttaattacc ataccattac accatgcatc aatatccata 60
tatatataaa ccctttcgca cgtacttata ctatgttttg tcatacatat atatgtgtcg 120
aacgatcgat ctatcactga tatgatatga ttgatccatc agcctgatct ctgtatcttg 180
ttatttgtat accgtcaaat aaaagtttct tccacttgtg ttaataatta gctactctca 240
tctcatgaac cctatatata actagtttaa tttgctgtca attgaacatg atgatcgatg 300

<210> SEQ ID NO 161
<211> LENGTH: 1204
<212> TYPE: DNA
<213> ORGANISM: Artificial sequence
<220> FEATURE:
<223> OTHER INFORMATION: Chimeric transcriptional regulatory expression element group.

<400> SEQUENCE: 161
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtggaaaag 360
gaaggtggct cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tccttcgcaa gacccttcct ctatataagg aagttcattt 600
catttggaga ggacacgctg acaagctgac tctagcagat cctctagaac catcttccac 660
acactcaagc cacactattg gagaacacac agggacaaca caccataaga tccaagggag 720
gcctccgccg ccgccggtaa ccaccccgcc cctctcctct ttctttctcc gttttttttt 780
ccgtctcggt ctcgatcttt ggccttggta gtttgggtgg gcgagaggcg gcttcgtgcg 840
cgcccagatc ggtgcgcggg aggggcggga tctcgcggct ggggctctcg ccggcgtgga 900
tccggcccgg atctcgcggg gaatggggct ctcggatgta gatctgcgat ccgccgttgt 960
tgggggagat gatggggggt ttaaaatttc cgccgtgcta aacaagatca ggaagagggg 1020
aaaagggcac tatggtttat atttttatat atttctgctg cttcgtcagg cttagatgtg 1080
ctagatcttt ctttcttctt tttgtgggta gaatttgaat ccctcagcat tgttcatcgg 1140
tagtttttct tttcatgatt tgtgacaaat gcagcctcgt gcggagcttt tttgtaggta 1200
gaag 1204

<210> SEQ ID NO 162
<211> LENGTH: 1396
<212> TYPE: DNA
<213> ORGANISM: Oryza sativa

<400> SEQUENCE: 162
tcgaggtcat tcatatgctt gagaagagag tcgggatagt ccaaaataaa acaaaggtaa 60
gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttagaaaaa cccatatgct aatttgacat aatttttgag 360
aaaaatatat attcaggcga attctcacaa tgaacaataa taagattaaa atagctttcc 420
cccgttgcag cgcatgggta ttttttctag taaaaataaa agataaactt agactcaaaa 480
catttacaaa aacaacccct aaagttccta aagcccaaag tgctatccac gatccatagc 540
aagcccagcc caacccaacc caacccagcc caccccagtc cagccaactg gacaatagtc 600
tccacacccc cccactatca ccgtgagttg tccgcacgca ccgcacgtct cgcagccaaa 660
aaaaaaaaga aagaaaaaaa agaaaaagaa aaaacagcag gtgggtccgg gtcgtggggg 720
ccggaaacgc gaggaggatc gcgagccagc gacgaggccg gccctccctc cgcttccaaa 780
gaaacgcccc ccatcgccac tatatacata cccccccctc tcctcccatc cccccaaccc 840
taccaccacc accaccacca cctccacctc ctcccccctc gctgccggac gacgagctcc 900 tccccccctcc ccctccgccg ccgccgcgcc ggtaaccacc ccgcccctct cctctttctt 960
tctccgtttt tttttccgtc tcggtctcga tctttggcct tggtagtttg ggtgggcgag 1020
aggcggcttc gtgccgccca gatcggtgcg cgggaggggc gggatctcgc ggctggctct 1080
cgcccccgtg gatccggccc ggatctcgcg gggaatgggg ctctcggatg tagatctgcg 1140
atccgccgtt gttggggccg atgatggggc ccttaaaatt tccgccgtgc taaacaagat 1200
caggaagagg ggaaaagggc actatggttt atatttttat atatttctgc tgcttcgtca 1260
ggcttagatg tgctagatct ttctttcttc tttttgtggg tagaatttaa tccctcagca 1320
ttgttcatcg gtagtttttc ttttcatgat tcgtgacaaa tgcagcctcg tgcggacgtt 1380
tttttgtagg tagaag 1396

<210> SEQ ID NO 163
<211> LENGTH: 1446
<212> TYPE: DNA
<213> ORGANISM: Artificial sequence
<220> FEATURE:
<223> OTHER INFORMATION: Chimeric transcriptional regulatory expression
element group.

<400> SEQUENCE: 163
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240

```
aagcaagtgg attgatgtga tggtccgatt gagacttttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacgctg acaagctgac tctagcagat ctaccgtctt cggtacgcgc    660
tcactccgcc ctctgccttt gttactgcca cgtttctctg aatgctctct tgtgtggtga    720
ttgctgagag tggtttagct ggatctagaa ttacactctg aaatcgtgtt ctgcctgtgc    780
tgattacttg ccgtcctttg tagcagcaaa atatagggac atggtagtac gaaacgaaga    840
tagaacctac acagcaatac gagaaatgtg taatttggtg cttagcggta tttatttaag    900
cacatgttgg tgttataggg cacttggatt cagaagtttg ctgttaattt aggcacaggc    960
ttcatactac atgggtcaat agtataggga ttcatattat aggcgatact ataataattt   1020
gttcgtctgc agagcttatt atttgccaaa attagatatt cctattctgt ttttgtttgt   1080
gtgctgttaa attgttaacg cctgaaggaa taaatataaa tgacgaaatt ttgatgttta   1140
tctctgctcc tttattgtga ccataagtca agatcagatg cacttgtttt aaatattgtt   1200
gtctgaagaa ataagtactg acagtatttt gatgcattga tctgcttgtt tgttgtaaca   1260
aaatttaaaa ataaagagtt tcctttttgt tgctctcctt acctcctgat ggtatctagt   1320
atctaccaac tgacactata ttgcttctct ttacatacgt atcttgctcg atgccttctc   1380
cctagtgttg accagtgtta ctcacatagt ctttgctcat ttcattgtaa tgcagatacc   1440
aagcgg                                                              1446
```

```
<210> SEQ ID NO 164
<211> LENGTH: 675
<212> TYPE: DNA
<213> ORGANISM: Artificial sequence
<220> FEATURE:
<223> OTHER INFORMATION: Chimeric transcriptional regulatory expression
      element group.

<400> SEQUENCE: 164

ggtccgatgt gagacttttc aacaaagggt aatatccgga aacctcctcg gattccattg     60
cccagctatc tgtcacttta ttgtgaagat agtggaaaag gaaggtggct cctacaaatg    120
ccatcattgc gataaaggaa aggccatcgt tgaagatgcc tctgccgaca gtggtcccaa    180
agatggaccc ccacccacga ggagcatcgt ggaaaaagaa gacgttccaa ccacgtcttc    240
aaagcaagtg gattgatgtg atggtccgat gtgagacttt tcaacaaagg gtaatatccg    300
gaaacctcct cggattccat tgcccagcta tctgtcactt tattgtgaag atagtggaaa    360
aggaaggtgg ctcctacaaa tgccatcatt gcgataaagg aaaggccatc gttgaagatg    420
cctctgccga cagtggtccc aaagatggac ccccacccac gaggagcatc gtggaaaaag    480
aagacgttcc aaccacgtct tcaaagcaag tggattgatg tgatatctcc actgacgtaa    540
gggatgacgc acaatcccac tatccttcgc aagacccttc ctctatataa ggaagttcat    600
ttcatttgga gaggaaccat cttccacaca ctcaagccac actattggag aacacacagg    660
gacaacacac cataa                                                     675
```

<210> SEQ ID NO 165
<211> LENGTH: 804
<212> TYPE: DNA
<213> ORGANISM: Zea mays

<400> SEQUENCE: 165
accgtcttcg gtacgcgctc actccgccct ctgcctttgt tactgccacg tttctctgaa 60
tgctctcttg tgtggtgatt gctgagagtg gtttagctgg atctagaatt acactctgaa 120
atcgtgttct gcctgtgctg attacttgcc gtcctttgta gcagcaaaat atagggacat 180
ggtagtacga aacgaagata gaacctacac agcaatacga gaaatgtgta atttggtgct 240
tagcggtatt tatttaagca catgttggtg ttatagggca cttggattca gaagtttgct 300
gttaatttag gcacaggctt catactacat gggtcaatag tatagggatt catattatag 360
gcgatactat aataatttgt tcgtctgcag agcttattat ttgccaaaat tagatattcc 420
tattctgttt ttgtttgtgt gctgttaaat tgttaacgcc tgaaggaata aatataaatg 480
acgaaatttt gatgtttatc tctgctcctt tattgtgacc ataagtcaag atcagatgca 540
cttgttttaa atattgttgt ctgaagaaat aagtactgac agtattttga tgcattgatc 600
tgcttgtttg ttgtaacaaa atttaaaaat aaagagtttc ctttttgttg ctctccttac 660
ctcctgatgg tatctagtat ctaccaactg acactatatt gcttctcttt acatacgtat 720
cttgctcgat gccttctccc tagtgttgac cagtgttact cacatagtct ttgctcattt 780
cattgtaatg cagataccaa gcgg 804

<210> SEQ ID NO 166
<211> LENGTH: 623
<212> TYPE: DNA
<213> ORGANISM: Cauliflower mosaic virus

<400> SEQUENCE: 166
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat gtgagacttt tcaacaaagg gtaatatccg 300
gaaacctcct cggattccat tgcccagcta tctgtcactt tattgtgaag atagtggaaa 360
aggaaggtgg ctcctacaaa tgccatcatt gcgataaagg aaaggccatc gttgaagatg 420
cctctgccga cagtggtccc aaagatggac ccccacccac gaggagcatc gtggaaaaag 480
aagacgttcc aaccacgtct tcaaagcaag tggattgatg tgatatctcc actgacgtaa 540
gggatgacgc acaatcccac tatccttcgc aagacccttc ctctatataa ggaagttcat 600
ttcatttgga gaggacacgc tga 623

<210> SEQ ID NO 167
<211> LENGTH: 8
<212> TYPE: DNA
<213> ORGANISM: Cauliflower mosaic virus

<400> SEQUENCE: 167 acacgctg 8

<210> SEQ ID NO 168
<211> LENGTH: 1790
<212> TYPE: DNA

<213> ORGANISM: Coix lacryma-jobi

<400> SEQUENCE: 168
gtgatgttca agatattgta atggtgttta ttttctatca aatagccata aaatgatata 60
caaaatgtta ttcatgattg atcctagtta cattcaaagt attaaatagc ttgcagatag 120
taaatagaca gtcattgtat aacctgtttt tttgactgtc tatgttcagt tccaagaact 180
tacagacaag aggttatgtg tagattgaac gtgcccttga cggcatccaa ctagcgaacc 240
acgagggaag cagatggtgg ccgttgaggg gctgttgacg caaagcatct ctctcggctg 300
ctctcgaaag ctccattgcg ggtggcggtc tggtggcacc aggaaattgc gtgagccaag 360
gcgggctcgt ctcggtctca caacacggca cgaaaccgtc acggcacacg gcaccaggat 420
ttccttcccc tcccctgccg ttctcctcat cataaatagc cacccccctcc tcgcctcttt 480 tccccaactc atctgttctt cgtctcacac agccagatcc caatccctct cctcgcgaac 540
ttcgtcgatc tcccttccct cgcctcgctt caaggtacgg cgatcatcct cccgctttcc 600
ctcctcctcc tctagatgta gtacggagta cttgccatca tgcatcatgc tacatcacgc 660
tcgtgcgagc tctgggtcct cgatctggga acggaactgt gggatgctgc tcgtgcgatt 720
tattattggg gatctgggtt ctcgatctgg gaacggaact gtgggatgct gctcgtgcga 780
tttattattg gggatctggg ttctcgatct gggaacggaa ctgtgggatg cttgtaggca 840
ggtcggagat gggtcggatc gttgcttagg gttcgatctg ctcgtggttt tcttttaatc 900
cctgatgcat gatttatcgg tcatcctatt agatggaacc agtagggtga ctctgatccg 960
atatacttaa cctcgatctg gttcgatgtt cctggctagg cttgtgcgtc tgtttcgtca 1020
gaccagtttt gctgttttttg gtatggttgt gatgcccgtc caaatatgac taagcgagtg 1080
tagaatcatt ttatgaacta actgctggtc ttattaaatc tagatctgca tacgttgatg 1140
tactacgttc atagttgata cagtatgtat gaactagttg ctggtcgtat taattttgga 1200
tctgcatgtg tggtagcata taatgttcat aatacaattg atacagtatg atgtatgaac 1260
tatctgctgg tttattaaat ttggatctgc ttgtggtaaa aaatatgttt tttatatagt 1320
taccatgatg gattaatcta tacttctgat gtatatgctg cagttttctg ctgaggctgt 1380 agtttttttcc agattaaaat acagcatgca tatttgctaa gctctgggcg tgtgaacgcc 1440
caccatggca ttgtccagta atagtaatga attttttttgt ttgcctgatg tgggagaaaa 1500
cacgcattgt ccagttattt tgttccatat gcattgtcct gttttgttgg atatgcatgc 1560
ttagaaaaca tatgcagcca ctgtttgata atgctttagc atctgcctgt tgaacatgca 1620
tgatctacct atctttattt tgtatgtact tgggtagtgg catgttgcta gttttccttg 1680
attctgtggc gtctacatgt tgagcttgca tatatgtttg ttgtccttct tttcctcctt 1740
ggtctactgc tatatgctta cccttttgtt tggctaattt tcaggtgcag 1790

<210> SEQ ID NO 169
<211> LENGTH: 481
<212> TYPE: DNA
<213> ORGANISM: Coix lacryma-jobi

<400> SEQUENCE: 169
gtgatgttca agatattgta atggtgttta ttttctatca aatagccata aaatgatata 60
caaaatgtta ttcatgattg atcctagtta cattcaaagt attaaatagc ttgcagatag 120
taaatagaca gtcattgtat aacctgtttt tttgactgtc tatgttcagt tccaagaact 180
tacagacaag aggttatgtg tagattgaac gtgcccttga cggcatccaa ctagcgaacc 240
acgagggaag cagatggtgg ccgttgaggg gctgttgacg caaagcatct ctctcggctg 300
ctctcgaaag ctccattgcg ggtggcggtc tggtggcacc aggaaattgc gtgagccaag 360
gcgggctcgt ctcggtctca caacacggca cgaaaccgtc acggcacacg gcaccaggat 420
ttccttcccc tcccctgccg ttctcctcat cataaatagc cacccccctcc tcgcctcttt 480 t 481

<210> SEQ ID NO 170
<211> LENGTH: 93
<212> TYPE: DNA
<213> ORGANISM: Coix lacryma-jobi

<400> SEQUENCE: 170
ccccaactca tctgttcttc gtctcacaca gccagatccc aatccctctc ctcgcgaact 60
tcgtcgatct cccttccctc gcctcgcttc aag 93

<210> SEQ ID NO 171
<211> LENGTH: 1216
<212> TYPE: DNA
<213> ORGANISM: Coix lacryma-jobi

<400> SEQUENCE: 171
gtacggcgat catcctcccg ctttccctcc tcctcctcta gatgtagtac ggagtacttg 60
ccatcatgca tcatgctaca tcacgctcgt gcgagctctg ggtcctcgat ctgggaacgg 120
aactgtggga tgctgctcgt gcgatttatt attggggatc tgggttctcg atctgggaac 180
ggaactgtgg gatgctgctc gtgcgattta ttattgggga tctgggttct cgatctggga 240
acggaactgt gggatgcttg taggcaggtc ggagatgggt cggatcgttg cttagggttc 300
gatctgctcg tggttttctt ttaatccctg atgcatgatt tatcggtcat cctattagat 360
ggaaccagta gggtgactct gatccgatat acttaacctc gatctggttc gatgttcctg 420
gctaggcttg tgcgtctgtt tcgtcagacc agttttgctg tttttggtat ggttgtgatg 480
cccgtccaaa tatgactaag cgagtgtaga atcattttat gaactaactg ctggtcttat 540
taaatctaga tctgcatacg ttgatgtact acgttcatag ttgatacagt atgtatgaac 600
tagttgctgg tcgtattaat tttggatctg catgtgtggt agcatataat gttcataata 660
caattgatac agtatgatgt atgaactatc tgctggttta ttaaatttgg atctgcttgt 720
ggtaaaaaat atgtttttta tatagttacc atgatggatt aatctatact tctgatgtat 780
atgctgcagt tttctgctga ggctgtagtt ttttccagat taaaatacag catgcatatt 840
tgctaagctc tgggcgtgtg aacgcccacc atggcattgt ccagtaatag taatgaattt 900
ttttgtttgc ctgatgtggg agaaaacacg cattgtccag ttattttgtt ccatatgcat 960
tgtcctgttt tgttggatat gcatgcttag aaaacatatg cagccactgt ttgataatgc 1020
tttagcatct gcctgttgaa catgcatgat ctacctatct ttattttgta tgtacttggg 1080
tagtggcatg ttgctagttt tccttgattc tgtggcgtct acatgttgag cttgcatata 1140
tgtttgttgt ccttcttttc ctccttggtc tactgctata tgcttaccct tttgtttggc 1200
taattttcag gtgcag 1216